(12) United States Patent
Barry

(10) Patent No.: US 11,485,767 B2
(45) Date of Patent: Nov. 1, 2022

(54) MULTIVALENT PD-L1 BINDING COMPOUNDS FOR TREATING CANCER

(71) Applicant: MAYO FOUNDATION FOR MEDICAL EDUCATION AND RESEARCH, Rochester, MN (US)

(72) Inventor: Michael A. Barry, Rochester, MN (US)

(73) Assignee: MAYO FOUNDATION FOR MEDICAL EDUCATION AND RESEARCH, Rochester, MN (US)

(*) Notice: Subject to any disclaimer, the term of this patent is extended or adjusted under 35 U.S.C. 154(b) by 0 days.

(21) Appl. No.: 16/860,637

(22) Filed: Apr. 28, 2020

(65) Prior Publication Data

US 2020/0339654 A1   Oct. 29, 2020

Related U.S. Application Data

(60) Provisional application No. 62/839,916, filed on Apr. 29, 2019.

(51) Int. Cl.
| | |
|---|---|
| *A61P 35/00* | (2006.01) |
| *C07K 14/005* | (2006.01) |
| *C07K 14/705* | (2006.01) |
| *C12N 7/00* | (2006.01) |
| *A61K 38/00* | (2006.01) |

(52) U.S. Cl.
CPC ........ *C07K 14/70521* (2013.01); *A61P 35/00* (2018.01); *C07K 14/005* (2013.01); *C12N 7/00* (2013.01); *A61K 38/00* (2013.01); *C12N 2710/10022* (2013.01)

(58) Field of Classification Search
CPC combination set(s) only.
See application file for complete search history.

(56) References Cited

U.S. PATENT DOCUMENTS

| | | | |
|---|---|---|---|
| 6,153,435 | A | 11/2000 | Crystal |
| 7,332,337 | B2 | 2/2008 | van Es |
| 7,741,099 | B2 | 6/2010 | Havenga et al. |
| 7,951,585 | B2 | 5/2011 | Ke |
| 8,834,863 | B2 | 9/2014 | Roy |
| 9,546,206 | B2 | 1/2017 | Ring et al. |
| 9,562,087 | B2 | 2/2017 | Ring et al. |
| 9,683,025 | B2 | 6/2017 | Zhang et al. |
| 10,588,938 | B2 | 3/2020 | Giaccia et al. |
| 10,800,830 | B2 | 10/2020 | Ring et al. |
| 2003/0219899 | A1 | 11/2003 | Korokhov |
| 2004/0191222 | A1 | 9/2004 | Emini |
| 2005/0265973 | A1 | 12/2005 | Harden |
| 2011/0318373 | A1* | 12/2011 | Sasikumar ............ A61P 1/04 424/185.1 |
| 2012/0264192 | A1 | 10/2012 | Yamamoto |
| 2013/0004461 | A1 | 1/2013 | Roy |
| 2015/0250837 | A1 | 9/2015 | Nolin |
| 2017/0157188 | A1 | 6/2017 | Silvestre |
| 2018/0346571 | A1 | 12/2018 | Gurney |
| 2019/0153471 | A1 | 5/2019 | Paul |
| 2019/0382793 | A1 | 12/2019 | Stewart |
| 2020/0157510 | A1 | 5/2020 | Barry |

FOREIGN PATENT DOCUMENTS

| | | |
|---|---|---|
| EP | 1786488 | 5/2007 |
| WO | WO 2011/043719 | 4/2011 |
| WO | WO 2012/083297 | 6/2012 |
| WO | WO2015166082 | 11/2015 |
| WO | WO2019202118 | 10/2019 |

OTHER PUBLICATIONS

McDermott et al., "PD-1 as a potential target in cancer therapy," Cancer Medicine 2(5): 662-673 (2013) (Year: 2013).*
Teng et al., "Classifying Cancers BasedonT-cell Infiltration and PD-L1," Am. Assoc. Cancer Res. J. 75:2139-2145 (2015) (Year: 2015).*
Kiesler, "Why a New Immunotherapy for Lung Cancer Works for Only Some People," accessed Feb. 12, 2018 at URL mskcc.org/blog/why-new-immunotherapy-lung-works-only-some-people (Apr. 2015; pp. 1-4)) (Year: 2015).*
National Institute of Cancer—understanding and related topics, accessed Aug. 21, 2014 at URL: cancer.gov/cancertopics/understandingcancer, 63 pages (Year: 2017).*
Merck Manuals Lung Carcinoma accessed Mar. 12, 2017 at URL merckmanuals.com/professional/pulmonary-disorders/tumors-of-the-lungs/lung-carcinoma, 18 pages (Year: 2017).*
Merck Manuals Neuroblastoma accessed Mar. 12, 2017 at URL merckmanuals.com/professional/ pediatrics/pediatric-cancers/neuroblastoma, 4 pages (Year: 2017).*
Merck Manual Colorectal Cancer accessed Aug. 21, 2014 at URL merckmanuals.com/home/digestive_disorders/tumors_of_the_digestive_system/colorectal_cancer.htm, 5 pages (Year: 2013).*

(Continued)

*Primary Examiner* — Julie Ha
*Assistant Examiner* — Kristina M Hellman
(74) *Attorney, Agent, or Firm* — Hueschen and Sage

(57) ABSTRACT

This invention provides methods and materials for treating cancer. The invention encompasses methods and materials for delivering programmed death-ligand 1 (PD-L1) binding compounds and/or compositions containing one or more monovalent or multivalent programmed death-ligand 1 (PD-L1) binding compounds which are administered to a mammal having cancer to treat the mammal. In some cases, a multivalent PD-L1 binding compound can include two or more programmed cell death protein 1 (PD-1) polypeptides (and/or fragments thereof having the ability to bind PD-L1). This invention also provides methods and materials for making multivalent PD-L1 binding compounds and methods and materials for making nucleic acid molecules that encode PD-L1 binding compounds.

16 Claims, 22 Drawing Sheets

Specification includes a Sequence Listing.

(56) References Cited

OTHER PUBLICATIONS

Merck Manual Prostate Cancer accessed Aug. 21, 2014 at URL: merckmanuals.com/home/kidney_and_urinary_tract_disorders/cancers_of_the_kidney_and_genitourinary_tract/prostate_cancer.html?qt=prostate cancer&alt=sh, 8 pages (Year: 2013).*
Cholangiocarcinoma accessed Mar. 12, 2017 at URL surgery.usc.edu/divisions/tumor/pancreasdiseases/web%20pages/BILIARY%20SYSTEM/cholangiocarcinoma, 2 pages, (Year: 2017).*
Thyroid cancer accessed Mar. 12, 2017 at URL www.merckmanuals.com/professional/endocrine-and-metabolic-disorders/thyroid-disorders/thyroid-cancers, 4 pages (Year: 2016).*
Renal cell carcinoma, accessed Mar. 12, 2017 at URL merckmanuals.com/professional/genitourinary-disorders/genitourinary-cancer/renal-cell-carcinoma, 6 pages (Year: 2017).*
Merck Manual Bladder Cancer accessed Aug. 21, 2014 at URL: merckmanuals.com/home/kidney_and_urinary_tract_disorders/cancers_of_the_kidney_and_genitourinary_tract/bladder_cancer.html, 2 pages (Year: 2014).*
Borovjagin et al. "Adenovirus-Based Vectors for the Development of Prophylactic and Therapeutic Vaccines," Novel Technologies for Vaccine Development, publisher-Springer-Verlag Wien, chptr8., pp. 203-271 (2014) (Year: 2014).*
Chen, Christopher, Y., et al., "Targeting adenoviruses with factor x-single-chain antibody fusion proteins",Human Gene Therapy, vol. 21, No. 6, Jun. 1, 2010, pp. 739-749.
Fromm, George, et al., "Agonist redirected checkpoint, PD1-Fc-OX40L, for cancer immunotherapy", Journal for Immunotheapy of Cancer, 6:149, 2018. pp. 1-16.
Gao, Wenda, et al., "Stimulating PD-1-negative signals concurrent with blocking CD154 co-stimulation induces long-term islet allograft survival", Transplantation, vol. 76, No. 6, Sep. 1, 2003, pp. 994-999.
Herrmann, Monika, et al., "Bifunctional PD-1 x αCD3 x αCD33 fusion protein reverses adaptive immune escape in acute myeloid leukemia", Blood, vol. 132, No. 23, Dec. 6, 2018, pp. 2484-2494
International Search Report for PCT/US2020/030240 dated Aug. 13, 2020

Nguyen, Tien, V., et al., "Oncolytic adenovirus Ad657 for systemic virotherapy against prostate cancer", Oncolytic Virotherapy, vol. 7, May 1, 2018, pp. 43-51.
Stepanenko, Aleksei, et al., "Tropism and transduction of oncolytic adenovirus 5 vectors in cancer therapy: focus on fiber chimerism and mosaicism, hexon and pIX", Virus Research, vol. 257, Sep. 1, 2018, pp. 40-51.
Wang, Gongze, et al., "Modification of sPD1 with CRT induces potent anti-tumor immune responses in vitro and in vivo", Biomedicine and Pharmacotherapy, vol. 76. Nov. 10, 2015, pp. 57-64.
Yoon, A-Rum, et al., "A vesicular stomatitis virus glycoprotein epitope-inmporated oncolytic adenovirus overcomes CAR-dependency and shows markedly enhanced cancer cell killing and suppression of tumor growth", Oncotarget, vol. 6, No. 33, Oct. 27, 2015, pp. 34875-34891.
Barry, Michael, "Single-cycle adenovirus vectors in the current vaccine landscape", Expert Rev Vaccines, 17(2), Feb. 2018, pp. 163-173.
International Search Report for PCT/US2019/062547 dated Feb. 5, 2020.
International Preliminary Report on Patentability for PCT/US2020/030240 dated Mar. 24, 2021.
Brahmer et al, The New England Journal of Medicine. 366:245-65, 2012 Brahmer et al., "Safety and activity of anti-PD-L1 antibody in patients with advanced cancer," New England Journal of Medicine 366: 2455-65 (2012).
Davison, AJ. Journal of General Virology, 84(11):2895-2908, 2003. Davison, "Genetic content and evolution of adenoviruses," J. General Virol. 84(11): 2895-2908 (2003).
Iwai, et al. "Involvement of PD-1 on tumor cells in the escape from host immune system and tumor immunotheapy by PD-L1 blockade", Proceedings of the National Academy of Sciences, 99(19):12293-97, 2002.
Maute, et al. Proceedings of the National Academy of Sciences, 112(47), E6506-E6514, published online Nov. 10, 2015.
Miao, et al. "Netralizing PD-L1 and PD-L2 Enhances teh Efficacy of Immune Checkpoint inhibitors in Ovarian Cancer", bioRxiv, published online Jan. 20, 2020.
Weaver, et al. Virology, 412(1):19-27, 2011. Weaver et al., "Characterization of species C human adenovirus serotype 6 (Ad6)," Virology 412(1): 19-27 (2011).

* cited by examiner

Fig. 2A
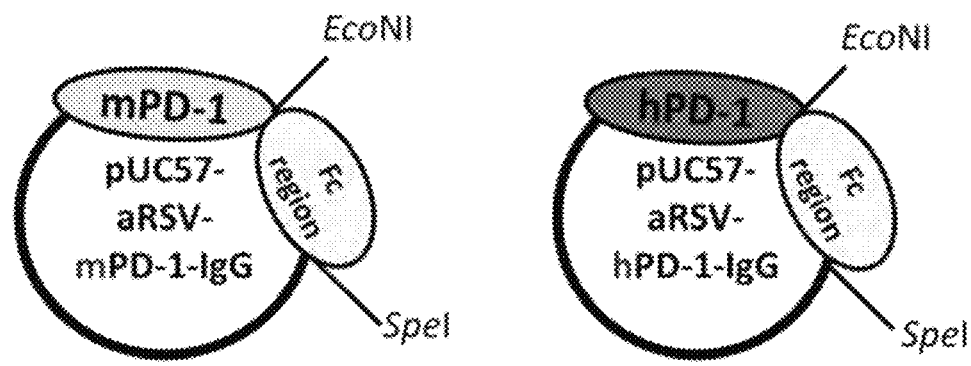
Inserts:
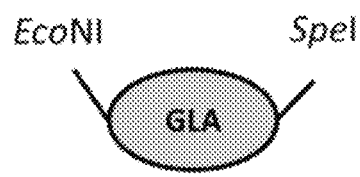
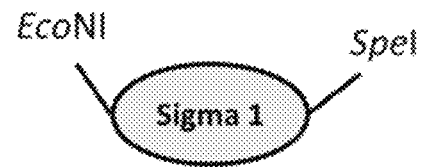
Fig. 2B
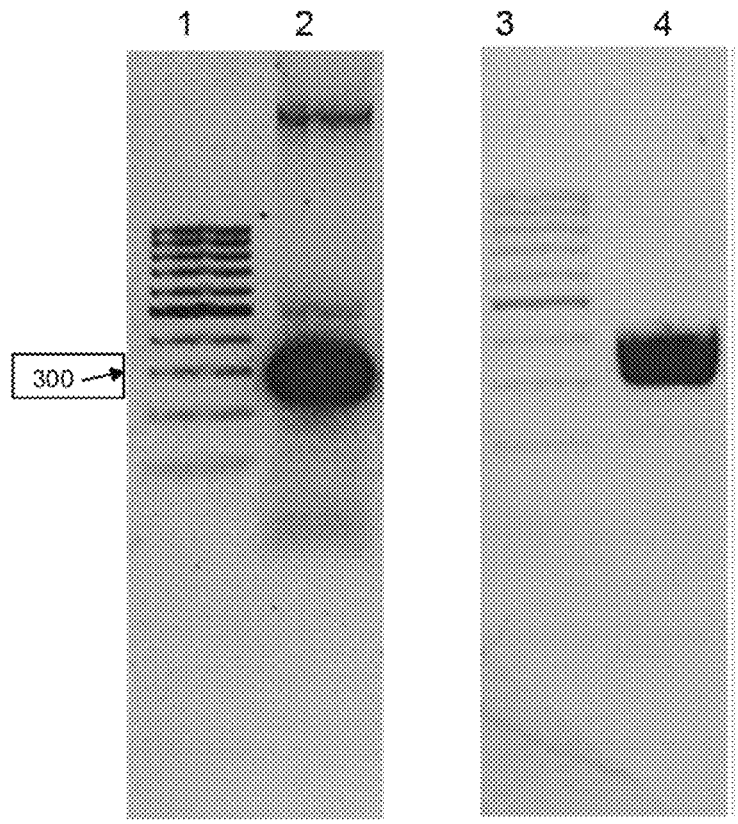

Figure 3
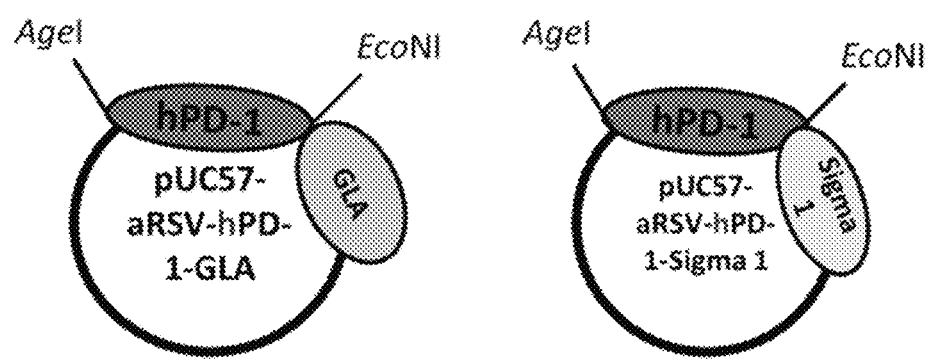
Inserts:

Figure 7 (Continued)
B

HVR 1

```
Ad5 hexon   YNALAPKGAPNPCEMDEAATL---ALEINLEEDDNEDEVDEQAEQCKTHVFSQAPYSGI
Ad6 hexon   YNALAPKGAPNSCEMEDNETAQVDAELEENEANEAQAEEQAKKTHVYAQAPLSGI
Ad57 hexon  YNALAPKGAPNSCEMDEDDIF-QVQMAEDQDDEEEQLPQQNGKKTHVYAQAPFAGE
```

HVR 2                                                    HVR 3

```
Ad5 hexon   NITKEQIQIG-----VEGQ-TPKYADKTFQPEPQIGESQWYETEINHAGGRVLKKTTPMK
Ad6 hexon   KITKEGLQIGTADATVAAGKEIFADKTFQPEPQVGESQWNEADATAAGGRVLKKTTPMK
Ad57 hexon  AINKNGLQIGNGAATEGN-KEIYADKTTYQPEPQIGESQWNEAESVAGGRVLKKTTPMK
```

HVR 4                                                    HVR 5

```
Ad5 hexon   PCYGSYAQPTNENGGQGILMKQONGKLESQVEMQFFSTIEATAGNGDILYKVVLYSEDV
Ad6 hexon   PCYGSYARPTNSNGGQGVMVEQ-NGKLESQVEMQFFSTSTNAINEVNNTQPTVVLYSEDV
Ad57 hexon  PCYGSYARPTNSNGGQGVMVEQ-NGKLESQVEMQFFSTSTNAVNEAIQPKDLVLYSEDV
```

HVR 6

```
Ad5 hexon   DIETPDTHLSYKFGQNSRELGQQSMPNRPNYIAFRDNFIGLMYYNSTGNMGVLAGQ
Ad6 hexon   NMETPDTHLSYKFMQKEGKNAKVMGQQAMPNRPNYIAFRDNFIGLMYYNSTGNMGVLAGQ
Ad57 hexon  NMETPDTHLSYKFGKSDDNSKAMGQQSMPNRPNYIAFRDNFIGLMYYNSTGNMGVLAGQ
```

```
Ad5 hexon   ASQLNAVVDLQDRNTELSYQLLLDSIGDRTRYFSMWNQAVDSYDPDVRIIENHGTEDELP
Ad6 hexon   ASQLNAVVDLQDRNTELSYQLLLDSIGDRTRYFSMWNQAVDSYDPDVRIIENHGTEDELP
Ad57 hexon  ASQLNAVVDLQDRNTELSYQLLLDSIGDRTRYFSMWNQAVDSYDPDVRIIENHGTEDELP
```

HVR 7

```
Ad5 hexon   NYCFPLSGVINTETLTKVKPKTGQE----NGMEKDATEFSDKNEIGNGNNFMEINLNAN
Ad6 hexon   NYCFPLSGIGITDTFQAVKTTAANGDQGNTTWQKDS-TFAERNEIGVGNNFMEINLNAN
Ad57 hexon  NYCFPLSGVDTYQAKATYNGNG-GATTVAQDN-TFAERNEIGVGNNFMEINLNAN
```

```
Ad5 hexon   LWRNFLYSNIALYLPDKLKYSPSNVKISDNPNTYDYMNKRVVAPGLVDCYINLGARWSLD   SEQ ID NO: 52
Ad6 hexon   LWRNFLYSNIALYLPDKLKYNPTNVEISDNPNTYDYMNKRVVAPGLVDCYINLGARWSLE   SEQ ID NO: 53
Ad57 hexon  LWRNFLYSNIALYLPDKLKYNPTNVEISDNPNTYDYMNKRVVAPGLVDCYINLGARWSLD   SEQ ID NO: 54
```

*E1 expression controlled by native E1 promoter*

CRAd-Probasin-E1A (Ad-PB)

*E1 expression
controlled by prostate-specific probasin promoter*

CRAd-dl1101

*p300 pathway binding ablated, susceptible to IFN pathway
in normal cells*

CRAd-dl1107

*pRB binding ablated allows virus to kill cancer cells with RB
pathway disruptions, but repressed in RB+ normal cells.*

CRAd-dl1101/07

*p300 pathway binding ablated, susceptible to IFN pathway
pRB binding ablated allows virus to kill cancer cells with
RB pathway disruptions, but repressed in RB+
normal cells.*

Figure 10 wild-type E1A N-terminus

MRHIICHGGVITEEMAASLLDQLIEEVLADNLPPPSHFEPPTLHELYDLD
VTAPEDPNEEAVSQIFPESVMLAVQEGIDLFTFPPAPGSPEPPHLSRQ
PEQPEQRALGPVSMPNLVPEVIDLTCHEAGFPPS (SEQ ID NO:31)

E1A dl1101 N-terminus

MRHIEEVLADNLPPPSHFEPPTLHELYDLDVTAPEDPNEEAVSQIFPES
VMLAVQEGIDLFTFPPAPGSPEPPHLSRQPEQPEQRALGPVSMPNLV
PEVIDLTCHEAGFPPS (SEQ ID NO:32)

E1A dl1107 N-terminus

MRHIICHGGVITEEMAASLLDQLIEEVLADNLPPPSHFEPPTLHELYDLD
VTAPEDPNEEAVSQIFPESVMLAVQEGIDLFTFPPAPGSPEPPHLSRQ
PEQPEQRALGPVCHEAGFPPS (SEQ ID NO:33)

E1A dl1101/1107 N-terminus

MRHIEEVLADNLPPPSHFEPPTLHELYDLDVTAPEDPNEEAVSQIFPES
VMLAVQEGIDLFTFPPAPGSPEPPHLSRQPEQPEQRALGPVCHEAGF
PPS (SEQ ID NO:34)

MULTIVALENT PD-L1 BINDING COMPOUNDS FOR TREATING CANCER

INCORPORATION-BY-REFERENCE OF MATERIAL SUBMITTED ELECTRONICALLY

Incorporated by reference in its entirety herein is a computer-readable nudeotide/amino acid sequence listing submitted concurrently herewith and identified as follows: One 262,711 Bytes ASCII (Text) file named "SEQUENCE_LISTING.TXT," created on 28 Apr. 2020.

BACKGROUND OF THE INVENTION

Technical Field

This invention relates to methods and materials for treating cancer. The invention provides methods and materials for making multivalent PD-L1 binding compounds. This invention also provides methods and materials for expressing PD-1 polypeptides in cells of a mammal having cancer. In particular, the invention relates to compositions comprising PD-1 polypeptides, the PD-1 polypeptides may be in the form of one or more multivalent programmed death-ligand 1 (PD-L1) binding compounds. In some cases, a multivalent PD-L1 binding compound can include two or more programmed cell death protein 1 (PD-1) polypeptides (and/or fragments thereof having the ability to bind PD-L1). The compositions comprising PD-L1 binding compounds are administered to a mammal having cancer in an amount effective to treat the cancer and, optionally, are administered in combination with one or more cancer therapies.

PD-L1, also called B7-H1, is an immune checkpoint protein that regulates the immune system through its binding of the PD-1 receptor. In the tumor microenvironment, over-expression of PD-L1 on tumor cells helps suppress antitumor immunity (Dong et al., Nat Med. 8:793-800, (2002); Hamanishi et al., Int. J. Clin. Oncol. 21:462-473 (2016); Dong et al., Nat. Med. 5:1365-1369 (1999); Chen et al., J. Clin. Invest. 125:3384-3391 (2015); He et al., Sci. Rep. 5:13110 (2015); Chen et al., Clin. Cancer Res. 18:6580-6587 (2012); Ohaegbulam et al., Trends Mol. Med. 21:24-33 (2015); and Postow et al., J. Clin. Oncol. 33:1974-1982 (2015)).

Antigen-presenting cells (APC) take up antigens released from cancer cells and present them to T cells. Cancer cells can also present antigens to activated T cells in the context of the major histocompatability complex. Upon T cell activation, PD-1 receptors are expressed on T cells and inhibit immune responses by engagement of PD-L1 and PD-L2 ligands on APC and PD-L1 on cancer cells. Therefore, monoclonal antibody (mAb)-mediated specific blockade of the PD-1/PD-L1/PD-L2 pathway can enhance anti-tumor immunity. In addition to T cells and APC, PD-1 and PD-L1 can be induced on other immune cells.

In the cancer disease state, the interaction of the PD-L1 which is present on a PD-L1 positive cancer cell with the PD-1 which is present on a T-cell can reduce T-cell function signals to prevent the immune system from attacking the PD-L1 positive cancer cell. Soluble PD-1 (sPD-1) can act as a decoy by binding to PD-L1 present on PD-L1 positive cancer cells. For example, when sPD-1 is bound to PD-L1 present on a PD-L1 positive cancer cell, the PD-L1 is not free to interact with a PD-1 present on a T-cell, thereby allowing the T-cell to function by attacking the PD-L1 positive cancer cell.

BRIEF SUMMARY OF THE INVENTION

This invention provides methods and materials for making one or more multivalent PD-L1 binding compounds. This invention provides compositions comprising PD-L1 binding compounds comprising PD-1 polypeptides, the PD-1 polypeptides may be in the form of one or more multivalent PD-L1 binding compounds. The PD-L1 binding compounds can act as a decoy by binding to PD-L1 present on PD-L1 positive cancer cells.

This invention provides methods and materials comprising PD-1 polypeptides, the PD-1 polypeptides may be in the form of one or more multivalent PD-L1 binding compounds which are administered to a mammal having cancer to treat the mammal. In some cases, a multivalent PD-L1 binding compound includes two or more amino acid segments that can bind PD-L1 (e.g., PD-1 polypeptides and/or fragments thereof). A multivalent PD-L1 binding compound includes two or more PD-1 polypeptides (or fragments thereof having the ability to bind PD-L1) such that the compound can bind two or more PD-L1 polypeptides. This invention also provides methods of making PD-L1 binding compounds and compositions comprising recombinant Ads comprising at least one amino acid segment comprising a PD-1 polypeptide which forms a PD-L1 binding compound or a multivalent PD-L1 binding compound described herein.

In an embodiment, mouse PD-1 polypeptides and/or human PD-1 polypeptides fused to a scaffold polypeptide can form a polypeptide conjugate (e.g., a polypeptide conjugate including a plurality of (e.g., two or more) associated amino acid chains) such that when the scaffold polypeptide fused to one or more PD-1 polypeptides is in a polypeptide conjugate, the polypeptide conjugate can form a multivalent PD-L1 binding compound that includes two or more PD-1 polypeptides.

In an embodiment, a polypeptide conjugate can include three amino acid chains, where the scaffold polypeptide can be a sigma-1 polypeptide derived from Mammalian orthoreovirus 3, and where the polypeptide conjugate can include three PD-1 polypeptides.

In an embodiment, a polypeptide conjugate can include four amino acid chains, where the scaffold polypeptide can be a streptavidin polypeptide, and where the polypeptide conjugate can include four PD-1 polypeptides.

This invention also provides compositions comprising recombinant Ads comprising nucleic acids encoding PD-1 polypeptides which bind PD-L1. In an embodiment, a mouse PD-1 polypeptide and/or a human PD-1 polypeptide is fused to a Vitamin K-dependent gamma-carboxyglutamic domain of a factor X single-chain antibody polypeptide (a GLA or GLA-EGF domain of an FX polypeptide) and is present on adenoviral hexon polypeptides such that when the polypeptide is present on two or more viral hexon polypeptides present on the capsid of a virus particle, the virus particle can form a multivalent PD-L1 binding compound that includes from about 240 to about 720 PD-1 polypeptides.

This invention provides methods and materials for treating cancer by administering one or more recombinant adenoviruses (Ads) expressing a PD-1 protein and/or amino acid segments which bind PD-L1 (e.g., PD-1 polypeptides and/or fragments thereof). The recombinant Ads expressing PD-1 may be administered in combination with a cancer immunotherapy according to a therapeutic treatment regime.

Using multivalent PD-L1 binding compounds (e.g., as compared to monomeric PD-1 polypeptides) can increase the efficacy of PD-1 to neutralize PD-L1 present on PD-L1 positive cancer cells, can prevent PD-L1 positive cancer cells from escaping the immune system, and/or can allow anti-cancer agents (e.g., cancer immunotherapies) to more effectively target PD-L1 positive cancer cells. In some cases, adenovirus presentation of PD-1 polypeptides can be used to retarget therapeutic Ads to PD-L1 on a cell for nucleic acid delivery or to kill PD-L1-expressing cells by oncolytic cell death.

In an embodiment, a PD-L1 binding compound also can include a targeting molecule. A targeting and cell fusion molecule can be a viral polypeptide such as a measles virus (MV) hemagglutinin (H) polypeptide, a MV fusion (F) polypeptide, or a vesicular stomatitis virus (VSV) glycoprotein (G) polypeptide.

The PD-L1 binding compound also can include one or more therapeutic polypeptides. The therapeutic polypeptide is selected from a 4-1BB ligand (4-1BBL) polypeptide, a OX40 ligand (OX40L) polypeptide, a CD40 ligand (CD40L) polypeptide, or a granulocyte-macrophage colony-stimulating factor (GM-CSF) polypeptide. The therapeutic polypeptide may also be a polypeptide which activates glucocorticoid-induced tumor necrosis factor receptor (TNFR)-related protein (GITR) signaling.

The PD-L1 binding compound also can include a detectable polypeptide. The detectable polypeptide can be a green fluorescent protein (GFP) or a luciferase polypeptide.

The invention encompasses recombinant vectors for the expression of PD-L1 binding compounds comprising nucleic acids encoding PD-1 polypeptides, the PD-1 polypeptides may be expressed with one or more targeting polypeptides, and/or one or more therapeutic polypeptides, and/or proteins (e.g., collagen, elastin, laminin, and fibrinogen). The PD-1 polypeptides may be expressed as fusion proteins with heterologous polypeptides. The nucleic acids encoding PD-1 polypeptides, as well as the nucleic acids encoding targeting polypeptides, therapeutic polypeptides and proteins, may be comprised in expression vectors, optionally comprising expression cassettes, which allow for expression of the polypeptides in prokaryotic or eukaryotic cells. The vector can be a viral vector. The viral vector can be an Ad, an adeno-associated virus (AAV), or a lentivirus. The viral vector may be an Ad selected from Ad657, Ad6/57/6, and variants thereof. The Ad may be a Conditionally Replicating Ad (CRAd). The viral vector can be an oncolytic viral vector.

In another aspect, the invention encompasses viral vectors for the expression of PD-L1 binding compounds comprising nucleic acids encoding an amino acid chain including a PD-1 polypeptide and a scaffold polypeptide as described herein (e.g., a polypeptide conjugate that can include a plurality of amino acid chains, where each amino acid chain includes a PD-1 polypeptide and a scaffold polypeptide; and where the plurality of amino acid chains can form the polypeptide conjugate).

In another aspect, the invention encompasses methods for treating a mammal having cancer. The methods can include, or consist essentially of, administering a composition comprising a PD-L1 binding compound to a mammal having cancer.

The method of the invention comprises administering an effective amount of compositions comprising PD-1 binding compounds described herein. In an embodiment, the PD-L1 binding compounds are administered in combination with one or more cancer therapeutics to the mammal, whereby the number of cancer cells present in the mammal is reduced. The one or more cancer therapeutics may include an immunotherapy which targets PD-1 or PD-L1. The immunotherapy may be selected from nivolumab. Pembrolizumab, atezolizumab, avelumab, cemiplimab, and durvalumab.

In another aspect, the invention relates to methods for treating a mammal having cancer comprising, or consisting essentially of, administering a composition comprising a multivalent PD-L1 binding compound to a mammal having cancer. The multivalent PD-L1 binding compound may comprise a polypeptide conjugate described herein (e.g., a polypeptide conjugate including a plurality of amino acid chains, where each amino acid chain includes a PD-1 polypeptide and a scaffold polypeptide). The cancer may be a prostate cancer, breast cancer, ovarian cancer, lung cancer (e.g., a non-small cell lung cancer), hepatocellular carcinoma, pancreatic cancer. Kidney cancer, melanoma, brain cancer, colon cancer, lymphoma, myeloma, lymphocytic leukemia, or myelogenous leukemia. The administering can include systemic or local administration (e.g. intravenous, intratumoral, intramuscular, intraorgan, intralymph node administration).

An aspect of the invention relates to multivalent programmed cell death protein ligand 1 (PD-L1) binding compounds comprising a plurality of amino acid chains, wherein each amino acid chain comprises at least one programmed cell death protein 1 (PD-1) polypeptide.

A further aspect of the invention relates to such a multivalent PD-L1 binding compound, wherein the multivalent PD-L1 binding compound is a polypeptide conjugate comprising a scaffold polypeptide selected from Ig polypeptides, sigma-1 polypeptides and streptavidin polypeptides.

A further aspect of the invention relates to such a multivalent PD-L1 binding compound, wherein the multivalent PD-L1 binding compound is a polypeptide conjugate comprising more than one scaffold polypeptide.

A further aspect of the invention relates to such a multivalent PD-L1 binding compound, wherein the PD-1 polypeptide is a human PD-1 or a murine PD-1.

A further aspect of the invention relates to such a multivalent PD-L1 binding compound, wherein the plurality of amino acid chains comprise a therapeutic polypeptide, a targeting polypeptide or an antigenic polypeptide.

A further aspect of the invention relates to such a multivalent PD-L1 binding compound, wherein the targeting polypeptide is selected from a measles virus hemagglutinin (MVH) polypeptide, a measles virus fusion (MVF) polypeptide, and a vesicular stomatitis virus glycoprotein (VSVG) polypeptide.

A further aspect of the invention relates to such a multivalent PD-L1 binding compound, wherein the therapeutic polypeptide is selected from a 4-1BB ligand (4-1BBL) polypeptide, a OX40 ligand (OX40L) polypeptide. A CD40 ligand (CD40L) polypeptide, a granulocyte-macrophage colony-stimulating factor (GM-CSF) polypeptide and a GITR agonist.

A further aspect of the invention relates to such a multivalent PD-L1 binding compound wherein each amino acid chain comprising at least one programmed cell death protein 1 (PD-1) polypeptide is associated with a recombinant Adenovirus (Ad) and the plurality of amino acid chains are present on a coat polypeptide of the recombinant Ad.

A further aspect of the invention relates to such a multivalent PD-L1 binding compound, wherein the recombinant Ad comprises capsid hexon polypeptides of an Ad strain Ad6 and at least one capsid hexon hypervariable region (HVR) polypeptide from Ad strain Ad57.

A further aspect of the invention relates to such a multivalent PD-L1 binding compound, wherein the capsid hexon polypeptides of an Ad strain Ad6 comprise HVR polypeptides 1-7 from Ad strain Ad57.

A further aspect of the invention relates to such a multivalent PD-L1 binding compound, wherein the capsid hexon polypeptides of an Ad strain Ad comprise HVR polypeptides 2-6 from Ad strain Ad57.

A further aspect of the invention relates to such a multivalent PD-L1 binding compound, wherein the programmed cell death protein 1 (PD-1) polypeptide is human PD-1.

A further aspect of the invention relates to such a multivalent PD-L1 binding compound, wherein the PD-1 polypeptide is fused to a Vitamin K-dependent gamma-carboxyglutamic domain of a factor X single-chain antibody polypeptide (a GLA domain of an FX polypeptide).

A further aspect of the invention relates to such a multivalent PD-L1 binding compound, wherein each amino acid chain comprises a targeting molecule selected from a measles virus hemagglutinin (MVH) polypeptide, a measles virus fusion (MVF) polypeptide, and a vesicular stomatitis virus glycoprotein (VSVG) polypeptide.

A further aspect of the invention relates to such a multivalent PD-L1 binding compound, wherein each amino acid chain comprises one or more therapeutic polypeptides selected from a 4-1BB ligand (4-1BBL) polypeptide, a OX40 ligand (OX40L) polypeptide, a CD40 ligand (CD40L) polypeptide, and a granulocyte-macrophage colony-stimulating factor (GM-CSF) polypeptide.

A further aspect of the invention relates to such a pharmaceutical composition comprising the multivalent PD-L1 binding compound and a pharmaceutically acceptable carrier.

A further aspect of the invention relates to a method of treating cancer in a subject in need thereof, comprising administering the multivalent PD-L1 binding compound.

A further aspect of the invention relates to such a method further comprising administering one or more cancer therapeutics to the mammal.

A further aspect of the invention relates to such a method wherein the cancer therapeutic is an immunotherapy which targets PD-1.

A further aspect of the invention relates to such a method wherein the immunotherapy is selected from the group consisting of nivolumab, pembrolizumab, atezolizumab, avelumab, cemiplimab, and durvalumab.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

An amino acid chain including one PD-1 polypeptide fused to a GLA domain of an FX polypeptide. The fusion proteins can be constructed with either entity on the N-terminus or the C-terminus. The fusion protein which is bound to the surface of an adenovirus particle generates a multivalent PD-L1 binding compound.

Figure 1A:
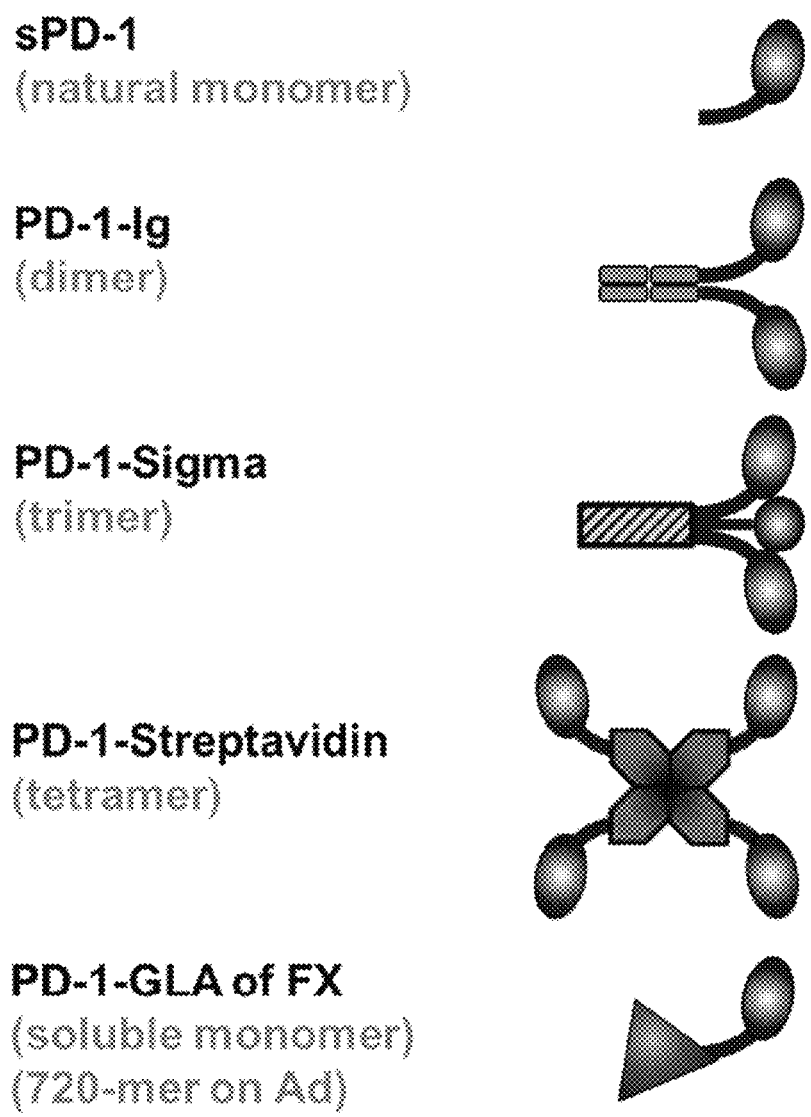
FIG. 1A shows schematics of exemplary engineered multivalent PD-L1 binding compounds. A multivalent PD-L1 binding compound comprising a PD-1 polypeptide fused to an Ig polypeptide which is a dimeric polypeptide conjugate that includes two amino acid chains that each include one PD-1 polypeptide. A multivalent PD-L1 binding compound that is a trimeric polypeptide conjugate comprising three amino acid chains that each include one PD-1 polypeptide fused to a sigma polypeptide. A multivalent PD-L1 binding compound that is a tetrameric polypeptide conjugate comprises four amino acid chains that each include one PD-1 polypeptide fused to a streptavidin polypeptide.
Figure 1B:
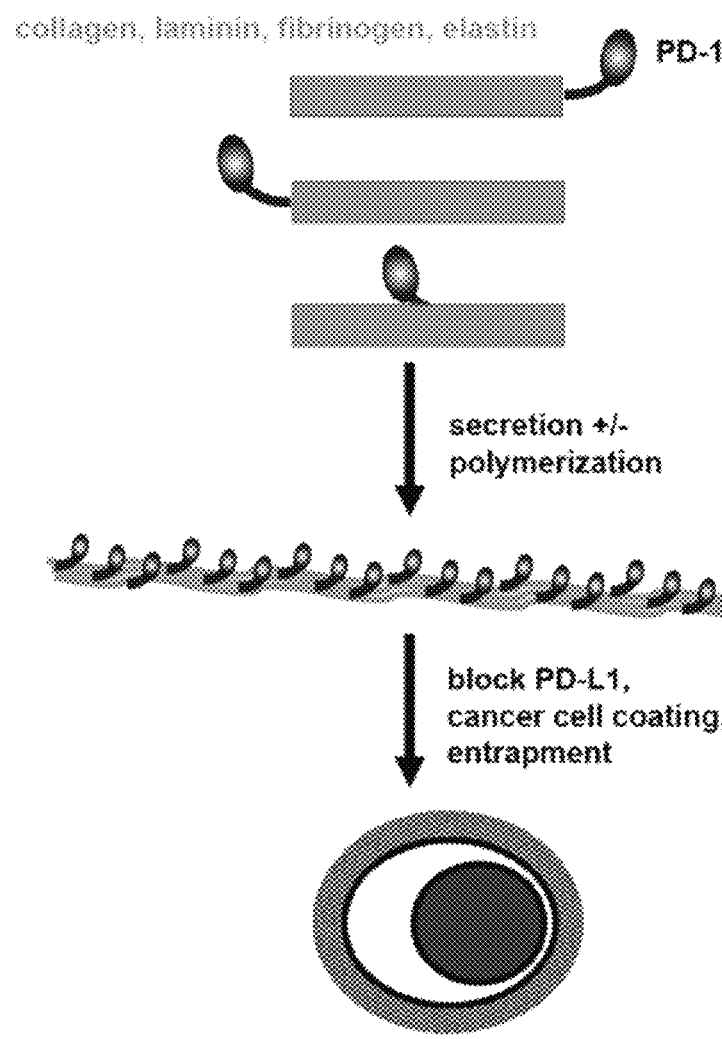

FIG. 1 shows engineered PD-L1 binding compounds by introduction of PD-1 motifs into natural biopolymers like collagen, laminin, fibronectin, or elastin. Fusion of PD-1 to protein monomers and expression in cells will allow their assembly into multivalent polymers displaying many PD-L1-binding motifs.

FIG. 2A shows nucleic acid vectors that can encode amino acid chains that can be used to generate multivalent PD-L1 binding compounds. FIG. 2A shows schematics of a nucleic acid vector that can encode an amino acid chain that includes one murine PD-1 (mPD-1) polypeptide fused to an IgG polypeptide (top left), a nucleic acid vector that can encode an amino acid chain that includes one human PD-1 (hPD-1) polypeptide fused to an IgG polypeptide (top right), and an exemplary cloning strategy (bottom) for replacing nucleic acid encoding the IgG with nucleic acid encoding a GLA domain of a FX polypeptide to generate a nucleic acid vector that can encode an amino acid chain that includes a PD-1 polypeptide fused to a GLA domain of an FX polypeptide, or for replacing nucleic acid encoding the IgG with nucleic acid encoding a sigma-1 polypeptide to generate a nucleic acid vector that can encode an amino acid chain that includes a PD-1 polypeptide fused to a sigma-1 polypeptide.

FIG. 2B contains images of gels showing expression of an amino acid chain comprising a PD-1 polypeptide. Lane 1: Molecular Weight Marker (base pairs; bp); Lane 2: a PD-1 polypeptide fused to a GLA domain of an FX polypeptide; Lane 3: Molecular Weight Marker (bp); Lane 4: an amino acid chain including a PD-1 polypeptide fused to a sigma-1 polypeptide.

FIG. 3 shows schematics of a nucleic acid vector that can encode an amino acid chain that includes a hPD-1 polypeptide fused to a GLA domain of an FX polypeptide (top left), a nucleic acid vector that can encode an amino acid chain that includes a hPD-1 polypeptide fused to a sigma-1 polypeptide (top right), and an exemplary cloning strategy (bottom) for replacing the nucleic acid encoding the hPD-1 polypeptide with nucleic acid encoding a mPD-1 polypeptide.

Figure 4:
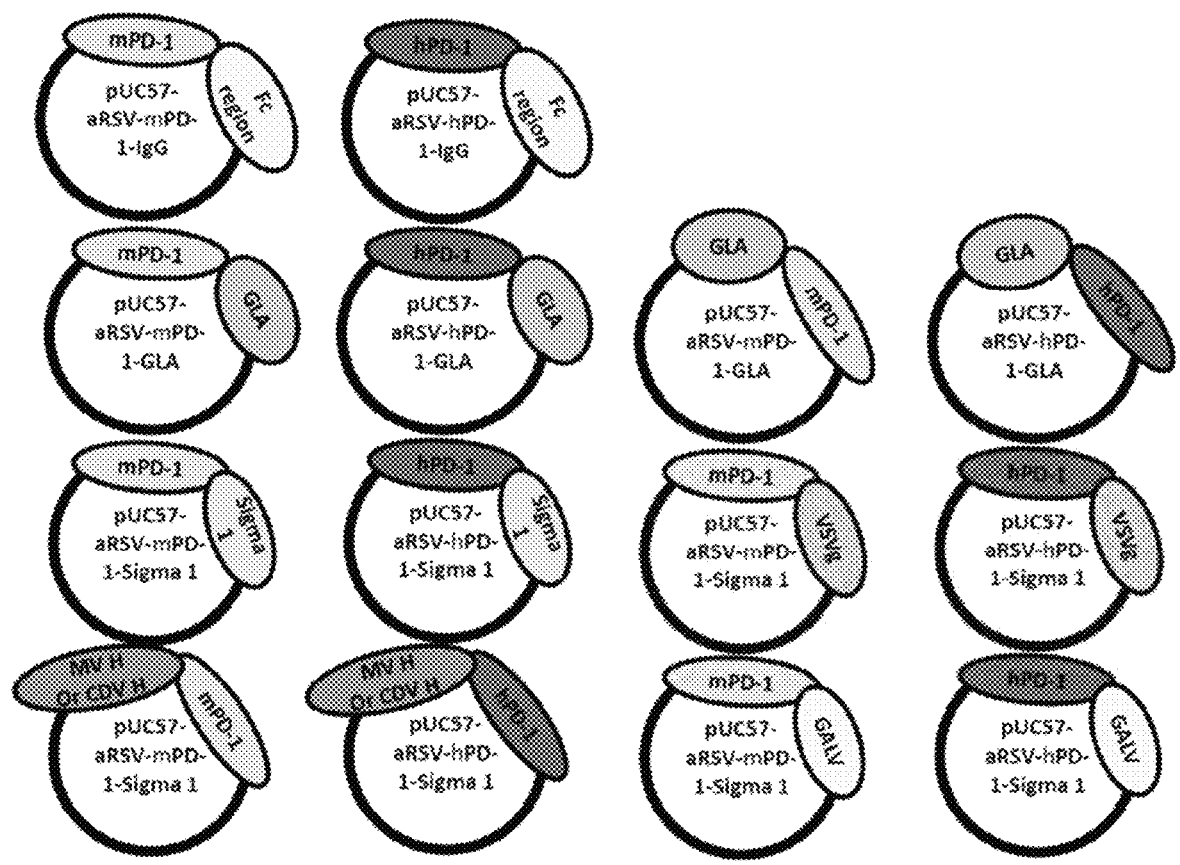

FIG. 4 shows schematics of exemplary nucleic acid vectors that can encode amino acid chains that can be used to generate multivalent PD-L1 binding compounds.

Figure 5:
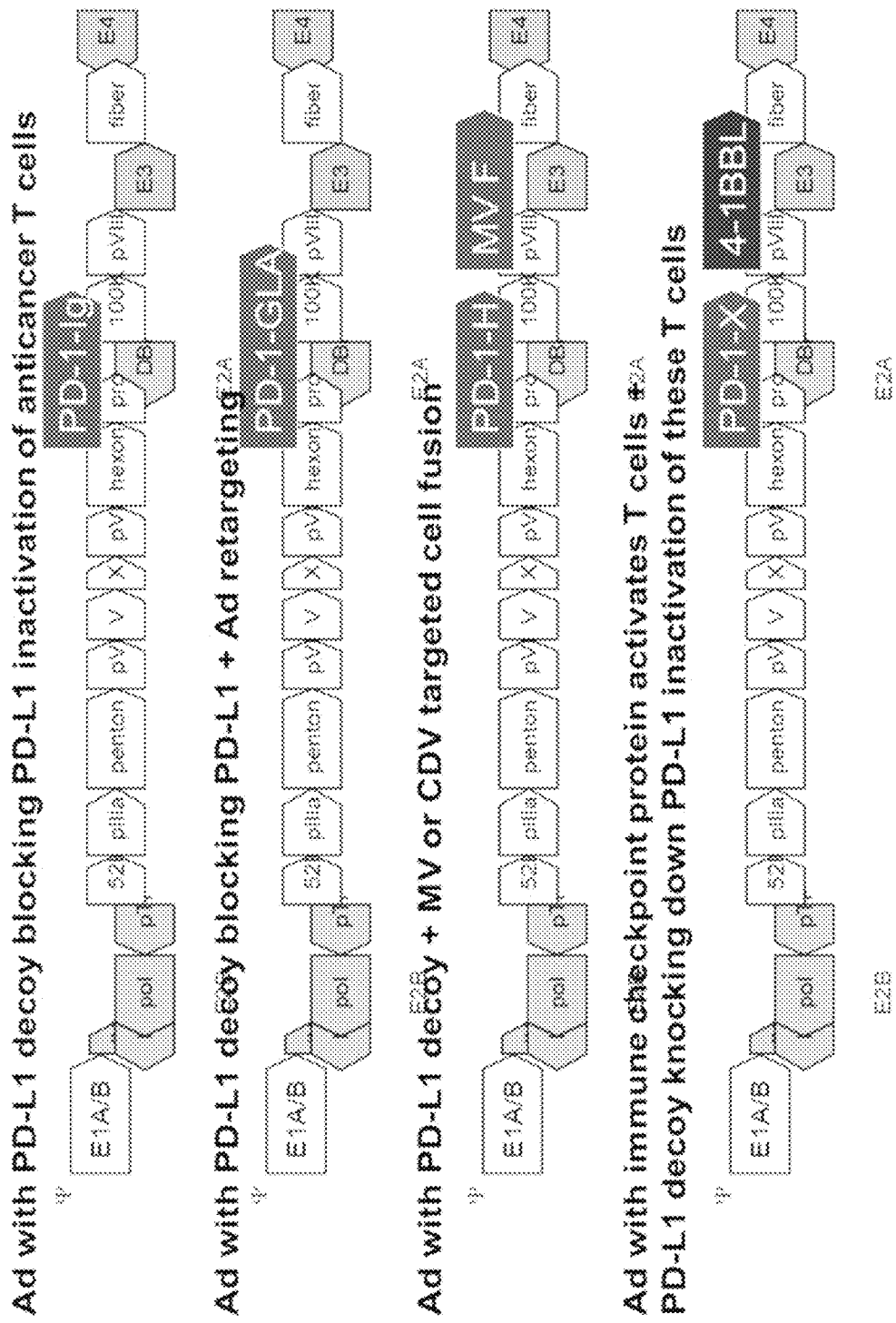

FIG. 5 shows schematics of exemplary adenoviral (Ad) vectors that can encode amino acid chains that can be used to generate multivalent PD-L1 binding compounds.

Figure 6:
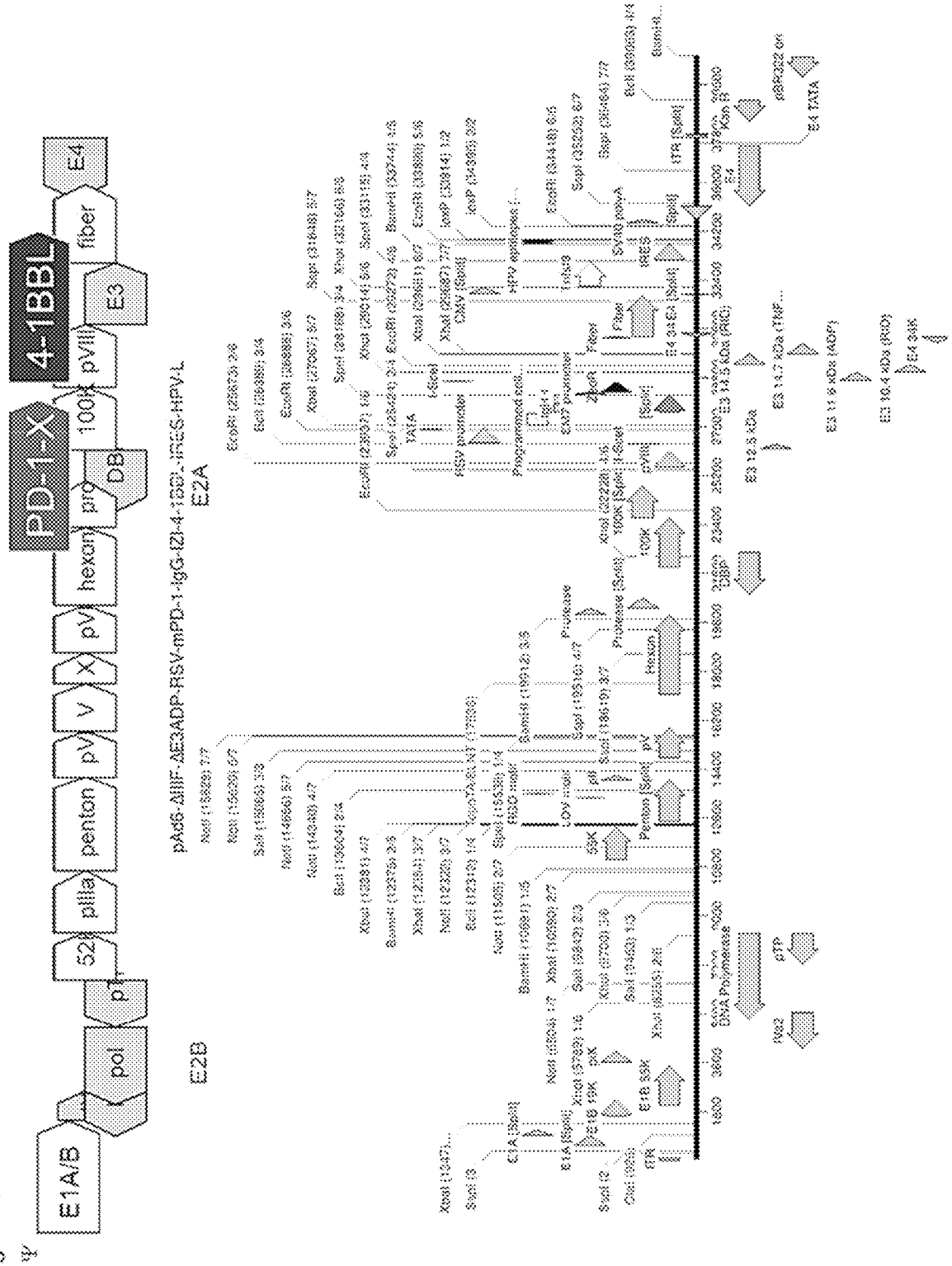

FIG. 6 shows a schematic of a genome of an Ad having nucleic acid encoding an immune checkpoint polypeptide that can activate T cells (4-1BBL), nucleic acid encoding one or more PD-1 polypeptides (PD-1-X, where X is a dimeric, trimeric, tetrameric, or polymeric binding scaffold), and nucleic acid encoding an antigen such as a cancer antigen or an infectious disease antigen (HPV epitope). Also shown is a restriction site map of the Ad genome.

Figure 7:
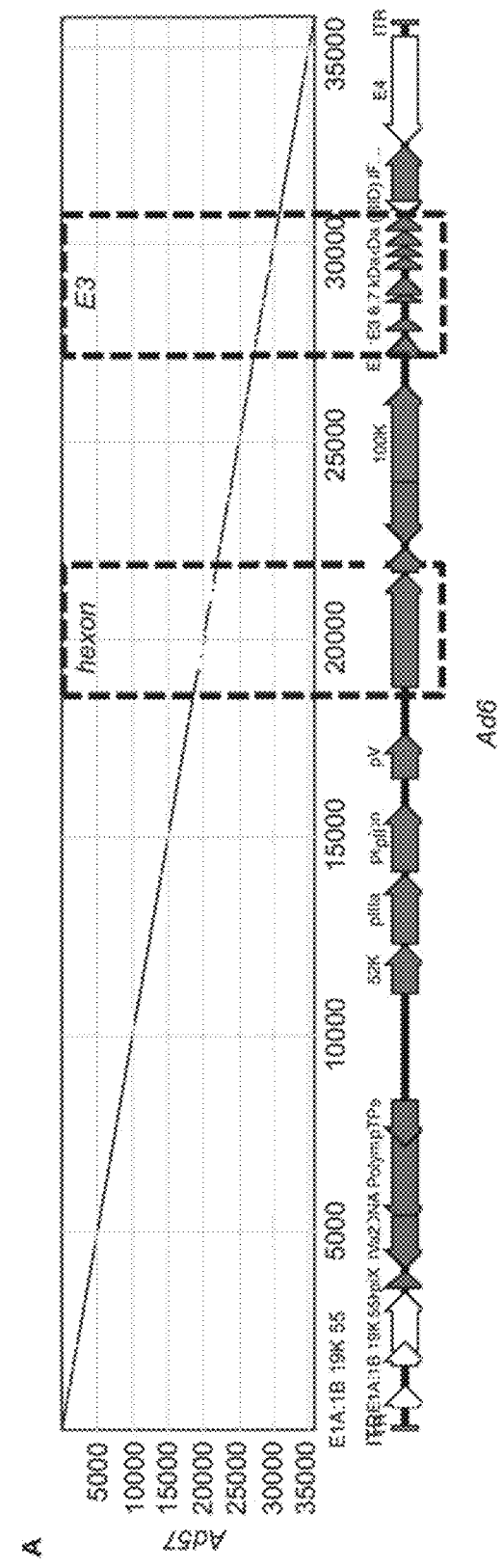

FIG. 7 shows an alignment of Ad5, 6, and 57 showing variation in hexon and E3 regions. (A) A Pustell DNA alignment of the genomes of Ad6 and Ad57. Boxes indicate hexon and E3 regions where variation is highest between the two viruses. (B) ClustaW amino acid alignment of the hypervariable region in hexon proteins from Ad5, Ad6, and Ad57.

Figure 8:
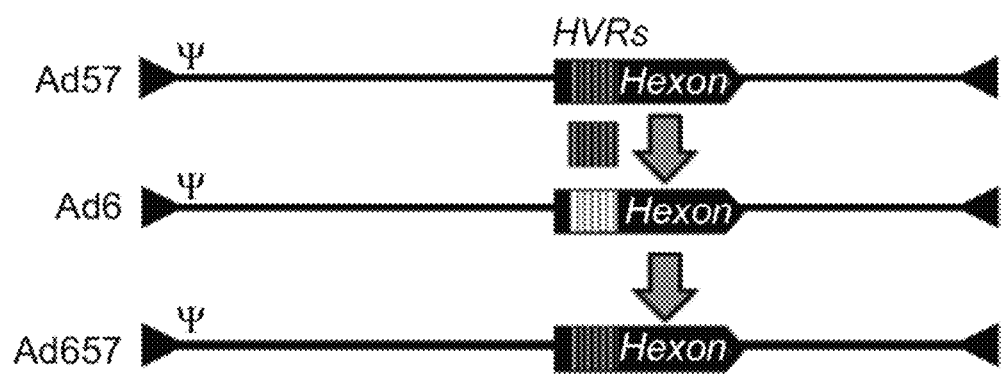

FIG. 8 shows the construction of Ad657 by replacement of the Ad HVRs with Ad57 HVRs. Abbreviation: HVRs, hypervariable regions.

FIG. 9 is a schematic of a replication competent Ad (RC-Ad), wherein E1 expression is controlled by the native E promoter; a variant CRAd-Probasin-E1A (Ad-PB), wherein E1 expression is controlled by prostate-specific probasin promoter; CRAd-dl101, wherein p300 pathway binding ablated, susceptible to IFN pathway in normal cells; CRAd-dl107, wherein pRB binding ablated allows virus to kill cancer cells with RB pathway disruptions, but is repressed in RB+ normal cells; CRAd-dl101/07, wherein p300 pathway binding ablated, susceptible to IFN pathway pRB binding ablated allows virus to kill cancer cells with RB pathway disruptions, but is repressed in RB+ normal cells.

FIG. 10 shows amino acid sequences of the N-terminal portion of the wild-type E1A polypeptide and the E1A N-terminus of the CRAd variants, dl1101, dl1107 and dl1101/1107.

Figure 11:
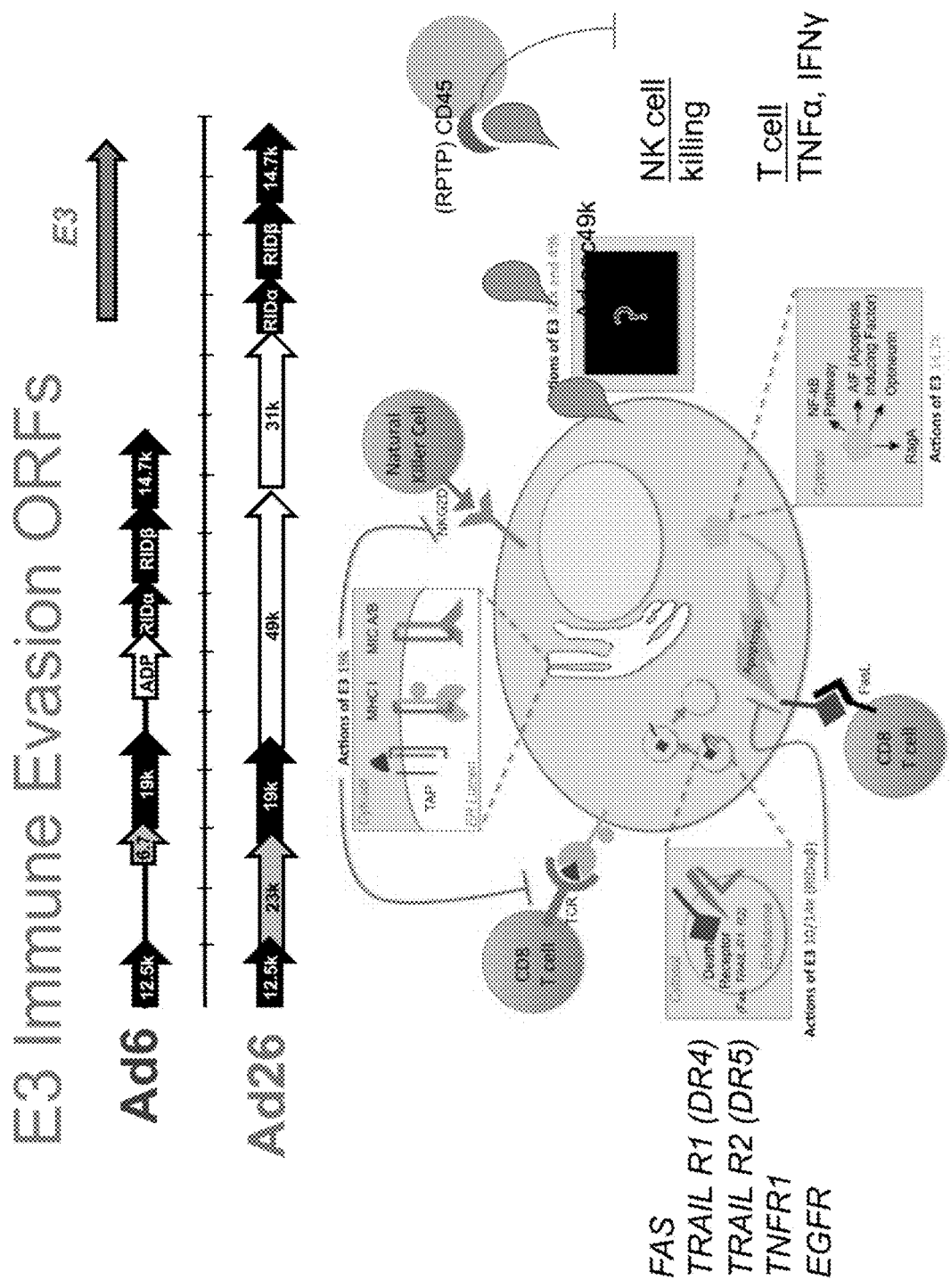

FIG. 11 shows as schematic of different E3 Immune evasion genes in Ad species C exemplar Ad6 and Ad species D exemplar Ad26. Both Ads express size and sequence variants of E3 12.5K, 6.7K, 19K, 10.4K (RIDα), 14.5K (RIDβ), and 14.7K genes, as well as a depiction of the functions of these E3 encoded proteins.

Figure 12:
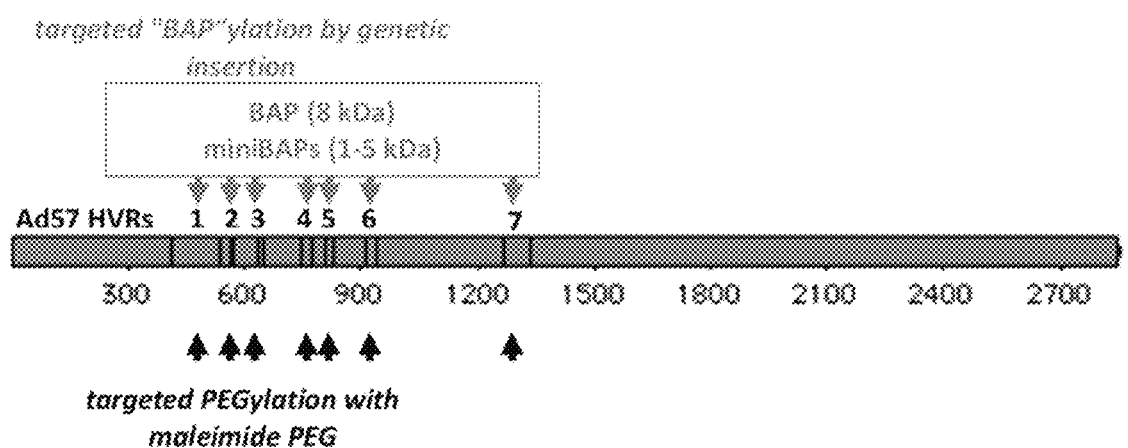

FIG. 12 depicts sites on Ad HVRs which may be modified, for example, by PEGylation or "BAPylation" with biotin acceptor peptides (BAPs).

Figure 13:
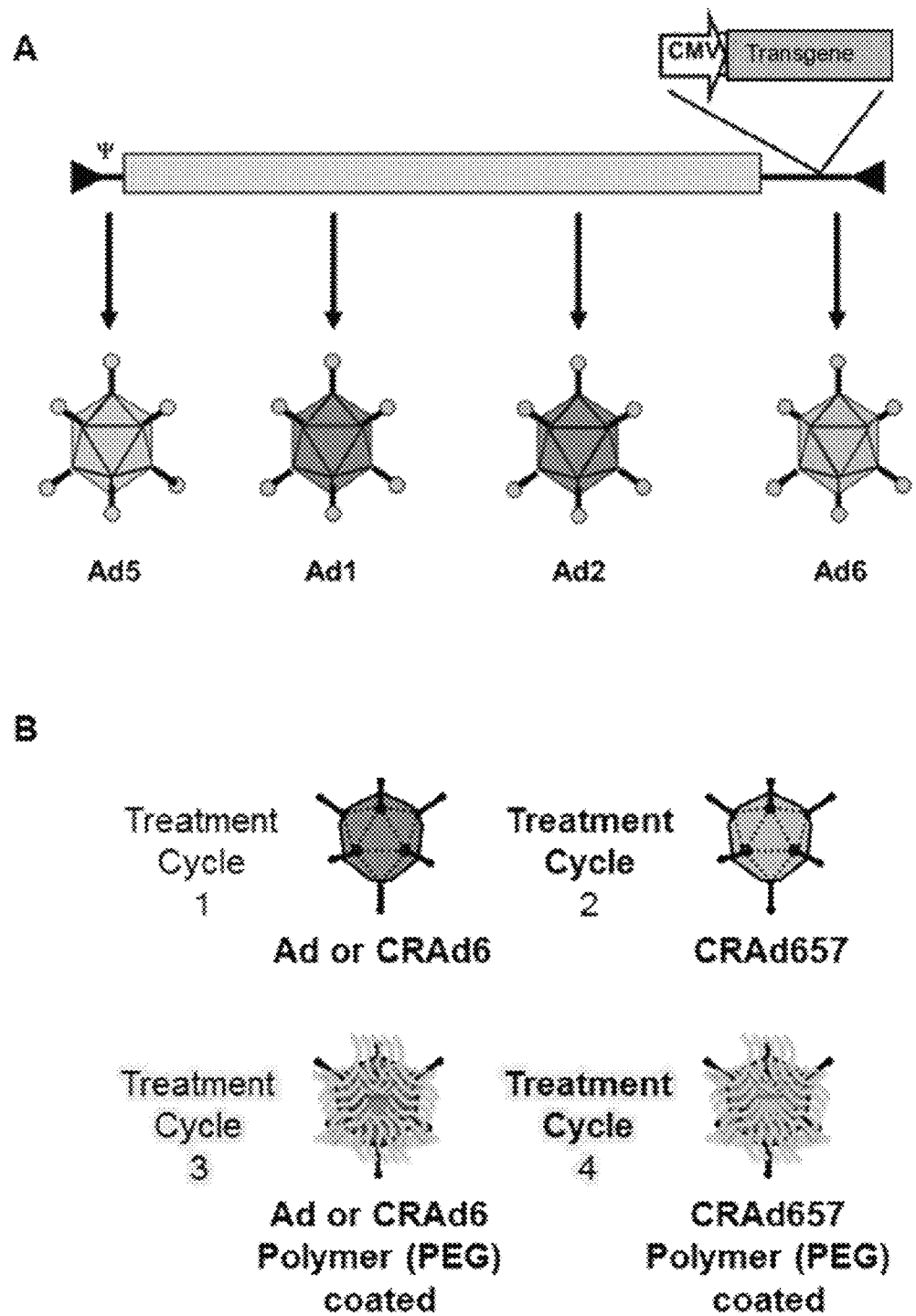

FIG. 13 is a schematic showing Ad therapeutic cycles. A) A schematic of serotype-switching with Ads. B) A schematic of an exemplary therapeutic cycle where Ad6 and Ad657 can be used for multiple rounds of treatment by serotype-switching in combination with covalent polymer conjugation.

Figure 14:
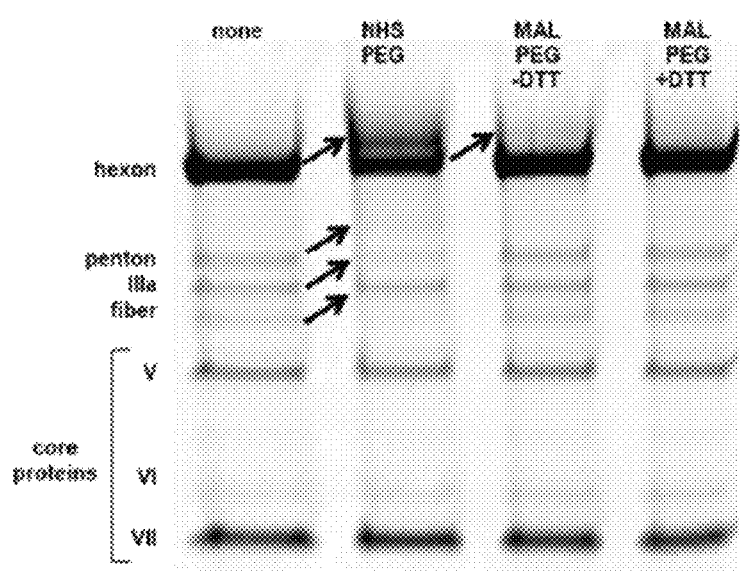

FIG. 14 shows conjugation of polyethylene glycol (PEG) to Ad657-HVR1-C. A) SDS-PAGE of Ad proteins with and without PEGylation. Arrows show size increases due to chemical attachment of PEG to hexon. B) Effects of targeted PEGylation by maleimide-PEG and non-targeting NHS-PEG on virus infection.

Figure 15:
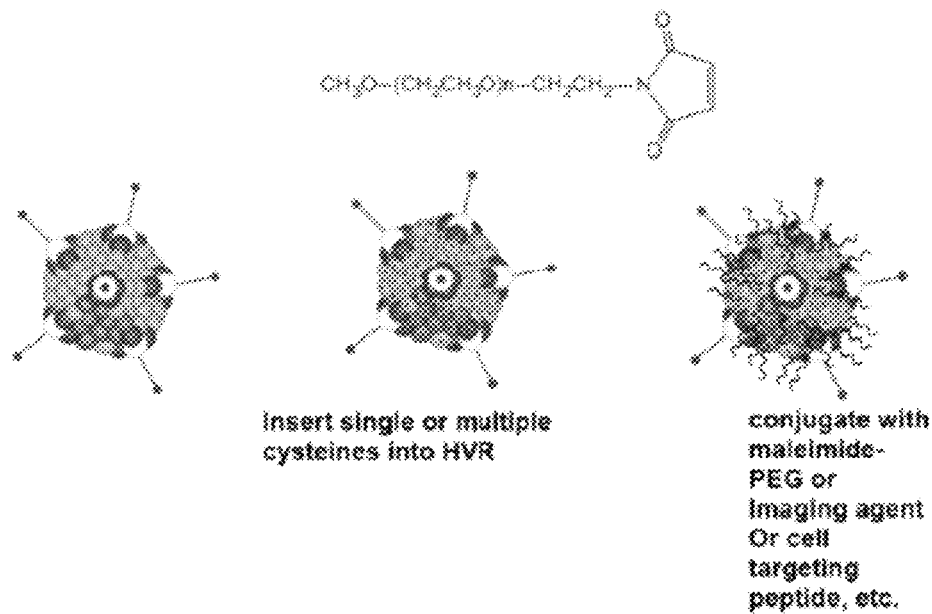

FIG. 15 shows chimeric HVR constructs that combine different HVRs from different Ad serotypes to modulate natural interactions with cells and blood factors improve pharmacology combined with insertion of cell binding and cell detargeting peptides in different HVRs to change cell entry and cell avoidance. In this example, a single cysteine amino acid is inserted into the HVR1 and HVR5 of Ad657 to modulate pharmacology and allow targeted conjugation of polymers like polyethylene glycol or other moieties like imaging agents like fluorophores.

Figure 16:
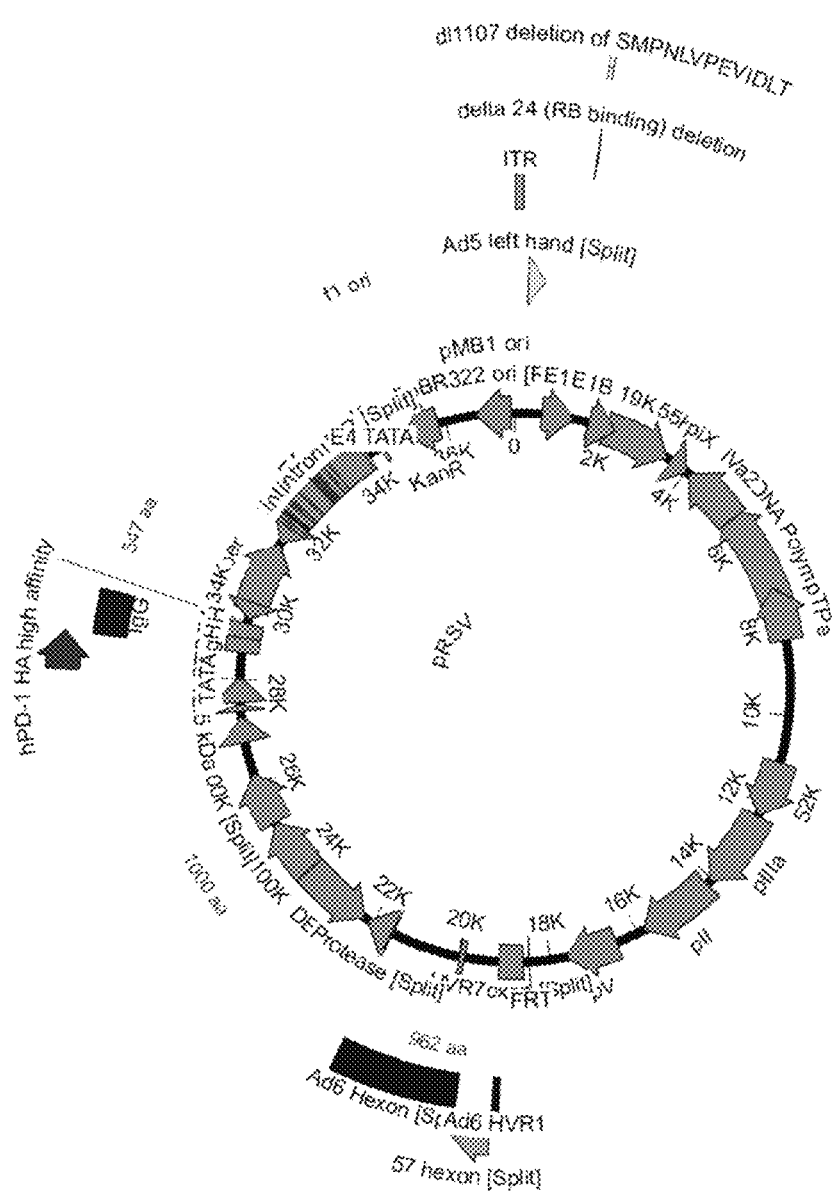

FIG. 16 shows plasmid maps for representative CRAds and peptide combinations. Shown are hexons as well as insertions of cell targeting peptides into individual HVRs.

Figure 17:
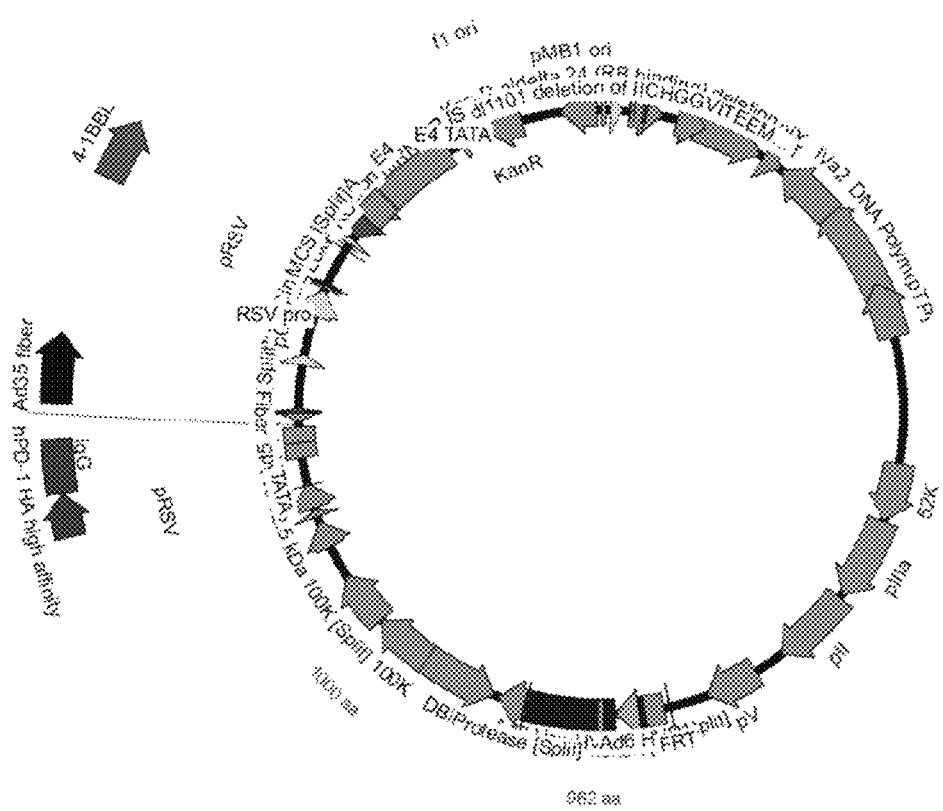

FIG. 17 shows plasmid maps for representative CRAds and peptide combinations. Shown are hexons as well as insertions of cell targeting peptides into individual HVRs.

Figure 18:
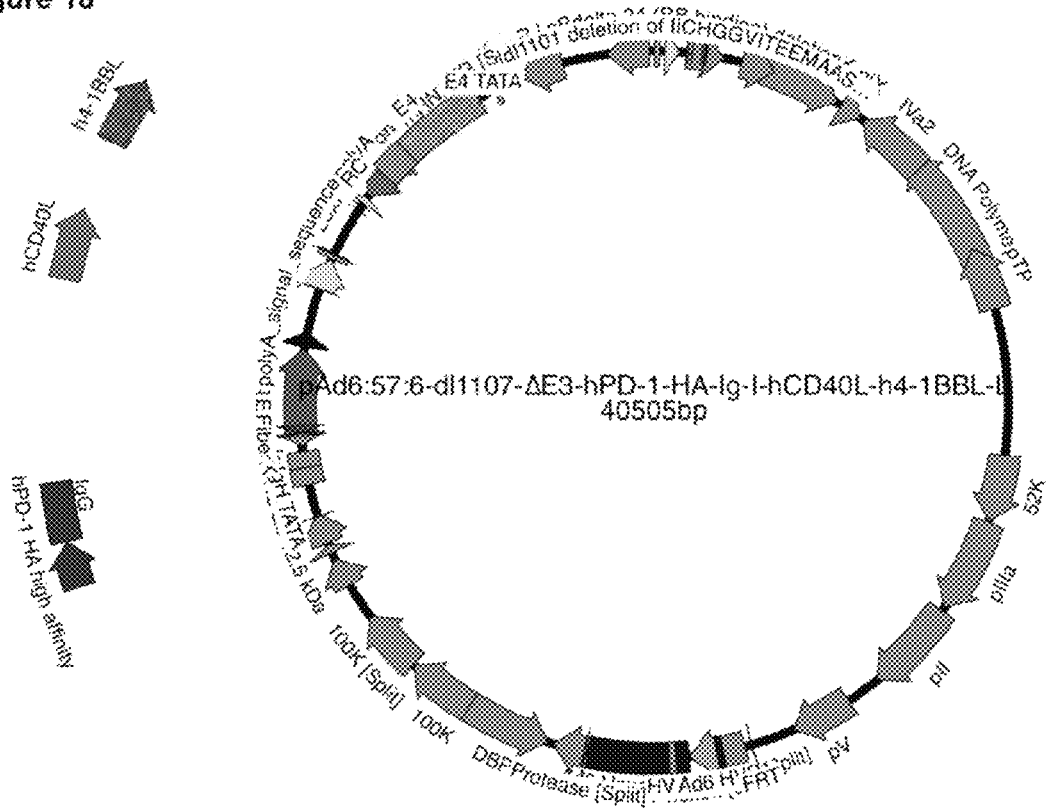

FIG. 18 shows plasmid maps for representative CRAds and peptide combinations. Shown are hexons as well as insertions of cell targeting peptides into individual HVRs.

Figure 19:
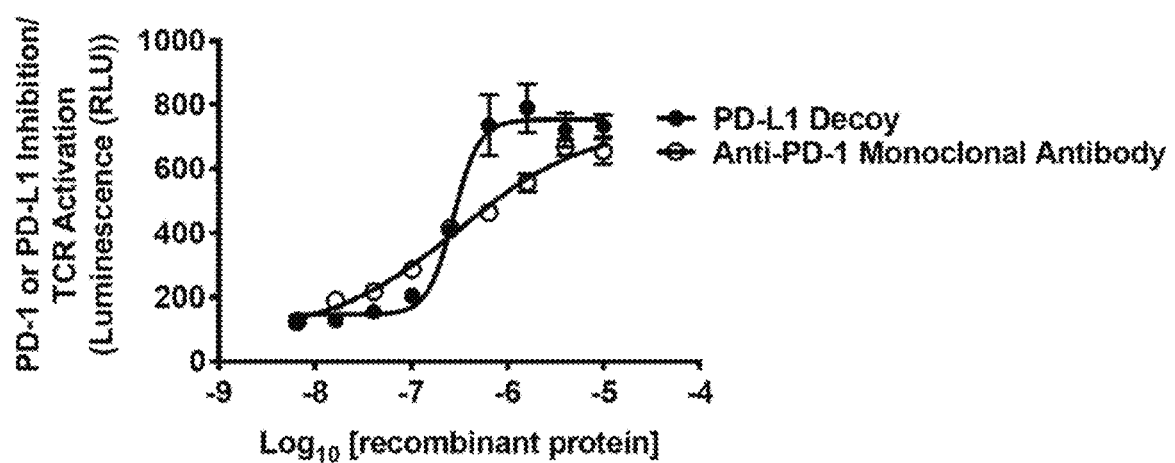

FIG. 19. PD-1 PD-L1 Blockade Assay—Fusion protein was purified from cells infected with pAd6/57/6-dl1107-DE3-RSV-hPD-1-HA-Ig-I on a protein A column. This protein was titrated along side positive control, anti-PD-1 monoclonal antibody from Promega (Madison, Wis. USA).

Figure 20:
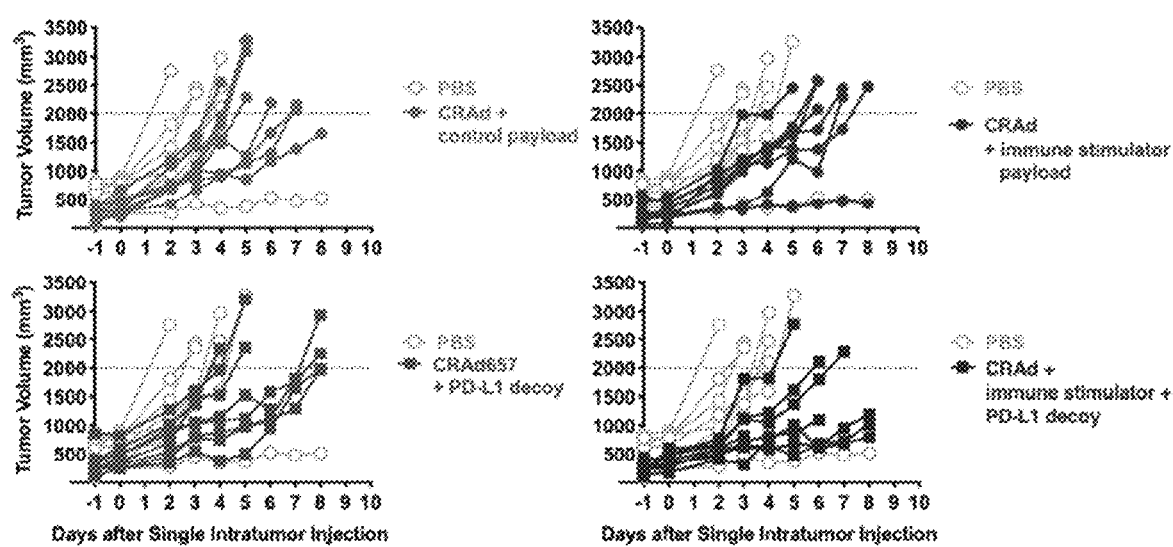

FIG. 20. Tumor Growth Assessment—B16-CAR melanoma cells were injected subcutaneously in C57BL/6 mice and tumors were injected with 3e11 viral particles of the indicated vectors. CRAd+PD-L1 decoy is pAd6/57/6-dl1107-ΔE3-RSV-hPD-1-HA-Ig-I. CRAd+PD-L1 decoy+immune simulator represent tumors that were co-injected with pAd6/57/6-dl1107-ΔE3-RSV-hPD-1-HA-Ig-I and a second adenovirus expressing 4-1BBL.

DETAILED DESCRIPTION OF THE INVENTION

This invention provides methods and compositions for treating cancer comprising PD-1 polypeptides. The PD-1 polypeptides may be in the form of multivalent PD-L1 binding compounds.

In some cases, a multivalent PD-L1 binding compound comprises two or more amino acid segments that can bind PD-L1 (e.g., PD-1 polypeptides and/or fragments thereof). For example, a multivalent PD-L1 binding compound that includes two or more PD-1 polypeptides (and/or fragments thereof having the ability to bind PD-L1) can bind two or more PD-L1 polypeptides. In some cases, a multivalent PD-L1 binding compound can include a single amino acid chain that includes two or more amino acid segments that can bind PD-L1.

In some cases, a multivalent PD-L1 binding compound can include a polypeptide conjugate including a plurality of (e.g., two or more) amino acid chains that each include one or more amino acid segments that can bind PD-L1. For example, an amino acid chain that includes one or more amino acid segments that can bind PD-L1 can be a fusion polypeptide that includes one or more PD-1 polypeptides fused to a scaffold polypeptide that can form a polypeptide conjugate with one or more other polypeptides that include one or more amino acid segments that can bind PD-L1 (e.g., a polypeptide conjugate including a plurality of associated amino acid chains). When the scaffold polypeptide fused to one or more PD-1 polypeptides is in a polypeptide conjugate, the polypeptide conjugate can include two or more PD-1 polypeptides.

In an embodiment, a virus particle comprising a PD-1 polypeptide may be in the form of a multivalent PD-L1 binding compound wherein two or more viral coat polypeptides are modified to include one or more amino acid chains that include one or more amino acid segments that can bind PD-L1.

In an embodiment, a PD-L1 binding compound comprises a recombinant virus which is genetically modified to express the PD-1 polypeptide, wherein the PD-1 polypeptide is displayed on the coat of the virus. In a further embodiment, the recombinant virus is genetically modified to express the PD-1 polypeptide in combination with one or more polypeptides which are heterologous to the recombinant virus backbone, for example, therapeutic polypeptides, targeting molecules/polypeptides and antigenic polypeptides.

In an embodiment, a PD-L1 binding compound comprises a recombinant Ad (i.e., Ad657, Ad6/57/6 and variants thereof) which is modified in one or more hexon hypervariable regions (HVRs) of the virus capsid protein and comprises at least one PD-1 polypeptide. In an embodiment, the recombinant Ad is further modified to comprise heterologous polypeptides such as targeting polypeptides, therapeutic polypeptides and/or antigens. The PD-1 polypeptides, as well as the heterologous polypeptides, are expressed upon viral replication. Upon virus assembly, the expressed polypeptides may be displayed on the surface of the virus as a component of the virus capsid structure.

In a further embodiment, a PD-L1 binding compound comprises a recombinant Ad which is genetically modified to express the PD-1 polypeptide as a fusion protein with one or more heterologous polypeptides, wherein the fusion protein is displayed on the capsid of the virus particle. Heterologous polypeptides may include a GLA domain from a FX polypeptide, CAR polypeptides, CD46 polypeptides, desmoglein polypeptides, integrin polypeptides, single-chain antibody polypeptides, camelid antibody polypeptides, capsid polypeptides, and envelope binding polypeptides.

In some cases, an amino acid chain that includes one or more PD-1 polypeptides and a polypeptide that can bind to a viral coat polypeptide can be a fusion polypeptide including one or more PD-1 polypeptides and a polypeptide that can bind to a viral coat polypeptide. In an embodiment, the fusion protein of PD-1 and a heterologous polypeptide may be expressed in a host cell, purified and admixed with an Ad such that the fusion protein is bound to the surface of the Ad via covalent attachment of the heterologous polypeptide to the Ad. When a first fusion polypeptide including one or more PD-1 polypeptides fused to a polypeptide that can bind to a viral coat polypeptide is bound to a first viral coat polypeptide on a virus particle and a second fusion polypeptide including one or more PD-1 polypeptides fused to a polypeptide that can bind to a viral coat polypeptide is bound to a second viral coat polypeptide on that virus particle, the virus particle will include two or more PD-1 polypeptides.

In some cases, a PD-L1 binding compound can include a virus particle where one or more viral coat polypeptides are modified to include one or more amino acid chains that include one or more amino acid segments that can bind PD-L1 (e.g., PD-1 polypeptides and/or fragments thereof). The PD-1 polypeptides may be expressed during viral replication and assembly and displayed on the coat of the virus. In an embodiment, the Ad (i.e., Ad657, Ad657/6 and variants thereof) is modified in an HVR region to express the PD-1 polypeptide in combination with one or more heterologous polypeptides selected from therapeutic polypeptides, targeting polypeptides and antigenic polypeptides. The PD-1 polypeptide may be expressed as a fusion protein with one or more heterologous polypeptides. For example, a virus particle is genetically modified to express two or more amino acid chains that each include at least one PD-1 polypeptide and a heterologous polypeptide, wherein the amino acid chains are displayed on the surface of the virus particle as a component of the virus capsid thereby forming a multivalent PD-L1 binding compound. In some cases, a virus particle is genetically modified to express two or more amino acid chains that each include a PD-1 polypeptide and is modified to express one or more amino acid chains that comprise a heterologous polypeptide, wherein the amino acid chains are displayed on the surface of the virus particle as a component of the virus capsid thereby forming a multivalent PD-L1 binding compound. In some cases, an amino acid chain includes two or more PD-1 polypeptides and a heterologous polypeptide that are displayed on the surface of the virus particle.

In an embodiment, an amino acid chain that comprises one or more PD-1 polypeptides can be a fusion protein that comprises one or more PD-1 polypeptides fused to a heterologous polypeptide. The heterologous polypeptide may bind to the surface of an Ad to coat the virus particle. In an embodiment, the fusion proteins are expressed in a host cell, purified and admixed with an Ad such that the fusion protein coats the surface of the Ad viral particle thereby forming a multivalent PD-L1 binding compound.

In some cases, a multivalent PD-L1 binding compound described herein can have increased affinity for PD-L1 (e.g., as compared to a monomeric PD-1 polypeptide). In some cases, a multivalent PD-L1 binding compound described herein can have increased avidity for PD-L1 (e.g., as compared to a monomeric PD-1 polypeptide).

This invention provides methods and materials for making compositions comprising PD-1 polypeptides and multivalent PD-L1 binding compounds, as well as methods and materials for making recombinant viruses comprising nucleic acid molecules that encode an amino acid chain that can be used to generate multivalent PD-L1 binding compounds described herein.

Multivalent PD-L1 binding compounds described herein (e.g., a fusion polypeptide that includes one or two or more PD-1 polypeptides, or a polypeptide conjugate that includes two or more amino acid chains that each include one or more PD-1 polypeptides, or a virus particle where viral coat proteins comprise one or more amino acid chains that include one or more PD-1 polypeptides, or a virus particle where one or more PD-1 polypeptides are bound to the surface of the virus particle) can include any appropriate number of amino acid segments that can bind PD-L1 (e.g., PD-1 polypeptides and/or fragments thereof that can bind PD-L1).

In some cases, a multivalent PD-L1 binding compound described herein can include two or more (e.g., 2, 3, 4, 5, 6, 240, 720, or more) amino acid segments that can bind PD-L1. In some cases, a multivalent PD-L1 binding compound described herein can include from about two to about 720 amino acid segments that can bind PD-L1. For example, when a multivalent PD-L1 binding compound described herein is a single amino acid chain that includes two or more amino acid segments that can bind PD-L1, the multivalent PD-L1 binding compound can include about 2, 3, 4, 5, 6, 7, or 8 PD-1 polypeptides (or fragments thereof that bind PD-L1). For example, when a multivalent PD-L1 binding compound described herein is a polypeptide conjugate including a plurality of amino acid chains that each include one or more amino acid segments that can bind PD-L1, the multivalent PD-L1 binding compound can include about 2, 3, 4, 5, 6, 7, or 8 PD-1 polypeptides (or fragments thereof that bind PD-L1).

For example, when a multivalent PD-L1 binding compound described herein is a virus particle where two or more viral coat polypeptides (e.g. capsid polypeptides) are modified to include one or more amino acid chains that include one or more amino acid segments that can bind PD-L1, the multivalent PD-L1 binding compound can include from about 240 PD-1 polypeptides to about 720 PD-1 polypeptides (or fragments thereof that bind PD-L1). In cases where a multivalent PD-L1 binding compound described herein includes two amino acid segments that can bind PD-L1 (or a virus particle where one or more viral coat polypeptides are modified to include one or more amino acid chains that include two or more amino acid segments that can bind PD-L1), the multivalent PD-L1 binding compound can be referred to as a dimeric or divalent PD-L1 binding compound. In cases where a multivalent PD-L1 binding compound described herein includes three amino acid segments that can bind PD-L1, the multivalent PD-L1 binding compound can be referred to as a trimeric or trivalent PD-L1 binding compound. In cases where a multivalent PD-L1 binding compound described herein includes four amino acid segments that can bind PD-L1, the multivalent PD-L1 binding compound can be referred to as a tetrameric or tetravalent PD-L1 binding compound.

Multivalent PD-L1 binding compounds described herein can include any appropriate amino acid segment(s) that can bind PD-L1.

In an embodiment, an amino acid segment that can bind PD-L1 can include a PD-1 polypeptide. In some cases, an amino acid segment that can bind PD-L1 can include any fragment of a PD-1 polypeptide provided that the fragment retains the ability to bind PD-L1. In some cases, a PD-1 polypeptide can be a sPD-1 polypeptide. A PD-1 polypeptide can be from any appropriate animal. In some cases, a PD-1 polypeptide can be from a mammal. For example, a PD-1 polypeptide can be an hPD-1 polypeptide. For example, a PD-1 polypeptide can be a mPD-1 polypeptide. A PD-1 polypeptide can include any appropriate PD-1 polypeptide sequence. In some cases, a PD-1 polypeptide can be modified (e.g., for higher affinity interactions with PD-L1). Exemplary PD-1 polypeptide sequences (and the nucleic acids encoding such polypeptides) can be as set forth in the National Center for Biotechnology Information (NCBI) databases at, for example, Accession No. AI928135 (Version AI928135.1), Accession No. AY238517 (Version AY238517.1), and Accession No. CR988122 (Version CR988122.1), Accession No. U64863 (Version U64883.1), Accession No. NM_008798 (Version NM_008798.2), and Accession No. NP_032824 (Version NP_032824.1). In some cases, a PD-1 polypeptide comprises the amino acid sequence set forth in SEQ ID NO:5. In some cases, a PD-1 polypeptide comprises the amino acid sequence set forth in SEQ ID NO: 6.

In some cases, an amino acid segment that can bind PD-L1 (e.g., PD-1 polypeptides and/or fragments thereof) can have a sequence that deviates from a wild type PD-1 polypeptide sequence (e.g., a wild type PD-1 polypeptide having the amino acid sequence set forth in SEQ ID NO:5 or SEQ ID NO:6), sometimes referred to as a variant sequence. For example, a PD-1 polypeptide sequence (and/ or a fragment thereof having the ability to bind PD-L1) can have at least 80% sequence identity to SEQ ID NO:5 or SEQ ID NO:6. In some embodiments, an amino acid segment that can bind PD-L1 can have at least 85% sequence identity, 90% sequence identity, 95% sequence identity, or at least 99% sequence identity to SEQ ID NO:5 or SEQ ID NO:6. Percent sequence identity is calculated by determining the number of matched positions in aligned polypeptide sequences, dividing the number of matched positions by the total number of aligned amino acids, respectively, and multiplying by 100. A matched position refers to a position in which identical amino acids occur at the same position in aligned sequences. The total number of aligned amino acids refers to the minimum number of amino acids in a PD-1 polypeptide that are necessary to align the second sequence, and does not include alignment (e.g., forced alignment) with non-PD-1 sequences, such as those fused to a PD-1 polypeptide (e.g., amino acids from an IgG polypeptide, a streptavidin polypeptide, sigma-1, or a GLA domain of an FX polypeptide that is fused to a PD-1 polypeptide). The total number of aligned amino acids may correspond to the entire PD-1 sequence or may correspond to fragments of the full-length PD-1 sequence. Sequences can be aligned using the algorithm described by Altschul et al. (*Nucleic Acids Res.*, 25:3389-3402 (1997)) as incorporated into BLAST (basic local alignment search tool) programs, available at ncbi.nlm.nih.gov on the World Wide Web. BLAST searches or alignments can be performed to determine percent sequence identity between a PD-1 polypeptide and any other sequence or portion thereof using the Altschul et al, algorithm. BLASTN is the program used to align and compare the identity between nucleic acid sequences, while BLASTP is the program used to align and compare the identity between amino acid sequences. When utilizing BLAST programs to calculate the percent identity between a PD-1 sequence and another sequence, the default parameters of the respective programs are used.

In some cases, a multivalent PD-L1 binding compound can include a polypeptide conjugate including a plurality of amino acid chains that each include one or more amino acid segments that can bind PD-L1 (e.g., PD-1 polypeptides and/or fragments thereof). As used herein, a plurality of amino acid chains that each include one or more amino acid segments that can bind PD-1 refers to two or more (e.g., 2, 3, 4, 5, 6, 7, 8, or more) amino acid chains that each include one or more amino acid segments that can bind PD-L1. For example, an amino acid chain that includes one or more PD-1 polypeptides can be a fusion polypeptide that includes one or more PD-1 polypeptides fused to a scaffold polypeptide that can form a polypeptide conjugate with one or more other polypeptides that include one or more amino acid segments that can bind PD-L1 (e.g., a polypeptide conjugate including a plurality of associated amino acid chains). When the scaffold polypeptide fused to one or more PD-1 polypeptides is in a polypeptide conjugate, the polypeptide conjugate can include two or more PD-1 polypeptides. In some cases, a polypeptide conjugate including a plurality amino acid chains that each include one or more PD-1 polypeptides can be a homomeric PD-1 polypeptide (e.g., can include two or more of the same amino acid chains that each include one or more PD-1 polypeptides). In some cases, a polypeptide conjugate including a plurality amino acid chains that each include one or more PD-1 polypeptides can be a heteromeric PD-1 polypeptide (e.g., can include two or more different amino acid chains that each include one or more PD-1 polypeptides).

An amino acid chain including one or more amino acid segments that can bind PD-L1 (e.g., PD-1 polypeptides and/or fragments thereof) present in a polypeptide conjugate described herein (e.g., a polypeptide conjugate including a plurality amino acid chains that each include one or more PD-1 polypeptides) can include one or more amino acid segments that can bind PD-L1 fused to any appropriate scaffold polypeptide. For example, an amino acid chain including one or more PD-1 polypeptides present in a polypeptide conjugate described herein can be a fusion polypeptide that includes one or more PD-1 polypeptides fused to any appropriate scaffold polypeptide. In some cases, a scaffold polypeptide can have the ability to form a polypeptide conjugate (e.g., a polypeptide conjugate including a plurality of associated amino acid chains). For example, two or more amino acid chains including one or more PD-1 polypeptides fused to a scaffold polypeptide can form a polypeptide conjugate that includes two or more PD-1 polypeptides. When two or more amino acid chains including one or more PD-1 polypeptides fused to a scaffold polypeptide form a polypeptide conjugate, the two or more amino acid chains can be bonded (e.g., by a covalent bond or an ionic bond). A scaffold polypeptide can be any appropriate polypeptide that can form a polypeptide conjugate with another polypeptide. A scaffold polypeptide can naturally form a polypeptide conjugate or can be engineered to form a polypeptide conjugate. Examples of scaffold polypeptides that can form a polypeptide conjugate can include, without limitation, Ig polypeptides (e.g., IgG polypeptides such as IgG2 polypeptides), sigma-1 polypeptides, and streptavidin polypeptides.

An amino acid chain including one or more amino acid segments that can bind PD-L1 (e.g., PD-1 polypeptides and/or fragments thereof) that can be present in a polypeptide conjugate described herein (e.g., a polypeptide conjugate including a plurality amino acid chains that each include one or more PD-1 polypeptides) can include any appropriate amino acid sequence. For example, an amino acid chain including one or more PD-1 polypeptides fused to a scaffold polypeptide can include any appropriate amino acid sequence. Exemplary amino acid sequences of amino acid chains including one or more PD-1 polypeptides and a scaffold polypeptide include, without limitation, those amino acid sequences set forth in SEQ ID NO: 7, 10, 11, 12, 13, 16, 17, 18, 19, 20, 21, 24, 25, 26, or 27. In some cases, the amino acid sequence of an amino acid chain including one or more PD-1 polypeptides and a scaffold polypeptide can have a sequence that deviates from one of the amino acid sequences set forth in SEQ ID NO: 7, 10, 11, 12, 13, 16, 17, 18, 19, 20, 21, 24, 25, 26, or 27. Sometimes referred to as a variant sequence. For example, an amino acid sequence of a fusion polypeptide containing one or more PD-1 polypeptides and a scaffold polypeptide can have at least 80% sequence identity to any one of the amino acid sequences set forth in SEQ ID NO: 7, 10, 11, 12, 13, 16, 17, 18, 19, 20, 21, 24, 25, 26, or 27. In some embodiments, an amino acid sequence of a fusion polypeptide containing one or more PD-1 polypeptides and a scaffold polypeptide can have at least 85% sequence identity, 90% sequence identity, 95% sequence identity, or at least 99% sequence identity to any one of the amino acid sequences set forth in SEQ ID NO: 7, 10, 11, 12, 13, 16, 17, 18, 19, 20, 21, 24, 25, 26, or 27. Percent sequence identity is calculated by determining the number of matched positions in aligned polypeptide sequences, dividing the number of matched positions by the total number of aligned amino acids, respectively, and multiplying by 100. A matched position refers to a position in which identical amino acids occur at the same position in aligned sequences. Sequences can be aligned using the algorithm described by Altschul et al. (*Nucleic Acids Res.,* 25:3389-3402 (1997)) as incorporated into BLAST (basic local alignment search tool) programs, available at ncbi.nlm-.nih.gov on the World Wide Web. BLAST searches or alignments can be performed to determine percent sequence identity between a polypeptide and any other sequence or portion thereof using the Altschul et al, algorithm. BLASTN is the program used to align and compare the identity between nucleic acid sequences, while BLASTP is the program used to align and compare the identity between amino acid sequences. When utilizing BLAST programs to calculate the percent identity between a polypeptide sequence and another sequence, the default parameters of the respective programs are used. In some cases, an amino acid chain including one or more PD-1 polypeptides that can be present in a polypeptide conjugate described herein (e.g., a polypeptide conjugate including a plurality amino acid chains that each include one or more PD-1 polypeptides) can be as set forth in Example 7.

In some cases, an amino acid chain including one or more amino acid segments that can bind PD-L1 (e.g., PD-1 polypeptides and/or fragments thereof) can be fused to a scaffold polypeptide that can form a polypeptide conjugate including two associated amino acid chains (e.g., an IgG polypeptide such as an IgG2 polypeptide). For example, two amino acid chains each including one PD-1 polypeptide fused to an IgG2 polypeptide can form a polypeptide conjugate that includes two PD-1 polypeptides. Exemplary amino acid sequences of amino acid chains including one PD-1 polypeptide fused to an IgG2 polypeptide include. Without limitation, those amino acid sequences set forth in SEQ ID NO:7, SEQ ID NO:13, or SEQ ID NO:21.

In some cases, an amino acid chain including one or more amino acid segments that can bind PD-L1 (e.g., PD-1 polypeptides and/or fragments thereof) can be fused to a scaffold polypeptide that can form a polypeptide conjugate including three associated amino acid chains (e.g., a sigma-1 polypeptide). For example, three amino acid chains each including one PD-1 polypeptide fused to a sigma-1 polypeptide can form a polypeptide conjugate that includes three PD-1 polypeptides. Exemplary amino acid sequences of amino acid chains including one PD-1 polypeptide fused to a sigma-1 polypeptide include, without limitation, those amino acid sequences set forth in SEQ ID NO:10, SEQ ID NO:16, or SEQ ID NO:24.

In some cases, an amino acid chain including one or more amino acid segments that can bind PD-L1 (e.g., PD-1 polypeptides and/or fragments thereof) can be fused to a scaffold polypeptide that can form a polypeptide conjugate including four associated amino acid chains (e.g., a streptavidin polypeptide). For example, four amino acid chains each including one PD-1 polypeptide fused to a streptavidin polypeptide can form a polypeptide conjugate that includes four PD-1 polypeptides. Exemplary amino acid sequences of amino acid chains including one PD-1 polypeptide fused to a streptavidin polypeptide include, without limitation, those amino acid sequences set forth in SEQ ID NO:11 or SEQ ID NO:17.

In some cases, a multivalent PD-L1 binding compound can include a virus particle where two or more viral coat polypeptides are modified to include one or more amino acid chains that include one or more amino acid segments that can bind PD-L1 (e.g., PD-1 polypeptides and/or fragments thereof). For example, a virus particle can be modified by coating the virus particle with two or more amino acid chains that each include one or more PD-1 polypeptides and a polypeptide that can bind to a viral coat polypeptide. An amino acid chain including one or more amino acid segments that can bind PD-L1 (e.g., PD-1 polypeptides and/or fragments thereof) that can be used to coat a virus particle to generate a multivalent PD-L1 binding compound (e.g., a virus particle where two or more viral coat polypeptides are modified to include one or more amino acid chains that include one or more PD-1 polypeptides) can include one or more amino acid segments that can bind PD-L1 fused to any appropriate polypeptide that can bind to a viral coat polypeptide. In some cases, a polypeptide that can bind to a viral coat polypeptide can covalently bind to one or more viral coat polypeptides. In some cases, a polypeptide that can bind to a viral coat polypeptide can bind to a viral coat polypeptide with high affinity (e.g., from about 0.25 μM to about 100 μM). A polypeptide that can bind to a viral coat polypeptide can naturally bind to a viral coat polypeptide or is engineered to bind to a viral coat polypeptide. A polypeptide that can bind to a viral coat polypeptide can bind to any appropriate viral coat polypeptide.

Examples of viral coat polypeptides include, without limitation. Capsid polypeptides (e.g., hexon polypeptides, fiber polypeptides, penton polypeptides), and adenovirus IX polypeptides. A polypeptide that can bind to a viral coat polypeptide can bind to a viral coat polypeptide present on any appropriate type of virus particle. A virus particle can be a replication competent (RC) virus particle (e.g., helper-dependent (HD) virus particles and single-cycle (SC) virus particles), a virus particle can be a replication-defective (RD) virus particle, or a virus can be a conditionally replicating virus particle (CRAd). In some cases, a virus particle can be an oncolytic virus particle.

In some cases, a virus particle can be a viral vector. Examples of virus particles that can be coated with one or more amino acid chains that include one or more PD-1 polypeptides and a polypeptide that can bind to a viral coat polypeptide include, without limitation, Ads, adeno-associated viruses (AAVs), lentiviruses, enteroviruses, reoviruses, poxviruses, measles virus, and herpes viruses.

Examples of polypeptides which may be present on a viral coat polypeptide include, without limitation, a GLA domain polypeptide (e.g., a GLA domain from a FX polypeptide), CAR polypeptides, CD46 polypeptides, desmoglein polypeptides, integrin polypeptides, single-chain antibody polypeptides, camelid antibody polypeptides. Capsid polypeptides, and envelope binding polypeptides.

An amino acid chain including one or more amino acid segments that can bind PD-L1 (e.g., PD-1 polypeptides and/or fragments thereof) that can be used to coat a virus particle to generate a multivalent PD-L1 binding compound (e.g., a virus particle where one or two or more viral coat polypeptides are modified to include one or more amino acid chains that include one or more PD-1 polypeptides) can include any appropriate amino acid sequence. For example, a virus particle can be contacted with a composition comprising two or more amino acid chains that each include one or more PD-1 polypeptides and a polypeptide that can covalently bind to a viral coat polypeptide such that the amino acid chains coat the virus particle. In some cases, an amino acid chain that includes one or more PD-1 polypeptides and a polypeptide that can bind to a viral coat polypeptide can be a fusion polypeptide including one or more PD-1 polypeptides and a polypeptide that can bind to a viral coat polypeptide. An amino acid chain that includes one or more PD-1 polypeptides and a polypeptide that can bind to a viral coat polypeptide can include any appropriate amino acid sequence. Exemplary amino acid sequences of amino acid chains including one or more PD-1 polypeptides and a polypeptide that can bind to a viral coat polypeptide include, without limitation, those amino acid sequences set forth in SEQ ID NO: 8, 9, 14, 15, 22, or 23. In some cases, the amino acid sequence of an amino acid chain including one or more PD-1 polypeptides and a polypeptide that can bind to a viral coat polypeptide can have a sequence that deviates from one of the amino acid sequences set forth in SEQ ID NO: 8, 9, 14, 15, 22, or 23 sometimes referred to as a variant sequence. For example, an amino acid sequence of a fusion polypeptide containing one or more PD-1 polypeptides and a polypeptide that can bind to a viral coat polypeptide can have at least 80% sequence identity to any one of the amino acid sequences set forth in SEQ ID NO: 8, 9, 14, 15, 22, or 23. In some embodiments, an amino acid sequence of a fusion polypeptide containing one or more PD-1 polypeptides and a polypeptide that can bind to a viral coat polypeptide can have at least 85% sequence identity, 90% sequence identity, 95% sequence identity, or at least 99% sequence identity to any one of the amino acid sequences set forth in SEQ ID NO: 8, 9, 14, 15, 22, or 23. Percent sequence identity is calculated by determining the number of matched positions in aligned polypeptide sequences, dividing the number of matched positions by the total number of aligned amino acids, respectively, and multiplying by 100. A matched position refers to a position in which identical amino acids occur at the same position in aligned sequences. Sequences can be aligned using the algorithm described by Altschul et a. (*Nucleic Acids Res.*, 25:3389-3402 (1997)) as incorporated into BLAST (basic local alignment search tool) programs. In some cases, an amino acid chain including one or more PD-1 polypeptides and a polypeptide that can bind to a viral coat polypeptide can be as set forth in the Examples.

In some cases, an amino acid chain including one or more amino acid segments that can bind PD-L1 (e.g., PD-1 polypeptides and/or fragments thereof) fused to a polypeptide that can bind to a viral coat polypeptide (e.g., a GLA domain of a FX polypeptide) can be used to coat (e.g., to modify one or more viral coat polypeptides) a virus particle to form a coated virus particle having two or more amino acid chains including one or more amino acid segments that can bind PD-L1 which is bound to one or more viral coat polypeptides present on the surface of the virus particle.

For example, one or more amino acid chains each including one PD-1 polypeptide fused to a GLA domain of a FX polypeptide can be bound to two or more viral hexon polypeptides and/or other viral coat proteins to coat a virus particle with two or more amino acid chains each including one PD-1 polypeptide fused to a GLA domain of a FX polypeptide. When a virus particle is an Ad, 240 hexon polypeptide homo-trimers (e.g., polypeptide conjugates including three hexon polypeptides) can be present on the virus particle (see, e.g., Chen et al., *Human gene therapy*, 21:739-749 (2010)). In some cases, a fusion polypeptide including one PD-1 polypeptide and a GLA domain of a FX polypeptide can be used to coat an Ad particle to generate a multivalent PD-L1 binding compound that includes about 240 PD-1 polypeptides. For example, when a fusion polypeptide including one PD-1 polypeptide fused to a GLA domain of a FX polypeptide is bound to each hexon polypeptide trimer on an Ad virus particle, the virus particle will include 240 PD-1 polypeptides. In some cases, a fusion polypeptide including one PD-1 polypeptide and a GLA domain of a FX polypeptide can be used to coat an Ad particle to generate a multivalent PD-L1 binding compound that may include between about 240 PD-1 polypeptides and about 720 PD-1 polypeptides. For example, when a fusion polypeptide including one PD-1 polypeptide fused to a GLA domain of a FX polypeptide is bound to each hexon polypeptide on an Ad virus particle, the virus particle will include 720 PD-1 polypeptides.

In some cases, multivalent PD-L1 binding compounds described herein (e.g., a fusion polypeptide that includes two or more PD-1 polypeptides, or a polypeptide conjugate that includes one or two or more amino acid chains that each include one or more PD-1 polypeptides, or a virus particle where two or more viral coat polypeptides include one or more amino acid chains that include one or more PD-1 polypeptides, or a virus particle where one or more viral coat polypeptides include one or more amino acid chains that include two or more PD-1 polypeptides) also can include one or more additional molecules/polypeptides.

Examples of molecules that can be included in a multivalent PD-L1 binding compound described herein include, without limitation, targeting molecules (e.g., targeting polypeptides and targeting nucleic acid sequences), antigens, therapeutic molecules, and detectable polypeptides. In some cases, when a multivalent PD-L1 binding compound is a polypeptide conjugate including a plurality of amino acid chains that each include one or more PD-1 polypeptides and/or PD-1 polypeptide fragments having the ability to bind PD-L1, and the polypeptide conjugate includes one or more additional molecules, the one or more additional molecules can be included in at least one (e.g., 1, 2, 3, 4, or more) amino acid chain including one or more PD-1 polypeptides and/or PD-1 polypeptide fragments having the ability to bind PD-L1 that is present in the polypeptide conjugate. For example, when a multivalent PD-L1 binding compound is a polypeptide conjugate including a plurality of amino acid chains that each include one or more PD-1 polypeptides and/or PD-1 polypeptide fragments having the ability to bind PD-L1, and the polypeptide conjugate includes one or more additional molecules, the one or more additional molecules can be included in each amino acid chain including one or more PD-1 polypeptides and/or PD-1 polypeptide fragments having the ability to bind PD-L1 that is present in the polypeptide conjugate. In some cases, when a multivalent PD-L1 binding compound is a virus particle where two or more viral coat polypeptides are modified to include one or more amino acid chains that include one or more PD-1 polypeptides and/or PD-1 polypeptide fragments having the ability to bind PD-L1 (or a virus particle where one or more viral coat polypeptides are include one or more amino acid chains that include two or more amino acid segments that include one or more PD-1 polypeptides and/or PD-1 polypeptides fragments having the ability to bind PD-L1), the one or more additional molecules can be included in at least one (e.g., 1, 2, 3, 4, or more) amino acid chain including one or more PD-1 polypeptides and/or PD-1 polypeptide fragments used to modify a viral coat polypeptide on a virus particle. For example, when a multivalent PD-L1 binding compound is a virus particle where two or more viral coat polypeptides are modified to include one or more amino acid chains that include one or more PD-1 polypeptides and/or PD-1 polypeptide fragments having the ability to bind PD-L1 (or a virus particle where one or more viral coat polypeptides are modified to include one or more amino acid chains that include two or more amino acid segments that include one or more PD-1 polypeptides and/or PD-1 polypeptides fragments having the ability to bind PD-L1), the one or more additional molecules can be included in each amino acid chain including one or more PD-1 polypeptides and/or PD-1 polypeptide fragments used to modify a viral coat polypeptide on a virus particle.

When PD-L1 binding compounds described herein also include one or more targeting molecules (e.g., targeting polypeptides and targeting nucleic acid sequences), a targeting molecule can be any appropriate targeting molecule. In some cases, a targeting molecule can be a polypeptide (e.g., a targeting polypeptide). In some cases, a targeting molecule can be nucleic acid sequence (e.g., a targeting nucleic acid sequence). In some cases, a targeting molecule can attract a T-cell to a PD-L1 positive cell (e.g., a PD-L1 positive cancer cell). For example, when a multivalent PD-L1 binding compound that includes a targeting molecule is bound to PD-L1 on a PD-L1 positive cell, the targeting molecule on the multivalent PD-L1 binding compound can attract T cells to the PD-L1 positive cell. For example, when a multivalent PD-L1 binding compound includes a targeting molecule, the targeting molecule on the multivalent PD-L1 binding compound can direct the multivalent PD-L1 binding compound to a target location (e.g., a target tissue) within a mammal. Examples of targeting molecules that can be included in a multivalent PD-L1 binding compound described herein include, viral polypeptides, antigens (e.g., peptide antigens), miRNA targeting sequences (e.g., tissue-specific miRNA targeting sequences), antibodies, growth factors, and carbohydrates. When a targeting polypeptide is a viral polypeptide, the viral polypeptide can be derived from any appropriate virus (e.g., measles virus (MV), canine distemper virus (CDV), vesicular stomatitis virus (VSV), gibbon ape leukemia virus (GALV), Zika virus, human immunodeficiency virus (HIV), and human endogenous retrovirus (HERV)). When a targeting polypeptide is a viral polypeptide, the viral polypeptide can be any appropriate viral polypeptide (e.g., a hemagglutinin (H) polypeptide such as a detargeted H polypeptide, a fusion (F) polypeptide, a viral glycoprotein (G) polypeptide, envelope (env; e.g., HERV env), syncytin-1, and syncytin-2. In some cases, a viral polypeptide can be a MV H polypeptide. In some cases, a viral polypeptide can be a MV F polypeptide. In some cases, a viral polypeptide can be a VSV G polypeptide.

When PD-L1 binding compounds described herein also include one or more therapeutic molecules, a therapeutic molecule can be any appropriate therapeutic molecule. In some cases, a therapeutic molecule can be a therapeutic polypeptide. In some cases, a therapeutic molecule can reduce or eliminate PD-L1 inactivation of one or more T cells. In some cases, a therapeutic molecule can activate and/or accumulate one or more pharmaceutical agents (e.g., anti-cancer drugs). Examples of therapeutic molecules that can be included in a multivalent PD-L1 binding compound described herein include, a 4-1BB ligand (4-1BBL) polypeptide, an OX40 ligand (OX40L) polypeptide, a granulocyte-macrophage colony-stimulating factor (GM-CSF) polypeptide, anti-PD-1 antibodies, nucleic acid encoding anti-PD-1 antibodies, thymidine kinase, cytosine deaminase, and iodide symporter. In some cases, a therapeutic molecule can be a therapeutic antibody. The therapeutic antibody may be an agonist antibody which targets GITR. Signaling through GITR enhances T-cell proliferation and effector functions and protects T cells from activation-induced cell death, which in turn increases the frequency of memory T cells. Combining GITR agonists with the PD-L1 binding compounds of the invention may demonstrate a strong synergy.

When PD-L1 binding compounds described herein also include one or more detectable polypeptides, a detectable polypeptide can be any appropriate detectable polypeptide. In some cases, a detectable polypeptide can be detected (e.g., by a clinician) to determine the location of one or more PD-L1 binding compounds described herein. In some cases, a detectable polypeptide can be detected (e.g., by a clinician) to monitor the persistence of one or more multivalent PD-L1 binding compounds described herein. Examples of detectable polypeptides that can be included in a PD-L1 binding compound described herein are selected from fluorescent polypeptides (e.g., green fluorescent protein (GFP), luciferase polypeptides, peptide labels, and sodium iodide symporter.

This document also provides nucleic acids (e.g., nucleic acid vectors) that can encode amino acid chains described herein (e.g., an amino acid chain that includes one or more PD-1 polypeptides fused to a scaffold polypeptide, or an amino acid chain that includes one or more PD-1 polypeptides fused to a polypeptide that can bind to a viral coat polypeptide) that can be used to generate multivalent PD-L1 binding compounds described herein (e.g., a fusion polypeptide that includes two or more PD-1 polypeptides, or a polypeptide conjugate that includes two or more amino acid chains that each include one or more PD-1 polypeptides, or a virus particle where one or two or more viral coat polypeptides are modified to include one or more amino acid chains that include one or more PD-1 polypeptides, or a virus particle where one or more viral coat polypeptides are modified to include one or more amino acid chains that include two or more PD-1 polypeptides). In some cases, nucleic acid can encode an amino acid chain that can be used to generate a polypeptide conjugate including two or more amino acid chains that each include one or more PD-1 polypeptides. For example, nucleic acid can encode an amino chain including one or more PD-1 polypeptides and a scaffold polypeptide. In some cases, nucleic acid can encode an amino acid chain that can be used to generate a virus particle where one or more viral coat polypeptides comprise one or more amino acid chains that include one or more PD-1 polypeptides. For example, nucleic acid can encode an amino chain including one or more PD-1 polypeptides and a polypeptide that can bind to a viral coat polypeptide.

Nucleic acid (e.g., nucleic acid vectors) encoding amino acid chains described herein (e.g., an amino acid chain that includes one or more PD-1 polypeptides fused to a scaffold polypeptide, or an amino acid chain that includes one or more PD-1 polypeptides fused to a polypeptide that can bind to a viral coat polypeptide) that can be used to generate multivalent PD-L1 binding compounds described herein can be a nucleic acid selected from DNA (e.g., a DNA construct), RNA (e.g., mRNA), or a combination thereof. In some cases, nucleic acid encoding an amino acid chain described herein can be a vector (e.g., an expression vector or a viral vector). A vector can be a RC vector (e.g., HD vectors and SC vectors) or a vector can be a RD vector. When a vector is a viral vector, the viral vector can be derived from any appropriate type of virus. In some cases, a viral vector can be derived from an oncolytic virus. Examples of viruses from which viral vectors can be derived include, without limitation, Ads, adeno-associated viruses (AAVs), lentiviruses, enteroviruses, reoviruses, poxviruses, measles virus, and herpes viruses.

In some cases, nucleic acid encoding an amino acid chain described herein also can include one or more regulatory elements (e.g., to regulate expression of the amino acid chain). Examples of regulatory elements that can be included in nucleic acid encoding an amino acid chain described herein include, without limitation, promoters (e.g., constitutive promoters, tissue/cell-specific promoters, and inducible promoters such as chemically-activated promoters and light-activated promoters), enhancers, nucleic acid sequences (e.g., suicide genes) whose expression can induce apoptosis, necrosis, and other forms of cell death.

In some cases, nucleic acids (e.g., nucleic acid vectors) encoding amino acid chains described herein (e.g., an amino acid chain that includes one or more PD-1 polypeptides fused to a scaffold polypeptide, or an amino acid chain that includes one or more PD-1 polypeptides fused to a polypeptide that can bind to a viral coat polypeptide) that can be used to generate multivalent PD-L1 binding compounds described herein (e.g., a fusion polypeptide that includes two or more PD-1 polypeptides, or a polypeptide conjugate that includes two or more amino acid chains that each include one or more PD-1 polypeptides, or a virus particle where two or more viral coat polypeptides are modified to include one or more amino acid chains that include one or more PD-1 polypeptides, or a virus particle where one or more viral coat polypeptides are modified to include one or more amino acid chains that include two or more PD-1 polypeptides) can produce two or more (e.g., 2, 3, 4, 5, 6, 7, 8, 9, 10, or more) amino acid chains described herein.

In some cases, nucleic acids (e.g., nucleic acid vectors) encoding amino acid chains described herein (e.g., an amino acid chain that includes one or more PD-1 polypeptides fused to a scaffold polypeptide, or an amino acid chain that includes one or more PD-1 polypeptides fused to a polypeptide that can bind to a viral coat polypeptide) that can be used to generate multivalent PD-L1 binding compounds described herein (e.g., a fusion polypeptide that includes two or more PD-1 polypeptides, or a polypeptide conjugate that includes two or more amino acid chains that each include one or more PD-1 polypeptides, or a virus particle where two or more viral coat polypeptides are modified to include one or more amino acid chains that include one or more PD-1 polypeptides, or a virus particle where one or more viral coat polypeptides are modified to include one or more amino acid chains that include two or more PD-1 polypeptides) can continuously produce one or more (e.g., 1, 2, 3, 4, 5, 6, 7, 8, 9, 10, or more) amino acid chains described herein.

In some cases, nucleic acids (e.g., nucleic acid vectors) encoding amino acid chains described herein (e.g., an amino acid chain that includes one or more PD-1 polypeptides fused to a scaffold polypeptide, or an amino acid chain that includes one or more PD-1 polypeptides fused to a polypeptide that can bind to a viral coat polypeptide) that can be used to generate multivalent PD-L1 binding compounds described herein (e.g., a fusion polypeptide that includes two or more PD-1 polypeptides, or a polypeptide conjugate that includes two or more amino acid chains that each include one or more PD-1 polypeptides, or a virus particle where two or more viral cost polypeptides are modified to include one or more amino acid chains that include one or more PD-1 polypeptides, or a virus particle where one or more viral coat polypeptides are modified to include one or more amino acid chains that include two or more PD-1 polypeptides) can produce one or more (e.g., 1, 2, 3, 4, 5, 6, 7, 8, 9, 10, or more) amino acid chains described herein for the duration of the persistence of the nucleic acid (e.g., until the nucleic acid is degraded).

In some cases, amino acid chains encoded by nucleic acid described herein can be used to generate multivalent PD-L1 binding compounds described herein. For example, two or more amino acid chains including one or more PD-1 polypeptides fused to a scaffold polypeptide can assemble (e.g., can self-assemble) into a polypeptide conjugate including two or more amino acid chains that each include one or more PD-1 polypeptides to generate a polypeptide conjugate described herein. When two or more amino acid chains including one or more PD-1 polypeptides fused to a scaffold polypeptide assemble into a polypeptide conjugate including two or more amino acid chains that each include one or more PD-1 polypeptides to generate a polypeptide conjugate, the amino acid chains can assemble in vivo or in vitro. For example, one or more amino acid chains including one or more PD-1 polypeptides fused to a polypeptide that can bind to a viral coat polypeptide can bind to two or more viral coat polypeptides present on the surface of a virus particle to coat to generate a coated virus particle described herein. When one or more amino acid chains including one or more PD-1 polypeptides fused to a polypeptide that can bind to a viral coat polypeptide coat virus particle to generate a coated virus particle, the virus particle can be coated in vivo or in vitro.

In some cases, multivalent PD-L1 binding compounds described herein can be purified. A "purified" polypeptide, protein or nucleic acid refers to a polypeptide or nucleic acid that constitutes the major component in a mixture of components, e.g., 30% or more, 40% or more, 50% or more, 60% or more, 70% or more, 80% or more, 90% or more, 95% or more, or 99% or more by weight. For example, a purified multivalent PD-L1 binding compound can constitute about 30% or more by weight of a composition containing one or more multivalent PD-L1 binding compounds. Polypeptides may be purified by methods including, but not limited to, affinity chromatography and immunosorbent affinity column. For example, a purified nucleic acid encoding an amino acid chain that can be used to generate a multivalent PD-L1 binding compound described herein can constitute about 30% or more by weight of a composition containing one or more amino acid chains that can be used to generate a multivalent PD-L1 binding compound described herein. Nucleic acid may be purified by methods including, but not limited to, phenol-chloroform extraction and column purification (e.g., mini-column purification).

Alternatively, the invention also provides multivalent PD-1 binding compounds that include two or more amino acid segments that can bind PD-1 (e.g., PD-L1 polypeptides and/or fragments thereof) as well as methods for making and using multivalent PD-1 binding compounds that include two or more amino acid segments that can bind PD-1 (e.g., PD-L1 polypeptides and/or fragments thereof). In some cases, a multivalent PD-1 binding compound can include two or more amino acid segments that can bind PD-1 (e.g., PD-L1 polypeptides and/or fragments thereof). For example, a multivalent PD-1 binding compound that includes two or more PD-L1 polypeptides (and/or fragments thereof having the ability to bind PD-1) can bind two or more PD-1 polypeptides. In some cases, a multivalent PD-1 binding compound can include a single amino acid chain that includes two or more amino acid segments that can bind PD-1.

Also provided herein are methods and materials for treating cancer, for example, administering a composition containing one or more multivalent PD-L1 binding compounds described herein. The one or more multivalent PD-L1 binding compounds may be administered to a subject in combination with therapeutic polypeptides. In an embodiment a multivalent PD-L1 binding compound comprises a therapeutic polypeptide which is administered to a subject for treating cancer. In another embodiment a multivalent PD-L1 binding compound is co-administered with an Ad expressing a therapeutic polypeptide to a subject for treating cancer.

The invention encompasses virus particles wherein two or more viral cost polypeptides comprise one or more amino acid chains that include one or more PD-1 polypeptides. The virus particle may be a recombinant virus particle comprising PD-1 polypeptides, including PD-1 fusion proteins, in the capsid protein of the virus particle. The virus particle may be a virus particle which has been coated with PD-1 polypeptides, for example, PD-1 fusion proteins.

In an embodiment, where the PD-L1 binding compound comprises a recombinant virus, the virus is a recombinant Ad, for example, Ad strain Ad657 or Ad strain Ad6/57/6, and variants thereof. The recombinant Ad may be modified to be a conditionally replicating Ad (CRAd). Such recombinant Ads are described in U.S. application Ser. No. 16/690,733, the disclosure of which is incorporated herein in its entirety by reference as if fully set forth herein.

In an embodiment, the invention encompasses a recombinant, conditionally replicating Ad virus particle which comprises one or more amino acid chains that each include one or two or more PD-1 polypeptides, or nucleic acid encoding amino acid chains that can be used to generate multivalent PD-L1 binding compounds.

In some cases, a recombinant Ad described herein (e.g., a recombinant Ad having oncolytic anti-cancer activity such as a recombinant Ad657) can include an Ad genome containing one or more nucleic acid deletions. A nucleic acid deletion can be a full deletion (e.g., deletion of a nucleic acid encoding a polypeptide) or a partial deletion (e.g., deletion of one or more nucleotides within a nucleic acid encoding a polypeptide). A nucleic acid deletion can reduce or eliminate transcription and translation of a polypeptide encoded by the deleted nucleic acid. In some cases, a nucleic acid encoding a polypeptide associated with production of infectious progeny can be deleted. Examples of nucleic acids that can be deleted and/or modified in a recombinant Ad described herein may encode E1 (e.g., E1A and E1B), E2, E3, E4, pIIIA, fiber, E1B, and include viral enhancers and promoters. For example, a recombinant Ad described herein (e.g., a recombinant Ad having oncolytic anti-cancer activity such as a recombinant Ad657) can include an Ad genome containing a deletion of one or more nucleotides within a nucleic acid encoding an E1 polypeptide. In some cases, a recombinant Ad described herein can include one or more substitutions in a nucleic acid encoding an E1 polypeptide.

In particular embodiments, a recombinant Ad described herein is modified to comprise a probasin promoter comprising, for example, a nucleic acid of SEQ ID NO:41, is modified to comprise a dl1101 deletion in a nucleic acid encoding an E polypeptide; a recombinant Ad described herein is modified to comprise a dl1107 deletion in a nucleic acid encoding an E1 polypeptide; a recombinant Ad described herein is modified to comprise a dl1101 deletion and a dl1107 deletion. The dl1101 modification to E1a prevents binding to p300 and to make virus susceptible to interferon (INF) repressions. The dl1107 mutation in E1a prevents its binding to pRB to block virus replication in cells with intact pRB pathways. See FIG. 10 for N-terminal amino acid sequences of the E1A polypeptide, for example, wild-type Ad E1A, and CRAd-657-dl1101, CRAd-657-dl107 and CRAd-657-dl1101/1107 variants.

Schematic of mutations in Ad6, Ad657 and variants thereof involving mutations in the E1 protein to convert the virus to a conditionally-replicating Ad (CRAd) is shown in FIG. 9 and FIG. 10. These include dl1101 and/or the dl1107 that block binding to p300 and pRB, respectively.

FIG. 10 shows the N-terminal amino acid sequences of E1A in a wild-type Ad, as well as Ad variants E1A dl1101, E1A dl1107 and E1A dl1101/1107.

Also shown is the replacement of the Ad E1 promoter with the prostate-specific promoter probasin-E1 DNA sequence (SEQ ID NO:41) to generate the CRAd, Ad-PB (FIG. 9). The probasin promoter is androgen dependent, so will work in androgen-sensitive tumors like LNCaP, but not in androgen-resistant tumors like DU145.

The replication competent Ads, as well as the CRAds, of the invention are genetically modified by methods known to those skilled in the art to express one or more therapeutic polypeptides. The therapeutic polypeptides may be immune stimulatory polypeptides, for example, CD40L, 4-1BBL, OX40, GM-CSF, and combinations thereof.

Moreover, in an embodiment, the replication competent Ads, as well as the CRAds, of the invention are genetically modified by methods known to those skilled in the art to express both PD-1 polypeptides and one or more therapeutic polypeptides as fusion proteins.

The replication competent Ads, as well as the CRAds, of the invention may be genetically modified by methods known to those skilled in the art to comprise modified fiber/knob capsid proteins. The Ad fiber protein is a complex of three apparently identical subunits which mediates the initial attachment step. The native Ad6 fiber protein (SEQ ID NO:35) binds CAR.

In a further aspect of the invention, fiber-modified recombinant Ads having different fiber proteins or modifications in the fiber/knob proteins which are not native to the parental Ad were generated. Recombinant Ads, including CRAds, comprising capsid proteins from different Ad strains and heterologous fiber/knob proteins were generated, for example, recombinant Ads comprising a heterologous Ad35 fiber polypeptide or Chimpanzee C68 fiber polypeptide, +/−a K7 peptide.

A chimeric Ad, AdF35 fiber chimera, has the amino acid sequence of SEQ ID NO:36 and is shorter than Ad5 and Ad6 fiber proteins and retargets virus to CD46.

A fiber-modified recombinant Ad, comprising K7 Fiber having the sequence of SEQ ID NO:37, targets virus to heparin sulfate proteoglycans and negative charges on cells.

A recombinant, chimeric Ad, 6/FC68 Fiber comprising the sequence of SEQ ID NO:38, is a chimeric Ad having a fiber protein from chimpanzee adenovirus C68. The fiber protein is shorter than Ad5 or Ad6 fiber proteins and binds CAR.

A recombinant, chimeric Ad, 6/FC68-K7 Fiber comprising the sequence of SEQ ID NO:39, is a chimeric Ad having a fiber protein from chimpanzee adenovirus C68. The fiber protein is shorter than Ad5 or Ad6 fiber proteins. The 6/FC68-K7 Fiber binds CAR and is retargeted to heparin sulfate and negative charges.

A recombinant, chimeric Ad, 6FC68-HI-K7 Fiber comprising the sequence of SEQ ID NO:40, is a chimeric Ad having a fiber protein from chimpanzee adenovirus C68. The fiber protein is shorter than Ad5 or Ad fiber proteins. The 6/FC68-HI-K7 Fiber binds CAR and is retargeted to heparin sulfate and negative charges.

In some cases, a recombinant Ad described herein (e.g., a recombinant Ad having oncolytic anti-cancer activity such as a recombinant Ad657) can include an Ad genome containing one or more nucleic acid insertions. For example, a nucleic acid insertion can include a nucleic acid encoding a polypeptide, for example a therapeutic polypeptide. A nucleic acid can be inserted into any appropriate location within a genome of a recombinant Ad described herein. In some cases, a nucleic acid encoding a polypeptide can be inserted into a HVR (e.g., HVR 5 loop) of a genome of a recombinant Ad described herein. For example, when a nucleic acid encoding a polypeptide is inserted into a HVR of a genome of a recombinant Ad described herein, the nucleic acid encoding a polypeptide can express one or more polypeptides, and the expressed polypeptide(s) can be incorporated into the capsid of the recombinant Ad. In cases where a nucleic acid encoding a polypeptide is inserted into a HVR region of a genome of a recombinant Ad described herein, the recombinant Ad can present from about 1 to about 720 polypeptides encoded by the inserted nucleic acid on its surface. A nucleic acid insertion can be nucleic acid encoding any appropriate polypeptide. In some cases, a nucleic acid insertion can encode a therapeutic polypeptide, a polypeptide antigen or a cytokine.

In general. Ads may be modified to include CRAd modifications described herein.

In an embodiment, a recombinant Ad is a conditionally replicating Ad with a dl1101 modification to E1a, which prevents binding to p300 and makes the virus susceptible to IFN repression, and a dl1107 mutation in E1a to prevent its binding to pRB to block virus replication in cells with intact pRB pathways, and an E3A deletion. The CRAd expresses human PD-1 fused to human immunoglobulin.

In an embodiment, a recombinant Ad (for example Ad657) is a conditionally replicating Ad with a dl1101 modification to E1a, which prevents binding to p300 and makes virus susceptible to IFN repression, and an E3A deletion. The CRAd expresses human PD-1 fused to human Factor X (GLA) on the surface of the virus particle, wherein the CRAd is retargeted to cells expressing PD-L1 on the surface of the cell.

In an embodiment, a recombinant Ad is a conditionally replicating Ad (for example Ad657) with a dl1101 modification to E1a, which prevents binding to p300 and makes virus susceptible to IFN repression, and a dl1107 mutation in E1a to prevent its binding to pRB to block virus replication in cells with intact pRB pathways, and an E3A deletion. The CRAd expresses human PD-1 fused to human Factor X (GLA) on the surface of the virus particle, wherein the CRAd is retargeted to cells expressing PD-L1 on the cell surface.

The virus particles having PD-1 polypeptides bound to the surface of the virus particle can be used for treating a mammal having cancer (e.g., a cancer including one or more PD-L1 positive cancer cells). The virus particles may be administered to a subject in an amount effective for the treatment of cancer and, optionally, may be administered in combination with cancer therapies, including immunotherapies and chemotherapeutic agents.

In an aspect of the invention, a composition containing one or more multivalent PD-L1 binding compounds or nucleic acid encoding an amino acid chain that can be used to generate multivalent PD-L1 binding compounds described herein and, optionally, one or more cancer therapies, can be administered to a mammal having cancer to treat the mammal. A multivalent PD-L1 binding compound described herein can bind to PD-L1 on PD-L1 positive cancer cells. Binding of a PD-1 polypeptides can neutralize PD-L1 function, and can thereby prevent PD-L1 positive cells (e.g., PD-L1 positive cancer cells) from escaping the immune system and/or can allow anti-cancer agents (e.g., cancer immunotherapies) to more effectively target PD-L1 positive cells. In cases where nucleic acid encoding a multivalent PD-L1 binding compound described herein is an oncolytic Ad vector encoding a multivalent PD-L1 binding compound described herein, the oncolytic Ad can infect cell and can drive T cell responses directed to the infected cell. An oncolytic Ad can infect any appropriate type of cell. In some cases, an oncolytic Ad can infect a PD-L1 positive cell (e.g., a PD-L1 positive cancer cell). In some cases, an oncolytic Ad can infect non-dividing cells (e.g., kidney cells).

In some cases, a composition comprising or consisting essentially of one or more PD-L1 binding compounds described herein can be used for treating a mammal having cancer (e.g., a cancer including one or more PD-L1 positive cancer cells). For example, a composition containing one or more multivalent PD-L1 binding compounds and, optionally, one or more cancer therapeutics, can be administered to a mammal having cancer to treat the mammal.

Alternatively, the methods and materials described herein can be used for treating other diseases or disorders associated with PD-L1 positive cells. In some cases, a composition containing one or more PD-L1 binding compounds described herein can be used for treating a mammal having an infectious disease (e.g., an infectious disease including one or more PD-L1 positive macrophages such as cancer infiltrating macrophages). Examples of infectious diseases that can include one or more PD-L1 positive cells include, without limitation, HIV, hepatitis, and malaria. In some cases, a composition containing one or more PD-L1 binding compounds described herein can be used for treating a mammal having an autoimmune disease (e.g., an autoimmune disease including one or more PD-L1 positive macrophages such as cancer infiltrating macrophages).

Any appropriate mammal having cancer can be treated as described herein. For example, humans and other primates such as monkeys having cancer can be treated with a composition containing one or more PD-L1 binding compounds described herein and, optionally, can be treated in combination with one or more cancer treatments to reduce the severity of the cancer, to reduce a symptom of the cancer, and/or to reduce the number of cancer cells present within the mammal within the human or other primate. In some cases, dogs, cats, horses, cows, pigs, sheep, mice, and rats having cancer can be treated with a composition containing one or more multivalent PD-L1 binding compounds described herein, viruses comprising PD-L1 binding compounds, or nucleic acid encoding an amino acid chain that can be used to generate multivalent PD-L1 binding compounds described herein, and, optionally, can be treated with one or more cancer treatments as described herein.

When treating a mammal (e.g., a human) having a cancer as described herein, the cancer can be any appropriate cancer. A cancer can include one or more PD-L1 positive cancer cells. A cancer can include one or more solid tumors. A cancer can be a blood cancer. Examples of cancers that can be treated as described herein include, without limitation, breast cancer, colorectal cancer, kidney cancer, lung cancer (e.g., non-small cell lung cancer), ovarian cancer, melanoma, brain cancer, sarcoma, prostate cancer, pancreatic cancer, head and neck cancer, liver cancer, retinoblastoma, lymphoma, and leukemia.

In some cases, a mammal can be identified as having a cancer (e.g., a cancer including one or more PD-L1 positive cancer cells). Any appropriate method can be used to identify a mammal having cancer. For example, imaging techniques and biopsy techniques can be used to identify mammals (e.g., humans) having cancer.

Once identified as having a cancer, a mammal can be administered a composition containing one or more PD-L1 binding compounds described herein, and, optionally, can be treated with one or more cancer therapeutics and/or cancer treatments. The one or more cancer therapeutics can include any appropriate cancer treatments. In some cases, a cancer treatment can include surgery. In some cases, a cancer treatment can include radiation therapy. In some cases, a cancer treatment can include administration of a pharmacotherapy such as a chemotherapy, hormone therapy, targeted therapy, and/or cytotoxic therapy. Examples of cancer treatments include, without limitation, administration of one or more receptor tyrosine kinase inhibitors (e.g., erlotinib), administration of one or more PD1/PD-L1 inhibitors (e.g., nivolumab, pembrolizumab, atezolizumab, avelumab, cemiplimab, and durvalumab), administration of one or more immunotherapies such as immunotherapies that can target PD1/PD-L1 (e.g., nivolumab, pembrolizumab, atezolizumab, avelumab, cemiplimab, durvalumab, alemtuzumab, ipilimumab, ofatumumab, and rituximab), administration of one or more antibodies which target GITR, administration of one or more platinum compounds (e.g., a cisplatin or carboplatin), administration of one or more taxanes (e.g., paclitaxel, docetaxel, or an albumin bound paclitaxel such as nab-paclitaxel), administration of altretamine, administration of capecitabine, administration of cyclophosphamide, administration of etoposide (vp-16), administration of gemcitabine, administration of ifosfamide, administration of irinotecan (cpt-11), administration of liposomal doxorubicin, administration of melphalan, administration of pemetrexed, administration of topotecan, administration of vinorelbine, administration of one or more luteinizing-hormone-releasing hormone (LHRH) agonists (such as goserelin and leuprolide), administration of one or more anti-estrogen therapies (such as tamoxifen), administration of one or more aromatase inhibitors (such as letrozole, anastrozole, and exemestane), administration of one or more angiogenesis inhibitors (such as bevacizumab), administration of one or more poly(ADP)-ribose polymerase (PARP) inhibitors (such as olaparib, rucaparib, and niraparib), administration of external beam radiation therapy, administration of brachytherapy, administration of radioactive phosphorus, and administration of any combinations thereof. In cases where a mammal having cancer is treated with a composition containing one or more multivalent PD-L1 binding compounds or nucleic acid encoding an amino acid chain that can be used to generate multivalent PD-L1 binding compounds described herein, and is treated with one or more cancer treatments, the composition containing one or more cancer treatments can be administered at the same time or independently. For example, the composition containing one or more multivalent PD-L1 binding compounds or nucleic acid encoding an amino acid chain that can be used to generate multivalent PD-L1 binding compounds described herein can be administered first, and the one or more cancer treatments administered second, or vice versa.

In some cases, a composition comprising one or more PD-L1 binding compounds described herein can be formulated into a pharmaceutically acceptable composition for administration to a mammal having cancer. For example, a therapeutically effective amount of one or more multivalent PD-L1 binding compounds or nucleic acid encoding an amino acid chain that can be used to generate multivalent PD-L1 binding compounds described herein can be formulated together with one or more pharmaceutically acceptable carriers (additives) and/or diluents. The pharmaceutical composition may further comprise a therapeutic polypeptide and/or a recombinant virus which is genetically modified to express a therapeutic polypeptide. A pharmaceutical composition comprising, or consisting essentially of a multivalent PD-L1 binding compound, and optionally a therapeutic polypeptide, can be formulated for administration in solid or liquid form including, without limitation, sterile solutions, suspensions, sustained-release formulations, tablets, capsules, pills, powders, nano-particles, and granules. Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition comprising or consisting essentially of one or more multivalent PD-L1 binding compounds as described herein, and optionally a therapeutic polypeptide, are formulated for oral or parenteral (including subcutaneous, intramuscular, intravenous, intratumoral, and intradermal) administration.

When being administered orally, a pharmaceutical composition comprising one or more PD-L1 binding compounds or nucleic acid encoding an amino acid chain that can be used to generate multivalent PD-L1 binding compounds described herein can be in the form of a pill, tablet, or capsule.

Compositions suitable for parenteral administration include aqueous and non-aqueous sterile injection solutions that can contain anti-oxidants, buffers, bacteriostatic agents, and solutes which render the formulation isotonic with the blood of the intended recipient; and aqueous and non-aqueous sterile suspensions which may include suspending agents and thickening agents. The formulations can be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules, and tablets. Such injection solutions can be in the form, for example, of a sterile injectable aqueous or oleaginous suspension. This suspension may be formulated using, for example, suitable dispersing or wetting agents (such as, for example, Tween 80) and suspending agents. The sterile injectable preparation can be a sterile injectable solution or suspension in a non-toxic parenterally-acceptable diluent or solvent, for example, as a solution in 1, 3-butanediol. Examples of acceptable vehicles and solvents that can be used include, without limitation, mannitol, water, Ringer's solution, and isotonic sodium chloride solution. In addition, sterile, fixed oils can be used as a solvent or suspending medium. In some cases, a bland fixed oil can be used such as synthetic mono- or di-glycerides. Fatty acids, such as oleic acid and its glyceride derivatives can be used in the preparation of injectables, as can natural pharmaceutically-acceptable oils, such as olive oil or castor oil, including those in their polyoxyethylated versions. In some cases, these oil solutions or suspensions can contain a long-chain alcohol diluent or dispersant.

Specific embodiments disclosed herein may be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s).

In some cases, a pharmaceutically acceptable composition comprising one or more PD-L1 binding compounds described herein can be administered locally or systemically. For example, a composition containing a compound that inhibits the function of an intracellular PD-L1 domain can be administered locally by injection into or near a cancer (e.g., a tumor) in a mammal (e.g., a human). For example, a composition containing a compound that inhibits the function of an intracellular PD-L1 domain can be administered systemically by oral administration or by injection (e.g., subcutaneous, intramuscular, intravenous, intratumoral, and intradermal injection) to a mammal (e.g., a human).

Effective doses can vary depending on the severity of the cancer, the route of administration, the age and general health condition of the subject, excipient usage, the possibility of co-usage with other therapeutic treatments such as use of other agents, and the judgment of the treating physician.

An effective amount of a composition containing one or more PD-L1 binding compounds described herein can be any amount that can reduce the severity of the cancer, to reduce a symptom of the cancer, and/or to reduce the number of cancer cells present within the mammal without producing significant toxicity to the mammal. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., cancer) may require an increase or decrease in the actual effective amount administered.

The frequency of administration can be any frequency that sensitizes cancer cells in the mammal to one or more cancer treatments (e.g., one or more cancer immunotherapies) without producing significant toxicity to the mammal. For example, the frequency of administration can be from about once a week to about three times a day, or from about twice a month to about six times a day, or from about twice a week to about once a day. The frequency of administration can remain constant or can be variable during the duration of treatment. A course of treatment with a composition containing one or more PD-L1 binding compounds described herein can include rest periods. For example, a composition containing one or more multivalent PD-L1 binding compounds or nucleic acid encoding an amino acid chain that can be used to generate multivalent PD-L1 binding compounds described herein can be administered daily over a two-week period followed by a two-week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., cancer) may require an increase or decrease in administration frequency.

An effective duration for administering a composition containing one or more PD-L1 binding compounds described herein can be any duration that can reduce the severity of the cancer, to reduce a symptom of the cancer, and/or to reduce the number of cancer cells present within the mammal without producing significant toxicity to the mammal. Thus, the effective duration can vary from several days to several weeks, months, or years. In general, the effective duration for the treatment of cancer can range in duration from six months to one year. Multiple factors can influence the actual effective duration used for a particular treatment. For example, an effective duration can vary with the frequency of administration, effective amount, use of multiple treatment agents, route of administration, and severity of the condition being treated.

In certain instances, a course of treatment and the severity of one or more symptoms related to the condition being treated (e.g., cancer) can be monitored. Any appropriate method can be used to determine whether or not the sensitivity of cancer cells in the mammal to one or more cancer treatments (e.g., one or more cancer immunotherapies) is increased. For example, the responsiveness of cancer (e.g., based on the size and/or number of tumors) can be assessed using office imaging techniques at different time points.

The invention will be further described in the following examples, which do not limit the scope of the invention described in the claims.

EXAMPLES

Example 1. Construction of Recombinant Adenoviruses: Insertion of Individual HVRs from Different Ad Serotypes with the Insertion of Cell Targeting/Detargeting Peptides or Novel Amino Acids Recombinant adenoviruses were constructed by recombinant DNA technology utilizing methods known to those skilled in the art. A recombinant Ad (Ad657) is derived from a first Ad strain Ad6 (e.g., can include a genome of a first Ad strain) and may include capsid hexon HVRs from a second Ad strain, Ad57, see FIG. 8. These embodiments have been applied generally in the context of Ads which combine different capsid hexon HVRs from different Ads (i.e., shuffling HVRs). FIG. 7 shows an alignment of Ad5, Ad6, and Ad57 showing variation in hexon regions. For example, HVR1 of Ad strain Ad with HVRs 2-7 of Ad strain Ad57 or HVR1 and 7 of Ad strain Ad6 with HVRs 2-6 of Ad strain Ad57. In a further embodiment, a Ad6/56/6 virus has HVRs 1 and 7 from Ad strain Ad6 and HVRs 2-6 from Ad strain Ad57.

In an aspect of the invention, chimeric Ads were generated which have an Ad6 HVR1 and Ad57 HVRs 2-7, the chimera, referred to as Ad6/57 HVR chimera, comprises the hexon having the amino acid sequence of SEQ ID NO:28.

In yet another aspect of the invention, chimeric Ads were generated which have Ad6 HVR1 and 7 and Ad57 HVRs 2-6, the chimera, referred to as Ad6/57/6 HVR chimera, comprises the hexon having the amino acid sequence of SEQ ID NO:29.

To obtain recombinant Ad strain Ad657, a nucleic acid encoding Ad57 HVRs 1-7 was synthesized and inserted into the Ad6 hexon in a plasmid with an FRT-Zeocin®-FRT cassette between pVI and hexon. This was recombined into various pAd6 plasmids to generate Ad657 and variants thereof. The amino acid sequence of the Ad657 hexon is set forth in SEQ ID NO:30.

With respect to variants of Ad657, the Ad57 HVR sequence was synthesized with HVR1 modified with a cysteine, flexibility amino acids, and restriction sites to allow insertions of other peptides. This was inserted into the Ad6 hexon in a plasmid with an FRT-Zeocin®-FRT cassette between pVI and hexon. This was recombined into various pAd6 plasmids to generate Ad657 variants with cysteine in HVR1, the variant referred to as Ad657-HVR1-XXA comprises the hexon having the amino acid sequence of SEQ ID NO:42.

With respect to variants of Ad657, the Ad57 HVR sequence was synthesized with HVR5 modified with a cysteine, flexibility amino acids, and restriction sites to allow insertions of other peptides. This was inserted into the Ad6 hexon in a plasmid with an FRT-Zeocin®-FRT cassette between pVI and hexon. This was recombined into various pAd6 plasmids to generate Ad657 variants with cysteine in HVR5, the variant referred to as Ad657-HVR5-XXA comprises the hexon having the amino acid sequence of SEQ ID NO:43.

With respect to variants of Ad657, the Ad57 HVR sequence was synthesized with HVR1 modified with a cysteine, flexibility amino acids, and restriction sites to allow insertions of other peptides. This was inserted into the Ad6 hexon in a plasmid with an FRT-Zeocin®-FRT cassette between pVI and hexon. This was recombined into various pAd6 plasmids to generate Ad657 variants without cysteine in HVR1, but with restriction sites allowing peptide insertions into HVR1, the variant referred to as Ad657-HVR1-XA comprises the hexon having the amino acid sequence of SEQ ID NO:44.

With respect to variants of Ad657, the Ad57 HVR sequence was synthesized with HVR5 modified with a cysteine, flexibility amino acids, and restriction sites to allow insertions of other peptides. This was inserted into the Ad6 hexon in a plasmid with an FRT-Zeocin®-FRT cassette between pVI and hexon. This was recombined into various pAd6 plasmids to generate Ad657 variants without cysteine in HVR5, but with restriction sites allowing peptide insertions into HVR5, the variant referred to as Ad657-HVR5-XA comprises the hexon having the amino acid sequence of SEQ ID NO:45.

With respect to variants of Ad657, the Ad657 HVR1-XA sequence was modified by insertion of a biotin acceptor peptide into HVR1. This was recombined into various pAd6 plasmids to generate Ad657 variants a BAP in HVR1, the variant referred to as Ad657-HVR1-PSTCD comprises the hexon having the amino acid sequence of SEQ ID NO:46.

The insertion of a biotin acceptor peptide detargets the virus variants from the liver, allows the virus to be retargeted with avidin or streptavidin and biotinylated ligands, and allows the virus to be purified on monomeric avidin or streptavidin columns.

With respect to variants of Ad657, the Ad657 HVR1-XA sequence was modified by insertion of a biotin acceptor peptide (BAP) into HVR1. This was recombined into various pAd6 plasmids to generate Ad657 variants a BAP in HVR1, the variant referred to as Ad657-HVR5-PSTCD comprises the hexon having the amino acid sequence of SEQ ID NO:47.

With respect to variants of Ad657, the Ad657 HVR5-XA sequence was modified by insertion of a synthetic V1/V2 loop from HIV envelope into HVR5, the variant referred to as Ad657-HVR5-V1/V2 comprises the hexon having the amino acid sequence of SEQ ID NO:48.

The insertion of a synthetic V1/V2 loop from HIV envelope allows display of this antigen to serve as a vaccine as well as retargeting by binding to proteins that interact with HIV envelope.

With respect to variants of Ad657, the Ad657 HVR5-XA sequence was modified by insertion of synthetic peptides from human papilloma virus (HPV) into HVR5, the variant referred to as Ad657-HVR5-HPV comprises the hexon having the amino acid sequence of SEQ ID NO:49.

The insertion of synthetic peptides from human papilloma virus allows display of HPV peptides as antigens for vaccine purposes as well as for retargeting by binding to proteins that interact with HPV peptides.

In another aspect of the invention, chimeric Ads were generated which have an Ad6 HVR1 and Ad57 HVRs 2-7, the chimera, referred to as Ad6/57 HVR chimera, comprises the hexon having the amino acid sequence of SEQ ID NO:50.

In yet another aspect of the invention, chimeric Ads were generated which have Ad6 HVR1 and 7 and Ad57 HVRs 2-6, the chimera, referred to as Ad6/57/6 HVR chimera, comprises the hexon having the amino acid sequence of SEQ ID NO:51.

The plasmid maps of FIGS. 16-18 show the combination of the insertion of individual HVRs from different Ad serotypes with the insertion of cell targeting/detargeting peptides, therapeutic polypeptides, or novel amino acids such as cysteine into the hexon for targeted chemical modification and shielding.

In certain embodiments, cell binding peptides are inserted into HVR 1 or HVR 5, which embodiments serve as examples of inserting these and other peptides in any of the HVRs of an Ad.

Example 2. Targeted Chemical Conjugation of Cysteine-Modified Hexon-Modified Ad657HVR5C FIG. 13 is a depiction of Ad variants showing the combination of insertion of individual HVRs from different Ad serotypes with the insertion of novel amino acids such as cysteine into the hexon for targeted chemical modification and shielding.

This example demonstrates the ability to target polymer and other chemical modifications to cysteines inserted into an Ad hexon (FIG. 15). Untargeted PEG inactivates virus infection whereas cysteine-targeting PEGylation retains virus functions.

In an aspect of the invention, the use of polymers or inserted peptides/proteins to detarget, retarget, and shield from antibodies, proteins, cells is contemplated. FIGS. 12 and 14 depict sites of Ad HVRs which may be modified, for example, by PEGylation or "BAPylation". Another example shows insertion of a biotin acceptor peptide (BAP) is inserted into these HVRs allowing for vector retargeting with avidin or streptavidin and biotinylated ligands or with avidin- or streptavidin fusion proteins. BAP insertion also allows the viruses to be purified on monomeric avidin or streptavidin columns for vector production. Likewise, Ad57-HVR1-XXA and XA shows the example of inserting a cysteine into this site to allow targeted chemical modification with maleimide or other cysteine-reactive agents.

In an embodiment, the different Ad serotypes and/or variants comprise polymer shielding to allow multi dosing of Ad6 and Ad657 variants. An exemplary therapeutic cycle where Ad and Ad657 can be used for multiple rounds of treatment by serotype-switching in combination with covalent polymer conjugation is shown (FIG. 13).

Ad657-HVR1C expressing GFPLuciferase was produced from cells and purified on CsCl gradients. The virus was covalently modified with 5 kDa polyethylene glycol (PEG). The virus was treated with either NHS-PEG that reacts randomly with amines/lysines on viral proteins or with maleimide PEG that reacts specifically with cysteine that was inserted into HVR1 using the XXA shuttle plasmid. These unmodified or modified viruses were then purified by a final CsCl spin followed by desalting. The indicated virus were separated on SDS-PAGE gels, stained with Sypro-Ruby, and visualized by imaging (FIG. 14). This shows that NHS-PEGylation randomly modifies many viral proteins as demonstrated by increases in the apparent mass of the proteins (indicated by arrows). In contrast, targeted maleimide PEG reaction with the cysteine in HVR1 modifies only hexon and does not damage other viral capsomer proteins. The effects of PEGylation on virus function is evaluated.

Example 3. Conditionally Replicating Ads (CRAds)

Schematic of mutations in Ad6, Ad657 and variants thereof involving mutations in the E protein to convert the virus to a conditionally-replicating Ad (CRAd) is shown in FIG. 9, FIG. 10 and FIG. 11. These include dl1101 and/or the dl1107 that block binding to p300 and pRB, respectively.

FIG. 10 shows the N-terminal amino acid sequences of E1A in a wild-type Ad, as well as Ad variants E1A dl1101, E1A dl1107 and EA dl1101/1107.

Also shown is the replacement of the Ad E1 promoter with the prostate-specific promoter probasin and the E1 DNA sequence of SEQ ID NO:31 to generate the CRAd, Ad-PB (FIG. 9). The probasin promoter is androgen dependent, so will work in androgen-sensitive tumors like LNCaP, but not in androgen-resistant tumors like DU145.

In an embodiment, a conditionally replicative Ad657 virus having a dl1101 modification to E1, and a dl1107 mutation in E1a, and an E3A deletion, is constructed to express human PD-1 fused to human immunoglobulin as a PD-L1 decoy protein. The virus also expresses GFPLuciferase from a CMV promoter. Such conditionally replicative Ad657 virus variant is referred to as CrAd6dl1101/1107DE3ADP-hPD-1-Ig-GL.

Example 4. Retargeted and Detargeted Recombinant Adenovirus

In vitro, Ads bind and enter cells through the combined interactions of its fiber and penton base proteins with cell surface receptors. The trimeric fiber binds the coxsackie-adenovirus receptor (CAR), and cells that lack CAR are relatively resistant to infection unless they also express $\alpha_v$ integrins that can be bound by an RGD motif on the penton base.

The Ad fiber protein is a complex of three apparently identical subunits which mediates the initial attachment step. The native Ad6 fiber protein comprises the amino acid sequence set forth in SEQ ID NO:35 and binds CAR.

In a further aspect of the invention, fiber-modified recombinant Ads having different fiber proteins which are not native to the parental Ad were generated. Recombinant Ads, including CRAds, comprising capsid proteins from different Ad strains were generated, for example, recombinant Ads comprising a heterologous Ad35 fiber polypeptide or Chimpanzee C68 fiber polypeptide, +/−a K7 peptide.

A chimeric Ad, AdF35 fiber chimera, has the amino acid sequence of SEQ ID NO:36 and is shorter than Ad5 and Ad6 fiber proteins and retargets virus to CD46.

A fiber-modified recombinant Ad, comprising K7 Fiber having the sequence of SEQ ID NO:37, targets virus to heparin sulfate proteoglycans and negative charges on cells.

A recombinant, chimeric Ad, 6FC68 Fiber comprising the sequence of SEQ ID NO:38, is a chimeric Ad having a fiber protein from chimpanzee adenovirus C68. The fiber protein is shorter than Ad5 or Ad6 fiber proteins and binds CAR.

A recombinant, chimeric Ad, 6FC68-K7 Fiber comprising the sequence of SEQ ID NO:39, is a chimeric Ad having a fiber protein from chimpanzee adenovirus C68. The fiber protein is shorter than Ad5 or Ad6 fiber proteins. The 6/FC68-K7 Fiber binds CAR and is retargeted to heparin sulfate and negative charges.

A recombinant, chimeric Ad, 6/FC68-HI-K7 Fiber comprising the sequence of SEQ ID NO:40, is a chimeric Ad having a fiber protein from chimpanzee adenovirus C68. The fiber protein is shorter than Ad5 or Ad6 fiber proteins. The 6/FC68-HI-K7 Fiber binds CAR and is retargeted to heparin sulfate and negative charges.

Blood factor X (FX) binds with nanomolar affinity to the hexons of species C adenovirus and, consequently, enables species C adenovirus to efficiently transduce liver hepatocytes after IV injection.

The following CRAd viruses are constructed which express human Factor X (GLA) fused to human PD-1.

Wild-type and high affinity mouse and human PD-1 domains were fused to the N- or C-termini of human FX GLA-EGF domain and their expression was driven by either RSV or CMV promoter. In some cases these fusion protein expression cassettes were inserted into the E3 domain of the indicated viruses. In others, they were inserted between the fiber and E4 genes of the viruses.

Conditionally replicative Ad657 with a dl101 modification to E1a prevent its binding to p300 and to become susceptible to IFN, an E3A deletion, with an RSV expression cassette inserted into the E3 deletion. This virus expresses human Factor X (GLA) fused to human PD-1 and an adenovirus retargeting protein to PD-L1+ cells (i.e., CrAd657d1101DE3ADP*hPD1-GLA-GL-L).

Conditionally replicative Ad657 with a dl1101 modification to E1a prevent its binding to p300 and to make virus susceptible to IFN repression and a dl1107 mutation in E1a to prevent its binding to pRB to block virus replication in cells with intact pRB pathways, with deleted E3, and comprises an RSV expression cassette inserted into the E3 deletion. This virus expresses human Factor X (GLA) fused to human PD-1 (i.e., CrAd657*1101/1107DE3BSTRSVhPD1-GLA*IgIZI). During viral replication, the PD-1 will be expressed in a cell as a monomer which is capable of binding PD-L1 when released from the cell. The PD-1 can also be bound to the surface of an Ad to retarget the Ad to PD-L1-expressing cells.

Conditionally replicative Ad6/57/6 with a dl1107 mutation in E1a, and an E3A deletion with an RSV expression cassette inserted into the E3 deletion, is constructed to express human PD-1 fused to human immunoglobulin as a PD-L1 decoy protein (i.e., pAd/57/6-dl107-ΔE3-RSV-hPD-1-HA-Ig-I). See FIG. 16.

The fusion protein was purified from cells infected with pAd6/57/6-dl1107-DE3-RSV-hPD-1-HA-g-Ion a protein A column. This protein was titrated along side positive control anti-PD-1 monoclonal antibody in the PD-1/PD-L1 Blockade Assay from Promega (Madison, Wis., USA). The high affinity human hPD-1-HA-Ig fusion protein inhibits PD-L1. See FIG. 19.

Example 5. Construction of Recombinant Ads for Expression of PD-L1 Binding Compounds in Combination with Heterologous Polypeptides A conditionally replicative Ad virus (CRAd657 or CRAd 6/57/6) is modified to express PD-1 polypeptides in combination with one or more heterologous polypeptides (e.g., therapeutic polypeptides and/or targeting polypeptides). In one embodiment, the RSV-PD-1 fusion cassette is inserted into an E3 deletion of the virus and the therapeutic transgenes are inserted as CMV or MCMV or RSV expression cassettes in between fiber and E4 genes according to methods known to those skilled in the art. See FIG. 17 and FIG. 18.

Example 6. Tumor Growth Assessment of CRAd Expressing High Affinity Human hPD-1-HA-Ig Fusion Protein Alone or in Combination with Immune Therapy Payloads B16-CAR melanoma cells are injected subcutaneously in C57BL/6 mice and resulting tumors are injected with 3e11 viral particles of the multivalent PD-L1 binding compounds of the invention. CRAd+PD-L1 decoy is pAd6/57/6-dl1107-ΔE3-RSV-hPD-1-HA-Ig-I. CRAd+PD-L1 decoy+immune simulator are co-injected into tumors using pAd6/57/6-dl1107-ΔE3-RSV-hPD-1-HA-Ig-I and a second adenovirus expressing 4-1BBL. CRAd expressing high affinity human hPD-1-HA-Ig fusion protein delays tumor growth by itself or in combination with immune therapy payloads. See FIG. 20.

In an embodiment, the CRAd657 or CRAd6/57/6 is modified to express PD-1 polypeptides in combination with one or more therapeutic polypeptides. The therapeutic polypeptide may be selected from GM-CSF, 4-1BBL, CD40L and OX40, and combinations thereof. In one aspect, the PD-1 polypeptide is expressed with the therapeutic polypeptide as a fusion protein. In a further aspect, a RSV-PD-1 fusion cassette is inserted into an E3 deletion of the virus and the therapeutic transgenes are inserted as CMV or MCMV or RSV expression cassettes in between the virus fiber and E4 genes. See FIGS. 17 and 18.

Example 7. Construction of Multivalent PD-L1 Binding Compounds

Fusion proteins including a PD-1 polypeptide and either a scaffold polypeptide or a GLA domain of an FX polypeptide are generated from genes that are PCR cloned with mutations and fusion junctions from wild-type, mutant, or synthetic genes according to methods known to those skilled in the art. Fusion proteins are assembled by cloning in expression vectors, culturing under conditions which allow expression and assembly of proteins and, optionally, purifying the proteins from the cellular milieu.

The fusion proteins may be produced by plasmid transfection or infection of cells with vectors expressing PD-1 polypeptides and/or fragments thereof fused to a polypeptide that can bind to a viral coat polypeptide, followed by purification with PD-1 or a fusion partner on antibody columns or on PD-L1 columns or on biotin columns.

In an embodiment, Ads may be contacted with the purified PD-1 fusion proteins under conditions which allow for coating of the Ad surface with the fusion protein. For example, the GLA domain of an FX polypeptide binds to the surface of the Ad such that the PD-1 is exposed on the surface of the Ad to bind to PD-L1 on the surface of a cell. An adenovirus wherein the fusion partner is bound to the Ad surface and the PD-1 is free to bind PD-L1 on a cell, provides a multimeric PD-L1 binding compound.

In an embodiment, nucleic acids encoding the fusion proteins are inserted into plasmids or viral vectors or are inserted in mRNA production vectors and these are transfected or infected in vitro into cell cultures or infected in vivo in animals. Samples are assayed for protein expression with antibodies against PD-1 and/or fusion protein partners.

Nucleic acid (e.g., DNA, mRNA, and viral vectors) encoding the fusion proteins are delivered into normal or cancer-bearing animals and changes in peripheral blood cells, lymph node cells, spleen cell, and tumor cell populations are assessed by staining with CD3, CD4, CD8, PD-L1, PD-L1, and T cell activation markers.

Nucleic acid (e.g., DNA, mRNA) or viral vectors encoding the fusion proteins are delivered into cancer-bearing animals and effects on tumor size, metastases, dissemination, and survival were assessed.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A multivalent programmed death ligand 1 (PD-L1) binding compound comprising,
a recombinant Adenovirus (Ad) comprising capsid hexon polypeptides of an Adenovirus strain Ad6 and at least one capsid hexon hypervariable region (HVR) polypeptide from Adenovirus strain Ad57,
wherein the recombinant Ad comprises a plurality of amino acid chains on the surface of the recombinant Ad,
wherein each amino acid chain comprises at least one programmed cell death protein 1 (PD-1) polypeptide.

2. The PD-L1 binding compound of claim 1, wherein the capsid hexon polypeptides of the Adenovirus strain Ad6 comprise HVR polypeptides 1-7 from Adenovirus strain Ad57.

3. The PD-L1 binding compound of claim 1, wherein the capsid hexon polypeptides of the Adenovirus strain Ad6 comprise HVR polypeptides 2-7 from Adenovirus strain Ad57.

4. The PD-L1 binding compound of claim 1, wherein the recombinant Ad is a conditionally-replicating Adenovirus (CRAd) which has been modified in an E1A gene encoding an E1A polypeptide, wherein the CRAd exhibits amino acid substitutions in the E1A polypeptide relative to wild-type E1A polypeptide of an Ad strain.

5. The PD-L1 binding compound of claim 4, wherein the recombinant Ad is a conditionally-replicating Adenovirus (CRAd) wherein the N-terminal portion of the E1A polypeptide comprises the amino acid sequence set forth in SEQ ID NO:32, SEQ ID NO:33 or SEQ ID NO:34.

6. The PD-L1 binding compound of claim 1, wherein the PD-1 polypeptide is in the form of a fusion protein with a heterologous polypeptide.

7. The PD-L1 binding compound of claim 1, wherein the PD-1 polypeptide is a human PD-1 or a murine PD-1.

8. The PD-L1 binding compound of claim 1, wherein the PD-1 polypeptide comprises one or more amino acid changes for higher affinity interactions with human PD-L1 compared to a wild type human PD-1.

9. The PD-L1 binding compound of claim 1, wherein the PD-1 polypeptide is a fragment of a human PD-1 polypeptide which retains the ability to bind PD-L1, wherein the fragment of the human PD-1 polypeptide comprises one or more amino acid changes relative to a wild type PD-1, which changes cause an increased affinity for human PD-L1.

10. The PD-L1 binding compound of claim 6, wherein the PD-1 polypeptide is fused to a heterologous polypeptide which is a Vitamin K-dependent gamma-carboxyglutamic domain of a factor X single-chain antibody polypeptide (a GLA domain of an FX polypeptide).

11. A pharmaceutical composition comprising the multivalent PD-L1 binding compound of claim 1 and a pharmaceutically acceptable carrier.

12. A method of treating cancer in a subject in need thereof, comprising administering the multivalent PD-L1 binding compound of claim 1 to a subject identified as having a cancer selected from the group consisting of breast cancer, lung cancer, melanoma and renal cancer.

13. The method of treating cancer of claim 12, further comprising administering one or more cancer therapeutics to the subject in need thereof.

14. The method of treating cancer of claim 13, wherein the cancer therapeutic is an immunotherapy which targets PD-1/PD-L1 pathways.

15. The method of treating cancer of claim 14, wherein the immunotherapy is selected from the group consisting of nivolumab, pembrolizumab, atezolizumab, avelumab, cemiplimab, and durvalumab.

16. A method of treating a subject having a cancer comprising administering to the subject having cancer, a multivalent programmed death ligand 1 (PD-L1) binding compound comprising a recombinant Adenovirus (Ad) comprising capsid hexon polypeptides of an Adenovirus strain Ad6 and at least one capsid hexon hypervariable region (HVR) polypeptide from Adenovirus strain Ad57,
wherein the recombinant Ad comprises a plurality of amino acid chains on the surface of the recombinant Ad, and
wherein each amino acid chain comprises at east one programmed cell death protein 1 (PD-1) polypeptide,
wherein cancer cells of the cancer are positive for PD-L1 expression.

* * * * *

SEQUENCE LISTING

<160> NUMBER OF SEQ ID NOS: 54

<210> SEQ ID NO 1
<211> LENGTH: 465
<212> TYPE: PRT
<213> ORGANISM: Human Adenovirus 6

<400> SEQUENCE: 1

```
Ala Tyr Asn Ala Leu Ala Pro Lys Gly Ala Pro Asn Ser Cys Glu Trp
1               5                   10                  15

Glu Gln Asn Glu Thr Ala Gln Val Asp Ala Gln Glu Leu Asp Glu Glu
            20                  25                  30

Glu Asn Glu Ala Asn Glu Ala Gln Ala Arg Glu Gln Glu Gln Ala Lys
        35                  40                  45

Lys Thr His Val Tyr Ala Gln Ala Pro Leu Ser Gly Ile Lys Ile Thr
    50                  55                  60

Lys Glu Gly Leu Gln Ile Gly Thr Ala Asp Ala Thr Val Ala Gly Ala
65                  70                  75                  80

Gly Lys Glu Ile Phe Ala Asp Lys Thr Phe Gln Pro Glu Pro Gln Val
                85                  90                  95

Gly Glu Ser Gln Trp Asn Glu Ala Asp Ala Thr Ala Ala Gly Gly Arg
            100                 105                 110

Val Leu Lys Lys Thr Thr Pro Met Lys Pro Cys Tyr Gly Ser Tyr Ala
        115                 120                 125

Arg Pro Thr Asn Ser Asn Gly Gly Gln Gly Val Leu Trp Leu Thr Asn
    130                 135                 140

Gly Lys Leu Glu Ser Gln Val Glu Met Gln Phe Phe Ser Thr Ser Thr
145                 150                 155                 160

Asn Ala Thr Asn Glu Val Asn Asn Ile Gln Pro Thr Val Val Leu Tyr
                165                 170                 175

Ser Glu Asp Val Asn Met Glu Thr Pro Asp Thr His Leu Ser Tyr Lys
            180                 185                 190

Pro Lys Met Gly Asp Lys Asn Ala Lys Val Ser Leu Gly Gln Gln Ala
        195                 200                 205

Met Pro Asn Arg Pro Asn Tyr Ile Ala Phe Arg Asp Asn Phe Ile Gly
    210                 215                 220

Leu Met Tyr Tyr Asn Ser Thr Gly Asn Met Gly Val Leu Ala Gly Gln
225                 230                 235                 240

Ala Ser Gln Leu Asn Ala Val Val Asp Leu Gln Asp Arg Asn Thr Glu
                245                 250                 255

Leu Ser Tyr Gln Leu Leu Leu Asp Ser Ile Gly Asp Arg Thr Arg Tyr
            260                 265                 270

Phe Ser Met Trp Asn Gln Ala Val Asp Ser Tyr Asp Pro Asp Val Arg
        275                 280                 285

Ile Ile Glu Asn His Gly Thr Glu Asp Glu Leu Pro Asn Tyr Cys Phe
    290                 295                 300

Pro Leu Gly Gly Ile Gly Ile Thr Asp Thr Phe Gln Ala Val Lys Thr
305                 310                 315                 320

Thr Ala Ala Asn Gly Asp Gln Gly Asn Thr Thr Trp Gln Lys Asp Ser
                325                 330                 335

Thr Phe Ala Glu Arg Asn Glu Ile Gly Val Gly Asn Asn Phe Ala Met
```

```
                    340                 345                 350
Glu Ile Asn Leu Asn Ala Asn Leu Trp Arg Asn Phe Leu Tyr Ser Asn
                355                 360                 365

Ile Ala Leu Tyr Leu Pro Asp Lys Leu Lys Tyr Asn Pro Thr Asn Val
            370                 375                 380

Asp Ile Ser Asp Asn Pro Asn Thr Tyr Asp His Met Lys Arg Val Val
385                 390                 395                 400

Ala Pro Gly Leu Val Asp Cys Tyr Ile Asn Leu Gly Ala Arg Trp Ser
                405                 410                 415

Leu Asp Tyr Met Asp Asn Val Asn Pro Phe Asn His His Arg Asn Ala
            420                 425                 430

Gly Leu Arg Tyr Arg Ser Met Leu Leu Gly Asn Gly Arg Tyr Val Pro
                435                 440                 445

Phe His Ile Gln Val Pro Gln Lys Phe Phe Ala Ile Lys Asn Leu Leu
            450                 455                 460

Leu
465

<210> SEQ ID NO 2
<211> LENGTH: 959
<212> TYPE: PRT
<213> ORGANISM: Artificial Sequence
<220> FEATURE:
<223> OTHER INFORMATION: Hexon Polypeptide

<400> SEQUENCE: 2

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Ser Cys Glu Trp Asp Glu Asp Thr Gln Val Gln Val
    130                 135                 140

Ala Ala Glu Asp Asp Gln Asp Asp Glu Glu Glu Gln Leu Pro
145                 150                 155                 160

Gln Gln Arg Asn Gly Lys Lys Thr His Val Tyr Ala Gln Ala Pro Phe
                165                 170                 175

Ala Gly Glu Ala Ile Asn Lys Asn Gly Leu Gln Ile Gly Thr Asn Gly
            180                 185                 190

Ala Ala Thr Glu Gly Asn Lys Glu Ile Tyr Ala Asp Lys Thr Tyr Gln
        195                 200                 205

Pro Glu Pro Gln Ile Gly Glu Ser Gln Trp Asn Glu Ala Glu Ser Ser
    210                 215                 220

Val Ala Gly Gly Arg Val Leu Lys Lys Thr Thr Pro Met Lys Pro Cys
```

-continued

```
            225                 230                 235                 240
Tyr Gly Ser Tyr Ala Arg Pro Thr Asn Ser Asn Gly Gln Gly Val
                245                 250                 255

Met Val Glu Gln Asn Gly Lys Leu Glu Ser Gln Val Glu Met Gln Phe
                260                 265                 270

Phe Ser Thr Ser Val Asn Ala Met Asn Glu Ala Asn Ala Ile Gln Pro
                275                 280                 285

Lys Leu Val Leu Tyr Ser Glu Asp Val Asn Met Glu Thr Pro Asp Thr
                290                 295                 300

His Leu Ser Tyr Lys Pro Gly Lys Ser Asp Asn Ser Lys Ala Met
305                 310                 315                 320

Leu Gly Gln Gln Ser Met Pro Asn Arg Pro Asn Tyr Ile Ala Phe Arg
                325                 330                 335

Asp Asn Phe Ile Gly Leu Met Tyr Tyr Asn Ser Thr Gly Asn Met Gly
                340                 345                 350

Val Leu Ala Gly Gln Ala Ser Gln Leu Asn Ala Val Val Asp Leu Gln
                355                 360                 365

Asp Arg Asn Thr Glu Leu Ser Tyr Gln Leu Leu Asp Ser Ile Gly
                370                 375                 380

Asp Arg Thr Arg Tyr Phe Ser Met Trp Asn Gln Ala Val Asp Ser Tyr
385                 390                 395                 400

Asp Pro Asp Val Arg Ile Ile Glu Asn His Gly Thr Glu Asp Glu Leu
                405                 410                 415

Pro Asn Tyr Cys Phe Pro Leu Gly Gly Ile Gly Val Thr Asp Thr Tyr
                420                 425                 430

Gln Ala Ile Lys Ala Thr Asn Gly Asn Gly Gly Ala Thr Thr Trp Ala
                435                 440                 445

Gln Asp Asn Thr Phe Ala Glu Arg Asn Glu Ile Gly Val Gly Asn Asn
                450                 455                 460

Phe Ala Met Glu Ile Asn Leu Asn Ala Asn Leu Trp Arg Asn Phe Leu
465                 470                 475                 480

Tyr Ser Asn Ile Ala Leu Tyr Leu Pro Asp Lys Leu Lys Tyr Asn Pro
                485                 490                 495

Thr Asn Val Glu Ile Ser Asp Asn Pro Asn Thr Tyr Asp Tyr Met Asn
                500                 505                 510

Lys Arg Val Val Ala Pro Gly Leu Val Asp Cys Tyr Ile Asn Leu Gly
                515                 520                 525

Ala Arg Trp Ser Leu Asp Tyr Met Asp Asn Val Asn Pro Phe Asn His
                530                 535                 540

His Arg Asn Ala Gly Leu Arg Tyr Arg Ser Met Leu Leu Gly Asn Gly
545                 550                 555                 560

Arg Tyr Val Pro Phe His Ile Gln Val Pro Gln Lys Phe Phe Ala Ile
                565                 570                 575

Lys Asn Leu Leu Leu Leu Pro Gly Ser Tyr Thr Tyr Glu Trp Asn Phe
                580                 585                 590

Arg Lys Asp Val Asn Met Val Leu Gln Ser Ser Leu Gly Asn Asp Leu
                595                 600                 605

Arg Val Asp Gly Ala Ser Ile Lys Phe Asp Ser Ile Cys Leu Tyr Ala
                610                 615                 620

Thr Phe Phe Pro Met Ala His Asn Thr Ala Ser Thr Leu Glu Ala Met
625                 630                 635                 640

Leu Arg Asn Asp Thr Asn Asp Gln Ser Phe Asn Asp Tyr Leu Ser Ala
                645                 650                 655
```

```
Ala Asn Met Leu Tyr Pro Ile Pro Ala Asn Ala Thr Asn Val Pro Ile
            660                 665                 670

Ser Ile Pro Ser Arg Asn Trp Ala Phe Arg Gly Trp Ala Phe Thr
    675                 680                 685

Arg Leu Lys Thr Lys Glu Thr Pro Ser Leu Gly Ser Gly Tyr Asp Pro
    690                 695                 700

Tyr Tyr Thr Tyr Ser Gly Ser Ile Pro Tyr Leu Asp Gly Thr Phe Tyr
705                 710                 715                 720

Leu Asn His Thr Phe Lys Lys Val Ala Ile Thr Phe Asp Ser Ser Val
                725                 730                 735

Ser Trp Pro Gly Asn Asp Arg Leu Leu Thr Pro Asn Glu Phe Glu Ile
            740                 745                 750

Lys Arg Ser Val Asp Gly Glu Gly Tyr Asn Val Ala Gln Cys Asn Met
        755                 760                 765

Thr Lys Asp Trp Phe Leu Val Gln Met Leu Ala Asn Tyr Asn Ile Gly
    770                 775                 780

Tyr Gln Gly Phe Tyr Ile Pro Glu Ser Tyr Lys Asp Arg Met Tyr Ser
785                 790                 795                 800

Phe Phe Arg Asn Phe Gln Pro Met Ser Arg Gln Val Val Asp Asp Thr
                805                 810                 815

Lys Tyr Lys Asp Tyr Gln Gln Val Gly Ile Ile His Gln His Asn Asn
            820                 825                 830

Ser Gly Phe Val Gly Tyr Leu Ala Pro Thr Met Arg Glu Gly Gln Ala
        835                 840                 845

Tyr Pro Ala Asn Val Pro Tyr Pro Leu Ile Gly Lys Thr Ala Val Asp
    850                 855                 860

Ser Ile Thr Gln Lys Lys Phe Leu Cys Asp Arg Thr Leu Trp Arg Ile
865                 870                 875                 880

Pro Phe Ser Ser Asn Phe Met Ser Met Gly Ala Leu Thr Asp Leu Gly
                885                 890                 895

Gln Asn Leu Leu Tyr Ala Asn Ser Ala His Ala Leu Asp Met Thr Phe
            900                 905                 910

Glu Val Asp Pro Met Asp Glu Pro Thr Leu Leu Tyr Val Leu Phe Glu
        915                 920                 925

Val Phe Asp Val Val Arg Val His Gln Pro His Arg Gly Val Ile Glu
    930                 935                 940

Thr Val Tyr Leu Arg Thr Pro Phe Ser Ala Gly Asn Ala Thr Thr
945                 950                 955

<210> SEQ ID NO 3
<211> LENGTH: 959
<212> TYPE: PRT
<213> ORGANISM: Artificial Sequence
<220> FEATURE:
<223> OTHER INFORMATION: Hexon Polypeptide

<400> SEQUENCE: 3

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60
```

```
Thr Leu Arg Phe Ile Pro Val Asp Arg Glu Asp Thr Ala Tyr Ser Tyr
 65                  70                  75                  80

Lys Ala Arg Phe Thr Leu Ala Val Gly Asp Asn Arg Val Leu Asp Met
             85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Ser Cys Glu Trp Asp Glu Asp Thr Gln Val Gln Val
        130                 135                 140

Ala Ala Glu Asp Asp Gln Asp Asp Glu Glu Glu Gln Leu Pro
145                 150                 155                 160

Gln Gln Arg Asn Gly Lys Lys Thr His Val Tyr Ala Gln Ala Pro Phe
                165                 170                 175

Ala Gly Glu Ala Ile Asn Lys Asn Gly Leu Gln Ile Gly Thr Asn Gly
            180                 185                 190

Ala Ala Thr Glu Gly Asn Lys Glu Ile Tyr Ala Asp Lys Thr Tyr Gln
        195                 200                 205

Pro Glu Pro Gln Ile Gly Glu Ser Gln Trp Asn Glu Ala Glu Ser Ser
210                 215                 220

Val Ala Gly Gly Arg Val Leu Lys Lys Thr Thr Pro Met Lys Pro Cys
225                 230                 235                 240

Tyr Gly Ser Tyr Ala Arg Pro Thr Asn Ser Asn Gly Gly Gln Gly Val
                245                 250                 255

Met Val Glu Gln Asn Gly Lys Leu Glu Ser Gln Val Glu Met Gln Phe
            260                 265                 270

Phe Ser Thr Ser Val Asn Ala Met Asn Glu Ala Asn Ala Ile Gln Pro
        275                 280                 285

Lys Leu Val Leu Tyr Ser Glu Asp Val Asn Met Glu Thr Pro Asp Thr
        290                 295                 300

His Leu Ser Tyr Lys Pro Gly Lys Ser Asp Asp Asn Ser Lys Ala Met
305                 310                 315                 320

Leu Gly Gln Gln Ser Met Pro Asn Arg Pro Asn Tyr Ile Ala Phe Arg
                325                 330                 335

Asp Asn Phe Ile Gly Leu Met Tyr Tyr Asn Ser Thr Gly Asn Met Gly
            340                 345                 350

Val Leu Ala Gly Gln Ala Ser Gln Leu Asn Ala Val Val Asp Leu Gln
        355                 360                 365

Asp Arg Asn Thr Glu Leu Ser Tyr Gln Leu Leu Leu Asp Ser Ile Gly
        370                 375                 380

Asp Arg Thr Arg Tyr Phe Ser Met Trp Asn Gln Ala Val Asp Ser Tyr
385                 390                 395                 400

Asp Pro Asp Val Arg Ile Ile Glu Asn His Gly Thr Glu Asp Glu Leu
                405                 410                 415

Pro Asn Tyr Cys Phe Pro Leu Gly Gly Ile Gly Val Thr Asp Thr Tyr
            420                 425                 430

Gln Ala Ile Lys Ala Thr Asn Gly Asn Gly Ala Thr Thr Trp Ala
        435                 440                 445

Gln Asp Asn Thr Phe Ala Glu Arg Asn Glu Ile Gly Val Gly Asn Asn
        450                 455                 460

Phe Ala Met Glu Ile Asn Leu Asn Ala Asn Leu Trp Arg Asn Phe Leu
465                 470                 475                 480
```

-continued

```
Tyr Ser Asn Ile Ala Leu Tyr Leu Pro Asp Lys Leu Lys Tyr Asn Pro
                485                 490                 495

Thr Asn Val Glu Ile Ser Asp Asn Pro Asn Thr Tyr Asp Tyr Met Asn
            500                 505                 510

Lys Arg Val Val Ala Pro Gly Leu Val Asp Cys Tyr Ile Asn Leu Gly
            515                 520                 525

Ala Arg Trp Ser Leu Asp Tyr Met Asp Asn Val Asn Pro Phe Asn His
            530                 535                 540

His Arg Asn Ala Gly Leu Arg Tyr Arg Ser Met Leu Leu Gly Asn Gly
545                 550                 555                 560

Arg Tyr Val Pro Phe His Ile Gln Val Pro Gln Lys Phe Phe Ala Ile
                565                 570                 575

Lys Asn Leu Leu Leu Leu Pro Gly Ser Tyr Thr Tyr Glu Trp Asn Phe
            580                 585                 590

Arg Lys Asp Val Asn Met Val Leu Gln Ser Ser Leu Gly Asn Asp Leu
            595                 600                 605

Arg Val Asp Gly Ala Ser Ile Lys Phe Asp Ser Ile Cys Leu Tyr Ala
610                 615                 620

Thr Phe Phe Pro Met Ala His Asn Thr Ala Ser Thr Leu Glu Ala Met
625                 630                 635                 640

Leu Arg Asn Asp Thr Asn Asp Gln Ser Phe Asn Asp Tyr Leu Ser Ala
                645                 650                 655

Ala Asn Met Leu Tyr Pro Ile Pro Ala Asn Ala Thr Asn Val Pro Ile
            660                 665                 670

Ser Ile Pro Ser Arg Asn Trp Ala Ala Phe Arg Gly Trp Ala Phe Thr
            675                 680                 685

Arg Leu Lys Thr Lys Glu Thr Pro Ser Leu Gly Ser Gly Tyr Asp Pro
690                 695                 700

Tyr Tyr Thr Tyr Ser Gly Ser Ile Pro Tyr Leu Asp Gly Thr Phe Tyr
705                 710                 715                 720

Leu Asn His Thr Phe Lys Lys Val Ala Ile Thr Phe Asp Ser Ser Val
                725                 730                 735

Ser Trp Pro Gly Asn Asp Arg Leu Leu Thr Pro Asn Glu Phe Glu Ile
            740                 745                 750

Lys Arg Ser Val Asp Gly Glu Gly Tyr Asn Val Ala Gln Cys Asn Met
            755                 760                 765

Thr Lys Asp Trp Phe Leu Val Gln Met Leu Ala Asn Tyr Asn Ile Gly
            770                 775                 780

Tyr Gln Gly Phe Tyr Ile Pro Glu Ser Tyr Lys Asp Arg Met Tyr Ser
785                 790                 795                 800

Phe Phe Arg Asn Phe Gln Pro Met Ser Arg Gln Val Val Asp Asp Thr
                805                 810                 815

Lys Tyr Lys Asp Tyr Gln Gln Val Gly Ile Ile His Gln His Asn Asn
            820                 825                 830

Ser Gly Phe Val Gly Tyr Leu Ala Pro Thr Met Arg Glu Gly Gln Ala
            835                 840                 845

Tyr Pro Ala Asn Val Pro Tyr Pro Leu Ile Gly Lys Thr Ala Val Asp
850                 855                 860

Ser Ile Thr Gln Lys Lys Phe Leu Cys Asp Arg Thr Leu Trp Arg Ile
865                 870                 875                 880

Pro Phe Ser Ser Asn Phe Met Ser Met Gly Ala Leu Thr Asp Leu Gly
                885                 890                 895

Gln Asn Leu Leu Tyr Ala Asn Ser Ala His Ala Leu Asp Met Thr Phe
```

```
                    900             905                 910
Glu Val Asp Pro Met Asp Glu Pro Thr Leu Leu Tyr Val Leu Phe Glu
                915                 920                 925

Val Phe Asp Val Val Arg Val His Gln Pro His Arg Gly Val Ile Glu
            930                 935                 940

Thr Val Tyr Leu Arg Thr Pro Phe Ser Ala Gly Asn Ala Thr Thr
945                 950                 955

<210> SEQ ID NO 4
<211> LENGTH: 962
<212> TYPE: PRT
<213> ORGANISM: Artificial Sequence
<220> FEATURE:
<223> OTHER INFORMATION: Hexon Polypeptide

<400> SEQUENCE: 4

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Ser Cys Glu Trp Glu Gln Asn Glu Thr Ala Gln Val Asp
    130                 135                 140

Ala Gln Glu Leu Asp Glu Glu Asn Glu Ala Asn Glu Ala Gln Ala
145                 150                 155                 160

Arg Glu Gln Glu Gln Ala Lys Lys Thr His Val Tyr Ala Gln Ala Pro
                165                 170                 175

Leu Ser Gly Glu Ala Ile Asn Lys Asn Gly Leu Gln Ile Gly Thr Asn
            180                 185                 190

Gly Ala Ala Thr Glu Gly Asn Lys Glu Ile Tyr Ala Asp Lys Thr Tyr
        195                 200                 205

Gln Pro Glu Pro Gln Ile Gly Glu Ser Gln Trp Asn Glu Ala Glu Ser
    210                 215                 220

Ser Val Ala Gly Gly Arg Val Leu Lys Lys Thr Thr Pro Met Lys Pro
225                 230                 235                 240

Cys Tyr Gly Ser Tyr Ala Arg Pro Thr Asn Ser Asn Gly Gly Gln Gly
                245                 250                 255

Val Met Val Glu Gln Asn Gly Lys Leu Glu Ser Gln Val Glu Met Gln
            260                 265                 270

Phe Phe Ser Thr Ser Val Asn Ala Met Asn Glu Ala Asn Ala Ile Gln
        275                 280                 285

Pro Lys Leu Val Leu Tyr Ser Glu Asp Val Asn Met Glu Thr Pro Asp
    290                 295                 300

Thr His Leu Ser Tyr Lys Pro Gly Lys Ser Asp Asp Asn Ser Lys Ala
```

```
              305                 310                 315                 320
Met Leu Gly Gln Gln Ser Met Pro Asn Arg Pro Asn Tyr Ile Ala Phe
                    325                 330                 335

Arg Asp Asn Phe Ile Gly Leu Met Tyr Tyr Asn Ser Thr Gly Asn Met
                340                 345                 350

Gly Val Leu Ala Gly Gln Ala Ser Gln Leu Asn Ala Val Val Asp Leu
            355                 360                 365

Gln Asp Arg Asn Thr Glu Leu Ser Tyr Gln Leu Leu Leu Asp Ser Ile
        370                 375                 380

Gly Asp Arg Thr Arg Tyr Phe Ser Met Trp Asn Gln Ala Val Asp Ser
385                 390                 395                 400

Tyr Asp Pro Asp Val Arg Ile Ile Glu Asn His Gly Thr Glu Asp Glu
                405                 410                 415

Leu Pro Asn Tyr Cys Phe Pro Leu Gly Gly Ile Gly Ile Thr Asp Thr
                420                 425                 430

Phe Gln Ala Val Lys Thr Thr Ala Ala Asn Gly Asp Gln Gly Asn Thr
            435                 440                 445

Thr Trp Gln Lys Asp Ser Thr Phe Ala Glu Arg Asn Glu Ile Gly Val
        450                 455                 460

Gly Asn Asn Phe Ala Met Glu Ile Asn Leu Asn Ala Asn Leu Trp Arg
465                 470                 475                 480

Asn Phe Leu Tyr Ser Asn Ile Ala Leu Tyr Leu Pro Asp Lys Leu Lys
                485                 490                 495

Tyr Asn Pro Thr Asn Val Glu Ile Ser Asp Asn Pro Asn Thr Tyr Asp
                500                 505                 510

Tyr Met Asn Lys Arg Val Val Ala Pro Gly Leu Val Asp Cys Tyr Ile
            515                 520                 525

Asn Leu Gly Ala Arg Trp Ser Leu Asp Tyr Met Asp Asn Val Asn Pro
        530                 535                 540

Phe Asn His Pro Arg His Ala Gly Leu Arg Tyr Arg Ser Met Leu Leu
545                 550                 555                 560

Gly Asn Gly Arg Tyr Val Pro Phe His Ile Gln Val Pro Gln Lys Phe
                565                 570                 575

Phe Ala Ile Lys Asn Leu Leu Leu Leu Pro Gly Ser Tyr Thr Tyr Glu
                580                 585                 590

Trp Asn Phe Arg Lys Asp Val Asn Met Val Leu Gln Ser Ser Leu Gly
            595                 600                 605

Asn Asp Leu Arg Val Asp Gly Ala Ser Ile Lys Phe Asp Ser Ile Cys
        610                 615                 620

Leu Tyr Ala Thr Phe Phe Pro Met Ala His Asn Thr Ala Ser Thr Leu
625                 630                 635                 640

Glu Ala Met Leu Arg Asn Asp Thr Asn Asp Gln Ser Phe Asn Asp Tyr
                645                 650                 655

Leu Ser Ala Ala Asn Met Leu Tyr Pro Ile Pro Ala Asn Ala Thr Asn
                660                 665                 670

Val Pro Ile Ser Ile Pro Ser Arg Asn Trp Ala Ala Phe Arg Gly Trp
            675                 680                 685

Ala Phe Thr Arg Leu Lys Thr Lys Glu Thr Pro Ser Leu Gly Ser Gly
        690                 695                 700

Tyr Asp Pro Tyr Tyr Thr Tyr Ser Gly Ser Ile Pro Tyr Leu Asp Gly
705                 710                 715                 720

Thr Phe Tyr Leu Asn His Thr Phe Lys Lys Val Ala Ile Thr Phe Asp
                725                 730                 735
```

-continued

```
Ser Ser Val Ser Trp Pro Gly Asn Asp Arg Leu Leu Thr Pro Asn Glu
            740                 745                 750

Phe Glu Ile Lys Arg Ser Val Asp Gly Glu Gly Tyr Asn Val Ala Gln
            755                 760                 765

Cys Asn Met Thr Lys Asp Trp Phe Leu Val Gln Met Leu Ala Asn Tyr
            770                 775                 780

Asn Ile Gly Tyr Gln Gly Phe Tyr Ile Pro Glu Ser Tyr Lys Asp Arg
785                 790                 795                 800

Met Tyr Ser Phe Phe Arg Asn Phe Gln Pro Met Ser Arg Gln Val Val
            805                 810                 815

Asp Asp Thr Lys Tyr Lys Asp Tyr Gln Gln Val Gly Ile Ile His Gln
            820                 825                 830

His Asn Asn Ser Gly Phe Val Gly Tyr Leu Ala Pro Thr Met Arg Glu
            835                 840                 845

Gly Gln Ala Tyr Pro Ala Asn Val Pro Tyr Pro Leu Ile Gly Lys Thr
            850                 855                 860

Ala Val Asp Ser Ile Thr Gln Lys Lys Phe Leu Cys Asp Arg Thr Leu
865                 870                 875                 880

Trp Arg Ile Pro Phe Ser Ser Asn Phe Met Ser Met Gly Ala Leu Thr
            885                 890                 895

Asp Leu Gly Gln Asn Leu Leu Tyr Ala Asn Ser Ala His Ala Leu Asp
            900                 905                 910

Met Thr Phe Glu Val Asp Pro Met Asp Glu Pro Thr Leu Leu Tyr Val
            915                 920                 925

Leu Phe Glu Val Phe Asp Val Val Arg Val His Gln Pro His Arg Gly
            930                 935                 940

Val Ile Glu Thr Val Tyr Leu Arg Thr Pro Phe Ser Ala Gly Asn Ala
945                 950                 955                 960

Thr Thr

<210> SEQ ID NO 5
<211> LENGTH: 288
<212> TYPE: PRT
<213> ORGANISM: Homo sapiens

<400> SEQUENCE: 5

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
            50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
            85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135                 140
```

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
            165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
        210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285

<210> SEQ ID NO 6
<211> LENGTH: 288
<212> TYPE: PRT
<213> ORGANISM: Mus musculus

<400> SEQUENCE: 6

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
            35                  40                  45

Asn Ala Thr Phe Thr Cys Ser Leu Ser Asn Trp Ser Glu Asp Leu Met
        50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
            115                 120                 125

His Pro Lys Ala Lys Ile Glu Glu Ser Pro Gly Ala Glu Leu Val Val
        130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
            165                 170                 175

Leu Val Gly Ile Pro Val Leu Leu Leu Leu Ala Trp Ala Leu Ala Val
            180                 185                 190

Phe Cys Ser Thr Ser Met Ser Glu Ala Arg Gly Ala Gly Ser Lys Asp
            195                 200                 205

Asp Thr Leu Lys Glu Glu Pro Ser Ala Ala Pro Val Pro Ser Val Ala
        210                 215                 220

Tyr Glu Glu Leu Asp Phe Gln Gly Arg Glu Lys Thr Pro Glu Leu Pro

```
              225                 230                 235                 240

Thr Ala Cys Val His Thr Glu Tyr Ala Thr Ile Val Phe Thr Glu Gly
                245                 250                 255

Leu Gly Ala Ser Ala Met Gly Arg Arg Gly Ser Ala Asp Gly Leu Gln
            260                 265                 270

Gly Pro Arg Pro Arg His Glu Asp Gly His Cys Ser Trp Pro Leu
        275                 280                 285

<210> SEQ ID NO 7
<211> LENGTH: 390
<212> TYPE: PRT
<213> ORGANISM: Artificial Sequence
<220> FEATURE:
<223> OTHER INFORMATION: PD-1 Fusion

<400> SEQUENCE: 7

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Cys Cys Val Glu Cys Pro Pro Cys Pro Ala Pro
                165                 170                 175

Pro Val Ala Gly Pro Ser Val Phe Leu Phe Pro Pro Lys Pro Lys Asp
            180                 185                 190

Thr Leu Met Ile Ser Arg Thr Pro Glu Val Thr Cys Val Val Val Asp
        195                 200                 205

Val Ser His Glu Asp Pro Glu Val Gln Phe Asn Trp Tyr Val Asp Gly
    210                 215                 220

Val Glu Val His Asn Ala Lys Thr Lys Pro Arg Glu Glu Gln Phe Asn
225                 230                 235                 240

Ser Thr Phe Arg Val Val Ser Val Leu Thr Val Val His Gln Asp Trp
                245                 250                 255

Leu Asn Gly Lys Glu Tyr Lys Cys Lys Val Ser Asn Lys Gly Leu Pro
            260                 265                 270

Ala Pro Ile Glu Lys Thr Ile Ser Lys Thr Lys Gly Gln Pro Arg Glu
        275                 280                 285

Pro Gln Val Tyr Thr Leu Pro Pro Ser Arg Glu Glu Met Thr Lys Asn
    290                 295                 300

Gln Val Ser Leu Thr Cys Leu Val Lys Gly Phe Tyr Pro Ser Asp Ile
```

```
                305                 310                 315                 320
Ala Val Glu Trp Glu Ser Asn Gly Gln Pro Glu Asn Asn Tyr Lys Thr
                    325                 330                 335

Thr Pro Pro Met Leu Asp Ser Asp Gly Ser Phe Phe Leu Tyr Ser Lys
                    340                 345                 350

Leu Thr Val Asp Lys Ser Arg Trp Gln Gln Gly Asn Val Phe Ser Cys
                    355                 360                 365

Ser Val Met His Glu Ala Leu His Asn His Tyr Thr Gln Lys Ser Leu
                    370                 375                 380

Ser Leu Ser Pro Gly Lys
385                 390

<210> SEQ ID NO 8
<211> LENGTH: 273
<212> TYPE: PRT
<213> ORGANISM: Artificial Sequence
<220> FEATURE:
<223> OTHER INFORMATION: PD-1 Fusion

<400> SEQUENCE: 8

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
                20                  25                  30

Arg Ser Leu Thr Phe Tyr Pro Ala Trp Leu Thr Val Ser Glu Gly Ala
                35                  40                  45

Asn Ala Thr Phe Thr Cys Ser Leu Ser Asn Trp Ser Glu Asp Leu Met
50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
                100                 105                 110

Thr Arg Arg Asn Asp Ser Gly Ile Tyr Leu Cys Gly Ala Ile Ser Leu
                115                 120                 125

His Pro Lys Ala Lys Ile Glu Glu Ser Pro Gly Ala Glu Leu Val Val
            130                 135                 140

Thr Glu Arg Ile Leu Glu Thr Ser Thr Arg Tyr Pro Ser Pro Ser Pro
145                 150                 155                 160

Lys Pro Glu Gly Arg Cys Cys Val Glu Cys Pro Pro Cys Pro Ala Pro
                165                 170                 175

Pro Val Ala Gly Gly Ser Ala Asn Ser Phe Leu Glu Glu Met Lys Lys
                180                 185                 190

Gly His Leu Glu Arg Glu Cys Met Glu Glu Thr Cys Ser Tyr Glu Glu
            195                 200                 205

Ala Arg Glu Val Phe Glu Asp Ser Asp Lys Thr Asn Glu Phe Trp Asn
            210                 215                 220

Lys Tyr Lys Asp Gly Asp Gln Cys Glu Thr Ser Pro Cys Gln Asn Gln
225                 230                 235                 240

Gly Lys Cys Lys Asp Gly Leu Gly Glu Tyr Thr Cys Thr Cys Leu Glu
                245                 250                 255

Gly Phe Glu Gly Lys Asn Cys Glu Leu Pro Val Gly Tyr Arg Gly Gly
                260                 265                 270

Ser
```

<210> SEQ ID NO 9
<211> LENGTH: 252
<212> TYPE: PRT
<213> ORGANISM: Artificial Sequence
<220> FEATURE:
<223> OTHER INFORMATION: PD-1 Fusion

<400> SEQUENCE: 9

```
Cys Cys Val Glu Cys Pro Pro Cys Pro Ala Pro Pro Val Ala Gly Gly
1               5                   10                  15

Ser Ala Asn Ser Phe Leu Glu Glu Met Lys Lys Gly His Leu Glu Arg
                20                  25                  30

Glu Cys Met Glu Glu Thr Cys Ser Tyr Glu Glu Ala Arg Glu Val Phe
            35                  40                  45

Glu Asp Ser Asp Lys Thr Asn Glu Phe Trp Asn Lys Tyr Lys Asp Gly
        50                  55                  60

Asp Gln Cys Glu Thr Ser Pro Cys Gln Asn Gln Gly Lys Cys Lys Asp
65                  70                  75                  80

Gly Leu Gly Glu Tyr Thr Cys Thr Cys Leu Glu Gly Phe Glu Gly Lys
                85                  90                  95

Asn Cys Glu Leu Pro Val Gly Tyr Arg Gly Gly Ser Gly Trp Leu Leu
            100                 105                 110

Glu Val Pro Asn Gly Pro Trp Arg Ser Leu Thr Phe Tyr Pro Ala Trp
        115                 120                 125

Leu Thr Val Ser Glu Gly Ala Asn Ala Thr Phe Thr Cys Ser Leu Ser
130                 135                 140

Asn Trp Ser Glu Asp Leu Met Leu Asn Trp Asn Arg Leu Ser Pro Ser
145                 150                 155                 160

Asn Gln Thr Glu Lys Gln Ala Ala Phe Cys Asn Gly Leu Ser Gln Pro
                165                 170                 175

Val Gln Asp Ala Arg Phe Gln Ile Ile Gln Leu Pro Asn Arg His Asp
            180                 185                 190

Phe His Met Asn Ile Leu Asp Thr Arg Arg Asn Asp Ser Gly Ile Tyr
        195                 200                 205

Leu Cys Gly Ala Ile Ser Leu His Pro Lys Ala Lys Ile Glu Glu Ser
210                 215                 220

Pro Gly Ala Glu Leu Val Val Thr Glu Arg Ile Leu Glu Thr Ser Thr
225                 230                 235                 240

Arg Tyr Pro Ser Pro Ser Pro Lys Pro Glu Gly Arg
                245                 250
```

<210> SEQ ID NO 10
<211> LENGTH: 310
<212> TYPE: PRT
<213> ORGANISM: Artificial Sequence
<220> FEATURE:
<223> OTHER INFORMATION: PD-1 Fusion

<400> SEQUENCE: 10

```
Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
                20                  25                  30

Arg Ser Leu Thr Phe Tyr Pro Ala Trp Leu Thr Val Ser Glu Gly Ala
            35                  40                  45

Asn Ala Thr Phe Thr Cys Ser Leu Ser Asn Trp Ser Glu Asp Leu Met
```

-continued

```
                50                  55                  60
Leu Asn Trp Asn Arg Leu Ser Pro Ser Asn Gln Thr Glu Lys Gln Ala
 65                  70                  75                  80

Ala Phe Cys Asn Gly Leu Ser Gln Pro Val Gln Asp Ala Arg Phe Gln
                    85                  90                  95

Ile Ile Gln Leu Pro Asn Arg His Asp Phe His Met Asn Ile Leu Asp
               100                 105                 110

Thr Arg Arg Asn Asp Ser Gly Ile Tyr Leu Cys Gly Ala Ile Ser Leu
               115                 120                 125

His Pro Lys Ala Lys Ile Glu Glu Ser Pro Gly Ala Glu Leu Val Val
           130                 135                 140

Thr Glu Arg Ile Leu Glu Thr Ser Thr Arg Tyr Pro Ser Pro Ser Pro
145                 150                 155                 160

Lys Pro Glu Gly Arg Cys Cys Val Glu Cys Pro Pro Cys Pro Ala Pro
                   165                 170                 175

Pro Val Ala Gly Ser Lys Gly Leu Glu Ser Arg Val Ser Ala Leu Glu
               180                 185                 190

Lys Thr Ser Gln Ile His Ser Asp Thr Ile Leu Arg Ile Thr Gln Gly
           195                 200                 205

Leu Asp Asp Ala Asn Lys Arg Ile Ile Ala Leu Glu Gln Ser Arg Asp
210                 215                 220

Asp Leu Val Ala Ser Val Ser Asp Ala Gln Leu Ala Ile Ser Arg Leu
225                 230                 235                 240

Glu Ser Ser Ile Gly Ala Leu Gln Thr Val Val Asn Gly Leu Asp Ser
                   245                 250                 255

Ser Val Thr Gln Leu Gly Ala Arg Val Gly Gln Leu Glu Thr Gly Leu
               260                 265                 270

Ala Glu Leu Arg Val Asp His Asp Asn Leu Val Ala Arg Val Asp Thr
           275                 280                 285

Ala Glu Arg Asn Ile Gly Ser Leu Thr Thr Glu Leu Ser Thr Leu Thr
       290                 295                 300

Leu Arg Val Thr Ser Ile
305                 310

<210> SEQ ID NO 11
<211> LENGTH: 599
<212> TYPE: PRT
<213> ORGANISM: Artificial Sequence
<220> FEATURE:
<223> OTHER INFORMATION: PD-1 Fusion Polypeptide

<400> SEQUENCE: 11

Met Trp Val Arg Gln Val Pro Trp Ser Phe Thr Trp Ala Val Leu Gln
 1               5                  10                  15

Leu Ser Trp Gln Ser Gly Trp Leu Leu Glu Val Pro Asn Gly Pro Trp
                20                  25                  30

Arg Ser Leu Thr Phe Tyr Pro Ala Trp Leu Thr Val Ser Glu Gly Ala
                35                  40                  45

Asn Ala Thr Phe Thr Cys Ser Leu Ser Asn Trp Ser Glu Asp Leu Met
         50                  55                  60

Leu Asn Trp Asn Arg Leu Ser Pro Ser Asn Gln Thr Glu Lys Gln Ala
 65                  70                  75                  80

Ala Phe Cys Asn Gly Leu Ser Gln Pro Val Gln Asp Ala Arg Phe Gln
                    85                  90                  95

Ile Ile Gln Leu Pro Asn Arg His Asp Phe His Met Asn Ile Leu Asp
```

-continued

```
                100                 105                 110
Thr Arg Arg Asn Asp Ser Gly Ile Tyr Leu Cys Gly Ala Ile Ser Leu
                115                 120                 125

His Pro Lys Ala Lys Ile Glu Glu Ser Pro Gly Ala Glu Leu Val Val
                130                 135                 140

Thr Glu Arg Ile Leu Glu Thr Ser Thr Arg Tyr Pro Ser Pro Ser Pro
145                 150                 155                 160

Lys Pro Glu Gly Arg Ser Gly Trp Leu Leu Glu Val Pro Asn Gly Pro
                165                 170                 175

Trp Arg Ser Leu Thr Phe Tyr Pro Ala Trp Leu Thr Val Ser Glu Gly
                180                 185                 190

Ala Asn Ala Thr Phe Thr Cys Ser Leu Ser Asn Trp Ser Glu Asp Leu
                195                 200                 205

Met Leu Asn Trp Asn Arg Leu Ser Pro Ser Asn Gln Thr Glu Lys Gln
                210                 215                 220

Ala Ala Phe Cys Asn Gly Leu Ser Gln Pro Val Gln Asp Ala Arg Phe
225                 230                 235                 240

Gln Ile Ile Gln Leu Pro Asn Arg His Asp Phe His Met Asn Ile Leu
                245                 250                 255

Asp Thr Arg Arg Asn Asp Ser Gly Ile Tyr Leu Cys Gly Ala Ile Ser
                260                 265                 270

Leu His Pro Lys Ala Lys Ile Glu Glu Ser Pro Gly Ala Glu Leu Val
                275                 280                 285

Val Thr Glu Arg Ile Leu Glu Thr Ser Thr Arg Tyr Pro Ser Pro Ser
                290                 295                 300

Pro Lys Pro Glu Gly Arg Cys Cys Val Glu Cys Pro Pro Cys Pro Ala
305                 310                 315                 320

Pro Pro Val Ala Gly Thr Met Gly Gly Ala Ala Gly Ser Gly Ala Ala
                325                 330                 335

Glu Ala Gly Ile Thr Gly Thr Trp Tyr Asn Gln Leu Gly Ser Thr Phe
                340                 345                 350

Ile Val Thr Ala Gly Ala Asp Gly Ala Leu Thr Gly Thr Tyr Glu Ser
                355                 360                 365

Ala Val Gly Asn Ala Glu Ser Arg Tyr Val Leu Thr Gly Arg Tyr Glu
                370                 375                 380

Ser Ala Pro Ala Thr Asp Gly Ser Gly Thr Ala Leu Gly Trp Thr Val
385                 390                 395                 400

Ala Trp Lys Asn Asn Tyr Arg Asn Ala His Ser Ala Thr Thr Trp Ser
                405                 410                 415

Gly Gln Tyr Val Gly Gly Ala Glu Ala Arg Ile Asn Thr Gln Trp Leu
                420                 425                 430

Leu Thr Ser Gly Thr Thr Glu Ala Asn Ala Trp Lys Ser Thr Leu Val
                435                 440                 445

Gly His Asp Thr Phe Thr Lys Val Lys Pro Ser Ala Ala Ser Gly Ser
                450                 455                 460

Ala Ala Gly Ser Gly Ala Glu Ala Gly Ile Thr Gly Thr Trp Tyr
465                 470                 475                 480

Asn Gln Leu Gly Ser Thr Phe Ile Val Thr Ala Gly Ala Asp Gly Ala
                485                 490                 495

Leu Thr Gly Thr Tyr Glu Ser Ala Val Gly Asn Ala Glu Ser Arg Tyr
                500                 505                 510

Val Leu Thr Gly Arg Tyr Glu Ser Ala Pro Ala Thr Asp Gly Ser Gly
                515                 520                 525
```

Thr Ala Leu Gly Trp Thr Val Ala Trp Lys Asn Asn Tyr Arg Asn Ala
                530                 535                 540

His Ser Ala Thr Thr Trp Ser Gly Gln Tyr Val Gly Gly Ala Glu Ala
545                 550                 555                 560

Arg Ile Asn Thr Gln Trp Leu Leu Thr Ser Gly Thr Thr Glu Ala Asn
                565                 570                 575

Ala Trp Lys Ser Thr Leu Val Gly His Asp Thr Phe Thr Lys Val Lys
                580                 585                 590

Pro Ser Ala Ala Ser Gly Ser
                595

<210> SEQ ID NO 12
<211> LENGTH: 765
<212> TYPE: PRT
<213> ORGANISM: Artificial Sequence
<220> FEATURE:
<223> OTHER INFORMATION: PD-1 Fusion Polypeptide

<400> SEQUENCE: 12

Met Ser Pro Gln Arg Asp Arg Ile Asn Ala Phe Tyr Lys Asp Asn Pro
1               5                   10                  15

His Pro Lys Gly Ser Arg Ile Val Ile Asn Arg Glu His Leu Met Ile
                20                  25                  30

Asp Arg Pro Tyr Val Leu Leu Ala Val Leu Phe Val Met Phe Leu Ser
                35                  40                  45

Leu Ile Gly Leu Leu Ala Ile Ala Gly Ile Arg Leu His Arg Ala Ala
            50                  55                  60

Ile Tyr Thr Ala Glu Ile His Lys Ser Leu Ser Thr Asn Leu Asp Val
65              70                  75                  80

Thr Asn Ser Ile Glu His Gln Val Lys Asp Val Leu Thr Pro Leu Phe
                85                  90                  95

Lys Ile Ile Gly Asp Glu Val Gly Leu Arg Thr Pro Gln Arg Phe Thr
                100                 105                 110

Asp Leu Val Lys Phe Ile Ser Asp Lys Ile Lys Phe Leu Asn Pro Asp
            115                 120                 125

Arg Glu Tyr Asp Phe Arg Asp Leu Thr Trp Cys Ile Asn Pro Pro Glu
            130                 135                 140

Arg Ile Lys Leu Asp Tyr Asp Gln Tyr Cys Ala Asp Val Ala Ala Glu
145                 150                 155                 160

Glu Leu Met Asn Ala Leu Val Asn Ser Thr Leu Leu Glu Thr Arg Thr
                165                 170                 175

Thr Asn Gln Phe Leu Ala Val Ser Lys Gly Asn Cys Ser Gly Pro Thr
            180                 185                 190

Thr Ile Arg Gly Gln Phe Ser Asn Met Ser Leu Ser Leu Leu Asp Leu
            195                 200                 205

Tyr Leu Gly Arg Gly Tyr Asn Val Ser Ser Ile Val Thr Met Thr Ser
        210                 215                 220

Gln Gly Met Tyr Gly Gly Thr Tyr Leu Val Glu Lys Pro Asn Leu Ser
225                 230                 235                 240

Ser Lys Arg Ser Glu Leu Ser Gln Leu Ser Met Tyr Arg Val Phe Glu
                245                 250                 255

Val Gly Val Ile Arg Asn Pro Gly Leu Gly Ala Pro Val Phe His Met
                260                 265                 270

Thr Asn Tyr Leu Glu Gln Pro Val Ser Asn Asp Leu Ser Asn Cys Met
            275                 280                 285

-continued

Val Ala Leu Gly Glu Leu Lys Leu Ala Ala Leu Cys His Gly Glu Asp
    290                 295                 300

Ser Ile Thr Ile Pro Tyr Gln Gly Ser Gly Lys Gly Val Ser Phe Gln
305                 310                 315                 320

Leu Val Lys Leu Gly Val Trp Lys Ser Pro Thr Asp Met Gln Ser Trp
                325                 330                 335

Val Pro Leu Ser Thr Asp Asp Pro Val Ile Asp Arg Leu Tyr Leu Ser
            340                 345                 350

Ser His Arg Gly Val Ile Ala Asp Asn Gln Ala Lys Trp Ala Val Pro
        355                 360                 365

Thr Thr Arg Thr Asp Asp Lys Leu Arg Met Glu Thr Cys Phe Gln Gln
    370                 375                 380

Ala Cys Lys Gly Lys Ile Gln Ala Leu Cys Glu Asn Pro Glu Trp Ala
385                 390                 395                 400

Pro Leu Lys Asp Asn Arg Ile Pro Ser Tyr Gly Val Leu Ser Val Asp
                405                 410                 415

Leu Ser Leu Thr Val Glu Leu Lys Ile Lys Ile Ala Ser Gly Phe Gly
            420                 425                 430

Pro Leu Ile Thr His Gly Ser Gly Met Asp Leu Tyr Lys Ser Asn His
        435                 440                 445

Asn Asn Val Tyr Trp Leu Thr Ile Pro Pro Met Lys Asn Leu Ala Leu
    450                 455                 460

Gly Val Ile Asn Thr Leu Glu Trp Ile Pro Arg Phe Lys Val Ser Pro
465                 470                 475                 480

Ala Leu Phe Asn Val Pro Ile Lys Glu Ala Gly Gly Asp Cys His Ala
                485                 490                 495

Pro Thr Tyr Leu Pro Ala Glu Val Asp Gly Asp Val Lys Leu Ser Ser
            500                 505                 510

Asn Leu Val Ile Leu Pro Gly Gln Asp Leu Gln Tyr Val Leu Ala Thr
        515                 520                 525

Tyr Asp Thr Ser Ala Val Glu His Ala Val Val Tyr Tyr Val Tyr Ser
    530                 535                 540

Pro Ser Arg Ser Phe Ser Tyr Phe Tyr Pro Phe Arg Leu Pro Ile Lys
545                 550                 555                 560

Gly Val Pro Ile Glu Leu Gln Val Glu Cys Phe Thr Trp Asp Gln Lys
                565                 570                 575

Leu Trp Cys Arg His Phe Cys Val Leu Ala Asp Ser Glu Ser Gly Gly
            580                 585                 590

His Ile Thr His Ser Gly Met Val Gly Met Gly Val Ser Cys Thr Val
        595                 600                 605

Thr Arg Glu Asp Gly Thr Asn Ile Glu Gly Arg Pro Gly Trp Phe Leu
    610                 615                 620

Asp Ser Pro Asp Arg Pro Trp Asn Pro Pro Thr Phe Ser Pro Ala Leu
625                 630                 635                 640

Leu Val Val Thr Glu Gly Asp Asn Ala Thr Phe Thr Cys Ser Phe Ser
                645                 650                 655

Asn Thr Ser Glu Ser Phe His Val Ile Trp His Arg Glu Ser Pro Ser
            660                 665                 670

Gly Gln Thr Asp Thr Leu Ala Ala Phe Pro Glu Asp Arg Ser Gln Pro
        675                 680                 685

Gly Gln Asp Cys Arg Phe Arg Val Thr Gln Leu Pro Asn Gly Arg Asp
    690                 695                 700

Phe His Met Ser Val Val Arg Ala Arg Arg Asn Asp Ser Gly Thr Tyr
705                 710                 715                 720

Val Cys Gly Val Ile Ser Leu Ala Pro Lys Ile Gln Ile Lys Glu Ser
            725                 730                 735

Leu Arg Ala Glu Leu Arg Val Thr Glu Arg Arg Ala Glu Val Pro Thr
        740                 745                 750

Ala His Pro Ser Pro Ser Pro His His His His His
        755                 760                 765

<210> SEQ ID NO 13
<211> LENGTH: 385
<212> TYPE: PRT
<213> ORGANISM: Artificial Sequence
<220> FEATURE:
<223> OTHER INFORMATION: PD-1 Fusion Polypeptide

<400> SEQUENCE: 13

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Cys Cys Val Glu Cys Pro Pro Cys Pro Ala Pro Pro Val Ala Gly Pro
                165                 170                 175

Ser Val Phe Leu Phe Pro Pro Lys Pro Lys Asp Thr Leu Met Ile Ser
            180                 185                 190

Arg Thr Pro Glu Val Thr Cys Val Val Val Asp Val Ser His Glu Asp
        195                 200                 205

Pro Glu Val Gln Phe Asn Trp Tyr Val Asp Gly Val Glu Val His Asn
    210                 215                 220

Ala Lys Thr Lys Pro Arg Glu Glu Gln Phe Asn Ser Thr Phe Arg Val
225                 230                 235                 240

Val Ser Val Leu Thr Val Val His Gln Asp Trp Leu Asn Gly Lys Glu
                245                 250                 255

Tyr Lys Cys Lys Val Ser Asn Lys Gly Leu Pro Ala Pro Ile Glu Lys
            260                 265                 270

Thr Ile Ser Lys Thr Lys Gly Gln Pro Arg Glu Pro Gln Val Tyr Thr
        275                 280                 285

Leu Pro Pro Ser Arg Glu Glu Met Thr Lys Asn Gln Val Ser Leu Thr
    290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Met Leu
            325                 330                 335

Asp Ser Asp Gly Ser Phe Phe Leu Tyr Ser Lys Leu Thr Val Asp Lys
            340                 345                 350

Ser Arg Trp Gln Gln Gly Asn Val Phe Ser Cys Ser Val Met His Glu
            355                 360                 365

Ala Leu His Asn His Tyr Thr Gln Lys Ser Leu Ser Leu Ser Pro Gly
            370                 375                 380

Lys
385

<210> SEQ ID NO 14
<211> LENGTH: 268
<212> TYPE: PRT
<213> ORGANISM: Artificial Sequence
<220> FEATURE:
<223> OTHER INFORMATION: PD-1 Fusion Polypeptide

<400> SEQUENCE: 14

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
130                 135                 140

Thr Glu Arg Arg Ala Glu Val Pro Thr Ala His Pro Ser Pro Ser Pro
145                 150                 155                 160

Cys Cys Val Glu Cys Pro Pro Cys Pro Ala Pro Val Ala Gly Gly
                165                 170                 175

Ser Ala Asn Ser Phe Leu Glu Glu Met Lys Lys Gly His Leu Glu Arg
            180                 185                 190

Glu Cys Met Glu Glu Thr Cys Ser Tyr Glu Glu Ala Arg Glu Val Phe
        195                 200                 205

Glu Asp Ser Asp Lys Thr Asn Glu Phe Trp Asn Lys Tyr Lys Asp Gly
210                 215                 220

Asp Gln Cys Glu Thr Ser Pro Cys Gln Asn Gln Gly Lys Cys Lys Asp
225                 230                 235                 240

Gly Leu Gly Glu Tyr Thr Cys Thr Cys Leu Glu Gly Phe Glu Gly Lys
                245                 250                 255

Asn Cys Glu Leu Pro Val Gly Tyr Arg Gly Gly Ser
            260                 265

<210> SEQ ID NO 15
<211> LENGTH: 248
<212> TYPE: PRT
<213> ORGANISM: Artificial Sequence
<220> FEATURE:
<223> OTHER INFORMATION: PD-1 Fusion Polypeptide

<400> SEQUENCE: 15

```
Cys Cys Val Glu Cys Pro Pro Cys Pro Ala Pro Pro Val Ala Gly Gly
1               5                   10                  15

Ser Ala Asn Ser Phe Leu Glu Met Lys Lys Gly His Leu Glu Arg
            20                  25                  30

Glu Cys Met Glu Glu Thr Cys Ser Tyr Glu Glu Ala Arg Glu Val Phe
            35                  40                  45

Glu Asp Ser Asp Lys Thr Asn Glu Phe Trp Asn Lys Tyr Lys Asp Gly
        50                  55                  60

Asp Gln Cys Glu Thr Ser Pro Cys Gln Asn Gln Gly Lys Cys Lys Asp
65                  70                  75                  80

Gly Leu Gly Glu Tyr Thr Cys Thr Cys Leu Glu Gly Phe Glu Gly Lys
                85                  90                  95

Asn Cys Glu Leu Pro Val Gly Tyr Arg Gly Gly Ser Pro Gly Trp Phe
            100                 105                 110

Leu Asp Ser Pro Asp Arg Pro Trp Asn Pro Pro Thr Phe Ser Pro Ala
        115                 120                 125

Leu Leu Val Val Thr Glu Gly Asp Asn Ala Thr Phe Thr Cys Ser Phe
130                 135                 140

Ser Asn Thr Ser Glu Ser Phe Val Leu Asn Trp Tyr Arg Met Ser Pro
145                 150                 155                 160

Ser Asn Gln Thr Asp Lys Leu Ala Ala Phe Pro Glu Asp Arg Ser Gln
                165                 170                 175

Pro Gly Gln Asp Cys Arg Phe Arg Val Thr Gln Leu Pro Asn Gly Arg
            180                 185                 190

Asp Phe His Met Ser Val Val Arg Ala Arg Arg Asn Asp Ser Gly Thr
        195                 200                 205

Tyr Leu Cys Gly Ala Ile Ser Leu Ala Pro Lys Ala Gln Ile Lys Glu
    210                 215                 220

Ser Leu Arg Ala Glu Leu Arg Val Thr Glu Arg Arg Ala Glu Val Pro
225                 230                 235                 240

Thr Ala His Pro Ser Pro Ser Pro
                245
```

<210> SEQ ID NO 16
<211> LENGTH: 305
<212> TYPE: PRT
<213> ORGANISM: Artificial Sequence
<220> FEATURE:
<223> OTHER INFORMATION: PD-1 Fusion Polypeptide

<400> SEQUENCE: 16

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60
```

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
130                 135                 140

Thr Glu Arg Arg Ala Glu Val Pro Thr Ala His Pro Ser Pro Ser Pro
145                 150                 155                 160

Cys Cys Val Glu Cys Pro Pro Cys Pro Ala Pro Val Ala Gly Ser
                165                 170                 175

Lys Gly Leu Glu Ser Arg Val Ser Ala Leu Glu Lys Thr Ser Gln Ile
            180                 185                 190

His Ser Asp Thr Ile Leu Arg Ile Thr Gln Gly Leu Asp Asp Ala Asn
        195                 200                 205

Lys Arg Ile Ile Ala Leu Glu Gln Ser Arg Asp Asp Leu Val Ala Ser
210                 215                 220

Val Ser Asp Ala Gln Leu Ala Ile Ser Arg Leu Glu Ser Ser Ile Gly
225                 230                 235                 240

Ala Leu Gln Thr Val Val Asn Gly Leu Asp Ser Ser Val Thr Gln Leu
            245                 250                 255

Gly Ala Arg Val Gly Gln Leu Glu Thr Gly Leu Ala Glu Leu Arg Val
        260                 265                 270

Asp His Asp Asn Leu Val Ala Arg Val Asp Thr Ala Glu Arg Asn Ile
    275                 280                 285

Gly Ser Leu Thr Thr Glu Leu Ser Thr Leu Thr Leu Arg Val Thr Ser
    290                 295                 300

Ile
305

<210> SEQ ID NO 17
<211> LENGTH: 594
<212> TYPE: PRT
<213> ORGANISM: Artificial Sequence
<220> FEATURE:
<223> OTHER INFORMATION: PD-1 Fusion Polypeptide

<400> SEQUENCE: 17

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

-continued

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
130                 135                 140

Thr Glu Arg Arg Ala Glu Val Pro Thr Ala His Pro Ser Pro Ser Pro
145                 150                 155                 160

Ser Gly Trp Leu Leu Glu Val Pro Asn Gly Pro Trp Arg Ser Leu Thr
                165                 170                 175

Phe Tyr Pro Ala Trp Leu Thr Val Ser Glu Gly Ala Asn Ala Thr Phe
            180                 185                 190

Thr Cys Ser Leu Ser Asn Trp Ser Glu Asp Leu Met Leu Asn Trp Asn
        195                 200                 205

Arg Leu Ser Pro Ser Asn Gln Thr Glu Lys Gln Ala Ala Phe Cys Asn
    210                 215                 220

Gly Leu Ser Gln Pro Val Gln Asp Ala Arg Phe Gln Ile Ile Gln Leu
225                 230                 235                 240

Pro Asn Arg His Asp Phe His Met Asn Ile Leu Asp Thr Arg Arg Asn
                245                 250                 255

Asp Ser Gly Ile Tyr Leu Cys Gly Ala Ile Ser Leu His Pro Lys Ala
            260                 265                 270

Lys Ile Glu Glu Ser Pro Gly Ala Glu Leu Val Val Thr Glu Arg Ile
        275                 280                 285

Leu Glu Thr Ser Thr Arg Tyr Pro Ser Pro Ser Pro Lys Pro Glu Gly
    290                 295                 300

Arg Cys Cys Val Glu Cys Pro Pro Cys Pro Ala Pro Pro Val Ala Gly
305                 310                 315                 320

Thr Met Gly Gly Ala Ala Gly Ser Gly Ala Ala Glu Ala Gly Ile Thr
                325                 330                 335

Gly Thr Trp Tyr Asn Gln Leu Gly Ser Thr Phe Ile Val Thr Ala Gly
            340                 345                 350

Ala Asp Gly Ala Leu Thr Gly Thr Tyr Glu Ser Ala Val Gly Asn Ala
        355                 360                 365

Glu Ser Arg Tyr Val Leu Thr Gly Arg Tyr Glu Ser Ala Pro Ala Thr
    370                 375                 380

Asp Gly Ser Gly Thr Ala Leu Gly Trp Thr Val Ala Trp Lys Asn Asn
385                 390                 395                 400

Tyr Arg Asn Ala His Ser Ala Thr Thr Trp Ser Gly Gln Tyr Val Gly
                405                 410                 415

Gly Ala Glu Ala Arg Ile Asn Thr Gln Trp Leu Leu Thr Ser Gly Thr
            420                 425                 430

Thr Glu Ala Asn Ala Trp Lys Ser Thr Leu Val Gly His Asp Thr Phe
        435                 440                 445

Thr Lys Val Lys Pro Ser Ala Ala Ser Gly Ser Ala Ala Gly Ser Gly
    450                 455                 460

Ala Ala Glu Ala Gly Ile Thr Gly Thr Trp Tyr Asn Gln Leu Gly Ser
465                 470                 475                 480

Thr Phe Ile Val Thr Ala Gly Ala Asp Gly Ala Leu Thr Gly Thr Tyr
                485                 490                 495

Glu Ser Ala Val Gly Asn Ala Glu Ser Arg Tyr Val Leu Thr Gly Arg
            500                 505                 510

Tyr Glu Ser Ala Pro Ala Thr Asp Gly Ser Gly Thr Ala Leu Gly Trp
        515                 520                 525

```
Thr Val Ala Trp Lys Asn Asn Tyr Arg Asn Ala His Ser Ala Thr Thr
            530                 535                 540

Trp Ser Gly Gln Tyr Val Gly Ala Glu Ala Arg Ile Asn Thr Gln
545                 550                 555                 560

Trp Leu Leu Thr Ser Gly Thr Thr Glu Ala Asn Ala Trp Lys Ser Thr
                565                 570                 575

Leu Val Gly His Asp Thr Phe Thr Lys Val Lys Pro Ser Ala Ala Ser
            580                 585                 590

Gly Ser

<210> SEQ ID NO 18
<211> LENGTH: 765
<212> TYPE: PRT
<213> ORGANISM: Artificial Sequence
<220> FEATURE:
<223> OTHER INFORMATION: PD-1 Fusion Polypeptide

<400> SEQUENCE: 18

Met Ser Pro Gln Arg Asp Arg Ile Asn Ala Phe Tyr Lys Asp Asn Pro
1               5                   10                  15

His Pro Lys Gly Ser Arg Ile Val Ile Asn Arg Glu His Leu Met Ile
            20                  25                  30

Asp Arg Pro Tyr Val Leu Leu Ala Val Leu Phe Val Met Phe Leu Ser
        35                  40                  45

Leu Ile Gly Leu Leu Ala Ile Ala Gly Ile Arg Leu His Arg Ala Ala
    50                  55                  60

Ile Tyr Thr Ala Glu Ile His Lys Ser Leu Ser Thr Asn Leu Asp Val
65                  70                  75                  80

Thr Asn Ser Ile Glu His Gln Val Lys Asp Val Leu Thr Pro Leu Phe
                85                  90                  95

Lys Ile Ile Gly Asp Glu Val Gly Leu Arg Thr Pro Gln Arg Phe Thr
            100                 105                 110

Asp Leu Val Lys Phe Ile Ser Asp Lys Ile Lys Phe Leu Asn Pro Asp
        115                 120                 125

Arg Glu Tyr Asp Phe Arg Asp Leu Thr Trp Cys Ile Asn Pro Pro Glu
    130                 135                 140

Arg Ile Lys Leu Asp Tyr Asp Gln Tyr Cys Ala Asp Val Ala Ala Glu
145                 150                 155                 160

Glu Leu Met Asn Ala Leu Val Asn Ser Thr Leu Leu Glu Thr Arg Thr
                165                 170                 175

Thr Asn Gln Phe Leu Ala Val Ser Lys Gly Asn Cys Ser Gly Pro Thr
            180                 185                 190

Thr Ile Arg Gly Gln Phe Ser Asn Met Ser Leu Ser Leu Leu Asp Leu
        195                 200                 205

Tyr Leu Gly Arg Gly Tyr Asn Val Ser Ser Ile Val Thr Met Thr Ser
    210                 215                 220

Gln Gly Met Tyr Gly Gly Thr Tyr Leu Val Glu Lys Pro Asn Leu Ser
225                 230                 235                 240

Ser Lys Arg Ser Glu Leu Ser Gln Leu Ser Met Tyr Arg Val Phe Glu
                245                 250                 255

Val Gly Val Ile Arg Asn Pro Gly Leu Gly Ala Pro Val Phe His Met
            260                 265                 270

Thr Asn Tyr Leu Glu Gln Pro Val Ser Asn Asp Leu Ser Asn Cys Met
        275                 280                 285

Val Ala Leu Gly Glu Leu Lys Leu Ala Ala Leu Cys His Gly Glu Asp
```

```
            290                 295                 300
Ser Ile Thr Ile Pro Tyr Gln Gly Ser Gly Lys Gly Val Ser Phe Gln
305                 310                 315                 320

Leu Val Lys Leu Gly Val Trp Lys Ser Pro Thr Asp Met Gln Ser Trp
                325                 330                 335

Val Pro Leu Ser Thr Asp Asp Pro Val Ile Asp Arg Leu Tyr Leu Ser
                340                 345                 350

Ser His Arg Gly Val Ile Ala Asp Asn Gln Ala Lys Trp Ala Val Pro
                355                 360                 365

Thr Thr Arg Thr Asp Asp Lys Leu Arg Met Glu Thr Cys Phe Gln Gln
        370                 375                 380

Ala Cys Lys Gly Lys Ile Gln Ala Leu Cys Glu Asn Pro Glu Trp Ala
385                 390                 395                 400

Pro Leu Lys Asp Asn Arg Ile Pro Ser Tyr Gly Val Leu Ser Val Asp
                405                 410                 415

Leu Ser Leu Thr Val Glu Leu Lys Ile Lys Ile Ala Ser Gly Phe Gly
                420                 425                 430

Pro Leu Ile Thr His Gly Ser Gly Met Asp Leu Tyr Lys Ser Asn His
            435                 440                 445

Asn Asn Val Tyr Trp Leu Thr Ile Pro Pro Met Lys Asn Leu Ala Leu
450                 455                 460

Gly Val Ile Asn Thr Leu Glu Trp Ile Pro Arg Phe Lys Val Ser Pro
465                 470                 475                 480

Ala Leu Phe Asn Val Pro Ile Lys Glu Ala Gly Gly Asp Cys His Ala
                485                 490                 495

Pro Thr Tyr Leu Pro Ala Glu Val Asp Gly Asp Val Lys Leu Ser Ser
                500                 505                 510

Asn Leu Val Ile Leu Pro Gly Gln Asp Leu Gln Tyr Val Leu Ala Thr
            515                 520                 525

Tyr Asp Thr Ser Ala Val Glu His Ala Val Tyr Tyr Val Tyr Ser
530                 535                 540

Pro Ser Arg Ser Phe Ser Tyr Phe Tyr Pro Phe Arg Leu Pro Ile Lys
545                 550                 555                 560

Gly Val Pro Ile Glu Leu Gln Val Glu Cys Phe Thr Trp Asp Gln Lys
                565                 570                 575

Leu Trp Cys Arg His Phe Cys Val Leu Ala Asp Ser Glu Ser Gly Gly
            580                 585                 590

His Ile Thr His Ser Gly Met Val Gly Met Gly Val Ser Cys Thr Val
            595                 600                 605

Thr Arg Glu Asp Gly Thr Asn Ile Glu Gly Arg Pro Gly Trp Phe Leu
    610                 615                 620

Asp Ser Pro Asp Arg Pro Trp Asn Pro Pro Thr Phe Ser Pro Ala Leu
625                 630                 635                 640

Leu Val Val Thr Glu Gly Asp Asn Ala Thr Phe Thr Cys Ser Phe Ser
                645                 650                 655

Asn Thr Ser Glu Ser Phe Val Leu Asn Trp Tyr Arg Met Ser Pro Ser
            660                 665                 670

Asn Gln Thr Asp Lys Leu Ala Ala Phe Pro Glu Asp Arg Ser Gln Pro
            675                 680                 685

Gly Gln Asp Cys Arg Phe Arg Val Thr Gln Leu Pro Asn Gly Arg Asp
        690                 695                 700

Phe His Met Ser Val Val Arg Ala Arg Arg Asn Asp Ser Gly Thr Tyr
705                 710                 715                 720
```

```
Leu Cys Gly Ala Ile Ser Leu Ala Pro Lys Ala Gln Ile Lys Glu Ser
                725                 730                 735

Leu Arg Ala Glu Leu Arg Val Thr Glu Arg Arg Ala Glu Val Pro Thr
            740                 745                 750

Ala His Pro Ser Pro Ser Pro His His His His His His
        755                 760                 765

<210> SEQ ID NO 19
<211> LENGTH: 765
<212> TYPE: PRT
<213> ORGANISM: Artificial Sequence
<220> FEATURE:
<223> OTHER INFORMATION: PD-1 Fusion Polypeptide

<400> SEQUENCE: 19

Met Ser Pro Gln Arg Asp Arg Ile Asn Ala Phe Tyr Lys Asp Asn Pro
1               5                   10                  15

His Pro Lys Gly Ser Arg Ile Val Ile Asn Arg Glu His Leu Met Ile
            20                  25                  30

Asp Arg Pro Tyr Val Leu Leu Ala Val Leu Phe Val Met Phe Leu Ser
        35                  40                  45

Leu Ile Gly Leu Leu Ala Ile Ala Gly Ile Arg Leu His Arg Ala Ala
    50                  55                  60

Ile Tyr Thr Ala Glu Ile His Lys Ser Leu Ser Thr Asn Leu Asp Val
65              70                  75                  80

Thr Asn Ser Ile Glu His Gln Val Lys Asp Val Leu Thr Pro Leu Phe
                85                  90                  95

Lys Ile Ile Gly Asp Glu Val Gly Leu Arg Thr Pro Gln Arg Phe Thr
            100                 105                 110

Asp Leu Val Lys Phe Ile Ser Asp Lys Ile Lys Phe Leu Asn Pro Asp
        115                 120                 125

Arg Glu Tyr Asp Phe Arg Asp Leu Thr Trp Cys Ile Asn Pro Pro Glu
    130                 135                 140

Arg Ile Lys Leu Asp Tyr Asp Gln Tyr Cys Ala Asp Val Ala Ala Glu
145             150                 155                 160

Glu Leu Met Asn Ala Leu Val Asn Ser Thr Leu Leu Glu Thr Arg Thr
                165                 170                 175

Thr Asn Gln Phe Leu Ala Val Ser Lys Gly Asn Cys Ser Gly Pro Thr
            180                 185                 190

Thr Ile Arg Gly Gln Phe Ser Asn Met Ser Leu Ser Leu Leu Asp Leu
        195                 200                 205

Tyr Leu Gly Arg Gly Tyr Asn Val Ser Ser Ile Val Thr Met Thr Ser
    210                 215                 220

Gln Gly Met Tyr Gly Gly Thr Tyr Leu Val Glu Lys Pro Asn Leu Ser
225             230                 235                 240

Ser Lys Arg Ser Glu Leu Ser Gln Leu Ser Met Tyr Arg Val Phe Glu
                245                 250                 255

Val Gly Val Ile Arg Asn Pro Gly Leu Gly Ala Pro Val Phe His Met
            260                 265                 270

Thr Asn Tyr Leu Glu Gln Pro Val Ser Asn Asp Leu Ser Asn Cys Met
        275                 280                 285

Val Ala Leu Gly Glu Leu Lys Leu Ala Ala Leu Cys His Gly Glu Asp
    290                 295                 300

Ser Ile Thr Ile Pro Tyr Gln Gly Ser Gly Lys Gly Val Ser Phe Gln
305             310                 315                 320
```

```
Leu Val Lys Leu Gly Val Trp Lys Ser Pro Thr Asp Met Gln Ser Trp
            325                 330                 335

Val Pro Leu Ser Thr Asp Pro Val Ile Asp Arg Leu Tyr Leu Ser
        340                 345                 350

Ser His Arg Gly Val Ile Ala Asp Asn Gln Ala Lys Trp Ala Val Pro
        355                 360                 365

Thr Thr Arg Thr Asp Asp Lys Leu Arg Met Glu Thr Cys Phe Gln Gln
370                 375                 380

Ala Cys Lys Gly Lys Ile Gln Ala Leu Cys Glu Asn Pro Glu Trp Ala
385                 390                 395                 400

Pro Leu Lys Asp Asn Arg Ile Pro Ser Tyr Gly Val Leu Ser Val Asp
                405                 410                 415

Leu Ser Leu Thr Val Glu Leu Lys Ile Lys Ile Ala Ser Gly Phe Gly
                420                 425                 430

Pro Leu Ile Thr His Gly Ser Gly Met Asp Leu Tyr Lys Ser Asn His
                435                 440                 445

Asn Asn Val Tyr Trp Leu Thr Ile Pro Pro Met Lys Asn Leu Ala Leu
        450                 455                 460

Gly Val Ile Asn Thr Leu Glu Trp Ile Pro Arg Phe Lys Val Ser Pro
465                 470                 475                 480

Ala Leu Phe Asn Val Pro Ile Lys Glu Ala Gly Gly Asp Cys His Ala
                485                 490                 495

Pro Thr Tyr Leu Pro Ala Glu Val Asp Gly Asp Val Lys Leu Ser Ser
                500                 505                 510

Asn Leu Val Ile Leu Pro Gly Gln Asp Leu Gln Tyr Val Leu Ala Thr
                515                 520                 525

Tyr Asp Thr Ser Ala Val Glu His Ala Val Val Tyr Tyr Val Tyr Ser
        530                 535                 540

Pro Ser Arg Leu Ser Ser Tyr Phe Tyr Pro Phe Arg Leu Pro Ile Lys
545                 550                 555                 560

Gly Val Pro Ile Glu Leu Gln Val Glu Cys Phe Thr Trp Asp Gln Lys
                565                 570                 575

Leu Trp Cys Arg His Phe Cys Val Leu Ala Asp Ser Glu Ser Gly Gly
                580                 585                 590

His Ile Thr His Ser Gly Met Val Gly Met Gly Val Ser Cys Thr Val
                595                 600                 605

Thr Arg Glu Asp Gly Thr Asn Ile Glu Gly Arg Pro Gly Trp Phe Leu
        610                 615                 620

Asp Ser Pro Asp Arg Pro Trp Asn Pro Pro Thr Phe Ser Pro Ala Leu
625                 630                 635                 640

Leu Val Val Thr Glu Gly Asp Asn Ala Thr Phe Thr Cys Ser Phe Ser
                645                 650                 655

Asn Thr Ser Glu Ser Phe Val Leu Asn Trp Tyr Arg Met Ser Pro Ser
                660                 665                 670

Asn Gln Thr Asp Lys Leu Ala Ala Phe Pro Glu Asp Arg Ser Gln Pro
                675                 680                 685

Gly Gln Asp Cys Arg Phe Arg Val Thr Gln Leu Pro Asn Gly Arg Asp
                690                 695                 700

Phe His Met Ser Val Val Arg Ala Arg Arg Asn Asp Ser Gly Thr Tyr
705                 710                 715                 720

Leu Cys Gly Ala Ile Ser Leu Ala Pro Lys Ala Gln Ile Lys Glu Ser
                725                 730                 735
```

```
Leu Arg Ala Glu Leu Arg Val Thr Glu Arg Arg Ala Glu Val Pro Thr
                740                 745                 750

Ala His Pro Ser Pro Ser Pro His His His His His His
        755                 760                 765

<210> SEQ ID NO 20
<211> LENGTH: 754
<212> TYPE: PRT
<213> ORGANISM: Artificial Sequence
<220> FEATURE:
<223> OTHER INFORMATION: PD-1 Fusion Polypeptide

<400> SEQUENCE: 20

Met Leu Pro Tyr Gln Asp Lys Val Gly Ala Phe Tyr Lys Asp Asn Ala
1               5                   10                  15

Arg Ala Asn Ser Thr Lys Leu Ser Leu Val Thr Glu Gly His Gly Gly
            20                  25                  30

Arg Arg Pro Pro Tyr Leu Leu Phe Val Leu Leu Ile Leu Leu Val Gly
        35                  40                  45

Ile Leu Ala Leu Leu Ala Ile Thr Gly Val Arg Phe His Gln Val Ser
    50                  55                  60

Thr Ser Asn Met Glu Phe Ser Arg Leu Leu Lys Glu Asp Met Glu Lys
65                  70                  75                  80

Ser Glu Ala Val His His Gln Val Ile Asp Val Leu Thr Pro Leu Phe
                85                  90                  95

Lys Ile Ile Gly Asp Glu Ile Gly Leu Arg Leu Pro Gln Lys Leu Asn
            100                 105                 110

Glu Ile Lys Gln Phe Ile Leu Gln Lys Thr Asn Phe Asn Pro Asn
        115                 120                 125

Arg Glu Phe Asp Phe Arg Asp Leu His Trp Cys Ile Asn Pro Pro Ser
130                 135                 140

Thr Val Lys Val Asn Phe Thr Asn Tyr Cys Glu Ser Ile Gly Ile Arg
145                 150                 155                 160

Lys Ala Ile Ala Ser Ala Ala Asn Pro Ile Leu Leu Ser Ala Leu Ser
                165                 170                 175

Gly Gly Arg Gly Asp Ile Phe Pro Pro His Arg Cys Ser Gly Ala Thr
            180                 185                 190

Thr Ser Val Gly Lys Val Phe Pro Leu Ser Val Ser Leu Ser Met Ser
        195                 200                 205

Leu Ile Ser Arg Thr Ser Glu Val Ile Asn Met Leu Thr Ala Ile Ser
    210                 215                 220

Asp Gly Val Tyr Gly Lys Thr Tyr Leu Leu Val Pro Asp Asp Ile Glu
225                 230                 235                 240

Arg Glu Phe Asp Thr Arg Glu Ile Arg Val Phe Glu Ile Gly Phe Ile
                245                 250                 255

Lys Arg Trp Leu Asn Asp Met Pro Leu Leu Gln Thr Thr Asn Tyr Met
            260                 265                 270

Val Leu Pro Lys Asn Ser Lys Ala Lys Val Cys Thr Ile Ala Val Gly
        275                 280                 285

Glu Leu Thr Leu Ala Ser Leu Cys Val Glu Glu Ser Thr Val Leu Leu
    290                 295                 300

Tyr His Asp Ser Ser Gly Ser Gln Asp Gly Ile Leu Val Val Thr Leu
305                 310                 315                 320

Gly Ile Phe Trp Ala Thr Pro Met Asp His Ile Glu Glu Val Ile Pro
                325                 330                 335
```

Val Ala His Pro Ser Met Lys Lys Ile His Ile Thr Asn His Arg Gly
                340                 345                 350

Phe Ile Lys Asp Ser Ile Ala Thr Trp Met Val Pro Ala Leu Ala Ser
            355                 360                 365

Glu Lys Gln Glu Glu Gln Lys Gly Cys Leu Glu Ser Ala Cys Gln Arg
        370                 375                 380

Lys Thr Tyr Pro Met Cys Asn Gln Ala Ser Trp Glu Pro Phe Gly Gly
385                 390                 395                 400

Arg Gln Leu Pro Ser Tyr Gly Arg Leu Thr Leu Pro Leu Asp Ala Ser
                405                 410                 415

Val Asp Leu Gln Leu Asn Ile Ser Phe Thr Tyr Gly Pro Val Ile Leu
            420                 425                 430

Asn Gly Asp Gly Met Asp Tyr Tyr Glu Ser Pro Leu Leu Asn Ser Gly
        435                 440                 445

Trp Leu Thr Ile Pro Pro Lys Asp Gly Thr Ile Ser Gly Leu Ile Asn
                450                 455                 460

Lys Ala Gly Arg Gly Asp Gln Phe Thr Val Leu Pro His Val Leu Thr
465                 470                 475                 480

Phe Ala Pro Arg Glu Ser Ser Gly Asn Cys Tyr Leu Pro Ile Gln Thr
                485                 490                 495

Ser Gln Ile Arg Asp Arg Asp Val Leu Ile Glu Ser Asn Ile Val Val
            500                 505                 510

Leu Pro Thr Gln Ser Ile Arg Tyr Val Ile Ala Thr Tyr Asp Ile Ser
        515                 520                 525

Arg Ser Asp His Ala Ile Val Tyr Tyr Val Tyr Asp Pro Ile Arg Thr
            530                 535                 540

Ile Ser Tyr Thr His Pro Phe Arg Leu Thr Thr Lys Gly Arg Pro Asp
545                 550                 555                 560

Phe Leu Arg Ile Glu Cys Phe Val Trp Asp Asp Asn Leu Trp Cys His
                565                 570                 575

Gln Phe Tyr Arg Phe Glu Ala Asp Ile Ala Asn Ser Thr Thr Ser Val
            580                 585                 590

Glu Asn Leu Val Arg Ile Arg Phe Ser Cys Asn Arg Ile Glu Gly Arg
        595                 600                 605

Pro Gly Trp Phe Leu Asp Ser Pro Asp Arg Pro Trp Asn Pro Pro Thr
    610                 615                 620

Phe Ser Pro Ala Leu Leu Val Val Thr Glu Gly Asp Asn Ala Thr Phe
625                 630                 635                 640

Thr Cys Ser Phe Ser Asn Thr Ser Glu Ser Phe Val Leu Asn Trp Tyr
                645                 650                 655

Arg Met Ser Pro Ser Asn Gln Thr Asp Lys Leu Ala Ala Phe Pro Glu
            660                 665                 670

Asp Arg Ser Gln Pro Gly Gln Asp Cys Arg Phe Arg Val Thr Gln Leu
        675                 680                 685

Pro Asn Gly Arg Asp Phe His Met Ser Val Val Arg Ala Arg Arg Asn
    690                 695                 700

Asp Ser Gly Thr Tyr Leu Cys Gly Ala Ile Ser Leu Ala Pro Lys Ala
705                 710                 715                 720

Gln Ile Lys Glu Ser Leu Arg Ala Glu Leu Arg Val Thr Glu Arg Arg
                725                 730                 735

Ala Glu Val Pro Thr Ala His Pro Ser Pro Ser Pro His His His His
            740                 745                 750

His His

<210> SEQ ID NO 21
<211> LENGTH: 385
<212> TYPE: PRT
<213> ORGANISM: Artificial Sequence
<220> FEATURE:
<223> OTHER INFORMATION: PD-1 Fusion Polypeptide

<400> SEQUENCE: 21

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe His
    50                  55                  60

Val Ile Trp His Arg Glu Ser Pro Ser Gly Gln Thr Asp Thr Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Val Cys Gly Val Ile Ser Leu
        115                 120                 125

Ala Pro Lys Ile Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Cys Cys Val Glu Cys Pro Pro Cys Pro Ala Pro Pro Val Ala Gly Pro
                165                 170                 175

Ser Val Phe Leu Phe Pro Pro Lys Pro Lys Asp Thr Leu Met Ile Ser
            180                 185                 190

Arg Thr Pro Glu Val Thr Cys Val Val Val Asp Val Ser His Glu Asp
        195                 200                 205

Pro Glu Val Gln Phe Asn Trp Tyr Val Asp Gly Val Glu Val His Asn
    210                 215                 220

Ala Lys Thr Lys Pro Arg Glu Glu Gln Phe Asn Ser Thr Phe Arg Val
225                 230                 235                 240

Val Ser Val Leu Thr Val Val His Gln Asp Trp Leu Asn Gly Lys Glu
                245                 250                 255

Tyr Lys Cys Lys Val Ser Asn Lys Gly Leu Pro Ala Pro Ile Glu Lys
            260                 265                 270

Thr Ile Ser Lys Thr Lys Gly Gln Pro Arg Glu Pro Gln Val Tyr Thr
        275                 280                 285

Leu Pro Pro Ser Arg Glu Glu Met Thr Lys Asn Gln Val Ser Leu Thr
    290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Met Leu
                325                 330                 335

Asp Ser Asp Gly Ser Phe Phe Leu Tyr Ser Lys Leu Thr Val Asp Lys
            340                 345                 350

Ser Arg Trp Gln Gln Gly Asn Val Phe Ser Cys Ser Val Met His Glu
        355                 360                 365
```

Ala Leu His Asn His Tyr Thr Gln Lys Ser Leu Ser Leu Ser Pro Gly
        370                 375                 380
Lys
385

<210> SEQ ID NO 22
<211> LENGTH: 268
<212> TYPE: PRT
<213> ORGANISM: Artificial Sequence
<220> FEATURE:
<223> OTHER INFORMATION: PD-1 Fusion Polypeptide

<400> SEQUENCE: 22

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe His
    50                  55                  60

Val Ile Trp His Arg Glu Ser Pro Ser Gly Gln Thr Asp Thr Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Val Cys Gly Val Ile Ser Leu
        115                 120                 125

Ala Pro Lys Ile Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Cys Cys Val Glu Cys Pro Pro Cys Pro Ala Pro Pro Val Ala Gly Gly
                165                 170                 175

Ser Ala Asn Ser Phe Leu Glu Glu Met Lys Lys Gly His Leu Glu Arg
            180                 185                 190

Glu Cys Met Glu Glu Thr Cys Ser Tyr Glu Glu Ala Arg Glu Val Phe
        195                 200                 205

Glu Asp Ser Asp Lys Thr Asn Glu Phe Trp Asn Lys Tyr Lys Asp Gly
    210                 215                 220

Asp Gln Cys Glu Thr Ser Pro Cys Gln Asn Gln Gly Lys Cys Lys Asp
225                 230                 235                 240

Gly Leu Gly Glu Tyr Thr Cys Thr Cys Leu Glu Gly Phe Glu Gly Lys
                245                 250                 255

Asn Cys Glu Leu Pro Val Gly Tyr Arg Gly Gly Ser
            260                 265

<210> SEQ ID NO 23
<211> LENGTH: 248
<212> TYPE: PRT
<213> ORGANISM: Artificial Sequence
<220> FEATURE:
<223> OTHER INFORMATION: PD-1 Fusion Polypeptide

<400> SEQUENCE: 23

Cys Cys Val Glu Cys Pro Pro Cys Pro Ala Pro Pro Val Ala Gly Gly

```
 1               5                   10                  15
Ser Ala Asn Ser Phe Leu Glu Glu Met Lys Lys Gly His Leu Glu Arg
            20                  25                  30

Glu Cys Met Glu Glu Thr Cys Ser Tyr Glu Glu Ala Arg Glu Val Phe
            35                  40                  45

Glu Asp Ser Asp Lys Thr Asn Glu Phe Trp Asn Lys Tyr Lys Asp Gly
        50                  55                  60

Asp Gln Cys Glu Thr Ser Pro Cys Gln Asn Gln Gly Lys Cys Lys Asp
65                  70                  75                  80

Gly Leu Gly Glu Tyr Thr Cys Thr Cys Leu Glu Gly Phe Glu Gly Lys
                85                  90                  95

Asn Cys Glu Leu Pro Val Gly Tyr Arg Gly Gly Ser Pro Gly Trp Phe
            100                 105                 110

Leu Asp Ser Pro Asp Arg Pro Trp Asn Pro Pro Thr Phe Ser Pro Ala
        115                 120                 125

Leu Leu Val Val Thr Glu Gly Asp Asn Ala Thr Phe Thr Cys Ser Phe
    130                 135                 140

Ser Asn Thr Ser Glu Ser Phe His Val Ile Trp His Arg Glu Ser Pro
145                 150                 155                 160

Ser Gly Gln Thr Asp Thr Leu Ala Ala Phe Pro Glu Asp Arg Ser Gln
                165                 170                 175

Pro Gly Gln Asp Cys Arg Phe Arg Val Thr Gln Leu Pro Asn Gly Arg
            180                 185                 190

Asp Phe His Met Ser Val Val Arg Ala Arg Arg Asn Asp Ser Gly Thr
        195                 200                 205

Tyr Val Cys Gly Val Ile Ser Leu Ala Pro Lys Ile Gln Ile Lys Glu
    210                 215                 220

Ser Leu Arg Ala Glu Leu Arg Val Thr Glu Arg Arg Ala Glu Val Pro
225                 230                 235                 240

Thr Ala His Pro Ser Pro Ser Pro
                245
```

<210> SEQ ID NO 24
<211> LENGTH: 305
<212> TYPE: PRT
<213> ORGANISM: Artificial Sequence
<220> FEATURE:
<223> OTHER INFORMATION: PD-1 Fusion Polypeptide

<400> SEQUENCE: 24

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe His
        50                  55                  60

Val Ile Trp His Arg Glu Ser Pro Ser Gly Gln Thr Asp Thr Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Val Cys Gly Val Ile Ser Leu
```

```
            115                 120                 125
Ala Pro Lys Ile Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Cys Cys Val Glu Cys Pro Pro Cys Pro Ala Pro Pro Val Ala Gly Ser
                165                 170                 175

Lys Gly Leu Glu Ser Arg Val Ser Ala Leu Glu Lys Thr Ser Gln Ile
            180                 185                 190

His Ser Asp Thr Ile Leu Arg Ile Thr Gln Gly Leu Asp Asp Ala Asn
            195                 200                 205

Lys Arg Ile Ile Ala Leu Glu Gln Ser Arg Asp Asp Leu Val Ala Ser
            210                 215                 220

Val Ser Asp Ala Gln Leu Ala Ile Ser Arg Leu Glu Ser Ser Ile Gly
225                 230                 235                 240

Ala Leu Gln Thr Val Val Asn Gly Leu Asp Ser Ser Val Thr Gln Leu
                245                 250                 255

Gly Ala Arg Val Gly Gln Leu Glu Thr Gly Leu Ala Glu Leu Arg Val
            260                 265                 270

Asp His Asp Asn Leu Val Ala Arg Val Asp Thr Ala Glu Arg Asn Ile
            275                 280                 285

Gly Ser Leu Thr Thr Glu Leu Ser Thr Leu Thr Leu Arg Val Thr Ser
            290                 295                 300

Ile
305

<210> SEQ ID NO 25
<211> LENGTH: 765
<212> TYPE: PRT
<213> ORGANISM: Artificial Sequence
<220> FEATURE:
<223> OTHER INFORMATION: PD-1 Fusion Polypeptide

<400> SEQUENCE: 25

Met Ser Pro Gln Arg Asp Arg Ile Asn Ala Phe Tyr Lys Asp Asn Pro
1               5                   10                  15

His Pro Lys Gly Ser Arg Ile Val Ile Asn Arg Glu His Leu Met Ile
                20                  25                  30

Asp Arg Pro Tyr Val Leu Leu Ala Val Leu Phe Val Met Phe Leu Ser
            35                  40                  45

Leu Ile Gly Leu Leu Ala Ile Ala Gly Ile Arg Leu His Arg Ala Ala
        50                  55                  60

Ile Tyr Thr Ala Glu Ile His Lys Ser Leu Ser Thr Asn Leu Asp Val
65                  70                  75                  80

Thr Asn Ser Ile Glu His Gln Val Lys Asp Val Leu Thr Pro Leu Phe
                85                  90                  95

Lys Ile Ile Gly Asp Glu Val Gly Leu Arg Thr Pro Gln Arg Phe Thr
            100                 105                 110

Asp Leu Val Lys Phe Ile Ser Asp Lys Ile Lys Phe Leu Asn Pro Asp
        115                 120                 125

Arg Glu Tyr Asp Phe Arg Asp Leu Thr Trp Cys Ile Asn Pro Pro Glu
    130                 135                 140

Arg Ile Lys Leu Asp Tyr Asp Gln Tyr Cys Ala Asp Val Ala Ala Glu
145                 150                 155                 160

Glu Leu Met Asn Ala Leu Val Asn Ser Thr Leu Leu Glu Thr Arg Thr
```

```
                       165                 170                 175
Thr Asn Gln Phe Leu Ala Val Ser Lys Gly Asn Cys Ser Gly Pro Thr
                180                 185                 190

Thr Ile Arg Gly Gln Phe Ser Asn Met Ser Leu Ser Leu Leu Asp Leu
                195                 200                 205

Tyr Leu Gly Arg Gly Tyr Asn Val Ser Ser Ile Val Thr Met Thr Ser
                210                 215                 220

Gln Gly Met Tyr Gly Gly Thr Tyr Leu Val Glu Lys Pro Asn Leu Ser
225                 230                 235                 240

Ser Lys Arg Ser Glu Leu Ser Gln Leu Ser Met Tyr Arg Val Phe Glu
                245                 250                 255

Val Gly Val Ile Arg Asn Pro Gly Leu Gly Ala Pro Val Phe His Met
                260                 265                 270

Thr Asn Tyr Leu Glu Gln Pro Val Ser Asn Asp Leu Ser Asn Cys Met
                275                 280                 285

Val Ala Leu Gly Glu Leu Lys Leu Ala Ala Leu Cys His Gly Glu Asp
                290                 295                 300

Ser Ile Thr Ile Pro Tyr Gln Gly Ser Gly Lys Gly Val Ser Phe Gln
305                 310                 315                 320

Leu Val Lys Leu Gly Val Trp Lys Ser Pro Thr Asp Met Gln Ser Trp
                325                 330                 335

Val Pro Leu Ser Thr Asp Asp Pro Val Ile Asp Arg Leu Tyr Leu Ser
                340                 345                 350

Ser His Arg Gly Val Ile Ala Asp Asn Gln Ala Lys Trp Ala Val Pro
                355                 360                 365

Thr Thr Arg Thr Asp Asp Lys Leu Arg Met Glu Thr Cys Phe Gln Gln
                370                 375                 380

Ala Cys Lys Gly Lys Ile Gln Ala Leu Cys Glu Asn Pro Glu Trp Ala
385                 390                 395                 400

Pro Leu Lys Asp Asn Arg Ile Pro Ser Tyr Gly Val Leu Ser Val Asp
                405                 410                 415

Leu Ser Leu Thr Val Glu Leu Lys Ile Lys Ile Ala Ser Gly Phe Gly
                420                 425                 430

Pro Leu Ile Thr His Gly Ser Gly Met Asp Leu Tyr Lys Ser Asn His
                435                 440                 445

Asn Asn Val Tyr Trp Leu Thr Ile Pro Pro Met Lys Asn Leu Ala Leu
450                 455                 460

Gly Val Ile Asn Thr Leu Glu Trp Ile Pro Arg Phe Lys Val Ser Pro
465                 470                 475                 480

Ala Leu Phe Asn Val Pro Ile Lys Glu Ala Gly Gly Asp Cys His Ala
                485                 490                 495

Pro Thr Tyr Leu Pro Ala Glu Val Asp Gly Asp Val Lys Leu Ser Ser
                500                 505                 510

Asn Leu Val Ile Leu Pro Gly Gln Asp Leu Gln Tyr Val Leu Ala Thr
                515                 520                 525

Tyr Asp Thr Ser Ala Val Glu His Ala Val Val Tyr Val Tyr Ser
                530                 535                 540

Pro Ser Arg Ser Phe Ser Tyr Phe Tyr Pro Phe Arg Leu Pro Ile Lys
545                 550                 555                 560

Gly Val Pro Ile Glu Leu Gln Val Glu Cys Phe Thr Trp Asp Gln Lys
                565                 570                 575

Leu Trp Cys Arg His Phe Cys Val Leu Ala Asp Ser Glu Ser Gly Gly
                580                 585                 590
```

-continued

```
His Ile Thr His Ser Gly Met Val Gly Met Gly Val Ser Cys Thr Val
        595                 600                 605

Thr Arg Glu Asp Gly Thr Asn Ile Glu Gly Arg Pro Gly Trp Phe Leu
    610                 615                 620

Asp Ser Pro Asp Arg Pro Trp Asn Pro Pro Thr Phe Ser Pro Ala Leu
625                 630                 635                 640

Leu Val Val Thr Glu Gly Asp Asn Ala Thr Phe Thr Cys Ser Phe Ser
                645                 650                 655

Asn Thr Ser Glu Ser Phe His Val Ile Trp His Arg Glu Ser Pro Ser
            660                 665                 670

Gly Gln Thr Asp Thr Leu Ala Ala Phe Pro Glu Asp Arg Ser Gln Pro
        675                 680                 685

Gly Gln Asp Cys Arg Phe Arg Val Thr Gln Leu Pro Asn Gly Arg Asp
    690                 695                 700

Phe His Met Ser Val Val Arg Ala Arg Arg Asn Asp Ser Gly Thr Tyr
705                 710                 715                 720

Val Cys Gly Val Ile Ser Leu Ala Pro Lys Ile Gln Ile Lys Glu Ser
                725                 730                 735

Leu Arg Ala Glu Leu Arg Val Thr Glu Arg Arg Ala Glu Val Pro Thr
            740                 745                 750

Ala His Pro Ser Pro Ser Pro His His His His His His
        755                 760                 765

<210> SEQ ID NO 26
<211> LENGTH: 765
<212> TYPE: PRT
<213> ORGANISM: Artificial Sequence
<220> FEATURE:
<223> OTHER INFORMATION: PD-1 Fusion Polypeptide

<400> SEQUENCE: 26

Met Ser Pro Gln Arg Asp Arg Ile Asn Ala Phe Tyr Lys Asp Asn Pro
1               5                   10                  15

His Pro Lys Gly Ser Arg Ile Val Ile Asn Arg Glu His Leu Met Ile
            20                  25                  30

Asp Arg Pro Tyr Val Leu Leu Ala Val Leu Phe Val Met Phe Leu Ser
        35                  40                  45

Leu Ile Gly Leu Leu Ala Ile Ala Gly Ile Arg Leu His Arg Ala Ala
    50                  55                  60

Ile Tyr Thr Ala Glu Ile His Lys Ser Leu Ser Thr Asn Leu Asp Val
65                  70                  75                  80

Thr Asn Ser Ile Glu His Gln Val Lys Asp Val Leu Thr Pro Leu Phe
                85                  90                  95

Lys Ile Ile Gly Asp Glu Val Gly Leu Arg Thr Pro Gln Arg Phe Thr
            100                 105                 110

Asp Leu Val Lys Phe Ile Ser Asp Lys Ile Lys Phe Leu Asn Pro Asp
        115                 120                 125

Arg Glu Tyr Asp Phe Arg Asp Leu Thr Trp Cys Ile Asn Pro Pro Glu
    130                 135                 140

Arg Ile Lys Leu Asp Tyr Asp Gln Tyr Cys Ala Asp Val Ala Ala Glu
145                 150                 155                 160

Glu Leu Met Asn Ala Leu Val Asn Ser Thr Leu Leu Glu Thr Arg Thr
                165                 170                 175

Thr Asn Gln Phe Leu Ala Val Ser Lys Gly Asn Cys Ser Gly Pro Thr
            180                 185                 190
```

```
                        -continued

Thr Ile Arg Gly Gln Phe Ser Asn Met Ser Leu Ser Leu Leu Asp Leu
            195                 200                 205

Tyr Leu Gly Arg Gly Tyr Asn Val Ser Ser Ile Val Thr Met Thr Ser
        210                 215                 220

Gln Gly Met Tyr Gly Thr Tyr Leu Val Glu Lys Pro Asn Leu Ser
225                 230                 235                 240

Ser Lys Arg Ser Glu Leu Ser Gln Leu Ser Met Tyr Arg Val Phe Glu
                245                 250                 255

Val Gly Val Ile Arg Asn Pro Gly Leu Gly Ala Pro Val Phe His Met
            260                 265                 270

Thr Asn Tyr Leu Glu Gln Pro Val Ser Asn Asp Leu Ser Asn Cys Met
        275                 280                 285

Val Ala Leu Gly Glu Leu Lys Leu Ala Ala Leu Cys His Gly Glu Asp
        290                 295                 300

Ser Ile Thr Ile Pro Tyr Gln Gly Ser Gly Lys Gly Val Ser Phe Gln
305                 310                 315                 320

Leu Val Lys Leu Gly Val Trp Lys Ser Pro Thr Asp Met Gln Ser Trp
                325                 330                 335

Val Pro Leu Ser Thr Asp Asp Pro Val Ile Asp Arg Leu Tyr Leu Ser
            340                 345                 350

Ser His Arg Gly Val Ile Ala Asp Asn Gln Ala Lys Trp Ala Val Pro
        355                 360                 365

Thr Thr Arg Thr Asp Asp Lys Leu Arg Met Glu Thr Cys Phe Gln Gln
        370                 375                 380

Ala Cys Lys Gly Lys Ile Gln Ala Leu Cys Glu Asn Pro Glu Trp Ala
385                 390                 395                 400

Pro Leu Lys Asp Asn Arg Ile Pro Ser Tyr Gly Val Leu Ser Val Asp
                405                 410                 415

Leu Ser Leu Thr Val Glu Leu Lys Ile Lys Ile Ala Ser Gly Phe Gly
            420                 425                 430

Pro Leu Ile Thr His Gly Ser Gly Met Asp Leu Tyr Lys Ser Asn His
        435                 440                 445

Asn Asn Val Tyr Trp Leu Thr Ile Pro Pro Met Lys Asn Leu Ala Leu
        450                 455                 460

Gly Val Ile Asn Thr Leu Glu Trp Ile Pro Arg Phe Lys Val Ser Pro
465                 470                 475                 480

Ala Leu Phe Asn Val Pro Ile Lys Glu Ala Gly Gly Asp Cys His Ala
                485                 490                 495

Pro Thr Tyr Leu Pro Ala Glu Val Asp Gly Asp Val Lys Leu Ser Ser
            500                 505                 510

Asn Leu Val Ile Leu Pro Gly Gln Asp Leu Gln Tyr Val Leu Ala Thr
        515                 520                 525

Tyr Asp Thr Ser Ala Val Glu His Ala Val Val Tyr Tyr Val Tyr Ser
        530                 535                 540

Pro Ser Arg Leu Ser Ser Tyr Phe Tyr Pro Phe Arg Leu Pro Ile Lys
545                 550                 555                 560

Gly Val Pro Ile Glu Leu Gln Val Glu Cys Phe Thr Trp Asp Gln Lys
                565                 570                 575

Leu Trp Cys Arg His Phe Cys Val Leu Ala Asp Ser Glu Ser Gly Gly
            580                 585                 590

His Ile Thr His Ser Gly Met Val Gly Met Gly Val Ser Cys Thr Val
        595                 600                 605
```

```
Thr Arg Glu Asp Gly Thr Asn Ile Glu Gly Arg Pro Gly Trp Phe Leu
    610                 615                 620

Asp Ser Pro Asp Arg Pro Trp Asn Pro Thr Phe Ser Pro Ala Leu
625                 630                 635                 640

Leu Val Val Thr Glu Gly Asp Asn Ala Thr Phe Thr Cys Ser Phe Ser
                645                 650                 655

Asn Thr Ser Glu Ser Phe Val Leu Asn Trp Tyr Arg Met Ser Pro Ser
            660                 665                 670

Asn Gln Thr Asp Lys Leu Ala Ala Phe Pro Glu Asp Arg Ser Gln Pro
        675                 680                 685

Gly Gln Asp Cys Arg Phe Arg Val Thr Gln Leu Pro Asn Gly Arg Asp
    690                 695                 700

Phe His Met Ser Val Val Arg Ala Arg Arg Asn Asp Ser Gly Thr Tyr
705                 710                 715                 720

Leu Cys Gly Ala Ile Ser Leu Ala Pro Lys Ala Gln Ile Lys Glu Ser
                725                 730                 735

Leu Arg Ala Glu Leu Arg Val Thr Glu Arg Arg Ala Glu Val Pro Thr
            740                 745                 750

Ala His Pro Ser Pro Ser Pro His His His His His
        755                 760                 765

<210> SEQ ID NO 27
<211> LENGTH: 754
<212> TYPE: PRT
<213> ORGANISM: Artificial Sequence
<220> FEATURE:
<223> OTHER INFORMATION: PD-1 Fusion Polypeptide

<400> SEQUENCE: 27

Met Leu Pro Tyr Gln Asp Lys Val Gly Ala Phe Tyr Lys Asp Asn Ala
1               5                   10                  15

Arg Ala Asn Ser Thr Lys Leu Ser Leu Val Thr Glu Gly His Gly Gly
            20                  25                  30

Arg Arg Pro Pro Tyr Leu Leu Phe Val Leu Leu Ile Leu Leu Val Gly
        35                  40                  45

Ile Leu Ala Leu Leu Ala Ile Thr Gly Val Arg Phe His Gln Val Ser
    50                  55                  60

Thr Ser Asn Met Glu Phe Ser Arg Leu Leu Lys Glu Asp Met Glu Lys
65                  70                  75                  80

Ser Glu Ala Val His His Gln Val Ile Asp Val Leu Thr Pro Leu Phe
                85                  90                  95

Lys Ile Ile Gly Asp Glu Ile Gly Leu Arg Leu Pro Gln Lys Leu Asn
            100                 105                 110

Glu Ile Lys Gln Phe Ile Leu Gln Lys Thr Asn Phe Asn Pro Asn
        115                 120                 125

Arg Glu Phe Asp Phe Arg Asp Leu His Trp Cys Ile Asn Pro Pro Ser
130                 135                 140

Thr Val Lys Val Asn Phe Thr Asn Tyr Cys Glu Ser Ile Gly Ile Arg
145                 150                 155                 160

Lys Ala Ile Ala Ser Ala Ala Asn Pro Ile Leu Leu Ser Ala Leu Ser
                165                 170                 175

Gly Gly Arg Gly Asp Ile Phe Pro Pro His Arg Cys Ser Gly Ala Thr
            180                 185                 190

Thr Ser Val Gly Lys Val Phe Pro Leu Ser Val Ser Leu Ser Met Ser
        195                 200                 205
```

```
Leu Ile Ser Arg Thr Ser Glu Val Ile Asn Met Leu Thr Ala Ile Ser
210                 215                 220

Asp Gly Val Tyr Gly Lys Thr Tyr Leu Val Pro Asp Asp Ile Glu
225                 230                 235                 240

Arg Glu Phe Asp Thr Arg Glu Ile Arg Val Phe Glu Ile Gly Phe Ile
                245                 250                 255

Lys Arg Trp Leu Asn Asp Met Pro Leu Leu Gln Thr Thr Asn Tyr Met
                260                 265                 270

Val Leu Pro Lys Asn Ser Lys Ala Lys Val Cys Thr Ile Ala Val Gly
                275                 280                 285

Glu Leu Thr Leu Ala Ser Leu Cys Val Glu Ser Thr Val Leu Leu
290                 295                 300

Tyr His Asp Ser Ser Gly Ser Gln Asp Gly Ile Leu Val Val Thr Leu
305                 310                 315                 320

Gly Ile Phe Trp Ala Thr Pro Met Asp His Ile Glu Glu Val Ile Pro
                325                 330                 335

Val Ala His Pro Ser Met Lys Lys Ile His Ile Thr Asn His Arg Gly
                340                 345                 350

Phe Ile Lys Asp Ser Ile Ala Thr Trp Met Val Pro Ala Leu Ala Ser
                355                 360                 365

Glu Lys Gln Glu Glu Gln Lys Gly Cys Leu Glu Ser Ala Cys Gln Arg
370                 375                 380

Lys Thr Tyr Pro Met Cys Asn Gln Ala Ser Trp Glu Pro Phe Gly Gly
385                 390                 395                 400

Arg Gln Leu Pro Ser Tyr Gly Arg Leu Thr Leu Pro Leu Asp Ala Ser
                405                 410                 415

Val Asp Leu Gln Leu Asn Ile Ser Phe Thr Tyr Gly Pro Val Ile Leu
                420                 425                 430

Asn Gly Asp Gly Met Asp Tyr Tyr Glu Ser Pro Leu Leu Asn Ser Gly
                435                 440                 445

Trp Leu Thr Ile Pro Pro Lys Asp Gly Thr Ile Ser Gly Leu Ile Asn
                450                 455                 460

Lys Ala Gly Arg Gly Asp Gln Phe Thr Val Leu Pro His Val Leu Thr
465                 470                 475                 480

Phe Ala Pro Arg Glu Ser Ser Gly Asn Cys Tyr Leu Pro Ile Gln Thr
                485                 490                 495

Ser Gln Ile Arg Asp Arg Asp Val Leu Ile Glu Ser Asn Ile Val Val
                500                 505                 510

Leu Pro Thr Gln Ser Ile Arg Tyr Val Ile Ala Thr Tyr Asp Ile Ser
                515                 520                 525

Arg Ser Asp His Ala Ile Val Tyr Tyr Val Tyr Asp Pro Ile Arg Thr
530                 535                 540

Ile Ser Tyr Thr His Pro Phe Arg Leu Thr Thr Lys Gly Arg Pro Asp
545                 550                 555                 560

Phe Leu Arg Ile Glu Cys Phe Val Trp Asp Asp Asn Leu Trp Cys His
                565                 570                 575

Gln Phe Tyr Arg Phe Glu Ala Asp Ile Ala Asn Ser Thr Thr Ser Val
                580                 585                 590

Glu Asn Leu Val Arg Ile Arg Phe Ser Cys Asn Arg Ile Glu Gly Arg
                595                 600                 605

Pro Gly Trp Phe Leu Asp Ser Pro Asp Arg Pro Trp Asn Pro Pro Thr
                610                 615                 620

Phe Ser Pro Ala Leu Leu Val Val Thr Glu Gly Asp Asn Ala Thr Phe
```

```
            625                 630                 635                 640
Thr Cys Ser Phe Ser Asn Thr Ser Glu Ser Phe His Val Ile Trp His
                645                 650                 655
Arg Glu Ser Pro Ser Gly Gln Thr Asp Thr Leu Ala Ala Phe Pro Glu
                660                 665                 670
Asp Arg Ser Gln Pro Gly Gln Asp Cys Arg Phe Arg Val Thr Gln Leu
                675                 680                 685
Pro Asn Gly Arg Asp Phe His Met Ser Val Val Arg Ala Arg Arg Asn
                690                 695                 700
Asp Ser Gly Thr Tyr Val Cys Gly Val Ile Ser Leu Ala Pro Lys Ile
705                 710                 715                 720
Gln Ile Lys Glu Ser Leu Arg Ala Glu Leu Arg Val Thr Glu Arg Arg
                725                 730                 735
Ala Glu Val Pro Thr Ala His Pro Ser Pro Ser Pro His His His His
                740                 745                 750
His His

<210> SEQ ID NO 28
<211> LENGTH: 959
<212> TYPE: PRT
<213> ORGANISM: Artificial Sequence
<220> FEATURE:
<223> OTHER INFORMATION: Hexon Polypeptide

<400> SEQUENCE: 28

Met Ala Thr Pro Ser Met Met Pro Gln Trp Ser Tyr Met His Ile Ser
1               5                   10                  15
Gly Gln Asp Ala Ser Glu Tyr Leu Ser Pro Gly Leu Val Gln Phe Ala
                20                  25                  30
Arg Ala Thr Glu Thr Tyr Phe Ser Leu Asn Asn Lys Phe Arg Asn Pro
            35                  40                  45
Thr Val Ala Pro Thr His Asp Val Thr Thr Asp Arg Ser Gln Arg Leu
        50                  55                  60
Thr Leu Arg Phe Ile Pro Val Asp Arg Glu Asp Thr Ala Tyr Ser Tyr
65                  70                  75                  80
Lys Ala Arg Phe Thr Leu Ala Val Gly Asp Asn Arg Val Leu Asp Met
                85                  90                  95
Ala Ser Thr Tyr Phe Asp Ile Arg Gly Val Leu Asp Arg Gly Pro Thr
                100                 105                 110
Phe Lys Pro Tyr Ser Gly Thr Ala Tyr Asn Ala Leu Ala Pro Lys Gly
            115                 120                 125
Ala Pro Asn Ser Cys Glu Trp Asp Glu Asp Thr Gln Val Gln Val
        130                 135                 140
Ala Ala Glu Asp Asp Gln Asp Asp Glu Glu Glu Gln Leu Pro
145                 150                 155                 160
Gln Gln Arg Asn Gly Lys Lys Thr His Val Tyr Ala Gln Ala Pro Phe
                165                 170                 175
Ala Gly Glu Ala Ile Asn Lys Asn Gly Leu Gln Ile Gly Thr Asn Gly
                180                 185                 190
Ala Ala Thr Glu Gly Asn Lys Glu Ile Tyr Ala Asp Lys Thr Tyr Gln
            195                 200                 205
Pro Glu Pro Gln Ile Gly Glu Ser Gln Trp Asn Glu Ala Glu Ser Ser
        210                 215                 220
Val Ala Gly Gly Arg Val Leu Lys Lys Thr Thr Pro Met Lys Pro Cys
225                 230                 235                 240
```

```
Tyr Gly Ser Tyr Ala Arg Pro Thr Asn Ser Asn Gly Gln Gly Val
                245                 250                 255

Met Val Glu Gln Asn Gly Lys Leu Glu Ser Gln Val Glu Met Gln Phe
                260                 265                 270

Phe Ser Thr Ser Val Asn Ala Met Asn Glu Ala Asn Ala Ile Gln Pro
                275                 280                 285

Lys Leu Val Leu Tyr Ser Glu Asp Val Asn Met Glu Thr Pro Asp Thr
                290                 295                 300

His Leu Ser Tyr Lys Pro Gly Lys Ser Asp Asp Asn Ser Lys Ala Met
305                 310                 315                 320

Leu Gly Gln Gln Ser Met Pro Asn Arg Pro Asn Tyr Ile Ala Phe Arg
                325                 330                 335

Asp Asn Phe Ile Gly Leu Met Tyr Tyr Asn Ser Thr Gly Asn Met Gly
                340                 345                 350

Val Leu Ala Gly Gln Ala Ser Gln Leu Asn Ala Val Val Asp Leu Gln
                355                 360                 365

Asp Arg Asn Thr Glu Leu Ser Tyr Gln Leu Leu Asp Ser Ile Gly
                370                 375                 380

Asp Arg Thr Arg Tyr Phe Ser Met Trp Asn Gln Ala Val Asp Ser Tyr
385                 390                 395                 400

Asp Pro Asp Val Arg Ile Ile Glu Asn His Gly Thr Glu Asp Glu Leu
                405                 410                 415

Pro Asn Tyr Cys Phe Pro Leu Gly Gly Ile Gly Val Thr Asp Thr Tyr
                420                 425                 430

Gln Ala Ile Lys Ala Thr Asn Gly Asn Gly Ala Thr Thr Trp Ala
                435                 440                 445

Gln Asp Asn Thr Phe Ala Glu Arg Asn Glu Ile Gly Val Gly Asn Asn
450                 455                 460

Phe Ala Met Glu Ile Asn Leu Asn Ala Asn Leu Trp Arg Asn Phe Leu
465                 470                 475                 480

Tyr Ser Asn Ile Ala Leu Tyr Leu Pro Asp Lys Leu Lys Tyr Asn Pro
                485                 490                 495

Thr Asn Val Glu Ile Ser Asp Asn Pro Asn Thr Tyr Asp Tyr Met Asn
                500                 505                 510

Lys Arg Val Val Ala Pro Gly Leu Val Asp Cys Tyr Ile Asn Leu Gly
                515                 520                 525

Ala Arg Trp Ser Leu Asp Tyr Met Asp Asn Val Asn Pro Phe Asn His
530                 535                 540

His Arg Asn Ala Gly Leu Arg Tyr Arg Ser Met Leu Leu Gly Asn Gly
545                 550                 555                 560

Arg Tyr Val Pro Phe His Ile Gln Val Pro Gln Lys Phe Phe Ala Ile
                565                 570                 575

Lys Asn Leu Leu Leu Leu Pro Gly Ser Tyr Thr Tyr Glu Trp Asn Phe
                580                 585                 590

Arg Lys Asp Val Asn Met Val Leu Gln Ser Ser Leu Gly Asn Asp Leu
                595                 600                 605

Arg Val Asp Gly Ala Ser Ile Lys Phe Asp Ser Ile Cys Leu Tyr Ala
                610                 615                 620

Thr Phe Phe Pro Met Ala His Asn Thr Ala Ser Thr Leu Glu Ala Met
625                 630                 635                 640

Leu Arg Asn Asp Thr Asn Asp Gln Ser Phe Asn Asp Tyr Leu Ser Ala
                645                 650                 655
```

-continued

```
Ala Asn Met Leu Tyr Pro Ile Pro Ala Asn Ala Thr Asn Val Pro Ile
            660                 665                 670

Ser Ile Pro Ser Arg Asn Trp Ala Ala Phe Arg Gly Trp Ala Phe Thr
        675                 680                 685

Arg Leu Lys Thr Lys Glu Thr Pro Ser Leu Gly Ser Gly Tyr Asp Pro
    690                 695                 700

Tyr Tyr Thr Tyr Ser Gly Ser Ile Pro Tyr Leu Asp Gly Thr Phe Tyr
705                 710                 715                 720

Leu Asn His Thr Phe Lys Lys Val Ala Ile Thr Phe Asp Ser Ser Val
                725                 730                 735

Ser Trp Pro Gly Asn Asp Arg Leu Leu Thr Pro Asn Glu Phe Glu Ile
            740                 745                 750

Lys Arg Ser Val Asp Gly Glu Gly Tyr Asn Val Ala Gln Cys Asn Met
        755                 760                 765

Thr Lys Asp Trp Phe Leu Val Gln Met Leu Ala Asn Tyr Asn Ile Gly
    770                 775                 780

Tyr Gln Gly Phe Tyr Ile Pro Glu Ser Tyr Lys Asp Arg Met Tyr Ser
785                 790                 795                 800

Phe Phe Arg Asn Phe Gln Pro Met Ser Arg Gln Val Val Asp Asp Thr
                805                 810                 815

Lys Tyr Lys Asp Tyr Gln Gln Val Gly Ile Ile His Gln His Asn Asn
            820                 825                 830

Ser Gly Phe Val Gly Tyr Leu Ala Pro Thr Met Arg Glu Gly Gln Ala
        835                 840                 845

Tyr Pro Ala Asn Val Pro Tyr Pro Leu Ile Gly Lys Thr Ala Val Asp
    850                 855                 860

Ser Ile Thr Gln Lys Lys Phe Leu Cys Asp Arg Thr Leu Trp Arg Ile
865                 870                 875                 880

Pro Phe Ser Ser Asn Phe Met Ser Met Gly Ala Leu Thr Asp Leu Gly
                885                 890                 895

Gln Asn Leu Leu Tyr Ala Asn Ser Ala His Ala Leu Asp Met Thr Phe
            900                 905                 910

Glu Val Asp Pro Met Asp Glu Pro Thr Leu Leu Tyr Val Leu Phe Glu
        915                 920                 925

Val Phe Asp Val Val Arg Val His Gln Pro His Arg Gly Val Ile Glu
    930                 935                 940

Thr Val Tyr Leu Arg Thr Pro Phe Ser Ala Gly Asn Ala Thr Thr
945                 950                 955

<210> SEQ ID NO 29
<211> LENGTH: 962
<212> TYPE: PRT
<213> ORGANISM: Artificial Sequence
<220> FEATURE:
<223> OTHER INFORMATION: Hexon Polypeptide

<400> SEQUENCE: 29

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60
```

```
Thr Leu Arg Phe Ile Pro Val Asp Arg Glu Asp Thr Ala Tyr Ser Tyr
 65                  70                  75                  80

Lys Ala Arg Phe Thr Leu Ala Val Gly Asp Asn Arg Val Leu Asp Met
                 85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Ser Cys Glu Trp Glu Gln Asn Glu Thr Ala Gln Val Asp
    130                 135                 140

Ala Gln Glu Leu Asp Glu Glu Asn Glu Ala Asn Glu Ala Gln Ala
145                 150                 155                 160

Arg Glu Gln Glu Gln Ala Lys Lys Thr His Val Tyr Ala Gln Ala Pro
                165                 170                 175

Leu Ser Gly Glu Ala Ile Asn Lys Asn Gly Leu Gln Ile Gly Thr Asn
            180                 185                 190

Gly Ala Ala Thr Glu Gly Asn Lys Glu Ile Tyr Ala Asp Lys Thr Tyr
        195                 200                 205

Gln Pro Glu Pro Gln Ile Gly Glu Ser Gln Trp Asn Glu Ala Glu Ser
    210                 215                 220

Ser Val Ala Gly Gly Arg Val Leu Lys Lys Thr Thr Pro Met Lys Pro
225                 230                 235                 240

Cys Tyr Gly Ser Tyr Ala Arg Pro Thr Asn Ser Asn Gly Gly Gln Gly
                245                 250                 255

Val Met Val Glu Gln Asn Gly Lys Leu Glu Ser Gln Val Glu Met Gln
            260                 265                 270

Phe Phe Ser Thr Ser Val Asn Ala Met Asn Glu Ala Asn Ala Ile Gln
        275                 280                 285

Pro Lys Leu Val Leu Tyr Ser Glu Asp Val Asn Met Glu Thr Pro Asp
    290                 295                 300

Thr His Leu Ser Tyr Lys Pro Gly Lys Ser Asp Asp Asn Ser Lys Ala
305                 310                 315                 320

Met Leu Gly Gln Gln Ser Met Pro Asn Arg Pro Asn Tyr Ile Ala Phe
                325                 330                 335

Arg Asp Asn Phe Ile Gly Leu Met Tyr Tyr Asn Ser Thr Gly Asn Met
            340                 345                 350

Gly Val Leu Ala Gly Gln Ala Ser Gln Leu Asn Ala Val Val Asp Leu
        355                 360                 365

Gln Asp Arg Asn Thr Glu Leu Ser Tyr Gln Leu Leu Leu Asp Ser Ile
    370                 375                 380

Gly Asp Arg Thr Arg Tyr Phe Ser Met Trp Asn Gln Ala Val Asp Ser
385                 390                 395                 400

Tyr Asp Pro Asp Val Arg Ile Ile Glu Asn His Gly Thr Glu Asp Glu
                405                 410                 415

Leu Pro Asn Tyr Cys Phe Pro Leu Gly Gly Ile Gly Ile Thr Asp Thr
            420                 425                 430

Phe Gln Ala Val Lys Thr Thr Ala Ala Asn Gly Asp Gln Gly Asn Thr
        435                 440                 445

Thr Trp Gln Lys Asp Ser Thr Phe Ala Glu Arg Asn Glu Ile Gly Val
    450                 455                 460

Gly Asn Asn Phe Ala Met Glu Ile Asn Leu Asn Ala Asn Leu Trp Arg
465                 470                 475                 480

Asn Phe Leu Tyr Ser Asn Ile Ala Leu Tyr Leu Pro Asp Lys Leu Lys
```

-continued

```
                485                 490                 495
Tyr Asn Pro Thr Asn Val Glu Ile Ser Asp Asn Pro Asn Thr Tyr Asp
            500                 505                 510
Tyr Met Asn Lys Arg Val Val Ala Pro Gly Leu Val Asp Cys Tyr Ile
            515                 520                 525
Asn Leu Gly Ala Arg Trp Ser Leu Asp Tyr Met Asp Asn Val Asn Pro
            530                 535                 540
Phe Asn His Pro Arg His Ala Gly Leu Arg Tyr Arg Ser Met Leu Leu
545                 550                 555                 560
Gly Asn Gly Arg Tyr Val Pro Phe His Ile Gln Val Pro Gln Lys Phe
                565                 570                 575
Phe Ala Ile Lys Asn Leu Leu Leu Pro Gly Ser Tyr Thr Tyr Glu
            580                 585                 590
Trp Asn Phe Arg Lys Asp Val Asn Met Val Leu Gln Ser Ser Leu Gly
            595                 600                 605
Asn Asp Leu Arg Val Asp Gly Ala Ser Ile Lys Phe Asp Ser Ile Cys
            610                 615                 620
Leu Tyr Ala Thr Phe Phe Pro Met Ala His Asn Thr Ala Ser Thr Leu
625                 630                 635                 640
Glu Ala Met Leu Arg Asn Asp Thr Asn Asp Gln Ser Phe Asn Asp Tyr
                645                 650                 655
Leu Ser Ala Ala Asn Met Leu Tyr Pro Ile Pro Ala Asn Ala Thr Asn
            660                 665                 670
Val Pro Ile Ser Ile Pro Ser Arg Asn Trp Ala Ala Phe Arg Gly Trp
            675                 680                 685
Ala Phe Thr Arg Leu Lys Thr Lys Glu Thr Pro Ser Leu Gly Ser Gly
            690                 695                 700
Tyr Asp Pro Tyr Tyr Thr Tyr Ser Gly Ser Ile Pro Tyr Leu Asp Gly
705                 710                 715                 720
Thr Phe Tyr Leu Asn His Thr Phe Lys Lys Val Ala Ile Thr Phe Asp
                725                 730                 735
Ser Ser Val Ser Trp Pro Gly Asn Asp Arg Leu Leu Thr Pro Asn Glu
            740                 745                 750
Phe Glu Ile Lys Arg Ser Val Asp Gly Glu Gly Tyr Asn Val Ala Gln
            755                 760                 765
Cys Asn Met Thr Lys Asp Trp Phe Leu Val Gln Met Leu Ala Asn Tyr
770                 775                 780
Asn Ile Gly Tyr Gln Gly Phe Tyr Ile Pro Glu Ser Tyr Lys Asp Arg
785                 790                 795                 800
Met Tyr Ser Phe Phe Arg Asn Phe Gln Pro Met Ser Arg Gln Val Val
                805                 810                 815
Asp Asp Thr Lys Tyr Lys Asp Tyr Gln Val Gly Ile Ile His Gln
            820                 825                 830
His Asn Asn Ser Gly Phe Val Gly Tyr Leu Ala Pro Thr Met Arg Glu
            835                 840                 845
Gly Gln Ala Tyr Pro Ala Asn Val Pro Tyr Pro Leu Ile Gly Lys Thr
            850                 855                 860
Ala Val Asp Ser Ile Thr Gln Lys Lys Phe Leu Cys Asp Arg Thr Leu
865                 870                 875                 880
Trp Arg Ile Pro Phe Ser Ser Asn Phe Met Ser Met Gly Ala Leu Thr
                885                 890                 895
Asp Leu Gly Gln Asn Leu Leu Tyr Ala Asn Ser Ala His Ala Leu Asp
            900                 905                 910
```

-continued

```
Met Thr Phe Glu Val Asp Pro Met Asp Glu Pro Thr Leu Leu Tyr Val
            915                 920                 925

Leu Phe Glu Val Phe Asp Val Val Arg Val His Gln Pro His Arg Gly
        930                 935                 940

Val Ile Glu Thr Val Tyr Leu Arg Thr Pro Phe Ser Ala Gly Asn Ala
945                 950                 955                 960

Thr Thr

<210> SEQ ID NO 30
<211> LENGTH: 959
<212> TYPE: PRT
<213> ORGANISM: Artificial Sequence
<220> FEATURE:
<223> OTHER INFORMATION: Hexon Polypeptide

<400> SEQUENCE: 30

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Ser Cys Glu Trp Asp Glu Asp Thr Gln Val Gln Val
    130                 135                 140

Ala Ala Glu Asp Asp Gln Asp Asp Glu Glu Glu Glu Gln Leu Pro
145                 150                 155                 160

Gln Gln Arg Asn Gly Lys Lys Thr His Val Tyr Ala Gln Ala Pro Phe
                165                 170                 175

Ala Gly Glu Ala Ile Asn Lys Asn Gly Leu Gln Ile Gly Thr Asn Gly
            180                 185                 190

Ala Ala Thr Glu Gly Asn Lys Glu Ile Tyr Ala Asp Lys Thr Tyr Gln
        195                 200                 205

Pro Glu Pro Gln Ile Gly Glu Ser Gln Trp Asn Glu Ala Glu Ser Ser
    210                 215                 220

Val Ala Gly Gly Arg Val Leu Lys Lys Thr Thr Pro Met Lys Pro Cys
225                 230                 235                 240

Tyr Gly Ser Tyr Ala Arg Pro Thr Asn Ser Asn Gly Gly Gln Gly Val
                245                 250                 255

Met Val Glu Gln Asn Gly Lys Leu Glu Ser Gln Val Glu Met Gln Phe
            260                 265                 270

Phe Ser Thr Ser Val Asn Ala Met Asn Glu Ala Asn Ala Ile Gln Pro
        275                 280                 285

Lys Leu Val Leu Tyr Ser Glu Asp Val Asn Met Glu Thr Pro Asp Thr
    290                 295                 300
```

His Leu Ser Tyr Lys Pro Gly Lys Ser Asp Asp Asn Ser Lys Ala Met
305                 310                 315                 320

Leu Gly Gln Gln Ser Met Pro Asn Arg Pro Asn Tyr Ile Ala Phe Arg
            325                 330                 335

Asp Asn Phe Ile Gly Leu Met Tyr Tyr Asn Ser Thr Gly Asn Met Gly
                340                 345                 350

Val Leu Ala Gly Gln Ala Ser Gln Leu Asn Ala Val Val Asp Leu Gln
            355                 360                 365

Asp Arg Asn Thr Glu Leu Ser Tyr Gln Leu Leu Asp Ser Ile Gly
    370                 375                 380

Asp Arg Thr Arg Tyr Phe Ser Met Trp Asn Gln Ala Val Asp Ser Tyr
385                 390                 395                 400

Asp Pro Asp Val Arg Ile Ile Glu Asn His Gly Thr Glu Asp Glu Leu
                405                 410                 415

Pro Asn Tyr Cys Phe Pro Leu Gly Gly Ile Gly Val Thr Asp Thr Tyr
                420                 425                 430

Gln Ala Ile Lys Ala Thr Asn Gly Asn Gly Ala Thr Thr Trp Ala
            435                 440                 445

Gln Asp Asn Thr Phe Ala Glu Arg Asn Glu Ile Gly Val Gly Asn Asn
450                 455                 460

Phe Ala Met Glu Ile Asn Leu Asn Ala Asn Leu Trp Arg Asn Phe Leu
465                 470                 475                 480

Tyr Ser Asn Ile Ala Leu Tyr Leu Pro Asp Lys Leu Lys Tyr Asn Pro
                485                 490                 495

Thr Asn Val Glu Ile Ser Asp Asn Pro Asn Thr Tyr Asp Tyr Met Asn
            500                 505                 510

Lys Arg Val Val Ala Pro Gly Leu Val Asp Cys Tyr Ile Asn Leu Gly
        515                 520                 525

Ala Arg Trp Ser Leu Asp Tyr Met Asp Asn Val Asn Pro Phe Asn His
    530                 535                 540

His Arg Asn Ala Gly Leu Arg Tyr Arg Ser Met Leu Leu Gly Asn Gly
545                 550                 555                 560

Arg Tyr Val Pro Phe His Ile Gln Val Pro Gln Lys Phe Phe Ala Ile
                565                 570                 575

Lys Asn Leu Leu Leu Pro Gly Ser Tyr Thr Tyr Glu Trp Asn Phe
            580                 585                 590

Arg Lys Asp Val Asn Met Val Leu Gln Ser Ser Leu Gly Asn Asp Leu
        595                 600                 605

Arg Val Asp Gly Ala Ser Ile Lys Phe Asp Ser Ile Cys Leu Tyr Ala
    610                 615                 620

Thr Phe Phe Pro Met Ala His Asn Thr Ala Ser Thr Leu Glu Ala Met
625                 630                 635                 640

Leu Arg Asn Asp Thr Asn Asp Gln Ser Phe Asn Asp Tyr Leu Ser Ala
                645                 650                 655

Ala Asn Met Leu Tyr Pro Ile Pro Ala Asn Ala Thr Asn Val Pro Ile
            660                 665                 670

Ser Ile Pro Ser Arg Asn Trp Ala Ala Phe Arg Gly Trp Ala Phe Thr
        675                 680                 685

Arg Leu Lys Thr Lys Glu Thr Pro Ser Leu Gly Ser Gly Tyr Asp Pro
    690                 695                 700

Tyr Tyr Thr Tyr Ser Gly Ser Ile Pro Tyr Leu Asp Gly Thr Phe Tyr
705                 710                 715                 720

Leu Asn His Thr Phe Lys Lys Val Ala Ile Thr Phe Asp Ser Ser Val

```
                725                 730                 735
Ser Trp Pro Gly Asn Asp Arg Leu Leu Thr Pro Asn Glu Phe Glu Ile
            740                 745                 750
Lys Arg Ser Val Asp Gly Glu Gly Tyr Asn Val Ala Gln Cys Asn Met
        755                 760                 765
Thr Lys Asp Trp Phe Leu Val Gln Met Leu Ala Asn Tyr Asn Ile Gly
    770                 775                 780
Tyr Gln Gly Phe Tyr Ile Pro Glu Ser Tyr Lys Asp Arg Met Tyr Ser
785                 790                 795                 800
Phe Phe Arg Asn Phe Gln Pro Met Ser Arg Gln Val Val Asp Thr
                805                 810                 815
Lys Tyr Lys Asp Tyr Gln Gln Val Gly Ile Ile His Gln His Asn Asn
                820                 825                 830
Ser Gly Phe Val Gly Tyr Leu Ala Pro Thr Met Arg Glu Gly Gln Ala
                835                 840                 845
Tyr Pro Ala Asn Val Pro Tyr Pro Leu Ile Gly Lys Thr Ala Val Asp
            850                 855                 860
Ser Ile Thr Gln Lys Lys Phe Leu Cys Asp Arg Thr Leu Trp Arg Ile
865                 870                 875                 880
Pro Phe Ser Ser Asn Phe Met Ser Met Gly Ala Leu Thr Asp Leu Gly
                885                 890                 895
Gln Asn Leu Leu Tyr Ala Asn Ser Ala His Ala Leu Asp Met Thr Phe
                900                 905                 910
Glu Val Asp Pro Met Asp Glu Pro Thr Leu Leu Tyr Val Leu Phe Glu
            915                 920                 925
Val Phe Asp Val Val Arg Val His Gln Pro His Arg Gly Val Ile Glu
        930                 935                 940
Thr Val Tyr Leu Arg Thr Pro Phe Ser Ala Gly Asn Ala Thr Thr
945                 950                 955

<210> SEQ ID NO 31
<211> LENGTH: 132
<212> TYPE: PRT
<213> ORGANISM: Artificial Sequence
<220> FEATURE:
<223> OTHER INFORMATION: Adenovirus E1A N-terminus polypeptide

<400> SEQUENCE: 31

Met Arg His Ile Ile Cys His Gly Gly Val Ile Thr Glu Glu Met Ala
1               5                   10                  15
Ala Ser Leu Leu Asp Gln Leu Ile Glu Glu Val Leu Ala Asp Asn Leu
            20                  25                  30
Pro Pro Pro Ser His Phe Glu Pro Thr Leu His Glu Leu Tyr Asp
        35                  40                  45
Leu Asp Val Thr Ala Pro Glu Asp Pro Asn Glu Glu Ala Val Ser Gln
50                  55                  60
Ile Phe Pro Glu Ser Val Met Leu Ala Val Gln Glu Gly Ile Asp Leu
65                  70                  75                  80
Phe Thr Phe Pro Pro Ala Pro Gly Ser Pro Glu Pro His Leu Ser
            85                  90                  95
Arg Gln Pro Glu Gln Pro Glu Gln Arg Ala Leu Gly Pro Val Ser Met
                100                 105                 110
Pro Asn Leu Val Pro Glu Val Ile Asp Leu Thr Cys His Glu Ala Gly
            115                 120                 125
Phe Pro Pro Ser
```

<210> SEQ ID NO 32
<211> LENGTH: 112
<212> TYPE: PRT
<213> ORGANISM: Artificial Sequence
<220> FEATURE:
<223> OTHER INFORMATION: E1A N-terminus polypeptide

<400> SEQUENCE: 32

Met Arg His Ile Glu Glu Val Leu Ala Asp Asn Leu Pro Pro Pro Ser
1               5                   10                  15

His Phe Glu Pro Pro Thr Leu His Glu Leu Tyr Asp Leu Asp Val Thr
            20                  25                  30

Ala Pro Glu Asp Pro Asn Glu Glu Ala Val Ser Gln Ile Phe Pro Glu
        35                  40                  45

Ser Val Met Leu Ala Val Gln Glu Gly Ile Asp Leu Phe Thr Phe Pro
    50                  55                  60

Pro Ala Pro Gly Ser Pro Glu Pro Pro His Leu Ser Arg Gln Pro Glu
65                  70                  75                  80

Gln Pro Glu Gln Arg Ala Leu Gly Pro Val Ser Met Pro Asn Leu Val
                85                  90                  95

Pro Glu Val Ile Asp Leu Thr Cys His Glu Ala Gly Phe Pro Pro Ser
            100                 105                 110

<210> SEQ ID NO 33
<211> LENGTH: 119
<212> TYPE: PRT
<213> ORGANISM: Artificial Sequence
<220> FEATURE:
<223> OTHER INFORMATION: E1A N-terminus polypeptide

<400> SEQUENCE: 33

Met Arg His Ile Ile Cys His Gly Gly Val Ile Thr Glu Glu Met Ala
1               5                   10                  15

Ala Ser Leu Leu Asp Gln Leu Ile Glu Glu Val Leu Ala Asp Asn Leu
            20                  25                  30

Pro Pro Pro Ser His Phe Glu Pro Pro Thr Leu His Glu Leu Tyr Asp
        35                  40                  45

Leu Asp Val Thr Ala Pro Glu Asp Pro Asn Glu Glu Ala Val Ser Gln
    50                  55                  60

Ile Phe Pro Glu Ser Val Met Leu Ala Val Gln Glu Gly Ile Asp Leu
65                  70                  75                  80

Phe Thr Phe Pro Pro Ala Pro Gly Ser Pro Glu Pro Pro His Leu Ser
                85                  90                  95

Arg Gln Pro Glu Gln Pro Glu Gln Arg Ala Leu Gly Pro Val Cys His
            100                 105                 110

Glu Ala Gly Phe Pro Pro Ser
        115

<210> SEQ ID NO 34
<211> LENGTH: 99
<212> TYPE: PRT
<213> ORGANISM: Artificial Sequence
<220> FEATURE:
<223> OTHER INFORMATION: E1A N-terminus polypeptide

<400> SEQUENCE: 34

Met Arg His Ile Glu Glu Val Leu Ala Asp Asn Leu Pro Pro Pro Ser
1               5                   10                  15

```
His Phe Glu Pro Pro Thr Leu His Glu Leu Tyr Asp Leu Asp Val Thr
            20                  25                  30

Ala Pro Glu Asp Pro Asn Glu Ala Val Ser Gln Ile Phe Pro Glu
        35                  40                  45

Ser Val Met Leu Ala Val Gln Glu Gly Ile Asp Leu Phe Thr Phe Pro
 50                  55                  60

Pro Ala Pro Gly Ser Pro Glu Pro Pro His Leu Ser Arg Gln Pro Glu
 65                  70                  75                  80

Gln Pro Glu Gln Arg Ala Leu Gly Pro Val Cys His Glu Ala Gly Phe
            85                  90                  95

Pro Pro Ser

<210> SEQ ID NO 35
<211> LENGTH: 528
<212> TYPE: PRT
<213> ORGANISM: Artificial Sequence
<220> FEATURE:
<223> OTHER INFORMATION: Fiber Polypeptide

<400> SEQUENCE: 35

Met Lys Arg Ala Arg Pro Ser Glu Asp Thr Phe Asn Pro Val Tyr Pro
 1               5                  10                  15

Tyr Asp Thr Glu Thr Gly Pro Pro Thr Val Pro Phe Leu Thr Pro Pro
            20                  25                  30

Phe Val Ser Pro Asn Gly Phe Gln Glu Ser Pro Pro Gly Val Leu Ser
        35                  40                  45

Leu Arg Leu Ser Glu Pro Leu Val Thr Ser His Gly Met Leu Ala Leu
 50                  55                  60

Lys Met Gly Ser Gly Leu Ser Leu Asp Gln Ala Gly Asn Leu Thr Ser
 65                  70                  75                  80

Asn Thr Ile Thr Val Ser Gln Pro Leu Lys Lys Thr Lys Ser Asn Ile
            85                  90                  95

Thr Leu Glu Thr Ser Ala Pro Leu Thr Val Ser Ser Gly Ala Leu Thr
        100                 105                 110

Met Ala Thr Thr Ser Pro Leu Val Val Ser Asp Asn Thr Leu Thr Met
        115                 120                 125

Gln Ser Gln Ala Pro Leu Thr Val Gln Asp Ser Lys Leu Ser Ile Ala
    130                 135                 140

Thr Lys Glu Pro Leu Thr Val Leu Asp Gly Lys Leu Ala Leu Gln Thr
145                 150                 155                 160

Ser Ala Pro Leu Ser Ala Thr Asp Asn Asn Ala Leu Thr Ile Thr Ala
                165                 170                 175

Ser Pro Pro Leu Thr Thr Ala Asn Gly Ser Leu Ala Val Thr Met Glu
            180                 185                 190

Asn Pro Leu Tyr Asn Asn Asn Gly Lys Leu Gly Leu Lys Ile Gly Gly
        195                 200                 205

Pro Leu Gln Val Ala Thr Asp Ser His Ala Leu Thr Leu Gly Thr Gly
    210                 215                 220

Gln Gly Val Ala Val His Asn Asn Leu Leu His Thr Lys Val Thr Gly
225                 230                 235                 240

Ala Ile Gly Phe Asp Thr Ser Gly Asn Met Glu Leu Lys Thr Gly Asp
                245                 250                 255

Gly Leu Tyr Val Asp Ser Ala Gly Pro Asn Gln Lys Leu His Ile Asn
            260                 265                 270
```

```
Leu Asn Thr Thr Lys Gly Leu Ala Phe Asp Asn Thr Ala Ile Thr Ile
            275                 280                 285

Asn Ala Gly Lys Gly Leu Glu Phe Glu Thr Asp Ser Ser Asn Gly Asn
290                 295                 300

Pro Ile Lys Thr Lys Ile Gly Ser Gly Ile Gln Tyr Asn Thr Asn Gly
305                 310                 315                 320

Ala Met Val Ala Lys Leu Gly Thr Gly Leu Ser Phe Asp Ser Ser Gly
                325                 330                 335

Ala Ile Thr Met Gly Ser Ile Asn Asn Asp Arg Leu Thr Leu Trp Thr
                340                 345                 350

Thr Pro Asp Pro Ser Pro Asn Cys Arg Ile Ala Ser Asp Lys Asp Cys
            355                 360                 365

Lys Leu Thr Leu Ala Leu Thr Lys Cys Gly Ser Gln Ile Leu Gly Thr
        370                 375                 380

Val Ser Ala Leu Ala Val Ser Gly Asn Met Ala Ser Ile Asn Gly Thr
385                 390                 395                 400

Leu Ser Ser Val Asn Leu Val Leu Arg Phe Asp Asp Asn Gly Val Leu
                405                 410                 415

Met Ser Asn Ser Ser Leu Asp Lys Gln Tyr Trp Asn Phe Arg Asn Gly
                420                 425                 430

Asp Ser Thr Asn Gly Gln Pro Tyr Thr Tyr Ala Val Gly Phe Met Pro
            435                 440                 445

Asn Leu Lys Ala Tyr Pro Lys Thr Gln Ser Lys Thr Ala Lys Ser Asn
        450                 455                 460

Ile Val Ser Gln Val Tyr Leu Asn Gly Asp Lys Ser Lys Pro Leu His
465                 470                 475                 480

Phe Thr Ile Thr Leu Asn Gly Thr Asp Glu Thr Asn Gln Val Ser Lys
                485                 490                 495

Tyr Ser Ile Ser Phe Ser Trp Ser Trp Asn Ser Gly Gln Tyr Thr Asn
                500                 505                 510

Asp Lys Phe Ala Thr Asn Ser Tyr Thr Phe Ser Tyr Ile Ala Gln Glu
            515                 520                 525

<210> SEQ ID NO 36
<211> LENGTH: 324
<212> TYPE: PRT
<213> ORGANISM: Artificial Sequence
<220> FEATURE:
<223> OTHER INFORMATION: Fiber Polypeptide

<400> SEQUENCE: 36

Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
            20                  25                  30

Phe Val Ser Pro Asn Gly Phe Gln Glu Ser Pro Pro Gly Val Leu Thr
        35                  40                  45

Leu Lys Cys Leu Thr Pro Leu Thr Thr Thr Gly Gly Ser Leu Gln Leu
    50                  55                  60

Lys Val Gly Gly Gly Leu Thr Val Asp Asp Thr Asp Gly Thr Leu Gln
65                  70                  75                  80

Glu Asn Ile Arg Ala Thr Ala Pro Ile Thr Lys Asn Asn His Ser Val
                85                  90                  95

Glu Leu Ser Ile Gly Asn Gly Leu Glu Thr Gln Asn Asn Lys Leu Cys
            100                 105                 110
```

```
Ala Lys Leu Gly Asn Gly Leu Lys Phe Asn Asn Gly Asp Ile Cys Ile
            115                 120                 125

Lys Asp Ser Ile Asn Thr Leu Trp Thr Gly Ile Asn Pro Pro Pro Asn
130                 135                 140

Cys Gln Ile Val Glu Asn Thr Asn Thr Asn Asp Gly Lys Leu Thr Leu
145                 150                 155                 160

Val Leu Val Lys Asn Gly Gly Leu Val Asn Gly Tyr Val Ser Leu Val
            165                 170                 175

Gly Val Ser Asp Thr Val Asn Gln Met Phe Thr Gln Lys Thr Ala Asn
            180                 185                 190

Ile Gln Leu Arg Leu Tyr Phe Asp Ser Ser Gly Asn Leu Leu Thr Asp
            195                 200                 205

Glu Ser Asp Leu Lys Ile Pro Leu Lys Asn Lys Ser Ser Thr Ala Thr
210                 215                 220

Ser Glu Thr Val Ala Ser Ser Lys Ala Phe Met Pro Ser Thr Thr Ala
225                 230                 235                 240

Tyr Pro Phe Asn Thr Thr Thr Arg Asp Ser Glu Asn Tyr Ile His Gly
            245                 250                 255

Ile Cys Tyr Tyr Met Thr Ser Tyr Asp Arg Ser Leu Phe Pro Leu Asn
            260                 265                 270

Ile Ser Ile Met Leu Asn Ser Arg Met Ile Ser Ser Asn Val Ala Tyr
            275                 280                 285

Ala Ile Gln Phe Glu Trp Asn Leu Asn Ala Ser Glu Ser Pro Glu Ser
            290                 295                 300

Asn Ile Ala Thr Leu Thr Thr Ser Pro Phe Phe Phe Ser Tyr Ile Thr
305                 310                 315                 320

Glu Asp Asp Asn

<210> SEQ ID NO 37
<211> LENGTH: 534
<212> TYPE: PRT
<213> ORGANISM: Artificial Sequence
<220> FEATURE:
<223> OTHER INFORMATION: Fiber Polypeptide

<400> SEQUENCE: 37

Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
            20                  25                  30

Phe Val Ser Pro Asn Gly Phe Gln Glu Ser Pro Pro Gly Val Leu Ser
            35                  40                  45

Leu Arg Leu Ser Glu Pro Leu Val Thr Ser His Gly Met Leu Ala Leu
        50                  55                  60

Lys Met Gly Ser Gly Leu Ser Leu Asp Gln Ala Gly Asn Leu Thr Ser
65                  70                  75                  80

Asn Thr Ile Thr Val Ser Gln Pro Leu Lys Lys Thr Lys Ser Asn Ile
                85                  90                  95

Thr Leu Glu Thr Ser Ala Pro Leu Thr Val Ser Ser Gly Ala Leu Thr
            100                 105                 110

Met Ala Thr Thr Ser Pro Leu Val Val Ser Asp Asn Thr Leu Thr Met
            115                 120                 125

Gln Ser Gln Ala Pro Leu Thr Val Gln Asp Ser Lys Leu Ser Ile Ala
        130                 135                 140

Thr Lys Glu Pro Leu Thr Val Leu Asp Gly Lys Leu Ala Leu Gln Thr
```

|  | 145 |  |  | 150 |  |  | 155 |  |  | 160 |  |

Ser Ala Pro Leu Ser Ala Thr Asp Asn Asn Ala Leu Thr Ile Thr Ala
            165                 170                 175

Ser Pro Pro Leu Thr Ala Asn Gly Ser Leu Ala Val Thr Met Glu
            180                 185                 190

Asn Pro Leu Tyr Asn Asn Gly Lys Leu Gly Leu Lys Ile Gly Gly
            195                 200                 205

Pro Leu Gln Val Ala Thr Asp Ser His Ala Leu Thr Leu Gly Thr Gly
210                 215                 220

Gln Gly Val Ala Val His Asn Asn Leu Leu His Thr Lys Val Thr Gly
225                 230                 235                 240

Ala Ile Gly Phe Asp Thr Ser Gly Asn Met Glu Leu Lys Thr Gly Asp
            245                 250                 255

Gly Leu Tyr Val Asp Ser Ala Gly Pro Asn Gln Lys Leu His Ile Asn
            260                 265                 270

Leu Asn Thr Thr Lys Gly Leu Ala Phe Asp Asn Thr Ala Ile Thr Ile
            275                 280                 285

Asn Ala Gly Lys Gly Leu Glu Phe Glu Thr Asp Ser Ser Asn Gly Asn
290                 295                 300

Pro Ile Lys Thr Lys Ile Gly Ser Gly Ile Gln Tyr Asn Thr Asn Gly
305                 310                 315                 320

Ala Met Val Ala Lys Leu Gly Thr Gly Leu Ser Phe Asp Ser Ser Gly
            325                 330                 335

Ala Ile Thr Met Gly Ser Ile Asn Asn Asp Arg Leu Thr Leu Trp Thr
            340                 345                 350

Thr Pro Asp Pro Ser Pro Asn Cys Arg Ile Ala Ser Asp Lys Asp Cys
            355                 360                 365

Lys Leu Thr Leu Ala Leu Thr Lys Cys Gly Ser Gln Ile Leu Gly Thr
            370                 375                 380

Val Ser Ala Leu Ala Val Ser Gly Asn Met Ala Ser Ile Asn Gly Thr
385                 390                 395                 400

Leu Ser Ser Val Asn Leu Val Leu Arg Phe Asp Asp Asn Gly Val Leu
            405                 410                 415

Met Ser Asn Ser Ser Leu Asp Lys Gln Tyr Trp Asn Phe Arg Asn Gly
            420                 425                 430

Asp Ser Thr Asn Gly Gln Pro Tyr Thr Tyr Ala Val Gly Phe Met Pro
            435                 440                 445

Asn Leu Lys Ala Tyr Pro Lys Thr Gln Ser Lys Thr Ala Lys Ser Asn
450                 455                 460

Ile Val Ser Gln Val Tyr Leu Asn Gly Asp Lys Ser Lys Pro Leu His
465                 470                 475                 480

Phe Thr Ile Thr Leu Asn Gly Thr Asp Glu Thr Asn Gln Val Ser Lys
            485                 490                 495

Tyr Ser Ile Ser Phe Ser Trp Ser Trp Asn Ser Gly Gln Tyr Thr Asn
            500                 505                 510

Asp Lys Phe Ala Thr Asn Ser Tyr Thr Phe Ser Tyr Ile Ala Gln Glu
            515                 520                 525

Lys Lys Lys Lys Lys Lys
    530

<210> SEQ ID NO 38
<211> LENGTH: 425
<212> TYPE: PRT
<213> ORGANISM: Artificial Sequence -continued
<220> FEATURE:
<223> OTHER INFORMATION: Fiber Polypeptide

<400> SEQUENCE: 38

```
Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
            20                  25                  30

Phe Val Ser Pro Asn Gly Phe Gln Glu Ser Pro Gly Val Leu Ser
        35                  40                  45

Leu Arg Leu Ser Glu Pro Leu Val Thr Lys Asn Gly Glu Ile Thr Leu
50                  55                  60

Lys Leu Gly Glu Gly Val Asp Leu Asp Ser Ser Gly Lys Leu Ile Ser
65                  70                  75                  80

Asn Thr Ala Thr Lys Ala Ala Pro Leu Ser Phe Ser Asn Asn Thr
                85                  90                  95

Ile Ser Leu Asn Met Asp His Pro Phe Tyr Thr Lys Asp Gly Lys Leu
            100                 105                 110

Ser Leu Gln Val Ser Pro Pro Leu Asn Ile Leu Arg Thr Ser Ile Leu
        115                 120                 125

Asn Thr Leu Ala Leu Gly Phe Gly Ser Gly Leu Gly Leu Arg Gly Ser
130                 135                 140

Ala Leu Ala Val Gln Leu Val Ser Pro Leu Thr Phe Asp Thr Asp Gly
145                 150                 155                 160

Asn Ile Lys Leu Thr Leu Asp Arg Gly Leu His Val Thr Thr Gly Asp
                165                 170                 175

Ala Ile Glu Ser Asn Ile Ser Trp Ala Lys Gly Leu Lys Phe Glu Asp
            180                 185                 190

Gly Ala Ile Ala Thr Asn Ile Gly Asn Gly Leu Glu Phe Gly Ser Ser
        195                 200                 205

Ser Thr Glu Thr Gly Val Asp Asp Ala Tyr Pro Ile Gln Val Lys Leu
210                 215                 220

Gly Ser Gly Leu Ser Phe Asp Ser Thr Gly Ala Ile Met Ala Gly Asn
225                 230                 235                 240

Lys Glu Asp Asp Lys Leu Thr Leu Trp Thr Thr Pro Asp Pro Ser Pro
                245                 250                 255

Asn Cys Gln Ile Leu Ala Glu Asn Asp Ala Lys Leu Thr Leu Cys Leu
            260                 265                 270

Thr Lys Cys Gly Ser Gln Ile Leu Ala Thr Val Ser Val Leu Val Val
        275                 280                 285

Gly Ser Gly Asn Leu Asn Pro Ile Thr Gly Thr Val Ser Ser Ala Gln
290                 295                 300

Val Phe Leu Arg Phe Asp Ala Asn Gly Val Leu Leu Thr Glu His Ser
305                 310                 315                 320

Thr Leu Lys Lys Tyr Trp Gly Tyr Arg Gln Gly Asp Ser Ile Asp Gly
                325                 330                 335

Thr Pro Tyr Thr Asn Ala Val Gly Phe Met Pro Asn Leu Lys Ala Tyr
            340                 345                 350

Pro Lys Ser Gln Ser Ser Thr Lys Asn Asn Ile Val Gly Gln Val
        355                 360                 365

Tyr Met Asn Gly Asp Val Ser Lys Pro Met Leu Leu Thr Ile Thr Leu
370                 375                 380

Asn Gly Thr Asp Asp Ser Asn Ser Thr Tyr Ser Met Ser Phe Ser Tyr
385                 390                 395                 400
```

```
Thr Trp Thr Asn Gly Ser Tyr Val Gly Ala Thr Phe Gly Ala Asn Ser
            405                 410                 415

Tyr Thr Phe Ser Tyr Ile Ala Gln Glu
            420                 425

<210> SEQ ID NO 39
<211> LENGTH: 432
<212> TYPE: PRT
<213> ORGANISM: Artificial Sequence
<220> FEATURE:
<223> OTHER INFORMATION: Fiber Polypeptide

<400> SEQUENCE: 39

Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
                20                  25                  30

Phe Val Ser Pro Asn Gly Phe Gln Glu Ser Pro Pro Gly Val Leu Ser
            35                  40                  45

Leu Arg Leu Ser Glu Pro Leu Val Thr Lys Asn Gly Glu Ile Thr Leu
        50                  55                  60

Lys Leu Gly Glu Gly Val Asp Leu Asp Ser Ser Gly Lys Leu Ile Ser
65                  70                  75                  80

Asn Thr Ala Thr Lys Ala Ala Pro Leu Ser Phe Ser Asn Asn Thr
                85                  90                  95

Ile Ser Leu Asn Met Asp His Pro Phe Tyr Thr Lys Asp Gly Lys Leu
                100                 105                 110

Ser Leu Gln Val Ser Pro Pro Leu Asn Ile Leu Arg Thr Ser Ile Leu
            115                 120                 125

Asn Thr Leu Ala Leu Gly Phe Gly Ser Gly Leu Gly Leu Arg Gly Ser
        130                 135                 140

Ala Leu Ala Val Gln Leu Val Ser Pro Leu Thr Phe Asp Thr Asp Gly
145                 150                 155                 160

Asn Ile Lys Leu Thr Leu Asp Arg Gly Leu His Val Thr Thr Gly Asp
                165                 170                 175

Ala Ile Glu Ser Asn Ile Ser Trp Ala Lys Gly Leu Lys Phe Glu Asp
            180                 185                 190

Gly Ala Ile Ala Thr Asn Ile Gly Asn Gly Leu Glu Phe Gly Ser Ser
        195                 200                 205

Ser Thr Glu Thr Gly Val Asp Asp Ala Tyr Pro Ile Gln Val Lys Leu
    210                 215                 220

Gly Ser Gly Leu Ser Phe Asp Ser Thr Gly Ala Ile Met Ala Gly Asn
225                 230                 235                 240

Lys Glu Asp Asp Lys Leu Thr Leu Trp Thr Thr Pro Asp Pro Ser Pro
                245                 250                 255

Asn Cys Gln Ile Leu Ala Glu Asn Asp Ala Lys Leu Thr Leu Cys Leu
            260                 265                 270

Thr Lys Cys Gly Ser Gln Ile Leu Ala Thr Val Ser Val Leu Val Val
        275                 280                 285

Gly Ser Gly Asn Leu Asn Pro Ile Thr Gly Thr Val Ser Ser Ala Gln
    290                 295                 300

Val Phe Leu Arg Phe Asp Ala Asn Gly Val Leu Leu Thr Glu His Ser
305                 310                 315                 320

Thr Leu Lys Lys Tyr Trp Gly Tyr Arg Gln Gly Asp Ser Ile Asp Gly
                325                 330                 335
```

```
Thr Pro Tyr Thr Asn Ala Val Gly Phe Met Pro Asn Leu Lys Ala Tyr
            340                 345                 350

Pro Lys Ser Gln Ser Ser Thr Thr Lys Asn Asn Ile Val Gly Gln Val
            355                 360                 365

Tyr Met Asn Gly Asp Val Ser Lys Pro Met Leu Leu Thr Ile Thr Leu
370                 375                 380

Asn Gly Thr Asp Asp Ser Asn Ser Thr Tyr Ser Met Ser Phe Ser Tyr
385                 390                 395                 400

Thr Trp Thr Asn Gly Ser Tyr Val Gly Ala Thr Phe Gly Ala Asn Ser
                405                 410                 415

Tyr Thr Phe Ser Tyr Ile Ala Gln Glu Lys Lys Lys Lys Lys Lys Lys
            420                 425                 430

<210> SEQ ID NO 40
<211> LENGTH: 441
<212> TYPE: PRT
<213> ORGANISM: Artificial Sequence
<220> FEATURE:
<223> OTHER INFORMATION: Fiber Polypeptide

<400> SEQUENCE: 40

Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
            20                  25                  30

Phe Val Ser Pro Asn Gly Phe Gln Glu Ser Pro Pro Gly Val Leu Ser
            35                  40                  45

Leu Arg Leu Ser Glu Pro Leu Val Thr Lys Asn Gly Glu Ile Thr Leu
50                  55                  60

Lys Leu Gly Glu Gly Val Asp Leu Asp Ser Ser Gly Lys Leu Ile Ser
65                  70                  75                  80

Asn Thr Ala Thr Lys Ala Ala Pro Leu Ser Phe Ser Asn Asn Thr
                85                  90                  95

Ile Ser Leu Asn Met Asp His Pro Phe Tyr Thr Lys Asp Gly Lys Leu
            100                 105                 110

Ser Leu Gln Val Ser Pro Pro Leu Asn Ile Leu Arg Thr Ser Ile Leu
            115                 120                 125

Asn Thr Leu Ala Leu Gly Phe Gly Ser Gly Leu Gly Leu Arg Gly Ser
            130                 135                 140

Ala Leu Ala Val Gln Leu Val Ser Pro Leu Thr Phe Asp Thr Asp Gly
145                 150                 155                 160

Asn Ile Lys Leu Thr Leu Asp Arg Gly Leu His Val Thr Thr Gly Asp
                165                 170                 175

Ala Ile Glu Ser Asn Ile Ser Trp Ala Lys Gly Leu Lys Phe Glu Asp
            180                 185                 190

Gly Ala Ile Ala Thr Asn Ile Gly Asn Gly Leu Glu Phe Gly Ser Ser
            195                 200                 205

Ser Thr Glu Thr Gly Val Asp Asp Ala Tyr Pro Ile Gln Val Lys Leu
            210                 215                 220

Gly Ser Gly Leu Ser Phe Asp Ser Thr Gly Ala Ile Met Ala Gly Asn
225                 230                 235                 240

Lys Glu Asp Asp Lys Leu Thr Leu Trp Thr Thr Pro Asp Pro Ser Pro
                245                 250                 255

Asn Cys Gln Ile Leu Ala Glu Asn Asp Ala Lys Leu Thr Leu Cys Leu
            260                 265                 270
```

```
Thr Lys Cys Gly Ser Gln Ile Leu Ala Thr Val Ser Val Leu Val Val
    275                 280                 285

Gly Ser Gly Asn Leu Asn Pro Ile Thr Gly Thr Val Ser Ser Ala Gln
290                 295                 300

Val Phe Leu Arg Phe Asp Ala Asn Gly Val Leu Leu Thr Glu His Ser
305                 310                 315                 320

Thr Leu Lys Lys Tyr Trp Gly Tyr Arg Gln Gly Asp Ser Ile Asp Gly
                325                 330                 335

Thr Pro Tyr Thr Asn Ala Val Gly Phe Met Pro Asn Leu Lys Ala Tyr
                340                 345                 350

Pro Lys Ser Gln Ser Ser Thr Thr Lys Asn Asn Ile Val Gly Gln Val
                355                 360                 365

Tyr Met Asn Gly Asp Val Ser Lys Pro Met Leu Leu Thr Ile Thr Leu
    370                 375                 380

Asn Gly Thr Asp Asp Ser Gly Gly Ser Ser Gly Lys Lys Lys Lys Lys
385                 390                 395                 400

Lys Lys Ala Ser Gly Gly Ser Ser Thr Tyr Ser Met Ser Phe Ser Tyr
                405                 410                 415

Thr Trp Thr Asn Gly Ser Tyr Val Gly Ala Thr Phe Gly Ala Asn Ser
                420                 425                 430

Tyr Thr Phe Ser Tyr Ile Ala Gln Glu
    435                 440
```

<210> SEQ ID NO 41
<211> LENGTH: 1608
<212> TYPE: DNA
<213> ORGANISM: Artificial Sequence
<220> FEATURE:
<223> OTHER INFORMATION: Probasin-E1

<400> SEQUENCE: 41

```
tcgagcgacg gtatcgataa gcttggagct tatgatagca tcttgttctt agtcttttc      60
ttaataggga cataaagccc acaaataaaa atatgcctga gaatgggac aggcattggg    120
cattgtccat gcctagtaaa gtactccaag aacctatttg tatactagat gacacaatgt   180
tctagccaag cttggtagtc atcatgttta acatctacc attccagtta agaaaatatg    240
atagcatctt gttcttagtc ttttttcttaa tagggacata aagcccacaa ataaaaatat   300
gcctgaagaa tgggacaggc attgggcatt gtccatgcct agtaaagtac tccaagaacc    360
tatttgtata ctagatgaca caatgtcaat gtctgtgtac aactgccaac tgggatgcaa    420
gacactgccc atgccaatca tcctgaaaag cagctataaa aagcaggaag ctactctgca    480
ccttgtcagt gaggtccaga tacctccctc gagcggccgc gacgcgcagt gtatttatac    540
ccggtgagtt cctcaagagg ccactcttga gtgccagcga gtagagtttt ctcctccgag    600
ccgctccgac accgggactg aaaatgagac atattatctg ccacggaggt gttattaccg    660
aagaaatggc cgccagtctt ttggaccagc tgatcgaaga ggtactggct gataatcttc    720
cacctcctag ccattttgaa ccacctaccc ttcacgaact gtatgattta cgtgacgg     780
cccccgaaga tcccaacgag gaggcggttt cgcagatttt tcccgagtct gtaatgttgg   840
cggtgcagga agggattgac ttattcactt ttccgccggc gccggttct ccggagccgc     900
ctcacctttc ccggcagccc gagcagccgg agcagagagc cttgggtccg gtttctatgc   960
caaaccttgt gccggaggtg atcgatctta cctgccacga ggctggcttt ccacccagtg  1020
acgacgagga tgaagagggt gaggagtttg tgttagatta tgtggagcac cccgggcacg  1080
```

```
gttgcaggtc ttgtcattat caccggagga atacggggga cccagatatt atgtgttcgc   1140
tttgctatat gaggacctgt ggcatgtttg tctacagtaa gtgaaaatta tgggcagtcg   1200
gtgatagagt ggtgggtttg gtgtggtaat ttttttttaa tttttacagt tttgtggttt   1260
aaagaatttt gtattgtgat tttttaaaag gtcctgtgtc tgaacctgag cctgagcccg   1320
agccagaacc ggagcctgca agacctaccc ggcgtcctaa attggtgcct gctatcctga   1380
gacgcccgac atcacctgtg tctagagaat gcaatagtag tacggatagc tgtgactccg   1440
gtccttctaa cacacctcct gagatacacc cggtggtccc gctgtgcccc attaaaccag   1500
ttgccgtgag agttggtggg cgtcgccagg ctgtggaatg tatcgaggac ttgcttaacg   1560
agtctgggca acctttggac ttgagctgta aacgccccag gccataag                1608
```

```
<210> SEQ ID NO 42
<211> LENGTH: 967
<212> TYPE: PRT
<213> ORGANISM: Artificial Sequence
<220> FEATURE:
<223> OTHER INFORMATION: Hexon Polypeptide

<400> SEQUENCE: 42
```

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Ser Cys Glu Trp Asp Glu Asp Thr Gln Val Gln Val
    130                 135                 140

Ala Ala Glu Asp Asp Gln Asp Asp Ser Ser Cys Ser Ser Gly Gly
145                 150                 155                 160

Thr Glu Glu Glu Glu Gln Leu Pro Gln Gln Arg Asn Gly Lys Lys Thr
                165                 170                 175

His Val Tyr Ala Gln Ala Pro Phe Ala Gly Glu Ala Ile Asn Lys Asn
            180                 185                 190

Gly Leu Gln Ile Gly Thr Asn Gly Ala Ala Thr Glu Gly Asn Lys Glu
        195                 200                 205

Ile Tyr Ala Asp Lys Thr Tyr Gln Pro Glu Pro Gln Ile Gly Glu Ser
    210                 215                 220

Gln Trp Asn Glu Ala Glu Ser Ser Val Ala Gly Gly Arg Val Leu Lys
225                 230                 235                 240

Lys Thr Thr Pro Met Lys Pro Cys Tyr Gly Ser Tyr Ala Arg Pro Thr
                245                 250                 255

Asn Ser Asn Gly Gly Gln Gly Val Met Val Glu Gln Asn Gly Lys Leu
            260                 265                 270

Glu Ser Gln Val Glu Met Gln Phe Phe Ser Thr Ser Val Asn Ala Met
            275                 280                 285

Asn Glu Ala Asn Ala Ile Gln Pro Lys Leu Val Leu Tyr Ser Glu Asp
    290                 295                 300

Val Asn Met Glu Thr Pro Asp Thr His Leu Ser Tyr Lys Pro Gly Lys
305                 310                 315                 320

Ser Asp Asp Asn Ser Lys Ala Met Leu Gly Gln Gln Ser Met Pro Asn
                325                 330                 335

Arg Pro Asn Tyr Ile Ala Phe Arg Asp Asn Phe Ile Gly Leu Met Tyr
            340                 345                 350

Tyr Asn Ser Thr Gly Asn Met Gly Val Leu Ala Gly Gln Ala Ser Gln
        355                 360                 365

Leu Asn Ala Val Val Asp Leu Gln Asp Arg Asn Thr Glu Leu Ser Tyr
    370                 375                 380

Gln Leu Leu Leu Asp Ser Ile Gly Asp Arg Thr Arg Tyr Phe Ser Met
385                 390                 395                 400

Trp Asn Gln Ala Val Asp Ser Tyr Asp Pro Asp Val Arg Ile Ile Glu
                405                 410                 415

Asn His Gly Thr Glu Asp Glu Leu Pro Asn Tyr Cys Phe Pro Leu Gly
            420                 425                 430

Gly Ile Gly Val Thr Asp Thr Tyr Gln Ala Ile Lys Ala Thr Asn Gly
        435                 440                 445

Asn Gly Gly Ala Thr Thr Trp Ala Gln Asp Asn Thr Phe Ala Glu Arg
    450                 455                 460

Asn Glu Ile Gly Val Gly Asn Asn Phe Ala Met Glu Ile Asn Leu Asn
465                 470                 475                 480

Ala Asn Leu Trp Arg Asn Phe Leu Tyr Ser Asn Ile Ala Leu Tyr Leu
                485                 490                 495

Pro Asp Lys Leu Lys Tyr Asn Pro Thr Asn Val Glu Ile Ser Asp Asn
            500                 505                 510

Pro Asn Thr Tyr Asp Tyr Met Asn Lys Arg Val Val Ala Pro Gly Leu
        515                 520                 525

Val Asp Cys Tyr Ile Asn Leu Gly Ala Arg Trp Ser Leu Asp Tyr Met
    530                 535                 540

Asp Asn Val Asn Pro Phe Asn His His Arg Asn Ala Gly Leu Arg Tyr
545                 550                 555                 560

Arg Ser Met Leu Leu Gly Asn Gly Arg Tyr Val Pro Phe His Ile Gln
                565                 570                 575

Val Pro Gln Lys Phe Phe Ala Ile Lys Asn Leu Leu Leu Leu Pro Gly
            580                 585                 590

Ser Tyr Thr Tyr Glu Trp Asn Phe Arg Lys Asp Val Asn Met Val Leu
        595                 600                 605

Gln Ser Ser Leu Gly Asn Asp Leu Arg Val Asp Gly Ala Ser Ile Lys
    610                 615                 620

Phe Asp Ser Ile Cys Leu Tyr Ala Thr Phe Phe Pro Met Ala His Asn
625                 630                 635                 640

Thr Ala Ser Thr Leu Glu Ala Met Leu Arg Asn Asp Thr Asn Asp Gln
                645                 650                 655

Ser Phe Asn Asp Tyr Leu Ser Ala Ala Asn Met Leu Tyr Pro Ile Pro
            660                 665                 670

Ala Asn Ala Thr Asn Val Pro Ile Ser Ile Pro Ser Arg Asn Trp Ala
        675                 680                 685

-continued

```
Ala Phe Arg Gly Trp Ala Phe Thr Arg Leu Lys Thr Lys Glu Thr Pro
    690                 695                 700
Ser Leu Gly Ser Gly Tyr Asp Pro Tyr Tyr Thr Tyr Ser Gly Ser Ile
705                 710                 715                 720
Pro Tyr Leu Asp Gly Thr Phe Tyr Leu Asn His Thr Phe Lys Lys Val
                725                 730                 735
Ala Ile Thr Phe Asp Ser Ser Val Ser Trp Pro Gly Asn Asp Arg Leu
            740                 745                 750
Leu Thr Pro Asn Glu Phe Glu Ile Lys Arg Ser Val Asp Gly Glu Gly
        755                 760                 765
Tyr Asn Val Ala Gln Cys Asn Met Thr Lys Asp Trp Phe Leu Val Gln
770                 775                 780
Met Leu Ala Asn Tyr Asn Ile Gly Tyr Gln Gly Phe Tyr Ile Pro Glu
785                 790                 795                 800
Ser Tyr Lys Asp Arg Met Tyr Ser Phe Phe Arg Asn Phe Gln Pro Met
                805                 810                 815
Ser Arg Gln Val Val Asp Asp Thr Lys Tyr Lys Asp Tyr Gln Gln Val
            820                 825                 830
Gly Ile Ile His Gln His Asn Asn Ser Gly Phe Val Gly Tyr Leu Ala
        835                 840                 845
Pro Thr Met Arg Glu Gly Gln Ala Tyr Pro Ala Asn Val Pro Tyr Pro
850                 855                 860
Leu Ile Gly Lys Thr Ala Val Asp Ser Ile Thr Gln Lys Lys Phe Leu
865                 870                 875                 880
Cys Asp Arg Thr Leu Trp Arg Ile Pro Phe Ser Ser Asn Phe Met Ser
                885                 890                 895
Met Gly Ala Leu Thr Asp Leu Gly Gln Asn Leu Leu Tyr Ala Asn Ser
            900                 905                 910
Ala His Ala Leu Asp Met Thr Phe Glu Val Asp Pro Met Asp Glu Pro
        915                 920                 925
Thr Leu Leu Tyr Val Leu Phe Glu Val Phe Asp Val Val Arg Val His
930                 935                 940
Gln Pro His Arg Gly Val Ile Glu Thr Val Tyr Leu Arg Thr Pro Phe
945                 950                 955                 960
Ser Ala Gly Asn Ala Thr Thr
                965
```

<210> SEQ ID NO 43
<211> LENGTH: 955
<212> TYPE: PRT
<213> ORGANISM: Artificial Sequence
<220> FEATURE:
<223> OTHER INFORMATION: Hexon Polypeptide

<400> SEQUENCE: 43

```
Met Ala Thr Pro Ser Met Met Pro Gln Trp Ser Tyr Met His Ile Ser
1               5                   10                  15
Gly Gln Asp Ala Ser Glu Tyr Leu Ser Pro Gly Leu Val Gln Phe Ala
            20                  25                  30
Arg Ala Thr Glu Thr Tyr Phe Ser Leu Asn Asn Lys Phe Arg Asn Pro
        35                  40                  45
Thr Val Ala Pro Thr His Asp Val Thr Thr Asp Arg Ser Gln Arg Leu
    50                  55                  60
Thr Leu Arg Phe Ile Pro Val Asp Arg Glu Asp Thr Ala Tyr Ser Tyr
65                  70                  75                  80
```

```
Lys Ala Arg Phe Thr Leu Ala Val Gly Asp Asn Arg Val Leu Asp Met
                85                  90                  95
Ala Ser Thr Tyr Phe Asp Ile Arg Gly Val Leu Asp Arg Gly Pro Thr
            100                 105                 110
Phe Lys Pro Tyr Ser Gly Thr Ala Tyr Asn Ala Leu Ala Pro Lys Gly
        115                 120                 125
Ala Pro Asn Ser Cys Glu Trp Asp Glu Asp Thr Gln Val Gln Val
130                 135                 140
Ala Ala Glu Asp Asp Gln Asp Asp Glu Glu Glu Gln Leu Pro
145                 150                 155                 160
Gln Gln Arg Asn Gly Lys Lys Thr His Val Tyr Ala Gln Ala Pro Phe
                165                 170                 175
Ala Gly Glu Ala Ile Asn Lys Asn Gly Leu Gln Ile Gly Thr Asn Gly
            180                 185                 190
Ala Ala Thr Glu Gly Asn Lys Glu Ile Tyr Ala Asp Lys Thr Tyr Gln
        195                 200                 205
Pro Glu Pro Gln Ile Gly Glu Ser Gln Trp Asn Glu Ala Glu Ser Ser
    210                 215                 220
Val Ala Gly Gly Arg Val Leu Lys Lys Thr Thr Pro Met Lys Pro Cys
225                 230                 235                 240
Tyr Gly Ser Tyr Ala Arg Pro Thr Asn Ser Asn Gly Gln Gly Val
                245                 250                 255
Met Val Glu Gln Asn Gly Lys Leu Glu Ser Gln Val Glu Met Gln Phe
            260                 265                 270
Phe Ser Thr Ser Ser Cys Ser Ser Gly Gly Thr Pro Lys Leu Val Leu
        275                 280                 285
Tyr Ser Glu Asp Val Asn Met Glu Thr Pro Asp Thr His Leu Ser Tyr
    290                 295                 300
Lys Pro Gly Lys Ser Asp Asp Asn Ser Lys Ala Met Leu Gly Gln Gln
305                 310                 315                 320
Ser Met Pro Asn Arg Pro Asn Tyr Ile Ala Phe Arg Asp Asn Phe Ile
                325                 330                 335
Gly Leu Met Tyr Tyr Asn Ser Thr Gly Asn Met Gly Val Leu Ala Gly
            340                 345                 350
Gln Ala Ser Gln Leu Asn Ala Val Val Asp Leu Gln Asp Arg Asn Thr
        355                 360                 365
Glu Leu Ser Tyr Gln Leu Leu Leu Asp Ser Ile Gly Asp Arg Thr Arg
    370                 375                 380
Tyr Phe Ser Met Trp Asn Gln Ala Val Asp Ser Tyr Asp Pro Asp Val
385                 390                 395                 400
Arg Ile Ile Glu Asn His Gly Thr Glu Asp Glu Leu Pro Asn Tyr Cys
                405                 410                 415
Phe Pro Leu Gly Gly Ile Gly Val Thr Asp Thr Tyr Gln Ala Ile Lys
            420                 425                 430
Ala Thr Asn Gly Asn Gly Gly Ala Thr Thr Trp Ala Gln Asp Asn Thr
        435                 440                 445
Phe Ala Glu Arg Asn Glu Ile Gly Val Gly Asn Asn Phe Ala Met Glu
    450                 455                 460
Ile Asn Leu Asn Ala Asn Leu Trp Arg Asn Phe Leu Tyr Ser Asn Ile
465                 470                 475                 480
Ala Leu Tyr Leu Pro Asp Lys Leu Lys Tyr Asn Pro Thr Asn Val Glu
                485                 490                 495
Ile Ser Asp Asn Pro Asn Thr Tyr Asp Tyr Met Asn Lys Arg Val Val
```

-continued

```
                500                 505                 510
Ala Pro Gly Leu Val Asp Cys Tyr Ile Asn Leu Gly Ala Arg Trp Ser
            515                 520                 525
Leu Asp Tyr Met Asp Asn Val Asn Pro Phe Asn His His Arg Asn Ala
            530                 535                 540
Gly Leu Arg Tyr Arg Ser Met Leu Leu Gly Asn Gly Arg Tyr Val Pro
545                 550                 555                 560
Phe His Ile Gln Val Pro Gln Lys Phe Ala Ile Lys Asn Leu Leu
            565                 570                 575
Leu Leu Pro Gly Ser Tyr Thr Tyr Glu Trp Asn Phe Arg Lys Asp Val
            580                 585                 590
Asn Met Val Leu Gln Ser Ser Leu Gly Asn Asp Leu Arg Val Asp Gly
            595                 600                 605
Ala Ser Ile Lys Phe Asp Ser Ile Cys Leu Tyr Ala Thr Phe Pro
            610                 615                 620
Met Ala His Asn Thr Ala Ser Thr Leu Glu Ala Met Leu Arg Asn Asp
625                 630                 635                 640
Thr Asn Asp Gln Ser Phe Asn Asp Tyr Leu Ser Ala Ala Asn Met Leu
            645                 650                 655
Tyr Pro Ile Pro Ala Asn Ala Thr Asn Val Pro Ile Ser Ile Pro Ser
            660                 665                 670
Arg Asn Trp Ala Ala Phe Arg Gly Trp Ala Phe Thr Arg Leu Lys Thr
            675                 680                 685
Lys Glu Thr Pro Ser Leu Gly Ser Gly Tyr Asp Pro Tyr Tyr Thr Tyr
            690                 695                 700
Ser Gly Ser Ile Pro Tyr Leu Asp Gly Thr Phe Tyr Leu Asn His Thr
705                 710                 715                 720
Phe Lys Lys Val Ala Ile Thr Phe Asp Ser Ser Val Ser Trp Pro Gly
            725                 730                 735
Asn Asp Arg Leu Leu Thr Pro Asn Glu Phe Glu Ile Lys Arg Ser Val
            740                 745                 750
Asp Gly Glu Gly Tyr Asn Val Ala Gln Cys Asn Met Thr Lys Asp Trp
            755                 760                 765
Phe Leu Val Gln Met Leu Ala Asn Tyr Asn Ile Gly Tyr Gln Gly Phe
            770                 775                 780
Tyr Ile Pro Glu Ser Tyr Lys Asp Arg Met Tyr Ser Phe Phe Arg Asn
785                 790                 795                 800
Phe Gln Pro Met Ser Arg Gln Val Val Asp Asp Thr Lys Tyr Lys Asp
            805                 810                 815
Tyr Gln Gln Val Gly Ile Ile His Gln His Asn Asn Ser Gly Phe Val
            820                 825                 830
Gly Tyr Leu Ala Pro Thr Met Arg Glu Gly Gln Ala Tyr Pro Ala Asn
            835                 840                 845
Val Pro Tyr Pro Leu Ile Gly Lys Thr Ala Val Asp Ser Ile Thr Gln
            850                 855                 860
Lys Lys Phe Leu Cys Asp Arg Thr Leu Trp Arg Ile Pro Phe Ser Ser
865                 870                 875                 880
Asn Phe Met Ser Met Gly Ala Leu Thr Asp Leu Gly Gln Asn Leu Leu
            885                 890                 895
Tyr Ala Asn Ser Ala His Ala Leu Asp Met Thr Phe Glu Val Asp Pro
            900                 905                 910
Met Asp Glu Pro Thr Leu Leu Tyr Val Leu Phe Glu Val Phe Asp Val
            915                 920                 925
```

```
Val Arg Val His Gln Pro His Arg Gly Val Ile Glu Thr Val Tyr Leu
    930                 935                 940

Arg Thr Pro Phe Ser Ala Gly Asn Ala Thr Thr
945                 950                 955

<210> SEQ ID NO 44
<211> LENGTH: 964
<212> TYPE: PRT
<213> ORGANISM: Artificial Sequence
<220> FEATURE:
<223> OTHER INFORMATION: Hexon Polypeptide

<400> SEQUENCE: 44

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Ser Cys Glu Trp Asp Glu Asp Thr Gln Val Gln Val
    130                 135                 140

Ala Ala Glu Asp Asp Gln Asp Asp Ser Ser Gly Gly Thr Glu Glu
145                 150                 155                 160

Glu Glu Gln Leu Pro Gln Gln Arg Asn Gly Lys Lys Thr His Val Tyr
                165                 170                 175

Ala Gln Ala Pro Phe Ala Gly Glu Ala Ile Asn Lys Asn Gly Leu Gln
            180                 185                 190

Ile Gly Thr Asn Gly Ala Ala Thr Glu Gly Asn Lys Glu Ile Tyr Ala
        195                 200                 205

Asp Lys Thr Tyr Gln Pro Glu Pro Gln Ile Gly Glu Ser Gln Trp Asn
    210                 215                 220

Glu Ala Glu Ser Ser Val Ala Gly Gly Arg Val Leu Lys Lys Thr Thr
225                 230                 235                 240

Pro Met Lys Pro Cys Tyr Gly Ser Tyr Ala Arg Pro Thr Asn Ser Asn
                245                 250                 255

Gly Gly Gln Gly Val Met Val Glu Gln Asn Gly Lys Leu Glu Ser Gln
            260                 265                 270

Val Glu Met Gln Phe Phe Ser Thr Ser Val Asn Ala Met Asn Glu Ala
        275                 280                 285

Asn Ala Ile Gln Pro Lys Leu Val Leu Tyr Ser Glu Asp Val Asn Met
    290                 295                 300

Glu Thr Pro Asp Thr His Leu Ser Tyr Lys Pro Gly Lys Ser Asp Asp
305                 310                 315                 320

Asn Ser Lys Ala Met Leu Gly Gln Gln Ser Met Pro Asn Arg Pro Asn
                325                 330                 335
```

```
Tyr Ile Ala Phe Arg Asp Asn Phe Ile Gly Leu Met Tyr Tyr Asn Ser
                340                 345                 350

Thr Gly Asn Met Gly Val Leu Ala Gly Gln Ala Ser Gln Leu Asn Ala
                355                 360                 365

Val Val Asp Leu Gln Asp Arg Asn Thr Glu Leu Ser Tyr Gln Leu Leu
        370                 375                 380

Leu Asp Ser Ile Gly Asp Arg Thr Arg Tyr Phe Ser Met Trp Asn Gln
385                 390                 395                 400

Ala Val Asp Ser Tyr Asp Pro Asp Val Arg Ile Ile Glu Asn His Gly
                405                 410                 415

Thr Glu Asp Glu Leu Pro Asn Tyr Cys Phe Pro Leu Gly Gly Ile Gly
                420                 425                 430

Val Thr Asp Thr Tyr Gln Ala Ile Lys Ala Thr Asn Gly Asn Gly Gly
                435                 440                 445

Ala Thr Thr Trp Ala Gln Asp Asn Thr Phe Ala Glu Arg Asn Glu Ile
                450                 455                 460

Gly Val Gly Asn Asn Phe Ala Met Glu Ile Asn Leu Asn Ala Asn Leu
465                 470                 475                 480

Trp Arg Asn Phe Leu Tyr Ser Asn Ile Ala Leu Tyr Leu Pro Asp Lys
                485                 490                 495

Leu Lys Tyr Asn Pro Thr Asn Val Glu Ile Ser Asp Asn Pro Asn Thr
                500                 505                 510

Tyr Asp Tyr Met Asn Lys Arg Val Val Ala Pro Gly Leu Val Asp Cys
                515                 520                 525

Tyr Ile Asn Leu Gly Ala Arg Trp Ser Leu Asp Tyr Met Asp Asn Val
                530                 535                 540

Asn Pro Phe Asn His His Arg Asn Ala Gly Leu Arg Tyr Arg Ser Met
545                 550                 555                 560

Leu Leu Gly Asn Gly Arg Tyr Val Pro Phe His Ile Gln Val Pro Gln
                565                 570                 575

Lys Phe Phe Ala Ile Lys Asn Leu Leu Leu Pro Gly Ser Tyr Thr
                580                 585                 590

Tyr Glu Trp Asn Phe Arg Lys Asp Val Asn Met Val Leu Gln Ser Ser
                595                 600                 605

Leu Gly Asn Asp Leu Arg Val Asp Gly Ala Ser Ile Lys Phe Asp Ser
                610                 615                 620

Ile Cys Leu Tyr Ala Thr Phe Phe Pro Met Ala His Asn Thr Ala Ser
625                 630                 635                 640

Thr Leu Glu Ala Met Leu Arg Asn Asp Thr Asn Asp Gln Ser Phe Asn
                645                 650                 655

Asp Tyr Leu Ser Ala Ala Asn Met Leu Tyr Pro Ile Pro Ala Asn Ala
                660                 665                 670

Thr Asn Val Pro Ile Ser Ile Pro Ser Arg Asn Trp Ala Ala Phe Arg
                675                 680                 685

Gly Trp Ala Phe Thr Arg Leu Lys Thr Lys Glu Thr Pro Ser Leu Gly
                690                 695                 700

Ser Gly Tyr Asp Pro Tyr Tyr Thr Tyr Ser Gly Ser Ile Pro Tyr Leu
705                 710                 715                 720

Asp Gly Thr Phe Tyr Leu Asn His Thr Phe Lys Lys Val Ala Ile Thr
                725                 730                 735

Phe Asp Ser Ser Val Ser Trp Pro Gly Asn Asp Arg Leu Leu Thr Pro
                740                 745                 750
```

```
Asn Glu Phe Glu Ile Lys Arg Ser Val Asp Gly Glu Gly Tyr Asn Val
            755                 760                 765

Ala Gln Cys Asn Met Thr Lys Asp Trp Phe Leu Val Gln Met Leu Ala
        770                 775                 780

Asn Tyr Asn Ile Gly Tyr Gln Gly Phe Tyr Ile Pro Glu Ser Tyr Lys
785                 790                 795                 800

Asp Arg Met Tyr Ser Phe Phe Arg Asn Phe Gln Pro Met Ser Arg Gln
            805                 810                 815

Val Val Asp Asp Thr Lys Tyr Lys Asp Tyr Gln Gln Val Gly Ile Ile
            820                 825                 830

His Gln His Asn Asn Ser Gly Phe Val Gly Tyr Leu Ala Pro Thr Met
            835                 840                 845

Arg Glu Gly Gln Ala Tyr Pro Ala Asn Val Pro Tyr Pro Leu Ile Gly
            850                 855                 860

Lys Thr Ala Val Asp Ser Ile Thr Gln Lys Lys Phe Leu Cys Asp Arg
865                 870                 875                 880

Thr Leu Trp Arg Ile Pro Phe Ser Ser Asn Phe Met Ser Met Gly Ala
            885                 890                 895

Leu Thr Asp Leu Gly Gln Asn Leu Leu Tyr Ala Asn Ser Ala His Ala
            900                 905                 910

Leu Asp Met Thr Phe Glu Val Asp Pro Met Asp Glu Pro Thr Leu Leu
            915                 920                 925

Tyr Val Leu Phe Glu Val Phe Asp Val Val Arg Val His Gln Pro His
            930                 935                 940

Arg Gly Val Ile Glu Thr Val Tyr Leu Arg Thr Pro Phe Ser Ala Gly
945                 950                 955                 960

Asn Ala Thr Thr

<210> SEQ ID NO 45
<211> LENGTH: 952
<212> TYPE: PRT
<213> ORGANISM: Artificial Sequence
<220> FEATURE:
<223> OTHER INFORMATION: Hexon Polypeptide

<400> SEQUENCE: 45

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
            85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
            115                 120                 125

Ala Pro Asn Ser Cys Glu Trp Asp Glu Asp Thr Gln Val Gln Val
        130                 135                 140

Ala Ala Glu Asp Asp Gln Asp Asp Asp Glu Glu Glu Gln Leu Pro
```

```
        145                 150                 155                 160
Gln Gln Arg Asn Gly Lys Lys Thr His Val Tyr Ala Gln Ala Pro Phe
                165                 170                 175
Ala Gly Glu Ala Ile Asn Lys Asn Gly Leu Gln Ile Gly Thr Asn Gly
                180                 185                 190
Ala Ala Thr Glu Gly Asn Lys Glu Ile Tyr Ala Asp Lys Thr Tyr Gln
                195                 200                 205
Pro Glu Pro Gln Ile Gly Glu Ser Gln Trp Asn Glu Ala Glu Ser Ser
    210                 215                 220
Val Ala Gly Gly Arg Val Leu Lys Lys Thr Thr Pro Met Lys Pro Cys
225                 230                 235                 240
Tyr Gly Ser Tyr Ala Arg Pro Thr Asn Ser Asn Gly Gly Gln Gly Val
                245                 250                 255
Met Val Glu Gln Asn Gly Lys Leu Glu Ser Gln Val Glu Met Gln Phe
                260                 265                 270
Phe Ser Thr Ser Ser Gly Gly Thr Pro Lys Leu Val Leu Tyr Ser Glu
                275                 280                 285
Asp Val Asn Met Glu Thr Pro Asp Thr His Leu Ser Tyr Lys Pro Gly
    290                 295                 300
Lys Ser Asp Asp Asn Ser Lys Ala Met Leu Gly Gln Gln Ser Met Pro
305                 310                 315                 320
Asn Arg Pro Asn Tyr Ile Ala Phe Arg Asp Asn Phe Ile Gly Leu Met
                325                 330                 335
Tyr Tyr Asn Ser Thr Gly Asn Met Gly Val Leu Ala Gly Gln Ala Ser
                340                 345                 350
Gln Leu Asn Ala Val Val Asp Leu Gln Asp Arg Asn Thr Glu Leu Ser
                355                 360                 365
Tyr Gln Leu Leu Leu Asp Ser Ile Gly Asp Arg Thr Arg Tyr Phe Ser
    370                 375                 380
Met Trp Asn Gln Ala Val Asp Ser Tyr Asp Pro Asp Val Arg Ile Ile
385                 390                 395                 400
Glu Asn His Gly Thr Glu Asp Glu Leu Pro Asn Tyr Cys Phe Pro Leu
                405                 410                 415
Gly Gly Ile Gly Val Thr Asp Thr Tyr Gln Ala Ile Lys Ala Thr Asn
                420                 425                 430
Gly Asn Gly Gly Ala Thr Thr Trp Ala Gln Asp Asn Thr Phe Ala Glu
                435                 440                 445
Arg Asn Glu Ile Gly Val Gly Asn Asn Phe Ala Met Glu Ile Asn Leu
    450                 455                 460
Asn Ala Asn Leu Trp Arg Asn Phe Leu Tyr Ser Asn Ile Ala Leu Tyr
465                 470                 475                 480
Leu Pro Asp Lys Leu Lys Tyr Asn Pro Thr Asn Val Glu Ile Ser Asp
                485                 490                 495
Asn Pro Asn Thr Tyr Asp Tyr Met Asn Lys Arg Val Val Ala Pro Gly
                500                 505                 510
Leu Val Asp Cys Tyr Ile Asn Leu Gly Ala Arg Trp Ser Leu Asp Tyr
                515                 520                 525
Met Asp Asn Val Asn Pro Phe Asn His His Arg Asn Ala Gly Leu Arg
    530                 535                 540
Tyr Arg Ser Met Leu Leu Gly Asn Gly Arg Tyr Val Pro Phe His Ile
545                 550                 555                 560
Gln Val Pro Gln Lys Phe Phe Ala Ile Lys Asn Leu Leu Leu Leu Pro
                565                 570                 575
```

Gly Ser Tyr Thr Tyr Glu Trp Asn Phe Arg Lys Asp Val Asn Met Val
              580                 585                 590

Leu Gln Ser Ser Leu Gly Asn Asp Leu Arg Val Asp Gly Ala Ser Ile
        595                 600                 605

Lys Phe Asp Ser Ile Cys Leu Tyr Ala Thr Phe Pro Met Ala His
    610                 615                 620

Asn Thr Ala Ser Thr Leu Glu Ala Met Leu Arg Asn Asp Thr Asn Asp
625                 630                 635                 640

Gln Ser Phe Asn Asp Tyr Leu Ser Ala Ala Asn Met Leu Tyr Pro Ile
                645                 650                 655

Pro Ala Asn Ala Thr Asn Val Pro Ile Ser Ile Pro Ser Arg Asn Trp
                660                 665                 670

Ala Ala Phe Arg Gly Trp Ala Phe Thr Arg Leu Lys Thr Lys Glu Thr
                675                 680                 685

Pro Ser Leu Gly Ser Gly Tyr Asp Pro Tyr Tyr Thr Tyr Ser Gly Ser
        690                 695                 700

Ile Pro Tyr Leu Asp Gly Thr Phe Tyr Leu Asn His Thr Phe Lys Lys
705                 710                 715                 720

Val Ala Ile Thr Phe Asp Ser Ser Val Ser Trp Pro Gly Asn Asp Arg
                725                 730                 735

Leu Leu Thr Pro Asn Glu Phe Glu Ile Lys Arg Ser Val Asp Gly Glu
                740                 745                 750

Gly Tyr Asn Val Ala Gln Cys Asn Met Thr Lys Asp Trp Phe Leu Val
        755                 760                 765

Gln Met Leu Ala Asn Tyr Asn Ile Gly Tyr Gln Gly Phe Tyr Ile Pro
    770                 775                 780

Glu Ser Tyr Lys Asp Arg Met Tyr Ser Phe Phe Arg Asn Phe Gln Pro
785                 790                 795                 800

Met Ser Arg Gln Val Val Asp Asp Thr Lys Tyr Lys Asp Tyr Gln Gln
                805                 810                 815

Val Gly Ile Ile His Gln His Asn Asn Ser Gly Phe Val Gly Tyr Leu
                820                 825                 830

Ala Pro Thr Met Arg Glu Gly Gln Ala Tyr Pro Ala Asn Val Pro Tyr
        835                 840                 845

Pro Leu Ile Gly Lys Thr Ala Val Asp Ser Ile Thr Gln Lys Lys Phe
    850                 855                 860

Leu Cys Asp Arg Thr Leu Trp Arg Ile Pro Phe Ser Ser Asn Phe Met
865                 870                 875                 880

Ser Met Gly Ala Leu Thr Asp Leu Gly Gln Asn Leu Leu Tyr Ala Asn
                885                 890                 895

Ser Ala His Ala Leu Asp Met Thr Phe Glu Val Asp Pro Met Asp Glu
                900                 905                 910

Pro Thr Leu Leu Tyr Val Leu Phe Glu Val Phe Asp Val Val Arg Val
        915                 920                 925

His Gln Pro His Arg Gly Val Ile Glu Thr Val Tyr Leu Arg Thr Pro
    930                 935                 940

Phe Ser Ala Gly Asn Ala Thr Thr
945                 950

<210> SEQ ID NO 46
<211> LENGTH: 1033
<212> TYPE: PRT
<213> ORGANISM: Artificial Sequence
<220> FEATURE:

<223> OTHER INFORMATION: Hexon Polypeptide

<400> SEQUENCE: 46

```
Met Ala Thr Pro Ser Met Met Pro Gln Trp Ser Tyr Met His Ile Ser
  1               5                  10                  15

Gly Gln Asp Ala Ser Glu Tyr Leu Ser Pro Gly Leu Val Gln Phe Ala
             20                  25                  30

Arg Ala Thr Glu Thr Tyr Phe Ser Leu Asn Asn Lys Phe Arg Asn Pro
         35                  40                  45

Thr Val Ala Pro Thr His Asp Val Thr Thr Asp Arg Ser Gln Arg Leu
     50                  55                  60

Thr Leu Arg Phe Ile Pro Val Asp Arg Glu Asp Thr Ala Tyr Ser Tyr
 65                  70                  75                  80

Lys Ala Arg Phe Thr Leu Ala Val Gly Asp Asn Arg Val Leu Asp Met
                 85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Ser Cys Glu Trp Asp Glu Asp Thr Gln Val Gln Val
    130                 135                 140

Ala Ala Glu Asp Asp Gln Asp Asp Ser Thr Gly Glu Ile Pro Ala
145                 150                 155                 160

Pro Leu Ala Gly Thr Val Ser Lys Ile Leu Val Lys Glu Gly Asp Thr
                165                 170                 175

Val Lys Ala Gly Gln Thr Val Leu Leu Glu Ala Met Lys Met Glu
            180                 185                 190

Thr Glu Ile Asn Ala Pro Thr Asp Gly Lys Val Glu Lys Val Leu Val
        195                 200                 205

Lys Glu Arg Asp Ala Val Gln Gly Gly Gln Gly Leu Ile Lys Ile Gly
210                 215                 220

Gly Gly Thr Glu Glu Glu Glu Gln Leu Pro Gln Gln Arg Asn Gly Lys
225                 230                 235                 240

Lys Thr His Val Tyr Ala Gln Ala Pro Phe Ala Gly Glu Ala Ile Asn
                245                 250                 255

Lys Asn Gly Leu Gln Ile Gly Thr Asn Gly Ala Ala Thr Glu Gly Asn
            260                 265                 270

Lys Glu Ile Tyr Ala Asp Lys Thr Tyr Gln Pro Glu Pro Gln Ile Gly
        275                 280                 285

Glu Ser Gln Trp Asn Glu Ala Glu Ser Ser Val Ala Gly Gly Arg Val
    290                 295                 300

Leu Lys Lys Thr Thr Pro Met Lys Pro Cys Tyr Gly Ser Tyr Ala Arg
305                 310                 315                 320

Pro Thr Asn Ser Asn Gly Gly Gln Gly Val Met Val Glu Gln Asn Gly
                325                 330                 335

Lys Leu Glu Ser Gln Val Glu Met Gln Phe Phe Ser Thr Ser Val Asn
            340                 345                 350

Ala Met Asn Glu Ala Asn Ala Ile Gln Pro Lys Leu Val Leu Tyr Ser
        355                 360                 365

Glu Asp Val Asn Met Glu Thr Pro Asp Thr His Leu Ser Tyr Lys Pro
    370                 375                 380

Gly Lys Ser Asp Asp Asn Ser Lys Ala Met Leu Gly Gln Gln Ser Met
385                 390                 395                 400
```

```
Pro Asn Arg Pro Asn Tyr Ile Ala Phe Arg Asp Asn Phe Ile Gly Leu
            405                 410                 415

Met Tyr Tyr Asn Ser Thr Gly Asn Met Gly Val Leu Ala Gly Gln Ala
            420                 425                 430

Ser Gln Leu Asn Ala Val Val Asp Leu Gln Asp Arg Asn Thr Glu Leu
            435                 440                 445

Ser Tyr Gln Leu Leu Leu Asp Ser Ile Gly Asp Arg Thr Arg Tyr Phe
            450                 455                 460

Ser Met Trp Asn Gln Ala Val Asp Ser Tyr Asp Pro Asp Val Arg Ile
465                 470                 475                 480

Ile Glu Asn His Gly Thr Glu Asp Glu Leu Pro Asn Tyr Cys Phe Pro
            485                 490                 495

Leu Gly Gly Ile Gly Val Thr Asp Thr Tyr Gln Ala Ile Lys Ala Thr
            500                 505                 510

Asn Gly Asn Gly Gly Ala Thr Thr Trp Ala Gln Asp Asn Thr Phe Ala
            515                 520                 525

Glu Arg Asn Glu Ile Gly Val Gly Asn Asn Phe Ala Met Glu Ile Asn
            530                 535                 540

Leu Asn Ala Asn Leu Trp Arg Asn Phe Leu Tyr Ser Asn Ile Ala Leu
545                 550                 555                 560

Tyr Leu Pro Asp Lys Leu Lys Tyr Asn Pro Thr Asn Val Glu Ile Ser
            565                 570                 575

Asp Asn Pro Asn Thr Tyr Asp Tyr Met Asn Lys Arg Val Val Ala Pro
            580                 585                 590

Gly Leu Val Asp Cys Tyr Ile Asn Leu Gly Ala Arg Trp Ser Leu Asp
            595                 600                 605

Tyr Met Asp Asn Val Asn Pro Phe Asn His His Arg Asn Ala Gly Leu
            610                 615                 620

Arg Tyr Arg Ser Met Leu Leu Gly Asn Gly Arg Tyr Val Pro Phe His
625                 630                 635                 640

Ile Gln Val Pro Gln Lys Phe Phe Ala Ile Lys Asn Leu Leu Leu Leu
            645                 650                 655

Pro Gly Ser Tyr Thr Tyr Glu Trp Asn Phe Arg Lys Asp Val Asn Met
            660                 665                 670

Val Leu Gln Ser Ser Leu Gly Asn Asp Leu Arg Val Asp Gly Ala Ser
            675                 680                 685

Ile Lys Phe Asp Ser Ile Cys Leu Tyr Ala Thr Phe Phe Pro Met Ala
690                 695                 700

His Asn Thr Ala Ser Thr Leu Glu Ala Met Leu Arg Asn Asp Thr Asn
705                 710                 715                 720

Asp Gln Ser Phe Asn Asp Tyr Leu Ser Ala Ala Asn Met Leu Tyr Pro
            725                 730                 735

Ile Pro Ala Asn Ala Thr Asn Val Pro Ile Ser Ile Pro Ser Arg Asn
            740                 745                 750

Trp Ala Ala Phe Arg Gly Trp Ala Phe Thr Arg Leu Lys Thr Lys Glu
            755                 760                 765

Thr Pro Ser Leu Gly Ser Gly Tyr Asp Pro Tyr Tyr Thr Tyr Ser Gly
            770                 775                 780

Ser Ile Pro Tyr Leu Asp Gly Thr Phe Tyr Leu Asn His Thr Phe Lys
785                 790                 795                 800

Lys Val Ala Ile Thr Phe Asp Ser Ser Val Ser Trp Pro Gly Asn Asp
            805                 810                 815

Arg Leu Leu Thr Pro Asn Glu Phe Glu Ile Lys Arg Ser Val Asp Gly
```

```
                820                 825                 830
Glu Gly Tyr Asn Val Ala Gln Cys Asn Met Thr Lys Asp Trp Phe Leu
            835                 840                 845

Val Gln Met Leu Ala Asn Tyr Asn Ile Gly Tyr Gln Gly Phe Tyr Ile
850                 855                 860

Pro Glu Ser Tyr Lys Asp Arg Met Tyr Ser Phe Phe Arg Asn Phe Gln
865                 870                 875                 880

Pro Met Ser Arg Gln Val Val Asp Asp Thr Lys Tyr Lys Asp Tyr Gln
                885                 890                 895

Gln Val Gly Ile Ile His Gln His Asn Asn Ser Gly Phe Val Gly Tyr
            900                 905                 910

Leu Ala Pro Thr Met Arg Glu Gly Gln Ala Tyr Pro Ala Asn Val Pro
            915                 920                 925

Tyr Pro Leu Ile Gly Lys Thr Ala Val Asp Ser Ile Thr Gln Lys Lys
            930                 935                 940

Phe Leu Cys Asp Arg Thr Leu Trp Arg Ile Pro Phe Ser Ser Asn Phe
945                 950                 955                 960

Met Ser Met Gly Ala Leu Thr Asp Leu Gly Gln Asn Leu Leu Tyr Ala
                965                 970                 975

Asn Ser Ala His Ala Leu Asp Met Thr Phe Glu Val Asp Pro Met Asp
            980                 985                 990

Glu Pro Thr Leu Leu Tyr Val Leu Phe Glu Val Phe Asp Val Val Arg
            995                 1000                1005

Val His Gln Pro His Arg Gly Val Ile Glu Thr Val Tyr Leu Arg
    1010                1015                1020

Thr Pro Phe Ser Ala Gly Asn Ala Thr Thr
                1025                1030

<210> SEQ ID NO 47
<211> LENGTH: 1021
<212> TYPE: PRT
<213> ORGANISM: Artificial Sequence
<220> FEATURE:
<223> OTHER INFORMATION: Hexon Polypeptide

<400> SEQUENCE: 47

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Ser Cys Glu Trp Asp Glu Asp Thr Gln Val Gln Val
    130                 135                 140

Ala Ala Glu Asp Asp Gln Asp Asp Asp Glu Glu Glu Gln Leu Pro
```

```
            145                 150                 155                 160
        Gln Gln Arg Asn Gly Lys Lys Thr His Val Tyr Ala Gln Ala Pro Phe
                        165                 170                 175
        Ala Gly Glu Ala Ile Asn Lys Asn Gly Leu Gln Ile Gly Thr Asn Gly
                        180                 185                 190
        Ala Ala Thr Glu Gly Asn Lys Glu Ile Tyr Ala Asp Lys Thr Tyr Gln
                        195                 200                 205
        Pro Glu Pro Gln Ile Gly Glu Ser Gln Trp Asn Glu Ala Glu Ser Ser
                210                 215                 220
        Val Ala Gly Gly Arg Val Leu Lys Lys Thr Thr Pro Met Lys Pro Cys
        225                 230                 235                 240
        Tyr Gly Ser Tyr Ala Arg Pro Thr Asn Ser Asn Gly Gly Gln Gly Val
                        245                 250                 255
        Met Val Glu Gln Asn Gly Lys Leu Glu Ser Gln Val Glu Met Gln Phe
                        260                 265                 270
        Phe Ser Thr Ser Thr Gly Glu Ile Pro Ala Pro Leu Ala Gly Thr Val
                    275                 280                 285
        Ser Lys Ile Leu Val Lys Glu Gly Asp Thr Val Lys Ala Gly Gln Thr
                290                 295                 300
        Val Leu Val Leu Glu Ala Met Lys Met Glu Thr Glu Ile Asn Ala Pro
        305                 310                 315                 320
        Thr Asp Gly Lys Val Glu Lys Val Leu Val Lys Glu Arg Asp Ala Val
                        325                 330                 335
        Gln Gly Gly Gln Gly Leu Ile Lys Ile Gly Gly Thr Pro Lys Leu
                    340                 345                 350
        Val Leu Tyr Ser Glu Asp Val Asn Met Glu Thr Pro Asp Thr His Leu
                    355                 360                 365
        Ser Tyr Lys Pro Gly Lys Ser Asp Asp Asn Ser Lys Ala Met Leu Gly
                    370                 375                 380
        Gln Gln Ser Met Pro Asn Arg Pro Asn Tyr Ile Ala Phe Arg Asp Asn
        385                 390                 395                 400
        Phe Ile Gly Leu Met Tyr Tyr Asn Ser Thr Gly Asn Met Gly Val Leu
                        405                 410                 415
        Ala Gly Gln Ala Ser Gln Leu Asn Ala Val Val Asp Leu Gln Asp Arg
                        420                 425                 430
        Asn Thr Glu Leu Ser Tyr Gln Leu Leu Leu Asp Ser Ile Gly Asp Arg
                        435                 440                 445
        Thr Arg Tyr Phe Ser Met Trp Asn Gln Ala Val Asp Ser Tyr Asp Pro
                450                 455                 460
        Asp Val Arg Ile Ile Glu Asn His Gly Thr Glu Asp Glu Leu Pro Asn
        465                 470                 475                 480
        Tyr Cys Phe Pro Leu Gly Gly Ile Gly Val Thr Asp Tyr Gln Ala
                        485                 490                 495
        Ile Lys Ala Thr Asn Gly Asn Gly Gly Ala Thr Thr Trp Ala Gln Asp
                        500                 505                 510
        Asn Thr Phe Ala Glu Arg Asn Glu Ile Gly Val Gly Asn Asn Phe Ala
                    515                 520                 525
        Met Glu Ile Asn Leu Asn Ala Asn Leu Trp Arg Asn Phe Leu Tyr Ser
                    530                 535                 540
        Asn Ile Ala Leu Tyr Leu Pro Asp Lys Leu Lys Tyr Asn Pro Thr Asn
        545                 550                 555                 560
        Val Glu Ile Ser Asp Asn Pro Asn Thr Tyr Asp Tyr Met Asn Lys Arg
                        565                 570                 575
```

-continued

Val Val Ala Pro Gly Leu Val Asp Cys Tyr Ile Asn Leu Gly Ala Arg
            580             585             590

Trp Ser Leu Asp Tyr Met Asp Asn Val Asn Pro Phe Asn His His Arg
        595             600             605

Asn Ala Gly Leu Arg Tyr Arg Ser Met Leu Leu Gly Asn Gly Arg Tyr
        610             615             620

Val Pro Phe His Ile Gln Val Pro Gln Lys Phe Phe Ala Ile Lys Asn
625             630             635             640

Leu Leu Leu Leu Pro Gly Ser Tyr Thr Tyr Glu Trp Asn Phe Arg Lys
                645             650             655

Asp Val Asn Met Val Leu Gln Ser Ser Leu Gly Asn Asp Leu Arg Val
            660             665             670

Asp Gly Ala Ser Ile Lys Phe Asp Ser Ile Cys Leu Tyr Ala Thr Phe
            675             680             685

Phe Pro Met Ala His Asn Thr Ala Ser Thr Leu Glu Ala Met Leu Arg
        690             695             700

Asn Asp Thr Asn Asp Gln Ser Phe Asn Asp Tyr Leu Ser Ala Ala Asn
705             710             715             720

Met Leu Tyr Pro Ile Pro Ala Asn Ala Thr Asn Val Pro Ile Ser Ile
                725             730             735

Pro Ser Arg Asn Trp Ala Ala Phe Arg Gly Trp Ala Phe Thr Arg Leu
            740             745             750

Lys Thr Lys Glu Thr Pro Ser Leu Gly Ser Gly Tyr Asp Pro Tyr Tyr
        755             760             765

Thr Tyr Ser Gly Ser Ile Pro Tyr Leu Asp Gly Thr Phe Tyr Leu Asn
        770             775             780

His Thr Phe Lys Lys Val Ala Ile Thr Phe Asp Ser Ser Val Ser Trp
785             790             795             800

Pro Gly Asn Asp Arg Leu Leu Thr Pro Asn Glu Phe Glu Ile Lys Arg
            805             810             815

Ser Val Asp Gly Glu Gly Tyr Asn Val Ala Gln Cys Asn Met Thr Lys
            820             825             830

Asp Trp Phe Leu Val Gln Met Leu Ala Asn Tyr Asn Ile Gly Tyr Gln
            835             840             845

Gly Phe Tyr Ile Pro Glu Ser Tyr Lys Asp Arg Met Tyr Ser Phe Phe
        850             855             860

Arg Asn Phe Gln Pro Met Ser Arg Gln Val Val Asp Asp Thr Lys Tyr
865             870             875             880

Lys Asp Tyr Gln Gln Val Gly Ile Ile His Gln His Asn Asn Ser Gly
                885             890             895

Phe Val Gly Tyr Leu Ala Pro Thr Met Arg Glu Gly Gln Ala Tyr Pro
            900             905             910

Ala Asn Val Pro Tyr Pro Leu Ile Gly Lys Thr Ala Val Asp Ser Ile
            915             920             925

Thr Gln Lys Lys Phe Leu Cys Asp Arg Thr Leu Trp Arg Ile Pro Phe
        930             935             940

Ser Ser Asn Phe Met Ser Met Gly Ala Leu Thr Asp Leu Gly Gln Asn
945             950             955             960

Leu Leu Tyr Ala Asn Ser Ala His Ala Leu Asp Met Thr Phe Glu Val
                965             970             975

Asp Pro Met Asp Glu Pro Thr Leu Leu Tyr Val Leu Phe Glu Val Phe
            980             985             990

Asp Val Val Arg Val His Gln Pro His Arg Gly Val Ile Glu Thr Val
            995                1000                1005

Tyr Leu Arg Thr Pro Phe Ser Ala Gly Asn Ala Thr Thr
    1010                1015                1020

<210> SEQ ID NO 48
<211> LENGTH: 1015
<212> TYPE: PRT
<213> ORGANISM: Artificial Sequence
<220> FEATURE:
<223> OTHER INFORMATION: Hexon Polypeptide

<400> SEQUENCE: 48

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Ser Cys Glu Trp Asp Glu Asp Asp Thr Gln Val Gln Val
    130                 135                 140

Ala Ala Glu Asp Asp Gln Asp Asp Glu Glu Glu Gln Leu Pro
145                 150                 155                 160

Gln Gln Arg Asn Gly Lys Lys Thr His Val Tyr Ala Gln Ala Pro Phe
                165                 170                 175

Ala Gly Glu Ala Ile Asn Lys Asn Gly Leu Gln Ile Gly Thr Asn Gly
            180                 185                 190

Ala Ala Thr Glu Gly Asn Lys Glu Ile Tyr Ala Asp Lys Thr Tyr Gln
        195                 200                 205

Pro Glu Pro Gln Ile Gly Glu Ser Gln Trp Asn Glu Ala Glu Ser Ser
    210                 215                 220

Val Ala Gly Gly Arg Val Leu Lys Lys Thr Thr Pro Met Lys Pro Cys
225                 230                 235                 240

Tyr Gly Ser Tyr Ala Arg Pro Thr Asn Ser Asn Gly Gly Gln Gly Val
                245                 250                 255

Met Val Glu Gln Asn Gly Lys Leu Glu Ser Gln Val Glu Met Gln Phe
            260                 265                 270

Phe Ser Thr Ser Ser Ser Asn Phe Thr Arg Glu Gly Asn Val Thr Tyr
        275                 280                 285

Lys Glu Glu Met Asp Lys Val Lys Asn Cys Ser Phe Asn Val Thr Thr
    290                 295                 300

Gly Ile Arg Asp Lys Lys Gln Lys Val Asn Ala Leu Phe Tyr Arg Leu
305                 310                 315                 320

Asp Ile Thr Pro Leu Asp Glu Asn Asn Asn Ser Ser Glu Tyr Arg
                325                 330                 335

-continued

```
Leu Ile Asn Ser Gly Gly Thr Pro Lys Leu Val Leu Tyr Ser Glu Asp
            340                 345                 350

Val Asn Met Glu Thr Pro Asp Thr His Leu Ser Tyr Lys Pro Gly Lys
        355                 360                 365

Ser Asp Asp Asn Ser Lys Ala Met Leu Gly Gln Gln Ser Met Pro Asn
    370                 375                 380

Arg Pro Asn Tyr Ile Ala Phe Arg Asp Asn Phe Ile Gly Leu Met Tyr
385                 390                 395                 400

Tyr Asn Ser Thr Gly Asn Met Gly Val Leu Ala Gly Gln Ala Ser Gln
                405                 410                 415

Leu Asn Ala Val Val Asp Leu Gln Asp Arg Asn Thr Glu Leu Ser Tyr
            420                 425                 430

Gln Leu Leu Leu Asp Ser Ile Gly Asp Arg Thr Arg Tyr Phe Ser Met
        435                 440                 445

Trp Asn Gln Ala Val Asp Ser Tyr Asp Pro Asp Val Arg Ile Ile Glu
    450                 455                 460

Asn His Gly Thr Glu Asp Glu Leu Pro Asn Tyr Cys Phe Pro Leu Gly
465                 470                 475                 480

Gly Ile Gly Val Thr Asp Thr Tyr Gln Ala Ile Lys Ala Thr Asn Gly
                485                 490                 495

Asn Gly Gly Ala Thr Thr Trp Ala Gln Asp Asn Thr Phe Ala Glu Arg
            500                 505                 510

Asn Glu Ile Gly Val Gly Asn Asn Phe Ala Met Glu Ile Asn Leu Asn
        515                 520                 525

Ala Asn Leu Trp Arg Asn Phe Leu Tyr Ser Asn Ile Ala Leu Tyr Leu
    530                 535                 540

Pro Asp Lys Leu Lys Tyr Asn Pro Thr Asn Val Glu Ile Ser Asp Asn
545                 550                 555                 560

Pro Asn Thr Tyr Asp Tyr Met Asn Lys Arg Val Val Ala Pro Gly Leu
                565                 570                 575

Val Asp Cys Tyr Ile Asn Leu Gly Ala Arg Trp Ser Leu Asp Tyr Met
            580                 585                 590

Asp Asn Val Asn Pro Phe Asn His His Arg Asn Ala Gly Leu Arg Tyr
        595                 600                 605

Arg Ser Met Leu Leu Gly Asn Gly Arg Tyr Val Pro Phe His Ile Gln
    610                 615                 620

Val Pro Gln Lys Phe Phe Ala Ile Lys Asn Leu Leu Leu Leu Pro Gly
625                 630                 635                 640

Ser Tyr Thr Tyr Glu Trp Asn Phe Arg Lys Asp Val Asn Met Val Leu
                645                 650                 655

Gln Ser Ser Leu Gly Asn Asp Leu Arg Val Asp Gly Ala Ser Ile Lys
            660                 665                 670

Phe Asp Ser Ile Cys Leu Tyr Ala Thr Phe Phe Pro Met Ala His Asn
        675                 680                 685

Thr Ala Ser Thr Leu Glu Ala Met Leu Arg Asn Asp Thr Asn Asp Gln
    690                 695                 700

Ser Phe Asn Asp Tyr Leu Ser Ala Ala Asn Met Leu Tyr Pro Ile Pro
705                 710                 715                 720

Ala Asn Ala Thr Asn Val Pro Ile Ser Ile Pro Ser Arg Asn Trp Ala
                725                 730                 735

Ala Phe Arg Gly Trp Ala Phe Thr Arg Leu Lys Thr Lys Glu Thr Pro
            740                 745                 750

Ser Leu Gly Ser Gly Tyr Asp Pro Tyr Tyr Thr Tyr Ser Gly Ser Ile
```

```
                     755                 760                 765
Pro Tyr Leu Asp Gly Thr Phe Tyr Leu Asn His Thr Phe Lys Lys Val
770                 775                 780

Ala Ile Thr Phe Asp Ser Ser Val Ser Trp Pro Gly Asn Asp Arg Leu
785                 790                 795                 800

Leu Thr Pro Asn Glu Phe Glu Ile Lys Arg Ser Val Asp Gly Glu Gly
                        805                 810                 815

Tyr Asn Val Ala Gln Cys Asn Met Thr Lys Asp Trp Phe Leu Val Gln
            820                 825                 830

Met Leu Ala Asn Tyr Asn Ile Gly Tyr Gln Gly Phe Tyr Ile Pro Glu
                835                 840                 845

Ser Tyr Lys Asp Arg Met Tyr Ser Phe Phe Arg Asn Phe Gln Pro Met
850                 855                 860

Ser Arg Gln Val Val Asp Asp Thr Lys Tyr Lys Asp Tyr Gln Gln Val
865                 870                 875                 880

Gly Ile Ile His Gln His Asn Asn Ser Gly Phe Val Gly Tyr Leu Ala
                    885                 890                 895

Pro Thr Met Arg Glu Gly Gln Ala Tyr Pro Ala Asn Val Pro Tyr Pro
                900                 905                 910

Leu Ile Gly Lys Thr Ala Val Asp Ser Ile Thr Gln Lys Lys Phe Leu
            915                 920                 925

Cys Asp Arg Thr Leu Trp Arg Ile Pro Phe Ser Ser Asn Phe Met Ser
930                 935                 940

Met Gly Ala Leu Thr Asp Leu Gly Gln Asn Leu Leu Tyr Ala Asn Ser
945                 950                 955                 960

Ala His Ala Leu Asp Met Thr Phe Glu Val Asp Pro Met Asp Glu Pro
                    965                 970                 975

Thr Leu Leu Tyr Val Leu Phe Glu Val Phe Asp Val Val Arg Val His
                980                 985                 990

Gln Pro His Arg Gly Val Ile Glu Thr Val Tyr Leu Arg Thr Pro Phe
            995                 1000                1005

Ser Ala  Gly Asn Ala Thr Thr
    1010                1015

<210> SEQ ID NO 49
<211> LENGTH: 987
<212> TYPE: PRT
<213> ORGANISM: Artificial Sequence
<220> FEATURE:
<223> OTHER INFORMATION: Hexon Polypeptide

<400> SEQUENCE: 49

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
```

```
                100                 105                 110
Phe Lys Pro Tyr Ser Gly Thr Ala Tyr Asn Ala Leu Ala Pro Lys Gly
            115                 120                 125

Ala Pro Asn Ser Cys Glu Trp Asp Glu Asp Thr Gln Val Gln Val
130                 135                 140

Ala Ala Glu Asp Asp Gln Asp Asp Glu Glu Glu Gln Leu Pro
145                 150                 155                 160

Gln Gln Arg Asn Gly Lys Lys Thr His Val Tyr Ala Gln Ala Pro Phe
                165                 170                 175

Ala Gly Glu Ala Ile Asn Lys Asn Gly Leu Gln Ile Gly Thr Asn Gly
            180                 185                 190

Ala Ala Thr Glu Gly Asn Lys Glu Ile Tyr Ala Asp Lys Thr Tyr Gln
                195                 200                 205

Pro Glu Pro Gln Ile Gly Glu Ser Gln Trp Asn Glu Ala Glu Ser Ser
210                 215                 220

Val Ala Gly Gly Arg Val Leu Lys Lys Thr Thr Pro Met Lys Pro Cys
225                 230                 235                 240

Tyr Gly Ser Tyr Ala Arg Pro Thr Asn Ser Asn Gly Gly Gln Gly Val
                245                 250                 255

Met Val Glu Gln Asn Gly Lys Leu Glu Ser Gln Val Glu Met Gln Phe
            260                 265                 270

Phe Ser Thr Ser Ser Gln Ala Glu Pro Asp Arg Ala His Tyr Asn Ile
        275                 280                 285

Val Thr Phe Cys Cys Lys Cys Asp Gln Leu Leu Arg Arg Glu Val Tyr
        290                 295                 300

Asp Phe Ala Phe Arg Asp Leu Ser Gly Gly Thr Pro Lys Leu Val Leu
305                 310                 315                 320

Tyr Ser Glu Asp Val Asn Met Glu Thr Pro Asp Thr His Leu Ser Tyr
                325                 330                 335

Lys Pro Gly Lys Ser Asp Asp Asn Ser Lys Ala Met Leu Gly Gln Gln
            340                 345                 350

Ser Met Pro Asn Arg Pro Asn Tyr Ile Ala Phe Arg Asp Asn Phe Ile
        355                 360                 365

Gly Leu Met Tyr Tyr Asn Ser Thr Gly Asn Met Gly Val Leu Ala Gly
        370                 375                 380

Gln Ala Ser Gln Leu Asn Ala Val Val Asp Leu Gln Asp Arg Asn Thr
385                 390                 395                 400

Glu Leu Ser Tyr Gln Leu Leu Leu Asp Ser Ile Gly Asp Arg Thr Arg
                405                 410                 415

Tyr Phe Ser Met Trp Asn Gln Ala Val Asp Ser Tyr Asp Pro Asp Val
            420                 425                 430

Arg Ile Ile Glu Asn His Gly Thr Glu Asp Glu Leu Pro Asn Tyr Cys
        435                 440                 445

Phe Pro Leu Gly Gly Ile Gly Val Thr Asp Thr Tyr Gln Ala Ile Lys
        450                 455                 460

Ala Thr Asn Gly Asn Gly Gly Ala Thr Thr Trp Ala Gln Asp Asn Thr
465                 470                 475                 480

Phe Ala Glu Arg Asn Glu Ile Gly Val Gly Asn Asn Phe Ala Met Glu
                485                 490                 495

Ile Asn Leu Asn Ala Asn Leu Trp Arg Asn Phe Leu Tyr Ser Asn Ile
            500                 505                 510

Ala Leu Tyr Leu Pro Asp Lys Leu Lys Tyr Asn Pro Thr Asn Val Glu
        515                 520                 525
```

Ile Ser Asp Asn Pro Asn Thr Tyr Asp Tyr Met Asn Lys Arg Val Val
530                 535                 540

Ala Pro Gly Leu Val Asp Cys Tyr Ile Asn Leu Gly Ala Arg Trp Ser
545                 550                 555                 560

Leu Asp Tyr Met Asp Asn Val Asn Pro Phe Asn His His Arg Asn Ala
            565                 570                 575

Gly Leu Arg Tyr Arg Ser Met Leu Leu Gly Asn Gly Arg Tyr Val Pro
            580                 585                 590

Phe His Ile Gln Val Pro Gln Lys Phe Phe Ala Ile Lys Asn Leu Leu
    595                 600                 605

Leu Leu Pro Gly Ser Tyr Thr Tyr Glu Trp Asn Phe Arg Lys Asp Val
610                 615                 620

Asn Met Val Leu Gln Ser Ser Leu Gly Asn Asp Leu Arg Val Asp Gly
625                 630                 635                 640

Ala Ser Ile Lys Phe Asp Ser Ile Cys Leu Tyr Ala Thr Phe Phe Pro
            645                 650                 655

Met Ala His Asn Thr Ala Ser Thr Leu Glu Ala Met Leu Arg Asn Asp
            660                 665                 670

Thr Asn Asp Gln Ser Phe Asn Asp Tyr Leu Ser Ala Ala Asn Met Leu
            675                 680                 685

Tyr Pro Ile Pro Ala Asn Ala Thr Asn Val Pro Ile Ser Ile Pro Ser
690                 695                 700

Arg Asn Trp Ala Ala Phe Arg Gly Trp Ala Phe Thr Arg Leu Lys Thr
705                 710                 715                 720

Lys Glu Thr Pro Ser Leu Gly Ser Gly Tyr Asp Pro Tyr Tyr Thr Tyr
            725                 730                 735

Ser Gly Ser Ile Pro Tyr Leu Asp Gly Thr Phe Tyr Leu Asn His Thr
            740                 745                 750

Phe Lys Lys Val Ala Ile Thr Phe Asp Ser Ser Val Ser Trp Pro Gly
    755                 760                 765

Asn Asp Arg Leu Leu Thr Pro Asn Glu Phe Glu Ile Lys Arg Ser Val
770                 775                 780

Asp Gly Glu Gly Tyr Asn Val Ala Gln Cys Asn Met Thr Lys Asp Trp
785                 790                 795                 800

Phe Leu Val Gln Met Leu Ala Asn Tyr Asn Ile Gly Tyr Gln Gly Phe
            805                 810                 815

Tyr Ile Pro Glu Ser Tyr Lys Asp Arg Met Tyr Ser Phe Phe Arg Asn
            820                 825                 830

Phe Gln Pro Met Ser Arg Gln Val Asp Asp Thr Lys Tyr Lys Asp
            835                 840                 845

Tyr Gln Gln Val Gly Ile Ile His Gln His Asn Asn Ser Gly Phe Val
850                 855                 860

Gly Tyr Leu Ala Pro Thr Met Arg Glu Gly Gln Ala Tyr Pro Ala Asn
865                 870                 875                 880

Val Pro Tyr Pro Leu Ile Gly Lys Thr Ala Val Asp Ser Ile Thr Gln
            885                 890                 895

Lys Lys Phe Leu Cys Asp Arg Thr Leu Trp Arg Ile Pro Phe Ser Ser
            900                 905                 910

Asn Phe Met Ser Met Gly Ala Leu Thr Asp Leu Gly Gln Asn Leu Leu
    915                 920                 925

Tyr Ala Asn Ser Ala His Ala Leu Asp Met Thr Phe Glu Val Asp Pro
930                 935                 940

Met Asp Glu Pro Thr Leu Leu Tyr Val Leu Phe Glu Val Phe Asp Val
945                 950                 955                 960

Val Arg Val His Gln Pro His Arg Gly Val Ile Glu Thr Val Tyr Leu
            965                 970                 975

Arg Thr Pro Phe Ser Ala Gly Asn Ala Thr Thr
                980                 985

<210> SEQ ID NO 50
<211> LENGTH: 959
<212> TYPE: PRT
<213> ORGANISM: Artificial Sequence
<220> FEATURE:
<223> OTHER INFORMATION: Hexon Polypeptide

<400> SEQUENCE: 50

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Ser Cys Glu Trp Asp Glu Asp Thr Gln Val Gln Val
    130                 135                 140

Ala Ala Glu Asp Asp Gln Asp Asp Glu Glu Glu Glu Gln Leu Pro
145                 150                 155                 160

Gln Gln Arg Asn Gly Lys Lys Thr His Val Tyr Ala Gln Ala Pro Phe
                165                 170                 175

Ala Gly Glu Ala Ile Asn Lys Asn Gly Leu Gln Ile Gly Thr Asn Gly
            180                 185                 190

Ala Ala Thr Glu Gly Asn Lys Glu Ile Tyr Ala Asp Lys Thr Tyr Gln
        195                 200                 205

Pro Glu Pro Gln Ile Gly Glu Ser Gln Trp Asn Glu Ala Glu Ser Ser
    210                 215                 220

Val Ala Gly Gly Arg Val Leu Lys Lys Thr Thr Pro Met Lys Pro Cys
225                 230                 235                 240

Tyr Gly Ser Tyr Ala Arg Pro Thr Asn Ser Asn Gly Gly Gln Gly Val
                245                 250                 255

Met Val Glu Gln Asn Gly Lys Leu Glu Ser Gln Val Glu Met Gln Phe
            260                 265                 270

Phe Ser Thr Ser Val Asn Ala Met Asn Glu Ala Asn Ala Ile Gln Pro
        275                 280                 285

Lys Leu Val Leu Tyr Ser Glu Asp Val Asn Met Glu Thr Pro Asp Thr
    290                 295                 300

His Leu Ser Tyr Lys Pro Gly Lys Ser Asp Asp Asn Ser Lys Ala Met
305                 310                 315                 320

```
Leu Gly Gln Gln Ser Met Pro Asn Arg Pro Asn Tyr Ile Ala Phe Arg
            325                 330                 335
Asp Asn Phe Ile Gly Leu Met Tyr Tyr Asn Ser Thr Gly Asn Met Gly
        340                 345                 350
Val Leu Ala Gly Gln Ala Ser Gln Leu Asn Ala Val Val Asp Leu Gln
    355                 360                 365
Asp Arg Asn Thr Glu Leu Ser Tyr Gln Leu Leu Asp Ser Ile Gly
370                 375                 380
Asp Arg Thr Arg Tyr Phe Ser Met Trp Asn Gln Ala Val Asp Ser Tyr
385                 390                 395                 400
Asp Pro Asp Val Arg Ile Ile Glu Asn His Gly Thr Glu Asp Glu Leu
                405                 410                 415
Pro Asn Tyr Cys Phe Pro Leu Gly Gly Ile Gly Val Thr Asp Thr Tyr
            420                 425                 430
Gln Ala Ile Lys Ala Thr Asn Gly Asn Gly Gly Ala Thr Thr Trp Ala
        435                 440                 445
Gln Asp Asn Thr Phe Ala Glu Arg Asn Glu Ile Gly Val Gly Asn Asn
    450                 455                 460
Phe Ala Met Glu Ile Asn Leu Asn Ala Asn Leu Trp Arg Asn Phe Leu
465                 470                 475                 480
Tyr Ser Asn Ile Ala Leu Tyr Leu Pro Asp Lys Leu Lys Tyr Asn Pro
                485                 490                 495
Thr Asn Val Glu Ile Ser Asp Asn Pro Asn Thr Tyr Asp Tyr Met Asn
            500                 505                 510
Lys Arg Val Val Ala Pro Gly Leu Val Asp Cys Tyr Ile Asn Leu Gly
        515                 520                 525
Ala Arg Trp Ser Leu Asp Tyr Met Asp Asn Val Asn Pro Phe Asn His
    530                 535                 540
His Arg Asn Ala Gly Leu Arg Tyr Arg Ser Met Leu Leu Gly Asn Gly
545                 550                 555                 560
Arg Tyr Val Pro Phe His Ile Gln Val Pro Gln Lys Phe Phe Ala Ile
                565                 570                 575
Lys Asn Leu Leu Leu Leu Pro Gly Ser Tyr Thr Tyr Glu Trp Asn Phe
            580                 585                 590
Arg Lys Asp Val Asn Met Val Leu Gln Ser Ser Leu Gly Asn Asp Leu
        595                 600                 605
Arg Val Asp Gly Ala Ser Ile Lys Phe Asp Ser Ile Cys Leu Tyr Ala
    610                 615                 620
Thr Phe Phe Pro Met Ala His Asn Thr Ala Ser Thr Leu Glu Ala Met
625                 630                 635                 640
Leu Arg Asn Asp Thr Asn Asp Gln Ser Phe Asn Asp Tyr Leu Ser Ala
                645                 650                 655
Ala Asn Met Leu Tyr Pro Ile Pro Ala Asn Ala Thr Asn Val Pro Ile
            660                 665                 670
Ser Ile Pro Ser Arg Asn Trp Ala Ala Phe Arg Gly Trp Ala Phe Thr
        675                 680                 685
Arg Leu Lys Thr Lys Glu Thr Pro Ser Leu Gly Ser Gly Tyr Asp Pro
    690                 695                 700
Tyr Tyr Thr Tyr Ser Gly Ser Ile Pro Tyr Leu Asp Gly Thr Phe Tyr
705                 710                 715                 720
Leu Asn His Thr Phe Lys Lys Val Ala Ile Thr Phe Asp Ser Ser Val
                725                 730                 735
Ser Trp Pro Gly Asn Asp Arg Leu Leu Thr Pro Asn Glu Phe Glu Ile
```

740                 745                 750
Lys Arg Ser Val Asp Gly Glu Gly Tyr Asn Val Ala Gln Cys Asn Met
                755                 760                 765

Thr Lys Asp Trp Phe Leu Val Gln Met Leu Ala Asn Tyr Asn Ile Gly
        770                 775                 780

Tyr Gln Gly Phe Tyr Ile Pro Glu Ser Tyr Lys Asp Arg Met Tyr Ser
785                 790                 795                 800

Phe Phe Arg Asn Phe Gln Pro Met Ser Arg Gln Val Val Asp Asp Thr
                805                 810                 815

Lys Tyr Lys Asp Tyr Gln Gln Val Gly Ile Ile His Gln His Asn Asn
            820                 825                 830

Ser Gly Phe Val Gly Tyr Leu Ala Pro Thr Met Arg Glu Gly Gln Ala
        835                 840                 845

Tyr Pro Ala Asn Val Pro Tyr Pro Leu Ile Gly Lys Thr Ala Val Asp
    850                 855                 860

Ser Ile Thr Gln Lys Lys Phe Leu Cys Asp Arg Thr Leu Trp Arg Ile
865                 870                 875                 880

Pro Phe Ser Ser Asn Phe Met Ser Met Gly Ala Leu Thr Asp Leu Gly
                885                 890                 895

Gln Asn Leu Leu Tyr Ala Asn Ser Ala His Ala Leu Asp Met Thr Phe
            900                 905                 910

Glu Val Asp Pro Met Asp Glu Pro Thr Leu Leu Tyr Val Leu Phe Glu
        915                 920                 925

Val Phe Asp Val Val Arg Val His Gln Pro His Arg Gly Val Ile Glu
    930                 935                 940

Thr Val Tyr Leu Arg Thr Pro Phe Ser Ala Gly Asn Ala Thr Thr
945                 950                 955

<210> SEQ ID NO 51
<211> LENGTH: 962
<212> TYPE: PRT
<213> ORGANISM: Artificial Sequence
<220> FEATURE:
<223> OTHER INFORMATION: Hexon Polypeptide

<400> SEQUENCE: 51

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Ser Cys Glu Trp Glu Gln Asn Glu Thr Ala Gln Val Asp
    130                 135                 140

Ala Gln Glu Leu Asp Glu Glu Glu Asn Glu Ala Asn Glu Ala Gln Ala

```
            145                 150                 155                 160
Arg Glu Gln Glu Gln Ala Lys Lys Thr His Val Tyr Ala Gln Ala Pro
                    165                 170                 175

Leu Ser Gly Glu Ala Ile Asn Lys Asn Gly Leu Gln Ile Gly Thr Asn
                180                 185                 190

Gly Ala Ala Thr Glu Gly Asn Lys Glu Ile Tyr Ala Asp Lys Thr Tyr
                195                 200                 205

Gln Pro Glu Pro Gln Ile Gly Glu Ser Gln Trp Asn Glu Ala Glu Ser
            210                 215                 220

Ser Val Ala Gly Gly Arg Val Leu Lys Lys Thr Thr Pro Met Lys Pro
225                 230                 235                 240

Cys Tyr Gly Ser Tyr Ala Arg Pro Thr Asn Ser Asn Gly Gln Gly
                245                 250                 255

Val Met Val Glu Gln Asn Gly Lys Leu Glu Ser Gln Val Glu Met Gln
                260                 265                 270

Phe Phe Ser Thr Ser Val Asn Ala Met Asn Glu Ala Asn Ala Ile Gln
            275                 280                 285

Pro Lys Leu Val Leu Tyr Ser Glu Asp Val Asn Met Glu Thr Pro Asp
        290                 295                 300

Thr His Leu Ser Tyr Lys Pro Gly Lys Ser Asp Asp Asn Ser Lys Ala
305                 310                 315                 320

Met Leu Gly Gln Gln Ser Met Pro Asn Arg Pro Asn Tyr Ile Ala Phe
                325                 330                 335

Arg Asp Asn Phe Ile Gly Leu Met Tyr Tyr Asn Ser Thr Gly Asn Met
                340                 345                 350

Gly Val Leu Ala Gly Gln Ala Ser Gln Leu Asn Ala Val Val Asp Leu
            355                 360                 365

Gln Asp Arg Asn Thr Glu Leu Ser Tyr Gln Leu Leu Asp Ser Ile
        370                 375                 380

Gly Asp Arg Thr Arg Tyr Phe Ser Met Trp Asn Gln Ala Val Asp Ser
385                 390                 395                 400

Tyr Asp Pro Asp Val Arg Ile Ile Glu Asn His Gly Thr Glu Asp Glu
                405                 410                 415

Leu Pro Asn Tyr Cys Phe Pro Leu Gly Ile Gly Ile Thr Asp Thr
                420                 425                 430

Phe Gln Ala Val Lys Thr Thr Ala Ala Asn Gly Asp Gln Gly Asn Thr
            435                 440                 445

Thr Trp Gln Lys Asp Ser Thr Phe Ala Glu Arg Asn Glu Ile Gly Val
        450                 455                 460

Gly Asn Asn Phe Ala Met Glu Ile Asn Leu Asn Ala Asn Leu Trp Arg
465                 470                 475                 480

Asn Phe Leu Tyr Ser Asn Ile Ala Leu Tyr Leu Pro Asp Lys Leu Lys
                485                 490                 495

Tyr Asn Pro Thr Asn Val Glu Ile Ser Asp Asn Pro Asn Thr Tyr Asp
                500                 505                 510

Tyr Met Asn Lys Arg Val Val Ala Pro Gly Leu Val Asp Cys Tyr Ile
            515                 520                 525

Asn Leu Gly Ala Arg Trp Ser Leu Asp Tyr Met Asp Asn Val Asn Pro
        530                 535                 540

Phe Asn His Pro Arg His Ala Gly Leu Arg Tyr Arg Ser Met Leu Leu
545                 550                 555                 560

Gly Asn Gly Arg Tyr Val Pro Phe His Ile Gln Val Pro Gln Lys Phe
                565                 570                 575
```

Phe Ala Ile Lys Asn Leu Leu Leu Pro Gly Ser Tyr Thr Tyr Glu
            580                 585                 590

Trp Asn Phe Arg Lys Asp Val Asn Met Val Leu Gln Ser Leu Gly
            595                 600                 605

Asn Asp Leu Arg Val Asp Gly Ala Ser Ile Lys Phe Asp Ser Ile Cys
610                 615                 620

Leu Tyr Ala Thr Phe Phe Pro Met Ala His Asn Thr Ala Ser Thr Leu
625                 630                 635                 640

Glu Ala Met Leu Arg Asn Asp Thr Asn Asp Gln Ser Phe Asn Asp Tyr
                645                 650                 655

Leu Ser Ala Ala Asn Met Leu Tyr Pro Ile Pro Ala Asn Ala Thr Asn
                660                 665                 670

Val Pro Ile Ser Ile Pro Ser Arg Asn Trp Ala Ala Phe Arg Gly Trp
                675                 680                 685

Ala Phe Thr Arg Leu Lys Thr Lys Glu Thr Pro Ser Leu Gly Ser Gly
                690                 695                 700

Tyr Asp Pro Tyr Tyr Thr Tyr Ser Gly Ser Ile Pro Tyr Leu Asp Gly
705                 710                 715                 720

Thr Phe Tyr Leu Asn His Thr Phe Lys Lys Val Ala Ile Thr Phe Asp
                725                 730                 735

Ser Ser Val Ser Trp Pro Gly Asn Asp Arg Leu Leu Thr Pro Asn Glu
                740                 745                 750

Phe Glu Ile Lys Arg Ser Val Asp Gly Glu Gly Tyr Asn Val Ala Gln
                755                 760                 765

Cys Asn Met Thr Lys Asp Trp Phe Leu Val Gln Met Leu Ala Asn Tyr
                770                 775                 780

Asn Ile Gly Tyr Gln Gly Phe Tyr Ile Pro Glu Ser Tyr Lys Asp Arg
785                 790                 795                 800

Met Tyr Ser Phe Phe Arg Asn Phe Gln Pro Met Ser Arg Gln Val Val
                805                 810                 815

Asp Asp Thr Lys Tyr Lys Asp Tyr Gln Gln Val Gly Ile Ile His Gln
                820                 825                 830

His Asn Asn Ser Gly Phe Val Gly Tyr Leu Ala Pro Thr Met Arg Glu
                835                 840                 845

Gly Gln Ala Tyr Pro Ala Asn Val Pro Tyr Pro Leu Ile Gly Lys Thr
850                 855                 860

Ala Val Asp Ser Ile Thr Gln Lys Lys Phe Leu Cys Asp Arg Thr Leu
865                 870                 875                 880

Trp Arg Ile Pro Phe Ser Ser Asn Phe Met Ser Met Gly Ala Leu Thr
                885                 890                 895

Asp Leu Gly Gln Asn Leu Leu Tyr Ala Asn Ser Ala His Ala Leu Asp
                900                 905                 910

Met Thr Phe Glu Val Asp Pro Met Asp Glu Pro Thr Leu Leu Tyr Val
                915                 920                 925

Leu Phe Glu Val Phe Asp Val Val Arg Val His Gln Pro His Arg Gly
                930                 935                 940

Val Ile Glu Thr Val Tyr Leu Arg Thr Pro Phe Ser Ala Gly Asn Ala
945                 950                 955                 960

Thr Thr

<210> SEQ ID NO 52
<211> LENGTH: 407
<212> TYPE: PRT

<213> ORGANISM: Human Adenovirus 5

<400> SEQUENCE: 52

| | | | | | | | | | | | | | | |
|---|---|---|---|---|---|---|---|---|---|---|---|---|---|---|
| Tyr | Asn | Ala | Leu | Ala | Pro | Lys | Gly | Ala | Pro | Asn | Pro | Cys | Glu | Trp | Asp |
| 1 | | | | 5 | | | | | 10 | | | | | 15 | |

Glu Ala Ala Thr Ala Leu Glu Ile Asn Leu Glu Glu Asp Asp Asp
            20                  25                  30

Asn Glu Asp Glu Val Asp Glu Gln Ala Glu Gln Gln Lys Thr His Val
        35                  40                  45

Phe Ser Gln Ala Pro Tyr Ser Gly Ile Asn Ile Thr Lys Glu Gly Ile
    50                  55                  60

Gln Ile Gly Val Glu Gly Gln Thr Pro Lys Tyr Ala Asp Lys Thr Phe
65                  70                  75                  80

Gln Pro Glu Pro Gln Ile Gly Glu Ser Gln Trp Tyr Glu Thr Glu Ile
                85                  90                  95

Asn His Ala Ala Gly Arg Val Leu Lys Lys Thr Thr Pro Met Lys Pro
            100                 105                 110

Cys Tyr Gly Ser Tyr Ala Lys Pro Thr Asn Glu Asn Gly Gly Gln Gly
        115                 120                 125

Ile Leu Val Lys Gln Gln Asn Gly Lys Leu Glu Ser Gln Val Glu Met
    130                 135                 140

Gln Phe Phe Ser Thr Thr Glu Ala Thr Ala Gly Asn Gly Asp Asn Leu
145                 150                 155                 160

Thr Pro Lys Val Val Leu Tyr Ser Glu Asp Val Asp Ile Glu Thr Pro
                165                 170                 175

Asp Thr His Ile Ser Tyr Met Pro Thr Ile Lys Glu Gly Asn Ser Arg
            180                 185                 190

Glu Leu Met Gly Gln Gln Ser Met Pro Asn Arg Pro Asn Tyr Ile Ala
        195                 200                 205

Phe Arg Asp Asn Phe Ile Gly Leu Met Tyr Tyr Asn Ser Thr Gly Asn
    210                 215                 220

Met Gly Val Leu Ala Gly Gln Ala Ser Gln Leu Asn Ala Val Val Asp
225                 230                 235                 240

Leu Gln Asp Arg Asn Thr Glu Leu Ser Tyr Gln Leu Leu Leu Asp Ser
                245                 250                 255

Ile Gly Asp Arg Thr Arg Tyr Phe Ser Met Trp Asn Gln Ala Val Asp
            260                 265                 270

Ser Tyr Asp Pro Asp Val Arg Ile Ile Glu Asn His Gly Thr Glu Asp
        275                 280                 285

Glu Leu Pro Asn Tyr Cys Phe Pro Leu Gly Gly Val Ile Asn Thr Glu
    290                 295                 300

Thr Leu Thr Lys Val Lys Pro Lys Thr Gly Gln Glu Asn Gly Trp Glu
305                 310                 315                 320

Lys Asp Ala Thr Glu Phe Ser Asp Lys Asn Glu Ile Arg Val Gly Asn
                325                 330                 335

Asn Phe Ala Met Glu Ile Asn Leu Asn Ala Asn Leu Trp Arg Asn Phe
            340                 345                 350

Leu Tyr Ser Asn Ile Ala Leu Tyr Leu Pro Asp Lys Leu Lys Tyr Ser
        355                 360                 365

Pro Ser Asn Val Lys Ile Ser Asp Asn Pro Asn Thr Tyr Asp Tyr Met
    370                 375                 380

Asn Lys Arg Val Val Ala Pro Gly Leu Val Asp Cys Tyr Ile Asn Leu
385                 390                 395                 400

Gly Ala Arg Trp Ser Leu Asp
                405

<210> SEQ ID NO 53
<211> LENGTH: 418
<212> TYPE: PRT
<213> ORGANISM: Human Adenovirus 6

<400> SEQUENCE: 53

Tyr Asn Ala Leu Ala Pro Lys Gly Ala Pro Asn Ser Cys Glu Trp Glu
1               5                   10                  15

Gln Asn Glu Thr Ala Gln Val Asp Ala Gln Glu Leu Asp Glu Glu Glu
            20                  25                  30

Asn Glu Ala Asn Glu Ala Gln Ala Arg Glu Gln Glu Gln Ala Lys Lys
        35                  40                  45

Thr His Val Tyr Ala Gln Ala Pro Leu Ser Gly Ile Lys Ile Thr Lys
    50                  55                  60

Glu Gly Leu Gln Ile Gly Thr Ala Asp Ala Thr Val Ala Gly Ala Gly
65              70                  75                  80

Lys Glu Ile Phe Ala Asp Lys Thr Phe Gln Pro Glu Pro Gln Val Gly
                85                  90                  95

Glu Ser Gln Trp Asn Glu Ala Asp Ala Thr Ala Ala Gly Gly Arg Val
            100                 105                 110

Leu Lys Lys Thr Thr Pro Met Lys Pro Cys Tyr Gly Ser Tyr Ala Arg
        115                 120                 125

Pro Thr Asn Ser Asn Gly Gly Gln Gly Val Met Val Glu Gln Asn Gly
    130                 135                 140

Lys Leu Glu Ser Gln Val Glu Met Gln Phe Phe Ser Thr Ser Thr Asn
145             150                 155                 160

Ala Thr Asn Glu Val Asn Asn Ile Gln Pro Thr Val Val Leu Tyr Ser
                165                 170                 175

Glu Asp Val Asn Met Glu Thr Pro Asp Thr His Leu Ser Tyr Lys Pro
            180                 185                 190

Lys Met Gly Asp Lys Asn Ala Lys Val Met Leu Gly Gln Gln Ala Met
        195                 200                 205

Pro Asn Arg Pro Asn Tyr Ile Ala Phe Arg Asp Asn Phe Ile Gly Leu
    210                 215                 220

Met Tyr Tyr Asn Ser Thr Gly Asn Met Gly Val Leu Ala Gly Gln Ala
225             230                 235                 240

Ser Gln Leu Asn Ala Val Val Asp Leu Gln Asp Arg Asn Thr Glu Leu
                245                 250                 255

Ser Tyr Gln Leu Leu Leu Asp Ser Ile Gly Asp Arg Thr Arg Tyr Phe
            260                 265                 270

Ser Met Trp Asn Gln Ala Val Asp Ser Tyr Asp Pro Asp Val Arg Ile
        275                 280                 285

Ile Glu Asn His Gly Thr Glu Asp Glu Leu Pro Asn Tyr Cys Phe Pro
    290                 295                 300

Leu Gly Gly Ile Gly Ile Thr Asp Thr Phe Gln Ala Val Lys Thr Thr
305             310                 315                 320

Ala Ala Asn Gly Asp Gln Gly Asn Thr Thr Trp Gln Lys Asp Ser Thr
                325                 330                 335

Phe Ala Glu Arg Asn Glu Ile Gly Val Gly Asn Asn Phe Ala Met Glu
            340                 345                 350

Ile Asn Leu Asn Ala Asn Leu Trp Arg Asn Phe Leu Tyr Ser Asn Ile
        355                 360                 365

```
Ala Leu Tyr Leu Pro Asp Lys Leu Lys Tyr Asn Pro Thr Asn Val Glu
        370                 375                 380

Ile Ser Asp Asn Pro Asn Thr Tyr Asp Tyr Met Asn Lys Arg Val Val
385                 390                 395                 400

Ala Pro Gly Leu Val Asp Cys Tyr Ile Asn Leu Gly Ala Arg Trp Ser
                405                 410                 415

Leu Glu

<210> SEQ ID NO 54
<211> LENGTH: 414
<212> TYPE: PRT
<213> ORGANISM: Human Adenovirus 57

<400> SEQUENCE: 54

Tyr Asn Ala Leu Ala Pro Lys Gly Ala Pro Asn Ser Cys Glu Trp Asp
1               5                   10                  15

Glu Asp Asp Thr Gln Val Gln Val Ala Ala Glu Asp Gln Asp Asp
            20                  25                  30

Asp Glu Glu Glu Gln Leu Pro Gln Gln Arg Asn Gly Lys Lys Thr
        35                  40                  45

His Val Tyr Ala Gln Ala Pro Phe Ala Gly Glu Ala Ile Asn Lys Asn
    50                  55                  60

Gly Leu Gln Ile Gly Thr Asn Gly Ala Ala Thr Glu Gly Asn Lys Glu
65                  70                  75                  80

Ile Tyr Ala Asp Lys Thr Tyr Gln Pro Glu Pro Gln Ile Gly Glu Ser
                85                  90                  95

Gln Trp Asn Glu Ala Glu Ser Ser Val Ala Gly Gly Arg Val Leu Lys
            100                 105                 110

Lys Thr Thr Pro Met Lys Pro Cys Tyr Gly Ser Tyr Ala Arg Pro Thr
        115                 120                 125

Asn Ser Asn Gly Gly Gln Gly Val Met Val Glu Gln Asn Gly Lys Leu
    130                 135                 140

Glu Ser Gln Val Glu Met Gln Phe Phe Ser Thr Ser Val Asn Ala Met
145                 150                 155                 160

Asn Glu Ala Asn Ala Ile Gln Pro Lys Leu Val Leu Tyr Ser Glu Asp
                165                 170                 175

Val Asn Met Glu Thr Pro Asp Thr His Leu Ser Tyr Lys Pro Gly Lys
            180                 185                 190

Ser Asp Asp Asn Ser Lys Ala Met Leu Gly Gln Gln Ser Met Pro Asn
        195                 200                 205

Arg Pro Asn Tyr Ile Ala Phe Arg Asp Asn Phe Ile Gly Leu Met Tyr
    210                 215                 220

Tyr Asn Ser Thr Gly Asn Met Gly Val Leu Ala Gly Gln Ala Ser Gln
225                 230                 235                 240

Leu Asn Ala Val Val Asp Leu Gln Asp Arg Asn Thr Glu Leu Ser Tyr
                245                 250                 255

Gln Leu Leu Leu Asp Ser Ile Gly Asp Arg Thr Arg Tyr Phe Ser Met
            260                 265                 270

Trp Asn Gln Ala Val Asp Ser Tyr Asp Pro Asp Val Arg Ile Ile Glu
        275                 280                 285

Asn His Gly Thr Glu Asp Glu Leu Pro Asn Tyr Cys Phe Pro Leu Gly
    290                 295                 300

Gly Ile Gly Val Thr Asp Thr Tyr Gln Ala Ile Lys Ala Thr Asn Gly
305                 310                 315                 320
```

```
Asn Gly Gly Ala Thr Thr Trp Ala Gln Asp Asn Thr Phe Ala Glu Arg
            325                 330                 335

Asn Glu Ile Gly Val Gly Asn Asn Phe Ala Met Glu Ile Asn Leu Asn
            340                 345                 350

Ala Asn Leu Trp Arg Asn Phe Leu Tyr Ser Asn Ile Ala Leu Tyr Leu
        355                 360                 365

Pro Asp Lys Leu Lys Tyr Asn Pro Thr Asn Val Glu Ile Ser Asp Asn
    370                 375                 380

Pro Asn Thr Tyr Asp Tyr Met Asn Lys Arg Val Val Ala Pro Gly Leu
385                 390                 395                 400

Val Asp Cys Tyr Ile Asn Leu Gly Ala Arg Trp Ser Leu Asp
                405                 410
```